US007220775B2

(12) United States Patent
Blackburn

(10) Patent No.: US 7,220,775 B2
(45) Date of Patent: May 22, 2007

(54) COMPOUND USEFUL FOR THE TREATMENT OF NEUROPATHIC PAIN

(75) Inventor: Thomas P. Blackburn, Hoboken, NJ (US)

(73) Assignee: H. Lundbeck A/S, Copenhagen-Valby (DK)

( * ) Notice: Subject to any disclaimer, the term of this patent is extended or adjusted under 35 U.S.C. 154(b) by 611 days.

(21) Appl. No.: 10/637,299

(22) Filed: Aug. 7, 2003

(65) Prior Publication Data
US 2004/0092570 A1    May 13, 2004

Related U.S. Application Data

(60) Provisional application No. 60/402,035, filed on Aug. 7, 2002.

(51) Int. Cl.
*A01N 43/38* (2006.01)
*A61K 31/4015* (2006.01)

(52) U.S. Cl. .................................... 514/416
(58) Field of Classification Search ................ 514/414
See application file for complete search history.

(56) References Cited

U.S. PATENT DOCUMENTS

| 5,576,296 | A | 11/1996 | Bartfai et al. ................. 514/13 |
| 6,511,827 | B1 | 1/2003 | Howard et al. ............ 434/69.1 |
| 7,081,470 | B2 * | 7/2006 | Konkel et al. .............. 514/411 |

FOREIGN PATENT DOCUMENTS

| EP | 514361 | 11/1992 |
| EP | 667340 | 8/1995 |
| WO | WO9212997 | 8/1992 |
| WO | WO9815570 | 4/1998 |
| WO | WO9931130 | 6/1999 |
| WO | WO0002865 | 1/2000 |
| WO | WO0260392 | 8/2002 |

OTHER PUBLICATIONS

U.S. Appl. No. 10/638,242, filed May 2004, Konkel et al.*
U.S. Appl. No. 10/723,961, filed Jul. 2004, Blackburn et al.*
U.S. Appl. No. 11/298,116, filed Dec. 2005, Blackburn et al.*
U.S. Appl. No. 11/343,810, filed Jan. 2006, Konkel et al.*
U.S. Appl. No. 11/343,989, filed Jan. 2006, Konkel et al.*
Swanson, C. J. et al. "Anxiolytic- and antidepressant-like profiles of the galanin-3 receptor (Gal3) antagonists SNAP 37889 and SNAP 398299" (2005) PNAS vol. 102, No. 48, pp. 17489-17494.*
Liu, H. X. et al. "Effect of intrathecal galanin and its putative antagonist M35 on pain begavior in a neuropathic pain model" (2000) Brain Research vol. 886, pp. 67-72.*
Silverman, Richard B. The Organic Chemistry of Drug Design and Drug Action, (1992) Published by Academic Press, pp. 65-71.*
Ahmad, A., et al., "Identification And Molecular Cloning Of ANovel Galanin Receptor (GALR-2) In Rat Sensory Neurons", Soc.Neurosci. Abstr. (1996) 22(3): 1682, Abstract No. 661.10 (Exhibit 10).

Ahmad, S., et al., "Molecular Cloning Of A Novel Widely Distributed Galanin Receptor Subtype (GALR2)," *International Association for the Study of Pain (IASP Press)*(1996) Abstract No. 81: 134 (Exhibit 11).
Ahmad, S. Et al., Astra Pain Control (1996), poster (Exhibit 12).
Bartfai, T., et al, "Galanin Receptor Ligand M40 Peptide Distinguishes Between Putative Galanin- Receptor Subtypes," *PNAS* (USA)(1993) 90: 11287-11291 (Exhibit 13).
Branchek, et al., "Galanin Receptor Subtypes," *Trends In Pharmacological Sciences. Elsevier Trends Journal.* (Mar. 2000) 21(3): 109-116 (Exhibit 14).
Gustafson, E., et al., "Distribution of a Rat Galanin Receptor mRNA in Rat Brain," *Neuroreport* (1996) 7: 953-957 (Exhibit 15).
Kahl, U., et al., "Galanin Receptors," *DN&P* (1995) 8(7): 404-410 (Exhibit 16).
O'Donnell, D., et al., "Neuroanatomical Distribution Of A Novel Rat Galanin Receptor Subtype," *Soc. Neurosci. Abstr.* (1996) 22(2):1304, Abstract No. 517.9 (Exhibit 17).
Selve et al., "Galanin receptor antagonists attenuate spinal antinociceptive effects of DAMGO, tramadol and non-opioid drugs in rats," *Brain Res.* (Oct. 7, 1996) 735(2): 177-187 (Exhibit 18).
Smith, et al., "Cloned Human and Rat Galanin GALR3 Receptors," *The Journal of Biological Chemistry.* (Sep. 1998) 273(36): 23321-23326 (Exhibit 19).
Xu, X.J., et al., "New High Affinity Peptide Antagonists to the Spinal Galanin Receptor," *Br. J. Pharmacol.* (1995) 116: 2076-2080 (Exhibit 20).
Bionet Research Ltd. Catalog #11L-312S (1-Phenyl-3-{[3-(trifluoromethyl)phenyl]imino}-1,3-dihydro-2H-indol-2-one) (Exhibit 21).
Chemical Abstracts Registry No. 61038-64-0 (Exhibit 22).
Chemical Abstracts Registry No. 41230-77-7 (Exhibit 23).
Chemical Abstracts Registry No. 130186-15-1 (Exhibit 24).
Chemical Abstracts Registry No. 130186-16-2 (Exhibit 25).
Chemical Abstracts Registry No. 130186-17-3 (Exhibit 26).
Chemical Abstracts Registry No. 130186-18-4 (Exhibit 27).
Chemical Abstracts Registry No. 130186-21-9 (Exhibit 28).
Chemical Abstracts Registry No. 130270-13-2 (Exhibit 29).
Chemical Abstracts Registry No. 133939-75-0 (Exhibit 30).

(Continued)

*Primary Examiner*—Shaojia Anna Jiang
*Assistant Examiner*—Eric S. Olson
(74) *Attorney, Agent, or Firm*—Stephen G. Kalinchak

(57) ABSTRACT

This invention is directed to pyrimidine and indolone derivatives which are selective antagonists for the GAL3 receptor and are useful for the treatment of neuropathic pain and other abnormalities. This invention also provides a method of treating a subject suffering from an abnormality which comprises administering to the subject an amount of a compound of the invention effective to treat the subject's abnormality. This invention also provides a method of treating an abnormality in a subject which comprises administering to the subject a composition comprising a pharmaceutically acceptable carrier and a therapeutically effective amount of a GAL3 receptor antagonist.

1 Claim, 5 Drawing Sheets

OTHER PUBLICATIONS

Chemical Abstracts Registry No. 56984-58-8 (Exhibit 31).
Chemical Abstracts Registry No. 77910-42-0 (Exhibit 32).
Chemical Abstracts Registry No. 70010-41-2 (Exhibit 33).
Chemical Abstracts Registry No. 189264-35-5 (Exhibit 34).
Chemical Abstracts Registry No. 88291-04-7 (Exhibit 35).
Chemical Abstracts Registry No. 88291-07-0 (Exhibit 36).
Chemical Abstracts Registry No. 154118-05-5 (Exhibit 37).
Chemical Abstracts Registry No. 155717-81-0 (Exhibit 38).
Chemical Abstracts Registry No. 155717-82-1 (Exhibit 39).
Chemical Abstracts Registry No. 159967-24-5 (Exhibit 40).
Chemical Abstracts Registry No. 138601-94-2 (Exhibit 41).
Chemical Abstracts Registry No. 136647-69-3 (Exhibit 42).
Chemical Abstracts Registry No. 136647-72-8 (Exhibit 43).
Chemical Abstracts Registry No. 77297-28-0 (Exhibit 44).
Chemical Abstracts Registry No. 43002-26-2 (Exhibit 45).
Chemical Abstracts Registry No. 303954-69-2 (Exhibit 46).
Chemical Abstracts Registry No. 122725-53-5 (Exhibit 47).
Chemical Abstracts Registry No. 122803-89-8 (Exhibit 48).
Chemical Abstracts Registry No. 303149-10-2 (Exhibit 49).
Chemical Abstracts Registry No. 303149-08-8 (Exhibit 50).
Chemical Abstracts Registry No. 303149-06-6 (Exhibit 51).
Chemical Abstracts Registry No. 303984-47-6 (Exhibit 52).
Chemical Abstracts Registry No. 303149-14-6 (Exhibit 53).
Chemical Abstracts Registry No. 303149-12-4 (Exhibit 54).
Chemical Abstracts Registry No. 303984-51-2 (Exhibit 55).
Chemical Abstracts Registry No. 303984-49-8 (Exhibit 56).
Chemical Abstracts Registry No. 303954-48-7 (Exhibit 57).
Chemical Abstracts Registry No. 303984-52-3 (Exhibit 58).
Chemical Abstracts Registry No. 303984-60-3 (Exhibit 59).
Chemical Abstracts Registry No. 303984-61-4 (Exhibit 60).
Chemical Abstracts Registry No. 303984-62-5 (Exhibit 61); and.
Chemical Abstracts Registry No. 303984-68-1 (Exhibit 62).

* cited by examiner

Figure 2. Effects of Example 92 on the Withdrawal Thresholds to Von Frey Monofilament Challenges of the (i) Contralateral and (ii) Nerve-injured Paw of Neuropathic Rats
(i) Contralateral Paw
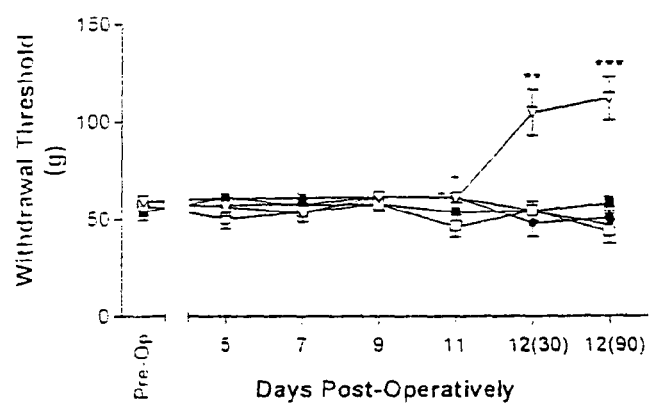
(ii) Nerve-injured Paw
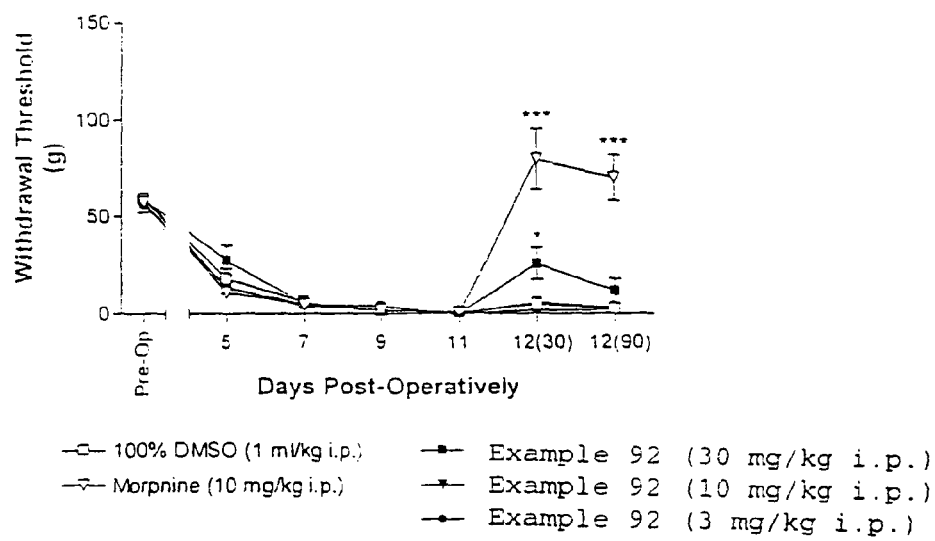

Figure 3. Effects of Example 92 on the Withdrawal Thresholds to Von Frey Monofilament Challenges of the (i) Contralateral and (ii) Nerve-injured Paw of Neuropathic Rats
(i) Contralateral Paw
(ii) Nerve-injured Paw
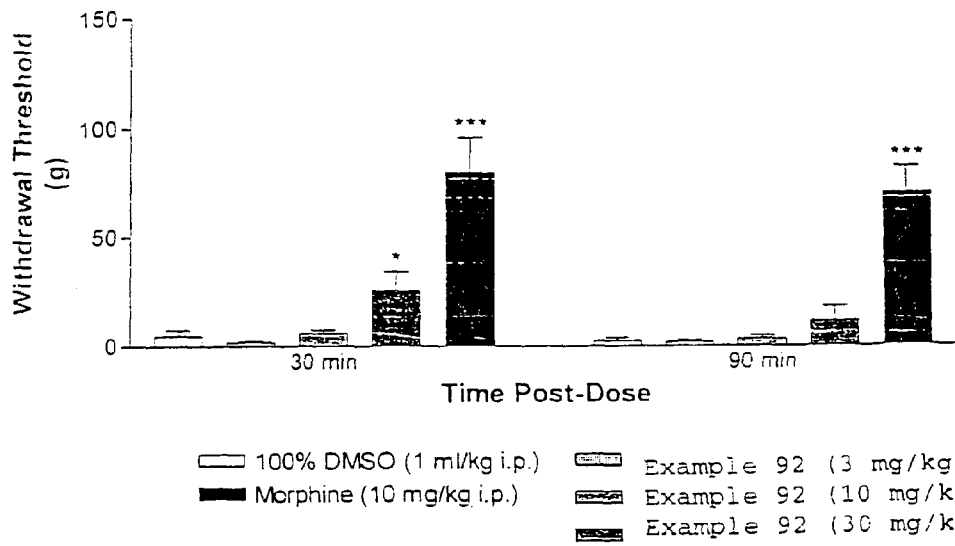

Figure 4. Effects of Example 92 on the Withdrawal Latency to a Thermal Plantar Stimulus of the (i) Contralateral and (ii) Nerve-injured Paw of Neuropathic Rats
(i) Contralateral Paw
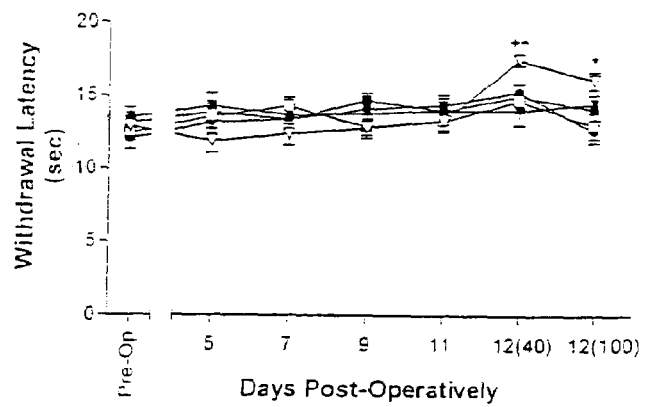
(ii) Nerve-injured Paw
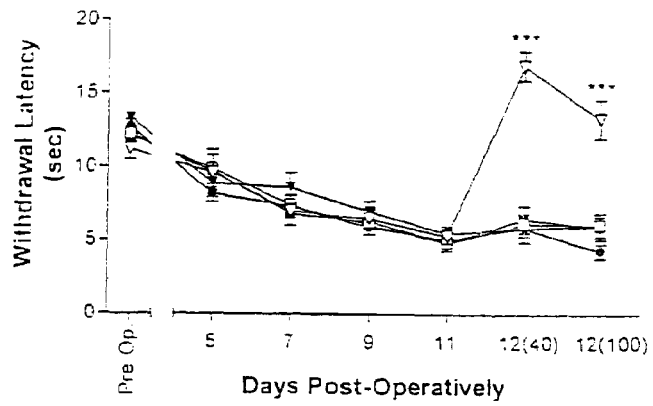
—□— 100% DMSO (1 ml/kg i.p.)  —■— Example 92 (30 mg/kg i.p.)
—▽— Morphine (10 mg/kg i.p.)  —▼— Example 92 (10 mg/kg i.p.)
                                —●— Example 92 (3 mg/kg i.p.)

Figure 5. Effects of Example 92 on the Withdrawal Latency to a Thermal Plantar Stimulus of the (i) Contralateral and (ii) Nerve-injured Paw of Neuropathic Rats
(i) Contralateral Paw
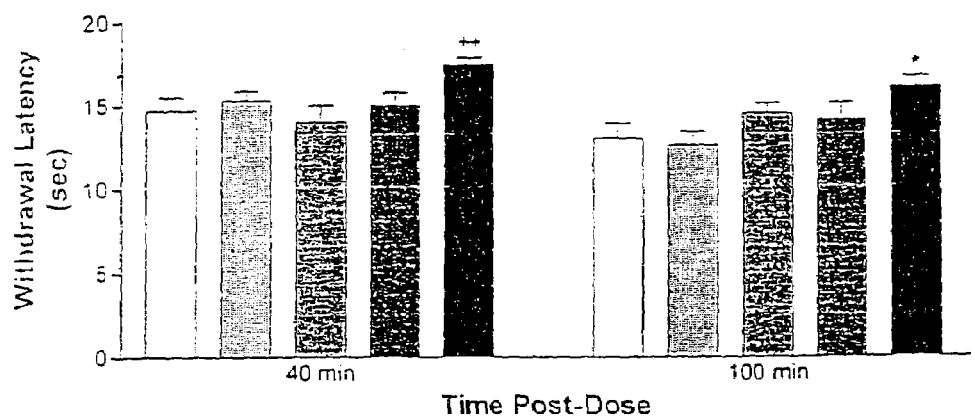
(ii) Nerve-injured Paw
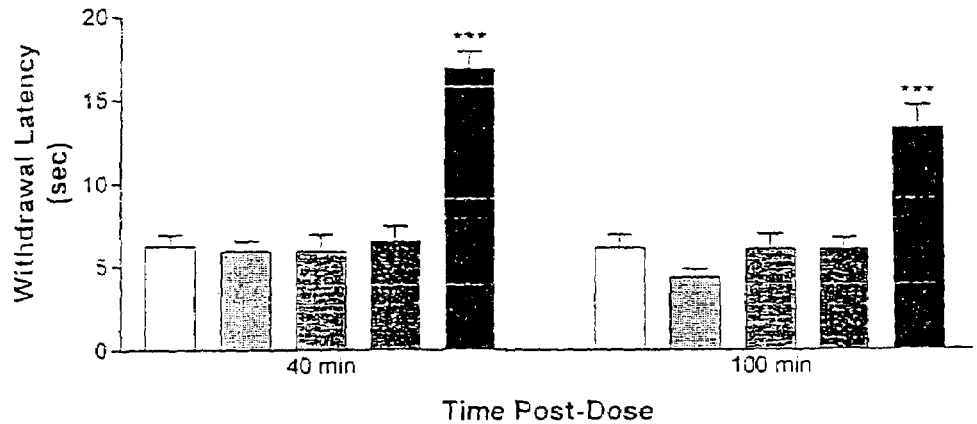
☐ 100% DMSO (1 ml/kg i.p.)   ▨ Example 92 (3 mg/kg i.p.)
■ Morphine (10 mg/kg i.p.)   ▨ Example 92 (10 mg/kg i.p.)
                              ▨ Example 92 (30 mg/kg i.p.)

COMPOUND USEFUL FOR THE TREATMENT OF NEUROPATHIC PAIN

This application claims priority of U.S. Provisional Application No. 60/402,035, filed Aug. 7, 2002, the contents of which are hereby incorporated by reference.

Throughout this application, various publications are referenced in parentheses by author and year. Full citations for these references may be found at the end of the specification immediately preceding the claims. The disclosures of these publications in their entireties are hereby incorporated by reference into this application to describe more fully the art to which this invention pertains.

BACKGROUND OF THE INVENTION

Discovery of GAL3 Receptor Subtype and its Role

The investigations leading to the present invention arose from the discovery that mRNA for the GAL3 receptor is localized to areas of the rat brain associated with analgesia (see PCT International Publication No. WO 98/15570, published Apr. 16, 1998), thus supporting the expression of GAL3 in those regions. Protein for the GAL3 receptor is also shown to localize to areas of the rat brain associated with analgesia (see Table 12 and discussion herein).

This discovery led to the hypothesis that the GAL3 receptor may be modulating nociceptive information. Galanin is known to be released from the terminals of sensory neurons as well as spinal interneurons and appears to play a role in the regulation of pain threshold (Wiesenfeld-Hallin et al. 1992). In light of these reports, in vivo behavioral experiments were carried out to evaluate the analgesic properties of a selective GAL3 receptor antagonist. An animal model of neuropathic pain was employed to evaluate the use of selective GAL3 receptor antagonists to treat neuropathic pain. The Chronic Constriction Nerve Injury Model of Neuropathic Pain is a behavioral test that is used to assess the potential analgesic effects of compounds (Bennett an Xie, 1988). This model monitors the development of allodynia and hyperalgesia and is considered by experts in the field to reflect the potential of analgesic agents to treat neuropathic pain (Fisher et al., 1998; Fisher et al., 2002). This model is widely used as it is reliable across laboratories, and is sensitive to the effects of some of the major classes of analgesic drugs.

In an embodiment of the present invention the synthesis of novel pyrimidines which bind selectively to the cloned human GAL3 receptor, compared to other cloned human G-protein coupled receptors, as measured in in vitro assays, is disclosed. In a further embodiment of the present invention the synthesis of indolones which bind selectively to the cloned human GAL3 receptor, compared to other cloned human G-protein coupled receptors, as measured in in vitro assays, is disclosed. The in vitro receptor assays described hereinafter were performed using various cultured cell lines, each transfected with and expressing only a single galanin-type receptor.

From the binding information described hereinafter, it has unexpectedly been discovered that compounds which are specific for the human GAL3 receptor with a binding affinity greater than ten-fold higher than the binding affinity with which the compounds bind to a human GAL1 receptor are effective in animal models of pain which are predictive of efficacy in humans. Thus, we demonstrate that the GAL3 receptor antagonists, which may be classified as neutral antagonists, inverse agonists or allosteric modulators, provide a novel method to treat neuropathic pain.

SUMMARY OF THE INVENTION

The present invention provides a method of treating a subject suffering from an abnormality which comprises administering to the subject an amount of compound effective to treat the subject's abnormality wherein the

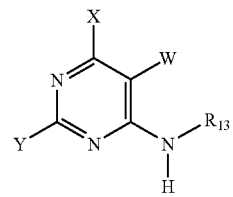

compound has the structure:
wherein W is H, —F, —Cl, —Br, —I, CN, methyl, ethyl, propyl, methoxy or ethoxy;

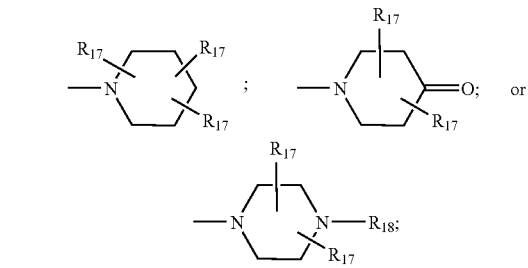

wherein X is; $NR_{11}R_{12}$;
wherein $R_{11}$ is H, straight chained or branched $C_1$-$C_7$ alkyl, $(CH_2)_q$—O—$(CH_2)_m$—$CH_3$, aryl, or aryl $(C_1$-$C_6)$alkyl;
wherein $R_{12}$ is straight chained or branched $C_1$-$C_7$ alkyl, $(CH_2)_q$—O—$(CH_2)_m$—$CH_3$, or —$(CH_2)_m$-Z;
wherein $R_{13}$ is a bicyclic alkyl ring system, adamantyl, noradamantyl, $C_3$-$C_{10}$ cycloalkyl, heteroaryl, aryl, aryl $(C_1$-$C_6)$alkyl, $Q_1$ or $Q_2$;
wherein aryl may be substituted with one or more $C_1$-$C_{10}$ straight chained or branched alkyl, aryl, heteroaryl, or $N(R_{19})$-Z;
wherein $Q_1$ is

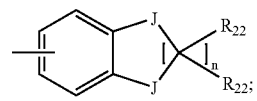

wherein $Q_2$ is

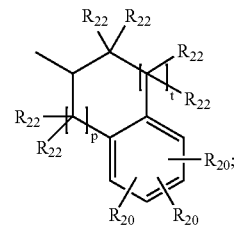

wherein each J is independently O, S, $C(R_{22})_2$ or $NR_4$;
wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

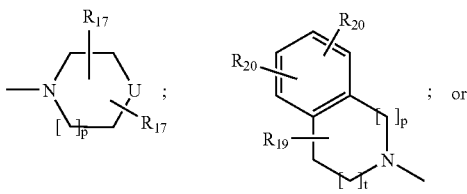

wherein Y is NR$_{14}$R$_{15}$;

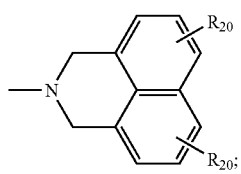

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;

wherein R$_{15}$ is straight chained or branched C$_3$-C$_6$ alkyl, (CH$_2$)$_q$—O—(CH$_2$)$_m$—CH$_3$, C$_3$-C$_6$ cycloalkyl, (C(R$_{19}$)$_2$)$_m$N(R$_{16}$)$_2$ or (C(R$_{19}$)$_2$)$_m$-Z;

wherein R$_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)$_q$—O—(CH$_2$)$_m$—CH$_3$;

wherein each R$_{17}$ is independently H; —OR$_{21}$, —OCOR$_{21}$, —COR$_{21}$, —NCOR$_{21}$, —N(R$_{21}$)$_2$, —CON(R$_{21}$)$_2$, —COOR$_{21}$, straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched C$_2$-C$_7$ alkenyl, straight chained or branched C$_2$-C$_7$ alkynyl, C$_5$-C$_7$ cycloalkenyl, —(CH$_2$)$_m$-Z, or (CH$_2$)—O—(CH)$_m$—CH$_3$;

wherein R$_{18}$ is straight chained or branched C$_1$-C$_6$ alkyl, —(CH$_2$)$_m$-Z, or (CH$_2$)$_q$—O—(CH$_2$)$_m$—CH$_3$;

wherein each R$_{19}$ is independently H, or straight chained or branched C$_1$-C$_6$ alkyl;

wherein each R$_{20}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl or C$_5$-C$_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COR$_{21}$; aryl or heteroaryl; or two R$_{20}$ groups present on adjacent carbon atoms can join together to form a methylenedioxy group;

wherein each R$_{21}$ is independently —H; straight chained or branched C$_1$-C$_7$ alkyl, monofluoroalkyl or polyfluoroalkyl; straight chained or branched C$_2$-C$_7$ alkenyl or alkynyl; C$_3$-C$_7$ cycloalkyl, C$_5$-C$_7$ cycloalkenyl, aryl, or aryl(C$_1$-C$_6$) alkyl;

wherein each R$_{22}$ is independently H, F, Cl or C$_1$-C$_4$ straight chained or branched alkyl;

wherein each m is an integer from 0 to 4 inclusive;
wherein each n is an integer from 1 to 4 inclusive;
wherein p is an integer from 0 to 2 inclusive;
wherein q is an integer from 2 to 4 inclusive;
wherein t is 1 or 2;

wherein U is O, —NR$_{16}$, S, C(R$_{17}$)$_2$, or —NSO$_2$R$_{16}$;
wherein Z is C$_3$-C$_{10}$ cycloalkyl, C$_4$-C$_7$ cyclic ether, C$_4$-C$_7$ cyclic thioether, aryl, or heteroaryl; or a pharmaceutically acceptable salt thereof.

The present invention provides a method of treating a subject suffering from an abnormality which comprises administering to the subject an amount of compound effective to treat the subject's abnormality wherein the compound has the structure:

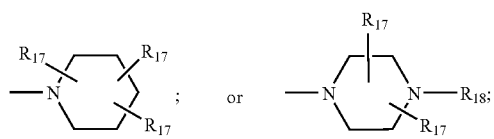

wherein W is H, —F, —Cl, —Br, —I, CN, methyl, ethyl, propyl, methoxy or ethoxy;
wherein X is NR$_{11}$R$_{12}$;

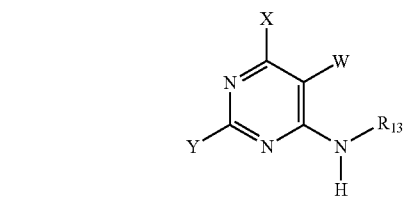

wherein R$_{11}$ is H, straight chained or branched C$_1$-C$_7$ alkyl, (CH$_2$)$_q$—O(CH$_2$)$_m$—CH$_3$, aryl or aryl(C$_1$-C$_6$)alkyl;
wherein R$_{12}$ is straight chained or branched C$_1$-C$_7$ alkyl, (CH$_2$)$_q$—O—(CH$_2$)$_m$—CH$_3$, or —(CH$_2$)$_m$-Z;
wherein R$_{13}$ is a bicyclic alkyl ring system, aryl or aryl (C$_1$-C$_6$) alkyl;
wherein Y is NR$_{14}$R$_{15}$;

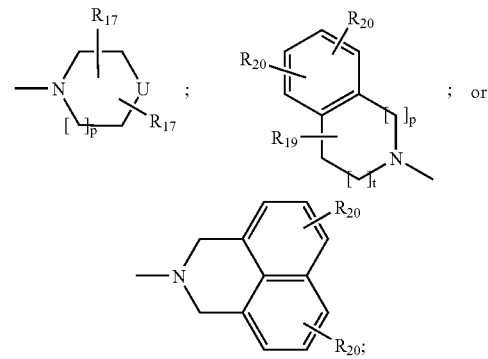

wherein R$_{14}$ is H, straight chained or branched C$_1$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;
wherein R$_{15}$ is straight chained or branched C$_3$-C$_6$ alkyl, (CH$_2$)$_q$—O—(CH$_2$)$_m$—CH$_3$, C$_3$-C$_6$ cycloalkyl, or (C(R$_{19}$)$_2$)$_m$-Z;
wherein U is O, —NR$_{16}$, S, C(R$_{17}$)$_2$, or —NSO$_2$R$_{16}$;
wherein Z is C$_3$-C$_{10}$ cycloalkyl, aryl, or heteroaryl;
wherein R$_{16}$ is straight chained or branched C$_1$-C$_7$ alkyl, straight chained or branched C$_1$-C$_7$ monofluoroalkyl, straight chained or branched C$_1$-C$_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_2)_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;
wherein each n is an integer from 1 to 4 inclusive;
wherein p is an integer from 0 to 2 inclusive;
wherein q is an integer from 2 to 4 inclusive;
wherein t is 1 or 2; or a pharmaceutically acceptable salt thereof.

The present invention provides a method of treating a subject suffering from an abnormality which comprises administering to the subject an amount of compound effective to treat the subject's abnormality wherein the compound has the structure:

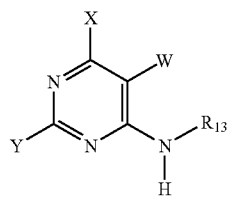

wherein W is H, —F, —Cl, —Br, —I, CN, methyl, ethyl, propyl, methoxy or ethoxy;
wherein X is $N(CH_3)_2$ or

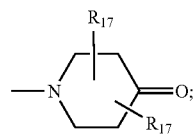

wherein $R_{13}$ is an aryl, adamantyl, noradamantyl, $C_3$-$C_{10}$ cycloalkyl, heteroaryl, $Q_1$ or $Q_2$;
wherein aryl may be substituted with one or more $C_1$-$C_{10}$ straight chained or branched alkyl, aryl, heteroaryl, or $N(R_{19})$-Z;

wherein $Q_1$ is

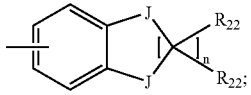

wherein $Q_2$ is

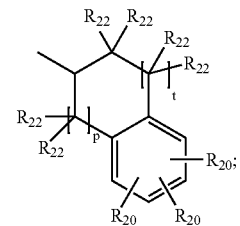

wherein each J is independently O, S, $C(R_{22})_2$ or $NR_4$;
wherein $R_4$ is —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;
wherein Y is $NR_{14}R_{15}$;

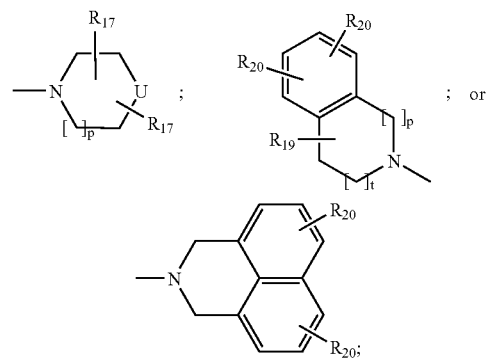

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;
wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;
wherein U is O, —$NR_{16}$, S, $C(R_{17})_2$, or —$NSO_2R_{16}$;
wherein Z is $C_3$-$C_{10}$ cycloalkyl, aryl, or heteroaryl;
wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;
wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;
wherein each n is an integer from 1 to 4 inclusive;
wherein p is an integer from 0 to 2 inclusive;
wherein q is an integer from 2 to 4 inclusive;
wherein t is 1 or 2; or a pharmaceutically acceptable salt thereof.

The present invention provides a method of treating a subject suffering from an abnormality which comprises administering to the subject an amount of compound effective to treat the subject's abnormality wherein the compound has the structure:

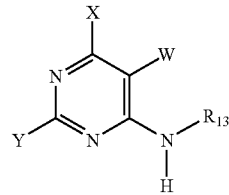

wherein W is H, —F, —CN, —Br, —I, CO, methyl, ethyl, propyl, methoxy or ethoxy;
wherein X is $N(CH_3)_2$ or

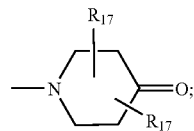

wherein $R_{13}$ is a bicyclic alkyl ring system, aryl or aryl ($C_1$-$C_6$) alkyl;
wherein Y is $NR_{14}R_{15}$;
wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;
wherein $R_{15}$ is $(C(R_{19})_2)_m$—$N(R_{16})_2$;
wherein Z is $C_3$-$C_{10}$ cycloalkyl, aryl, or heteroaryl;
wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently —H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{19}$ is independently H, or straight chained or branched $C_1$-$C_6$ alkyl;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;
wherein each n is an integer from 1 to 4 inclusive;

The invention provides a method of treating a subject suffering from an abnormality which comprises administering to the subject an amount of compound effective to treat the subject's abnormality wherein the compound has the structure:

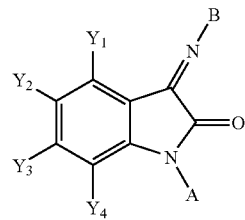

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein A is A', $Q_3$, $Q_4$, $Q_5$, straight chained or branched $C_1$-$C_7$ alkyl, aryl, heteroaryl, aryl($C_1$-$C_6$) alkyl, heteroaryl ($C_1$-$C_6$) alkyl, aryl substituted with an aryl or heteroaryl, heteroaryl substituted with an aryl or heteroaryl; or $(CHR_{17})$—$(CHR_{17})_n$-Z;

wherein A' is

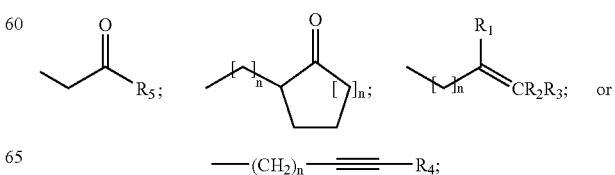

wherein $Q_3$ is

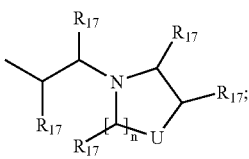

wherein $Q_4$ is

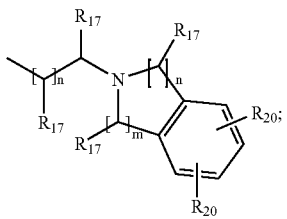

wherein $Q_5$ is

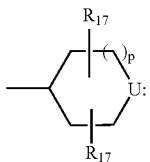

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two R$_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;
wherein each n is an integer from 1 to 4 inclusive;
wherein each p is an integer from 0 to 2 inclusive;
wherein U is O, —NR$_{16}$, S, C(R$_{17}$)$_2$, or —NSO$_2$R$_{16}$;
wherein Z is $C_3$-$C_{10}$ cycloalkyl, $C_4$-$C_7$ cyclic ether, $C_4$-$C_7$ cyclic thioether, aryl, or heteroaryl;
wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;
wherein q is an integer from 2 to 4 inclusive;
wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;
wherein a tricyclic heteroaryl is a fused three member aromatic system in which one or more of the rings is heteroaryl; carbazole; or acridine;
wherein $Q_6$ is

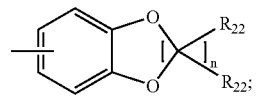

wherein each $R_{22}$ is independently H, F, Cl, or straight chained or branched $C_1$-$C_4$ alkyl;
or a pharmaceutically acceptable salt thereof.

The invention provides a method of treating a subject suffering from an abnormality which comprises administering to the subject an amount or compound effective to treat the subject's abnormality wherein the compound has the structure:

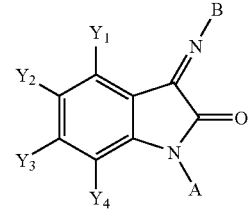

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

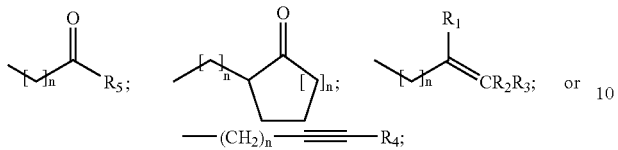

wherein $R_1$ and $R_2$ are each independently H, straight chaired or branched $C_1$-$C_7$ alkyl, —F, —Cl, —Br, —I, —$NO_2$, or —CN;

wherein $R_3$ is H, straight chained or branched $C_1$-$C_7$ alkyl, —F, —Cl, —Br, —I, —$NO_2$, —CN, —$OR_6$ aryl or heteroaryl;

wherein $R_5$ is straight chained or branched $C_1$-$C_7$ alkyl, —$N(R_4)_2$, —$OR_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

The invention provides a method of treating a subject suffering from an abnormality which comprises administering to the subject an amount of compound effective to treat the subject's abnormality wherein the

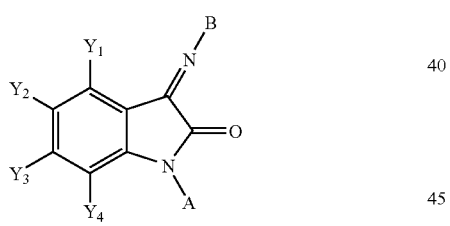

compound has the structure:

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

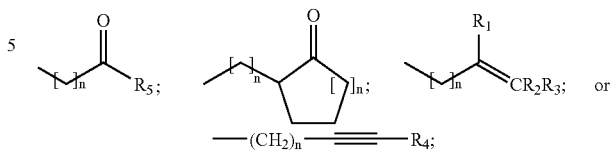

wherein B is aryl substituted with an aryl or heteroaryl, heteroaryl substituted with an aryl or heteroaryl, tricyclic heteroaryl or $Q_6$;

wherein a tricyclic heteroaryl is a fused three ring aromatic system in which one or more of the rings is heteroaryl; carbazole; or acridine;

wherein $Q_6$ is

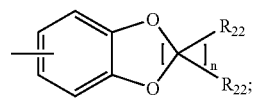

wherein n is an integer from 1 to 4 inclusive;

wherein each $R_{22}$ is independently H, F, Cl, or straight chained or branched $C_1$-$C_4$ alkyl;

or a pharmaceutically acceptable salt thereof.

The invention provides a method of treating a subject suffering from an abnormality which comprises administering to the subject an amount of compound effective to treat the subject's abnormality wherein the

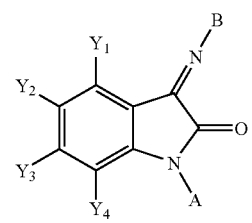

compound has the structure:

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is $Q_3$, $Q_4$, $Q_5$, aryl substituted with an aryl or heteroaryl, heteroaryl substituted with an aryl or heteroaryl, or $(CHR_{17})$—$(CHR_{17})_n$-Z;

wherein $Q_3$ is

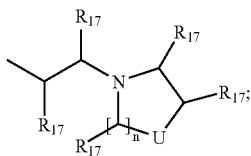

wherein $Q_4$ is

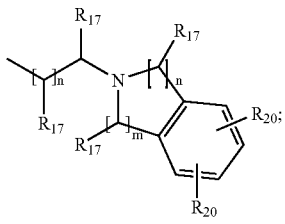

wherein $Q_5$ is

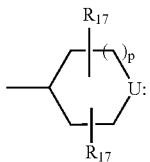

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$COOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained of branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

wherein q is an integer from 2 to 4 inclusive; or a pharmaceutically acceptable salt thereof.

The invention provides a method of treating a subject suffering from an abnormality which comprises administering to the subject an amount of compound effective to treat the subject's abnormality wherein the compound has the structure:

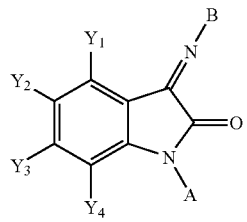

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl ($C_1$-$C_6$)alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

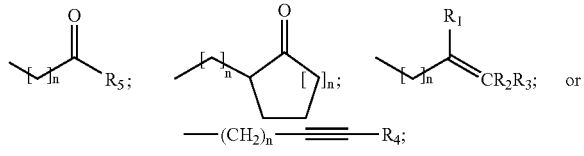

wherein $R_1$ and $R_2$ are each independently H, straight chained or branched $C_1$-$C_7$ alkyl, —F, —Cl, —Br, —I, —$NO_2$, or —CN;

wherein $R_3$ is H, straight chained or branched $C_1$-$C_7$ alkyl, —F, —Cl, —Br, —I, —$NO_2$, —CN, —$OR_6$, aryl or heteroaryl;

wherein $R_5$ is straight chained or branched $C_1$-$C_7$ alkyl, —$N(R_4)_2$, —$OR_4$ or aryl;

wherein $R_6$ is straight chained or branched $C_1$-$C_7$ alkyl or aryl;

wherein B is $C_3$-$C_7$ cycloalkyl, $C_5$-$C_7$ cycloalkenyl, adamantyl, aryl, pyridyl, pyridazinyl, pyrimidinyl, pyrazinyl, triazinyl, indolizinyl, indol-4-yl, indol-5-yl, indol-6-yl, indol-7-yl, isoindolyl, benzo[b]furan-4-yl, benzo[b]furan-5-yl, benzo[b]furan-6-yl, benzo[b]furan-7-yl, benzo[b]thiophen-4-yl, benzo[b]thiophen-5-yl, benzo[b]thiophen-6-yl, benzo[b]thiophen-7-yl, indazolyl, benzimidazolyl, benzo[b]thiazolyl, purinyl, imidazo[2,1-b]thiazolyl, quinolinyl, isoquinolinyl, quinazolinyl, 2,1,3-benzothiazolyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, benzoxazolyl, benzisoxazolyl, cinnolinyl, quinoxalinyl, 1,8-naphthridinyl, pteridinyl, or phthalimidyl; provided however, if B is aryl, pyridyl, pyridazinyl, pyrimidinyl, pyrazinyl, triazinyl, indolizinyl, indol-4-yl, indol-5-yl, indol-6-yl, indol-7-yl, isoindolyl, benzo[b]furan-4-yl, benzo[b]furan-5-yl, benzo[b]furan-6-yl, benzo[b]furan-7-yl, benzo[b]thiophen-4-yl, benzo[b]thiophen-5-yl, benzo[b]thiophen-6-yl, benzo[b]thiophen-7-yl, indazolyl, benzimidazolyl, benzo[b]thiazolyl, purinyl, imidazo[2,1-b]thiazolyl, quinolinyl, isoquinolinyl, quinazolinyl, 2,1,3-benzothiazolyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, benzoxazolyl, benzisoxazolyl, cinnolinyl, quinoxalinyl, 1,8-napthyridinyl, pteridinyl, or phthalimidyl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive.

Figure 1:
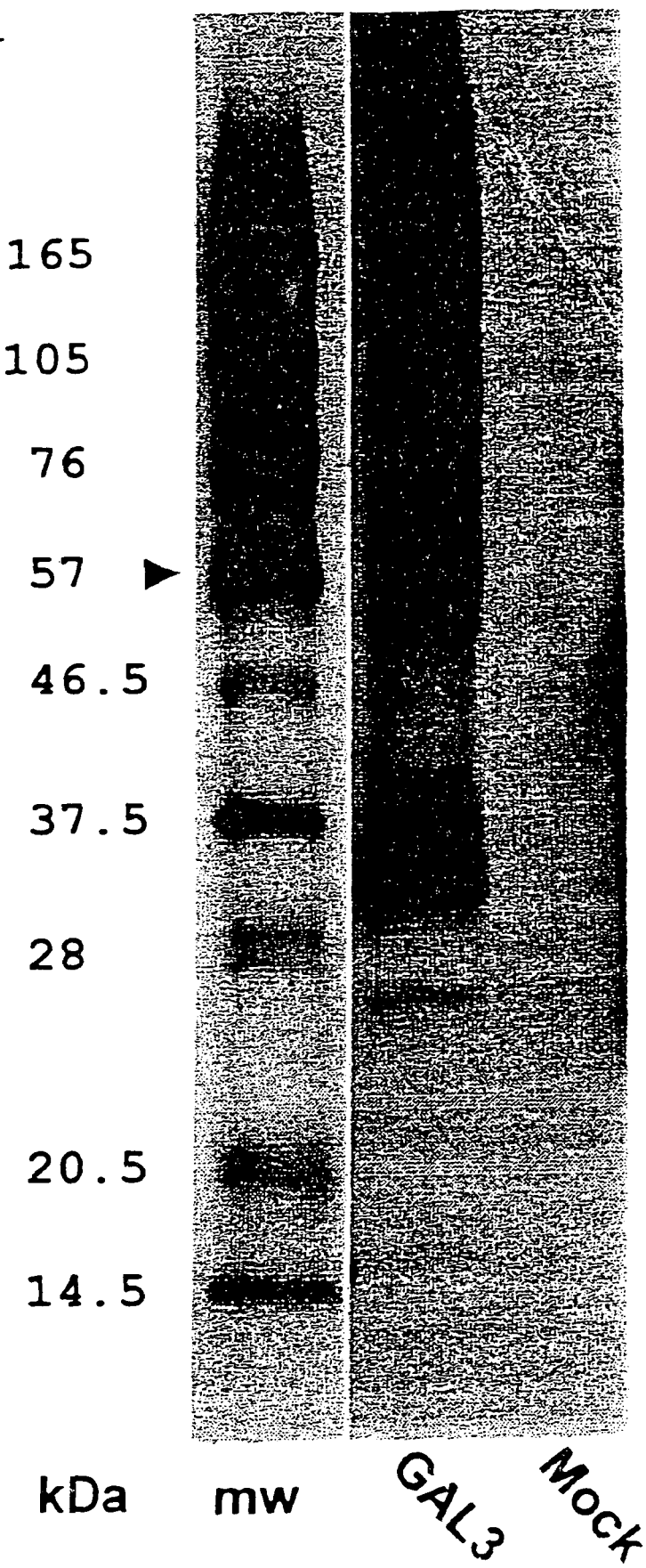
FIG. 1: Western Blot Results

In order to establish the specificity of the anti-GAL3 antiserum, membranes prepared from COS-7 cells transiently transfected with the rat recombinant GAL3 (Borowsky et al., 1999) (Lane 2) or mock-transfected (vector only) (Lane 3) were applied to an SDS-PAGE gel and blotted using the GAL3 receptor polyclonal antibody. Lane 1 corresponds to molecular weight marker. The anti-GAL3 antiserum labeled proteins in membranes only from rat GAL3-transfected cells (Lane 2); a predominant band was evident with an apparent molecular weight of approximately 56 kDa, (somewhat higher than the amino acid-derived value of 40.4 kDa). The apparently high molecular weight observed for rat GAL3 very likely reflects post-translational processing such as glycosylation; note that rat GAL3 contains multiple N-terminal glycosylation sites (Smith et al., 1998). Relative to the predominant band, additional species of higher molecular weight as well as lower molecular weight were labeled by the GAL3 antiserum. These are interpreted as protein aggregates of C-terminal fragments, as they are absent in mock-transfected cells.

FIG. 2: Effects of Example 92 on the Withdrawal Thresholds to Von Frey Monofilament Challenges of the (i) Contralateral and (ii) Nerve-injured Paw of Neuropathic Rats. Data plotted represents the group mean withdrawal threshold (grams) to Von Frey filament challenges on the days prior to and following a chronic constriction nerve injury. The animals were dosed with test substance (Example 92), reference sustance (morphine) or vehicle (100% DMSO) on day 12 PO. *$P \leq 0.05$, $P \leq 0.01$, *$P \leq 0.001$ compared to vehicle control group (ANOVA and Dunnett's tests or Unpaired t-test). *$P \leq 0.05$ compared to the vehicle group (Kruskal-Wallis and Dunn's test or Mann-Whitney U-test).

FIG. 3: Effects of Example 92 on the Withdrawal Thresholds to Von Frey Monofilament Challenges of the (i) Contralateral and (ii) Nerve-injured Paw of Neuropathic Rats. Data are expressed as mean±SEM; n=10 rats per group. *$P \leq 0.05$, $P \leq 0.01$, *$P \leq 0.001$ compared to vehicle control group (ANOVA and Dunnett's tests or Unpaired t-test).

FIG. 4: Effects of Example 92 on the Withdrawal Latency to a Thermal Plantar Stimulus of the (i) Contralateral and (ii) Nerve-injured Paw of Neuropathic Rats. Data plotted represents the group mean withdrawal latency (seconds) to a thermal plantar stimulus on the days prior to and following a chronic constriction nerve injury. The animals were dosed with test substance (Example 92), reference sustance (morphine) or vehicle (100% DMSO) on day 12 PO. *$P \leq 0.05$, *$P \leq 0.001$ compared to vehicle control group (Unpaired t-test). $P \leq 0.01$ compared to the vehicle group (Mann-Whitney U-test).

FIG. 5: Effects of Example 92 on the Withdrawal Latency to a Thermal Plantar Stimulus of the (i) Contralateral and (ii) Nerve-injured Paw of Neuropathic Rats. Data are expressed as mean±SEM; n=10 rats per group. *$P \leq 0.05$, *$P \leq 0.001$ compared to the vehicle control group (Unpaired t-test). $P \leq 0.01$ compared to the vehicle control group (Mann-Whitney U-test).

DETAILED DESCRIPTION OF THE INVENTION

The present invention provides a method of treating a subject suffering from an abnormality which comprises administering to the subject an amount of compound effective to treat the subject's abnormality wherein the

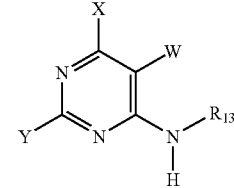

compound has the structure:

wherein W is H, —F, —Cl, —Br, —I, CN, methyl, ethyl, propyl, methoxy or ethoxy;

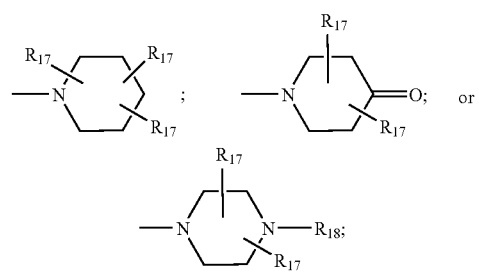

wherein X is; $NR_{11}R_{12}$;

wherein $R_{11}$ is H, straight chained or branched $C_1$-$C_7$ alkyl, $(CH_2)_q$—O—$(CH)_m$—$CH_3$, aryl, or aryl ($C_1$-$C_6$) alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, adamantyl, noradamantyl, $C_3$-$C_{10}$ cycloalkyl, heteroaryl, aryl, aryl($C_1$-$C_6$)alkyl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

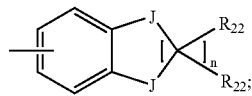

wherein $Q_2$ is

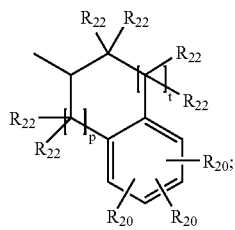

wherein each J is independently O, S, $C(R_{22})_2$ or $NR_4$;

wherein $R_4$ is H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

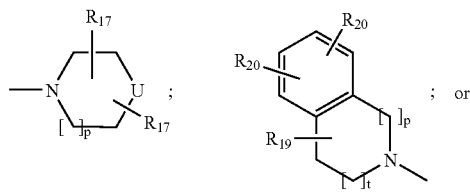

wherein Y is $NR_{14}R_{15}$;

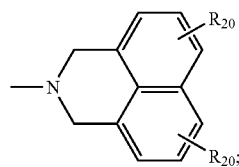

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m CH_3$, $C_3$-$C_6$ cycloalkyl, $(C(R_{19})_2)_m N(R_{16})_2$ or $(C(R_{19})_2)_m$-Z;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl, or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2;

wherein U is O, —$NR_{16}$, S, $C(R_{17})_2$, or —$NSO_2R_{16}$;

wherein Z is $C_3$-$C_{10}$ cycloalkyl, $C_4$-$C_7$ cyclic ether, $C_4$-$C_7$ cyclic thioether, aryl, or heteroaryl; or a pharmaceutically acceptable salt thereof.

The invention provides a method of treating a subject suffering from an abnormality which comprises administering to the subject an amount of compound effective to treat the subject's abnormality wherein the compound has the structure:

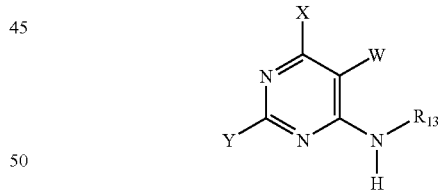

wherein W is H, —F, —Cl, —Br, —I, CN, methyl, ethyl, propyl, methoxy or ethoxy;

wherein X is $NR_{11}R_{12}$;

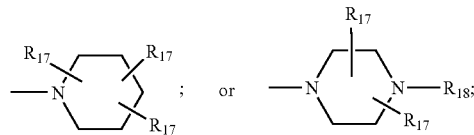

wherein $R_{11}$ is H, straight chained or branched $C_1$-$C_7$ alkyl, $(CH_2)_q$—O—$(CH_2)_m$—$CH_3$, aryl or aryl($C_1$-$C_6$)alkyl;

wherein $R_{12}$ is straight chained or branched $C_1$-$C_7$ alkyl, $(CH_2)_q$—O—$(CH_2)_m$—$CH_3$, or —$(CH_2)_m$-Z;

wherein $R_{13}$ is a bicyclic alkyl ring system, aryl or aryl $(C_1$-$C_6)$ alkyl;

wherein Y is $NR_{14}R_{15}$;

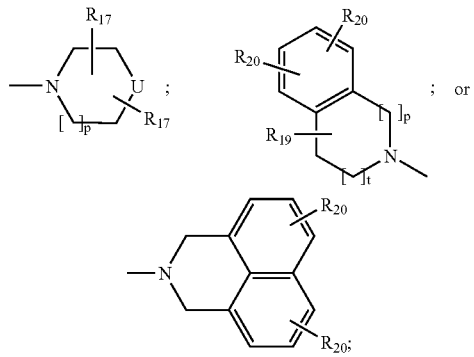

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$, polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_2$-$C_7$ cycloalkenyl; —F, —Cl, —Br, or —I; —$NO_2$; —$N_3$; —CN; —$O_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a method of treating a subject suffering from an abnormality which comprises administering to the subject an amount of compound effective to treat the subject's abnormality wherein the compound has the structure:

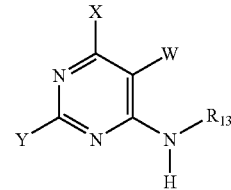

wherein W is H, —F, —Cl, —Br, —I, CN, methyl, ethyl, propyl, methoxy or ethoxy;

wherein X is $N(CH_3)_2$ or

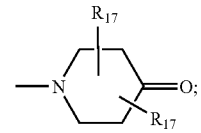

wherein $R_{13}$ is an aryl, adamantyl, noradamantyl, $C_3$-$C_{10}$ cycloalkyl, heteroaryl, $Q_1$ or $Q_2$;

wherein aryl may be substituted with one or more $C_1$-$C_{10}$ straight chained or branched alkyl, aryl, heteroaryl, or $N(R_{19})$-Z;

wherein $Q_1$ is

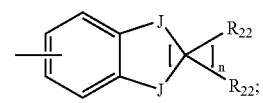

wherein $Q_2$ is

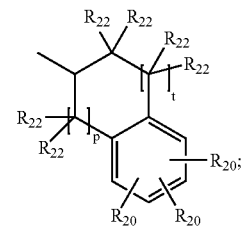

wherein each J is independently O, S, $C(R_{22})_2$ or $NR_4$;

wherein $R_4$ is —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein Y is $NR_{14}R_{15}$;

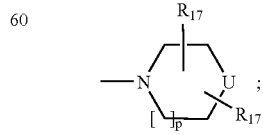 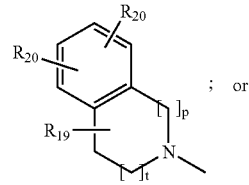

-continued

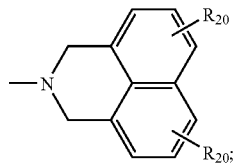

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is straight chained or branched $C_3$-$C_6$ alkyl, $(CH_2)_q$—O—$(CH_2)_m$—$CH_3$, $C_3$-$C_6$ cycloalkyl, or $(C(R_{19})_2)_m$-Z;

wherein U is O, —$NR_{16}$, S, $C(R_{17})_2$, or —$NSO_2R_{16}$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H; —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein $R_{18}$ is straight chained or branched $C_1$-$C_6$ alkyl, —$(CH_2)_m$-Z, or $(CH_2)_q$—O—$(CH_2)_m$—$CH_3$;

wherein each $R_{19}$ is independently H, or straight chained or branched $C_1$-$C_6$ alkyl;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —$NO_2$; —$N_3$; —CN; —$OR_{21}$, —$OCOR_{21}$, —$COR_{21}$, —$NCOR_{21}$, —$N(R_{21})_2$, —$CON(R_{21})_2$, or —$COOR_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each $R_{22}$ is independently H, F, Cl or $C_1$-$C_4$ straight chained or branched alkyl;

wherein each m is an integer from 0 to 4 inclusive;

wherein each n is an integer from 1 to 4 inclusive;

wherein p is an integer from 0 to 2 inclusive;

wherein q is an integer from 2 to 4 inclusive;

wherein t is 1 or 2; or a pharmaceutically acceptable salt thereof.

The invention provides a method of treating a subject suffering from an abnormality which comprises administering to the subject an amount of compound effective to treat the subject's abnormality wherein the compound has the structure:

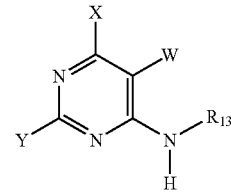

wherein W is H, —F, —Cl, —Br, —I, CN, methyl, ethyl, propyl, methoxy or ethoxy;

wherein X is $N(CH_3)_2$ or

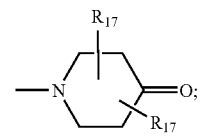

wherein $R_{13}$ is a bicyclic alkyl ring system, aryl or aryl ($C_1$-$C_6$) alkyl;

wherein Y is $NR_{14}R_{15}$;

wherein $R_{14}$ is H, straight chained or branched $C_1$-$C_6$ alkyl, $(CH_2)_q$—O—$(CH_2)_m$—$CH_3$, $C_3$-$C_6$ cycloalkyl, or $(C(R_{19})_2)_m$-Z;

wherein $R_{15}$ is $(C(R_{19})_2)_m$—$N(R_{16})_2$;

wherein Z is $C_3$-$C_{10}$ cycloalkyl, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_q$—O—$(CH_2)_m$—$CH_3$;

wherein each $R_{17}$ is independently H, —$OR_{21}$, —$OCOR_{21}$, —$COR_{21}$, —$NCOR_{21}$, —$N(R_{21})_2$, —$CON(R_{21})_2$, —$COOR_{21}$, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —$(CH_2)_m$-Z, or $(CH_2)_n$—O—$(CH_2)_m$—$CH_3$;

wherein each $R_{19}$ is independently H, or straight chained or branched $C_1$-$C_6$ alkyl;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein each m is an integer from 0 to 4 inclusive;

wherein each n is an integer from 1 to 4 inclusive;

wherein q is an integer from 2 to 4 inclusive; or a pharmaceutically acceptable salt thereof.

As used in the present invention, the term "bicyclic alkyl ring systems" includes, but is not limited to, bicyclo[2.2.1]heptane, bicyclo[3.1.1]heptane and bicyclo[2.2.2]octane. In addition, the bicyclic alkyl ring systems may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_5$-$C_7$ cycloalkenyl, —$N(R_{21})_2$, —$OR_{21}$, —$COR_{21}$, —$CO_2R_{21}$, —$CON(R_{21})_2$ or $(CH_2)_n$—O—$(CH_2)_m$—$CH_3$.

As used in the present invention, the term "cycloalkyl" includes, $C_3$-$C_7$ cycloalkyl moieties which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cyclohexyl" includes, cyclohexyl groups which may be substituted with one or more of the following: —F, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

As used in the present invention, the term "cycloalkenyl" includes, $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$SR_4$, —$OCOR_4$, —$COR_4$, —$NCOR_4$, —$CO_2R_4$, —$CON(R_4)_2$ or $(CH_2)_n$—O—$(CH_2)_m$—$CH_3$.

In one embodiment of any of the methods described herein, the compound is enantiomerically and diasteriomerically pure. In one embodiment, the compound is enantiomerically or diasteriomerically pure.

In one embodiment of any of the methods described herein, the compound can be administered orally.

In one embodiment, X is:

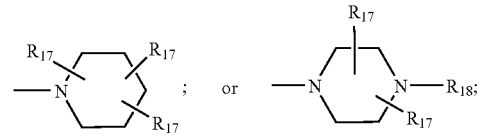

In one embodiment, X is $NR_{11}R_{12}$ and $R_{11}$ is H or straight chained or branched $C_1$-$C_7$ alkyl.

In one embodiment, the compound has the structure:

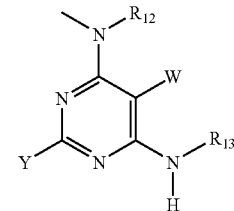

In one embodiment, $R_{13}$ is a bicyclic alkyl ring system, cyclohexyl or aryl.

In one embodiment, $R_{14}$ is H, straight chained or branched $C_1$-$C_6$ alkyl or $(CH_2)_q$—O—$(CH_2)_m$—$CH_3$.

In one embodiment, the compound is selected from the

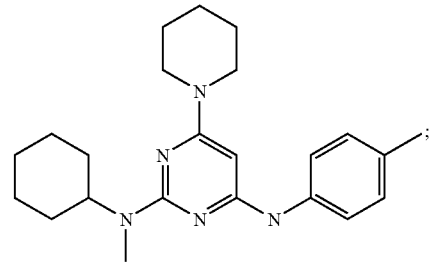

group consisting of:
In one embodiment, Y is
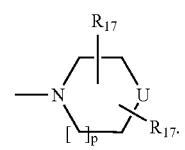
In one embodiment, U is $NR_{16}$.
In one embodiment, $R_{16}$ is $(CH_2)_m$-Z.
In one embodiment, Z is aryl or heteroaryl.

In one embodiment, the compound is selected from the group consisting of:
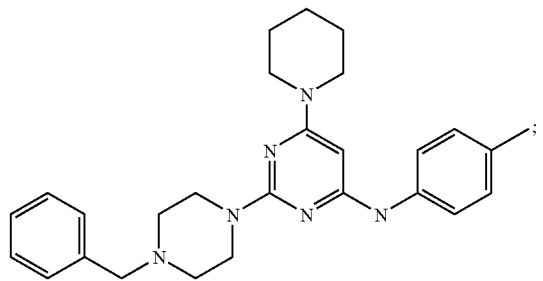
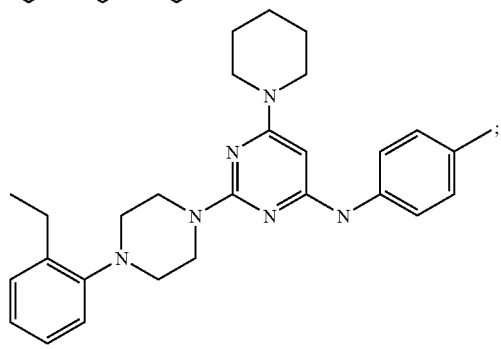
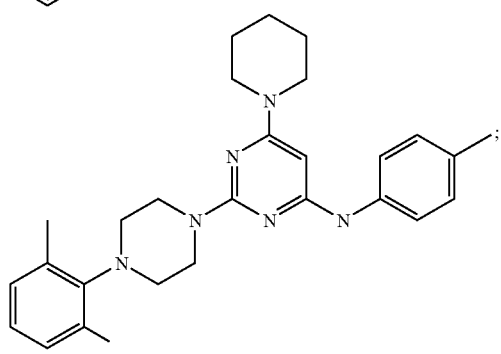
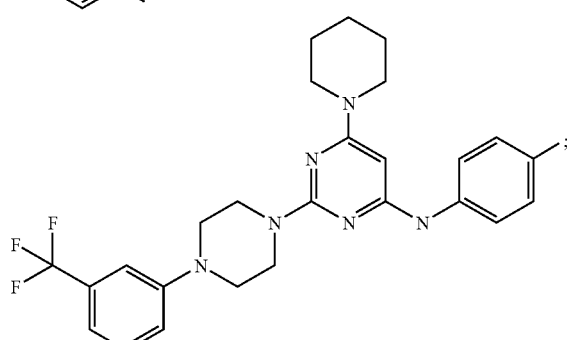
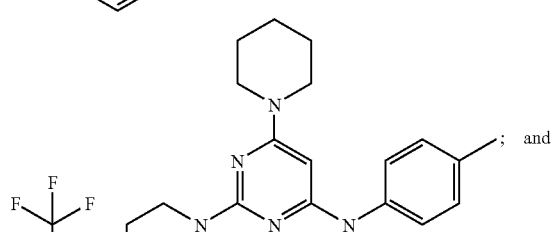
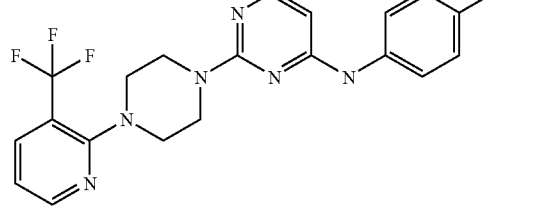
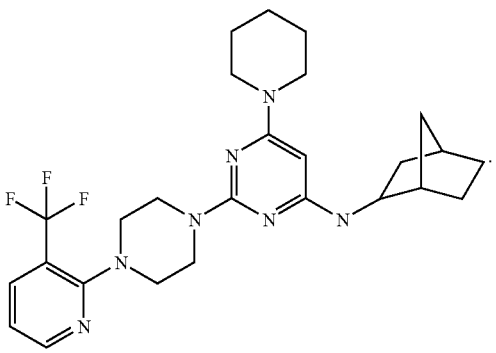
In one embodiment, the compound is selected from the group consisting of:
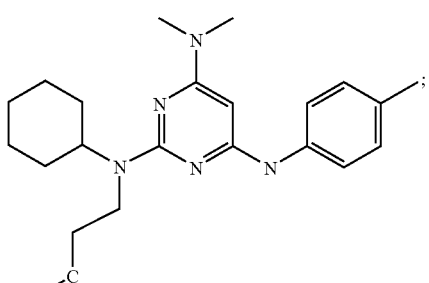
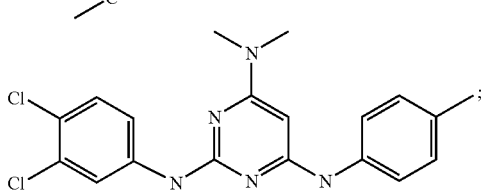
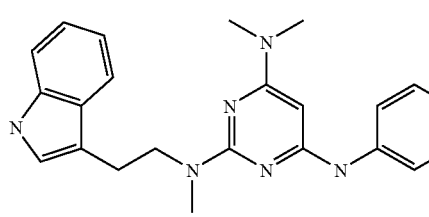
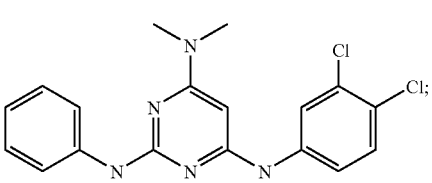
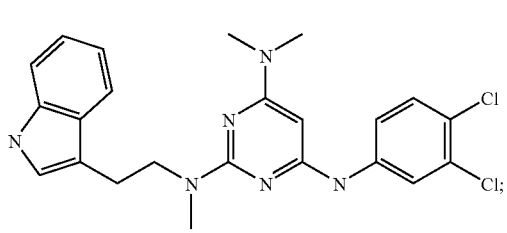

-continued
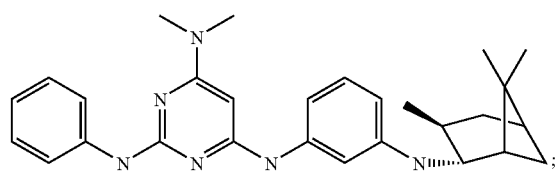
In one embodiment, Y is
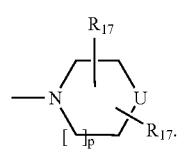
In one embodiment, U is NR$_{16}$.
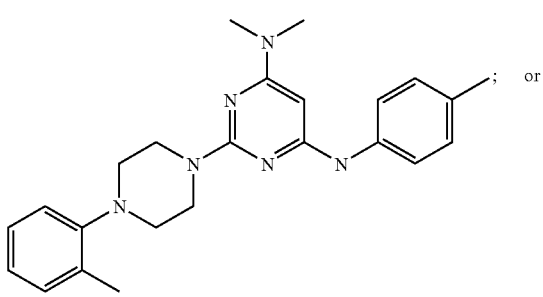
In one embodiment, the compound is
In one embodiment, the compound is
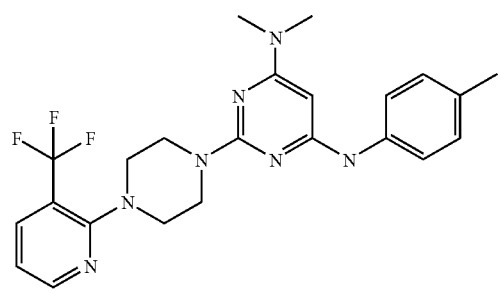
In one embodiment, the compound is selected from the group consisting of:
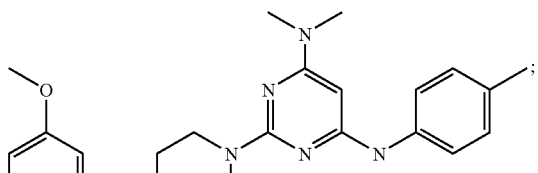
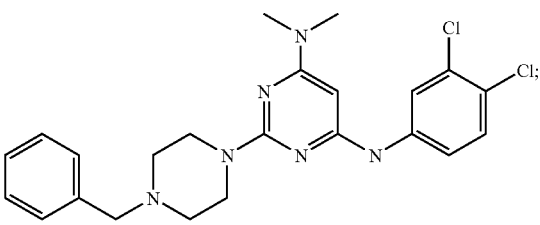
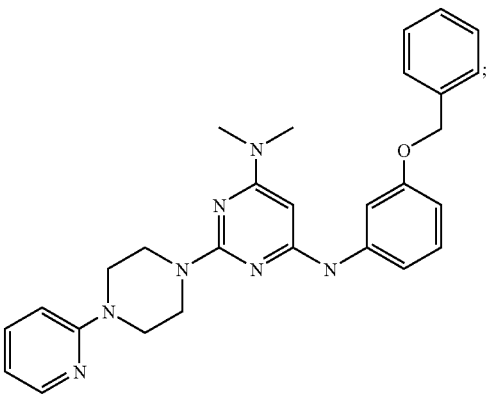
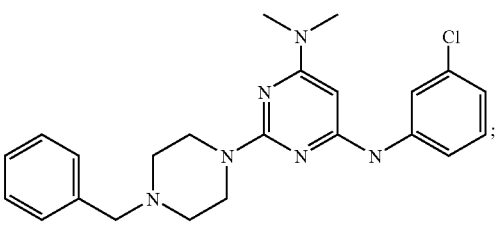
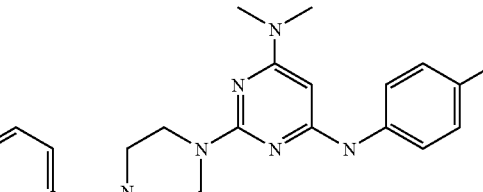
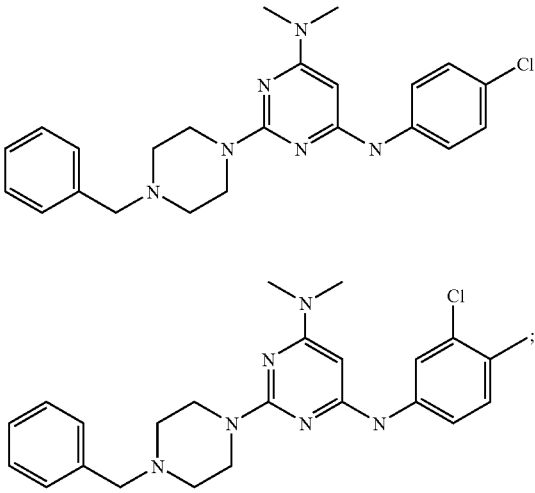

-continued
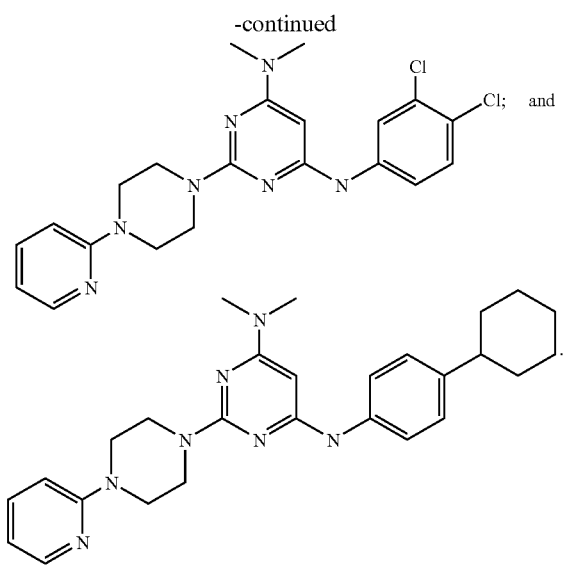
In one embodiment, the compound is selected from the group consisting of:
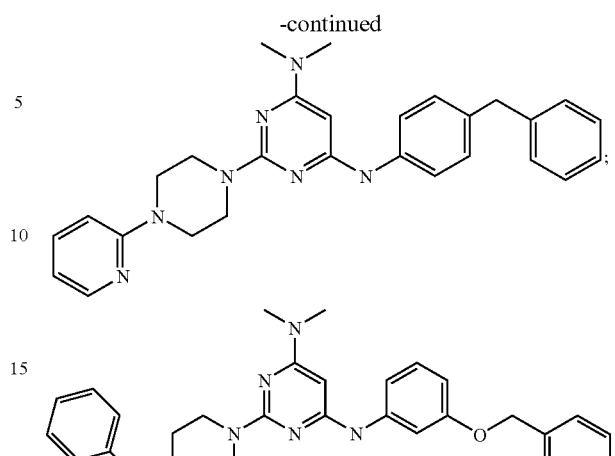
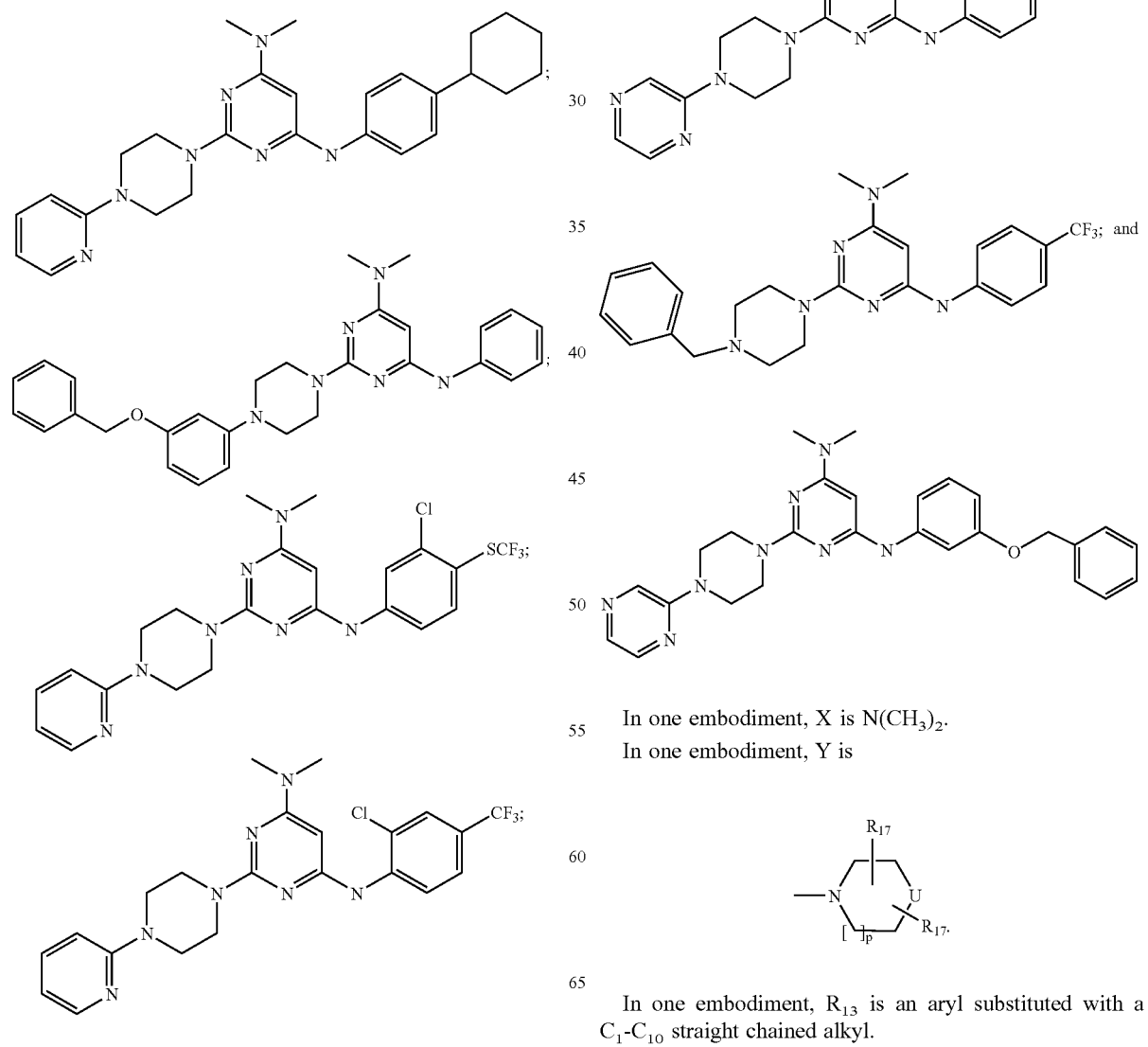
In one embodiment, X is $N(CH_3)_2$.
In one embodiment, Y is
In one embodiment, $R_{13}$ is an aryl substituted with a $C_1$-$C_{10}$ straight chained alkyl.

In one embodiment, the compound is selected from a group consisting of:

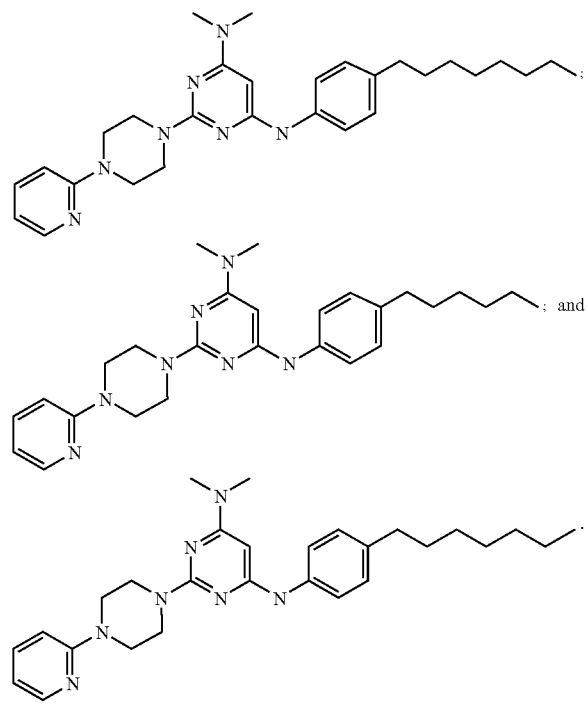

The invention provides a pharmaceutical composition comprising a therapeutically effective amount of any of the compounds described herein and a pharmaceutically acceptable carrier.

The invention provides a pharmaceutical composition made by combining a therapeutically effective amount of any of the compounds described herein and a pharmaceutically acceptable carrier.

The invention provides a process for making a pharmaceutical composition comprising combining a therapeutically effective amount of any of the compounds described herein and a pharmaceutically acceptable carrier.

The invention provides a method of treating a subject suffering from an abnormality which comprises administering to the subject an amount of any of the compounds described herein effective to treat the subject's abnormality.

In separate embodiments, the abnormality is a regulation of a steroid or pituitary hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder such as Alzheimer's disease, a learning disorder, a sleep disorder, a sensory modulation and transmission disorder, a motor coordination disorder, Huntington's disease, a sensory integration disorder, a motor integration disorder, a dopaminergic function disorder such as Parkinson's disease, a sensory transmission disorder, an olfaction disorder, a sympathetic innervation disorder, a stress-related disorder, a fluid-balance disorder, a seizure disorder, pain, inflammatory pain, chronic pain, psychotic behavior such as schizophrenia, morphine tolerance, drug addition particularly opiate addiction, migraine, an appetite disorder, such as obesity, or an eating/body weight disorders, such as bulimia or bulimia nervosa.

In preferred embodiments, the abnormality is Alzheimer's disease, obesity, diabetes, or pain, particularly neuropathic pain.

The invention provides a method of treating a subject suffering from pain which comprises administering to the subject an amount of any of the compounds described herein effective to treat the subject's pain.

The invention provides a method of treating a subject suffering from neuropathic pain which comprises administering to the subject an amount of any of the compounds described herein effective to treat the subject's neuropathic pain.

The invention provides a method of treating a subject suffering from an abnormality which comprises administering to the subject an amount of compound effective to treat the subject's abnormality wherein the compound has the structure:

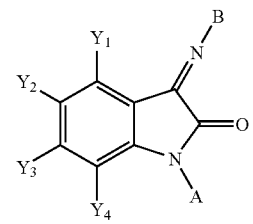

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', $Q_3$, $Q_4$, $Q_5$, straight chained or branched $C_1$-$C_7$ alkyl, aryl, heteroaryl, aryl($C_1$-$C_6$)alkyl, heteroaryl($C_1$-$C_6$)alkyl, aryl substituted with an aryl or heteroaryl, heteroaryl substituted with an aryl or heteroaryl; or $(CHR_{17})$—$(CHR_{17})_n$-Z;

wherein A' is

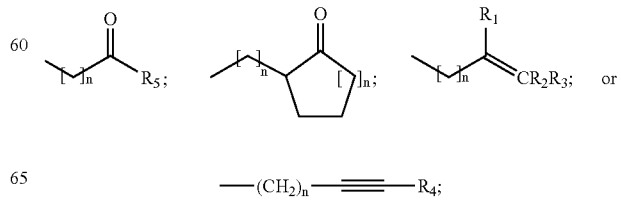

wherein $Q_3$ is

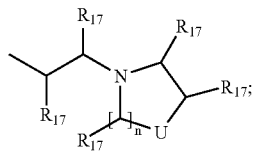

wherein $Q_4$ is

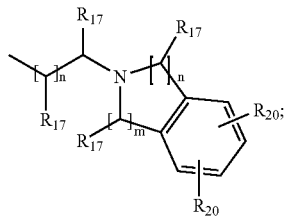

wherein $Q_5$ is

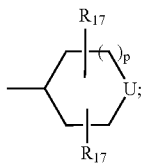

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl, straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein each m is an integer from 0 to 4 inclusive;
wherein each n is an integer from 1 to 4 inclusive;
wherein each p is an integer from 0 to 2 inclusive;
wherein U is O, —NR$_{16}$, S, C(R$_{17}$)$_2$, or —NSO$_2$R$_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or (CH$_2$)$_q$—O—(CH$_2$)$_m$—CH$_3$;

wherein q is an integer from 2 to 4 inclusive;

wherein B is aryl, heteroaryl, aryl substituted with an aryl or heteroaryl, heteroaryl substituted with an aryl or heteroaryl, tricyclic heteroaryl or $Q_6$; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein a tricyclic heteroaryl is a fused three member aromatic system in which one or more of the rings is heteroaryl; carbazole; or acridine;

wherein $Q_6$ is

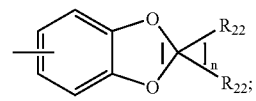

wherein each $R_{22}$ is independently H, F, Cl, or straight chained or branched $C_1$-$C_4$ alkyl;

or a pharmaceutically acceptable salt thereof.

The invention provides a method of treating a subject suffering from an abnormality which comprises administering to the subject an amount of compound effective to treat the subject's abnormality wherein the compound has the structure:

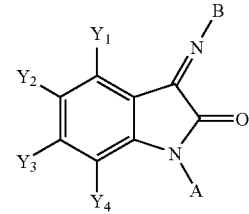

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_3$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl ($C_1$-$C_6$) alkyl;

wherein A is A', straight chained or branched $C_1$-$C_7$ alkyl, aryl, heteroaryl, aryl($C_1$-$C_6$)alkyl or heteroaryl($C_1$-$C_6$) alkyl;

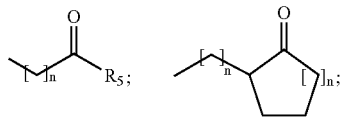

wherein A' is

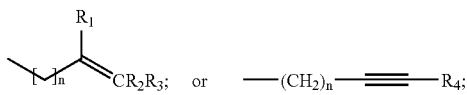

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$ aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

The invention provides a method of treating a subject suffering from an abnormality which comprises administering to the subject an amount of compound effective to treat the subject's abnormality wherein the

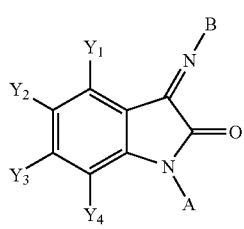

compound has the structure:

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl ($C_1$-$C_6$) alkyl;

wherein A is A', straight chained or branched $C_1$-$C_7$ alkyl, aryl, heteroaryl, aryl ($C_1$-$C_6$) alkyl or heteroaryl ($C_1$-$C_6$) alkyl;

wherein A' is

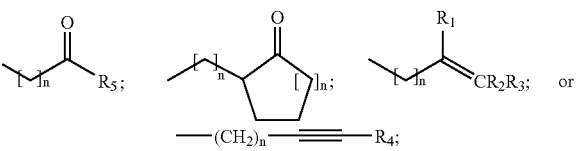

wherein B is aryl substituted with an aryl or heteroaryl, heteroaryl substituted with an aryl or heteroaryl, tricyclic heteroaryl or $Q_6$;

wherein a tricyclic heteroaryl is a fused three ring aromatic system in which one or more of the rings is heteroaryl; carbazole; or acridine;

wherein $Q_6$ is

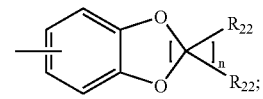

wherein n is an integer from 1 to 4 inclusive;

wherein each $R_{22}$ is independently H, F, Cl, or straight chained or branched $C_1$-$C_4$ alkyl;

or a pharmaceutically acceptable salt thereof.

The invention provides a method of treating a subject suffering from an abnormality which comprises administering to the subject an amount of compound effective to treat the subject's abnormality wherein the

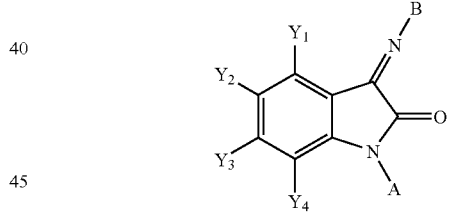

compound has the structure:

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is $Q_3$, $Q_4$, $Q_5$, aryl substituted with an aryl or heteroaryl, heteroaryl substituted with an aryl or heteroaryl, or (CHR$_{17}$)—(CHR$_{17}$)$_n$-Z;

wherein $Q_3$ is

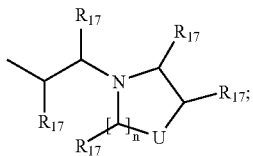

wherein $Q_4$ is

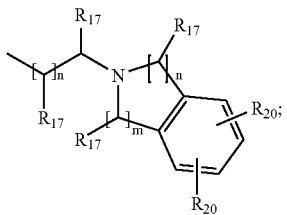

wherein $Q_5$ is

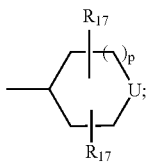

wherein each $R_{17}$ is independently H; straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_n$-Z, or —(CH$_2$)$_n$—O—(CH$_2$)$_m$—CH$_3$;

wherein each $R_{20}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_{21}$, —OCOR$_{21}$, —COR$_{21}$, —NCOR$_{21}$, —N(R$_{21}$)$_2$, —CON(R$_{21}$)$_2$, or —COOR$_{21}$; aryl or heteroaryl; or two $R_{20}$ groups present on adjacent carbon atoms can join together to form a methylenedioxy group;

wherein each $R_{21}$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl or aryl;

wherein each $R_{22}$ is independently H, F, Cl, or straight chained or branched $C_1$-$C_4$ alkyl;

wherein q is an integer from 2 to 4 inclusive;

wherein each m is an integer from 0 to 4 inclusive;

wherein each n is an integer from 1 to 4 inclusive;

wherein each p is an integer from 0 to 2 inclusive;

wherein U is O, —NR$_{16}$, S, C(R$_{17}$)$_2$, or —NSO$_2$R$_{16}$;

wherein Z is $C_3$-$C_{10}$ cycloalkyl, $C_4$-$C_7$ cyclic ether, $C_4$-$C_7$ cyclic thioether, aryl, or heteroaryl;

wherein $R_{16}$ is straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_5$-$C_7$ cycloalkenyl, —(CH$_2$)$_m$-Z, or —(CH$_2$)$_q$—O—(CH$_2$)$_m$—CH$_3$;

wherein B is aryl, or heteroaryl; provided however, if B is aryl or heteroaryl the carbon atom or carbon atoms ortho to the nitrogen atom of the imine bond may only be substituted with one or more of the following —F, —Cl, —Br, —I, —CN, methyl, ethyl or methoxy;

or a pharmaceutically acceptable salt thereof.

As used in the present invention, the term "cycloalkyl" includes $C_3$-$C_7$ cycloalkyl moieties which may be substituted with one or more of the following: —F, —NO$_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —N(R$_4$)$_2$, —OR$_4$, —COR$_4$, —NCOR$_4$, —CO$_2$R$_4$, —CON(R$_4$)$_2$ or (CH$_2$)$_n$—O—(CH$_2$)$_m$—CH$_3$.

As used in the present invention, the term "cycloalkenyl" includes $C_5$-$C_7$ cycloalkenyl moieties which may be substituted with one or more of the following: —F, —Cl, —Br, —I, —NO$_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —N(R$_4$)$_2$, —OR$_4$, —COR$_4$, —NCOR$_4$, —CO$_2$R$_4$, —CON(R$_4$)$_2$ or (CH$_2$)$_n$—O—(CH$_2$)$_m$—CH$_3$.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —NO$_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —N(R$_4$)$_2$, —OR$_4$, —COR$_4$, —NCOR$_4$, —CO$_2$R$_4$, —CON(R$_4$)$_2$ or (CH$_2$)$_n$—O—(CH$_2$)$_m$—CH$_3$.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —NO$_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —N($R_4$)$_2$, —O$R_4$, —S$R_4$, —OCO$R_4$, —CO$R_4$, —NCO$R_4$, —CO$_2R_4$, —CON($R_4$)$_2$ or (CH$_2$)$_n$—O—(CH$_2$)$_m$—CH$_3$.

The present invention also provides a method of treating a subject suffering from an abnormality which compromises administering to the subject an amount of compound effective to treat the subject's abnormality where in the compound has the structure:

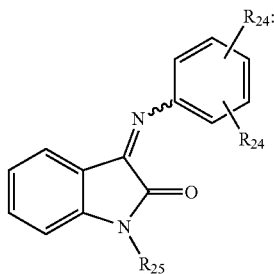

wherein each $R_{24}$ is independently one or more of the following: H, F, Cl, Br, I, CF$_3$, OCH$_3$ or N$_2$;

wherein $R_{25}$ is methyl, ethyl, alkyl, phenyl and the phenyl is optionally substituted with a F, Cl, Br, CF$_3$, NO$_2$.

In one embodiment of any of the methods described herein, the compound is enantiomerically and diastereomerically pure. In one embodiment of any of the methods described herein, the compound is enantiomerically or diastereomerically pure.

In one embodiment of any of the methods described herein, the compound is a pure Z imine isomer or a pure Z alkene isomer. In one embodiment, the compound is a pure E imine isomer or a pure E alkene isomer.

In one embodiment, the compound has the structure:

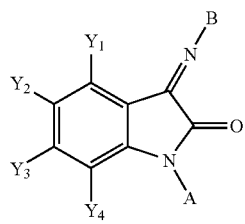

wherein each of $Y_1$, $Y_2$, $Y_3$, and $Y_4$ is independently —H; straight chained or branched $C_1$-$C_7$ alkyl, —CF$_3$, —F, —Cl, —Br, —I, —O$R_4$, —N($R_4$)$_2$, or —CON($R_4$)$_2$;

wherein each $R_4$ is independently —H; straight chained or branched $C_1$-$C_7$ alkyl, —CF$_3$, or phenyl;

wherein A is A', straight chained or branched $C_1$-$C_7$ alkyl, aryl, heteroaryl, aryl($C_1$-$C_6$)alkyl or heteroaryl ($C_1$-$C_6$) alkyl; and wherein A' is

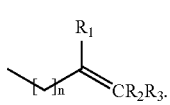

In one embodiment, B is heteroaryl. In another embodiment, B is aryl.

In one embodiment, B is phenyl and the phenyl is optionally substituted with one or more of the following:

—F, —Cl, —Br, —CF$_3$, straight chained or branched $C_1$-$C_7$ alkyl, —N($R_4$)$_2$, —O$R_4$, —CO$R_4$, —NCO$R_4$, —CO$_2R_4$, or —CON($R_4$)$_2$.

In one embodiment, A is aryl. In another embodiment, A is heteroaryl.

In some embodiments, the compound is selected from the group consisting of:

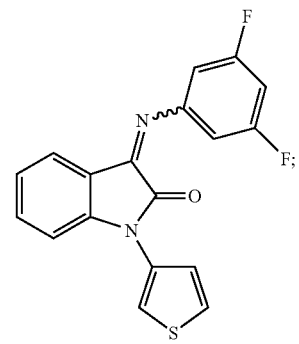

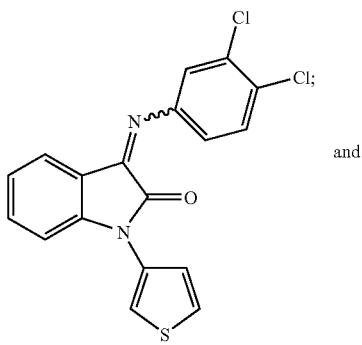

and

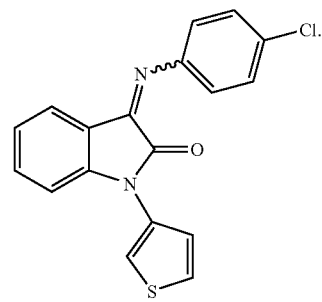

In certain embodiments, the compound is selected from the group consisting of:

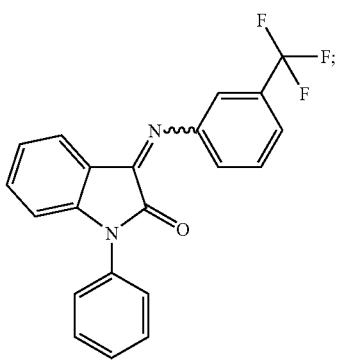

-continued
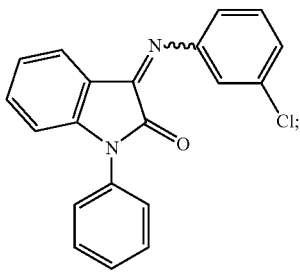
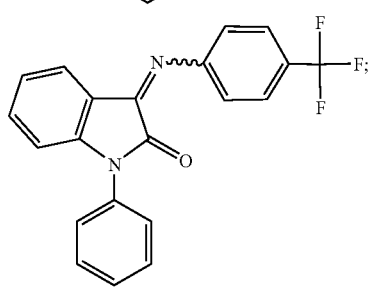
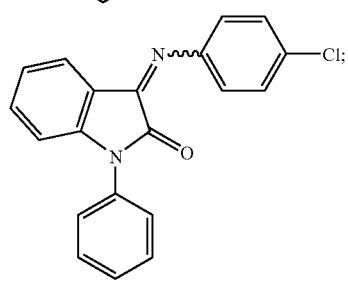
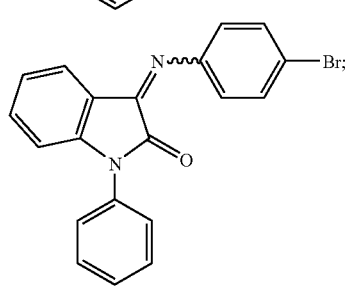
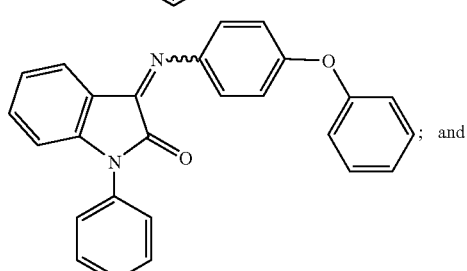; and
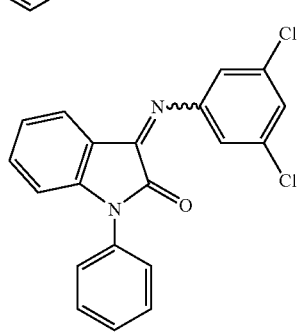
In one embodiment, A is A' and A' is
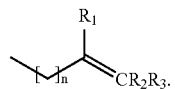
In other embodiments, the compound is:
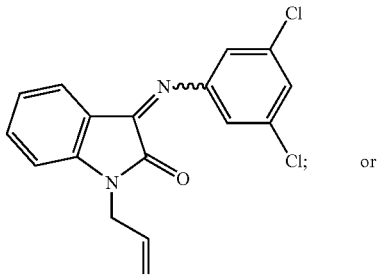  or
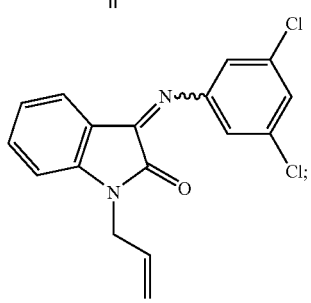
In still other embodiments, B is $Q_6$.
In one embodiment, A is aryl.
In another embodiment, the compound has the structure:
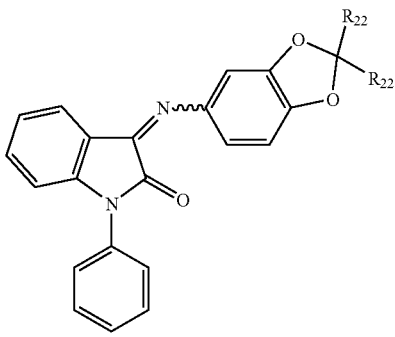
In other embodiments, the compound is:
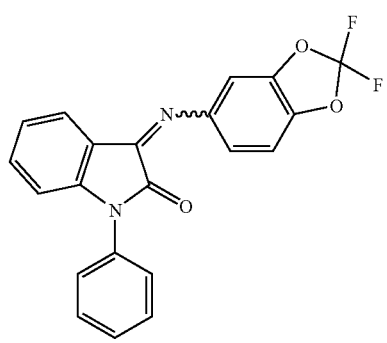
In another embodiment, B is aryl.
In certain embodiments, A is $(CHR_{17})$—$(CHR_{17})_n$-Z.

In one embodiment, the compound is:

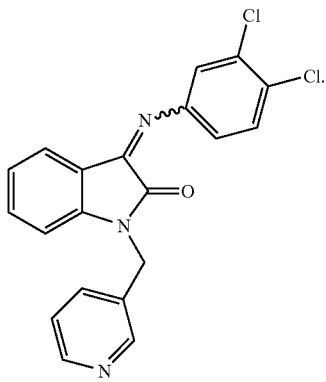

The invention provides a method of treating a subject suffering from an abnormality which comprises administering to the subject an amount of compound effective to treat the subject's abnormality wherein the compound has the structure:

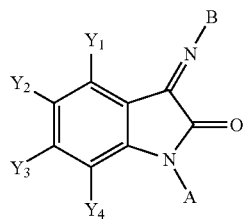

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$, alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl($C_1$-$C_6$) alkyl;

wherein A' is

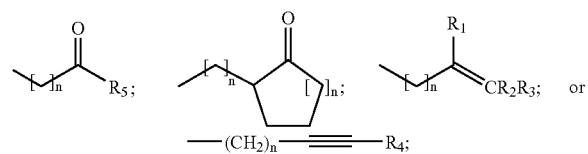

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$, aryl or heteroaryl;

wherein $R_5$ is straight chained or branched $C_1$-$C_7$ alkyl, —N(R$_4$)$_2$, —OR$_4$ or aryl;

wherein $R_6$ is straight chained or branched $C_1$-$C_7$ alkyl or aryl;

wherein B is $C_3$-$C_7$ cycloalkyl, $C_5$-$C_7$ cycloalkenyl, adamantyl, aryl, pyridyl, pyridazinyl, pyrimidinyl, pyrazinyl, triazinyl, indolizinyl, indol-4-yl, indol-5-yl, indol-6-yl, indol-7-yl, isoindolyl, benzo[b]furan-4-yl, benzo[b]furan-5-yl, benzo[b]furan-6-yl, benzo[b]furan-7-yl, benzo[b]thiophen-4-yl, benzo[b]thiophen-5-yl, benzo[b]thiophen-6-yl, benzo[b]thiophen-7-yl, indazolyl, benzimidazolyl, benzo[b]thiazolyl, purinyl, imidazo[2,1-b]thiazolyl, quinolinyl, isoquinolinyl, quinazolinyl, 2,1,3-benzothiazolyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, benzoxazolyl, benzisoxazolyl, cinnolinyl, quinoxalinyl, 1,8-naphthridinyl, pteridinyl, or phthalimidyl; provided however, if B is aryl, pyridyl, pyridazinyl, pyrimidinyl, pyrazinyl, triazinyl, indolizinyl, indol-4-yl, indol-5-yl, indol-6-yl, indol-7-yl, isoindolyl, benzo[b]furan-4-yl, benzo[b]furan-5-yl, benzo[b]furan-6-yl, benzo[b]furan-7-yl, benzo[b]thiophen-4-yl, benzo[b]thiophen-5-yl, benzo[b]thiophen-6-yl, benzo[b]thiophen-7-yl, indazolyl, benzimidazolyl, benzo[b]thiazolyl, purinyl, imidazo[2,1-b]thiazolyl, quinolinyl, isoquinolinyl, quinazolinyl, 2,1,3-benzothiazolyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, benzoxazolyl, benzisoxazolyl, cinnolinyl, quinoxalinyl, 1,8-napthyridinyl, pteridinyl, or phthalimidyl the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive.

In one embodiment of the invention, A is aryl, heteroaryl, heteroaryl($C_1$-$C_6$)alkyl or (CH$_2$)$_n$—CC—R$_4$; wherein the aryl is substituted with —OH;

In one embodiment of the invention, A is aryl, heteroaryl, or heteroaryl($C_1$-$C_6$)alkyl; and wherein aryl is substituted with —F, —Cl, —Br, —I, —NO$_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —N(R$_4$)$_2$, —OR$_4$, —SR$_4$, OCOR$_9$, —COR$_4$, —NCOR$_4$, —CO$_2$R$_4$, —CON(R$_4$)$_2$ or —(CH$_2$)$_n$O(CH$_2$)$_m$CH$_3$.

In another embodiment of the invention, each of $Y_1$, $Y_2$, $Y_3$, and $Y_4$ is independently —H; straight chained or branched $C_1$-$C_7$ alkyl, —CF$_3$, —F, —Cl, —Br, —I, —OR$_4$, —N(R$_4$)$_2$, or —CON(R$_4$)$_2$;

wherein each $R_4$ is independently —H; straight chained or branched $C_1$-$C_7$ alkyl, —CF$_3$, or phenyl;

wherein A is A', straight chained or branched $C_1$-$C_7$ alkyl, aryl, heteroaryl, aryl($C_1$-$C_6$)alkyl or heteroaryl ($C_1$-$C_6$) alkyl; and wherein A' is

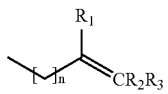

In another embodiment of the invention, B is $C_3$-$C_7$ cycloalkyl or adamantyl.

In still another embodiment of the invention, B is pyridyl, pyridazinyl, pyrimidinyl, pyrazinyl, triazinyl, indolizinyl, indol-4-yl, indol-5-yl, indol-6-yl, indol-7-yl, isoindolyl, benzo[b]furan-4-yl, benzo[b]furan-5-yl, benzo[b]furan-6-yl, benzo[b]furan-7-yl, benzo[b]thiophen-4-yl, benzo[b]thiophen-5-yl, benzo[b]thiophen-6-yl, benzo[b]thiophen-7-yl, indazolyl, benzimidazolyl, benzo[b]thiazolyl, purinyl, imidazo[2,1-b]thiazolyl, quinolinyl, isoquinolinyl; quinazolinyl, 2,1,3-benzothiazolyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, benzoxazolyl, benzisoxazolyl, cinnolinyl, quinoxalinyl, 1,8-napthyridinyl, pteridinyl, or phthalimidyl.

In another embodiment of the invention, B is aryl.

In still another embodiment of the invention, B is phenyl and the phenyl is optionally substituted with one or more of the following: —F, —Cl, —Br, —$CF_3$, straight chained or branched $C_1$-$C_7$ alkyl, —$N(R_4)_2$, —$OR_4$, —$COR_4$, —$NCOR_4$, —$CO_2R_4$, or —$CON(R_4)_2$.

In some embodiments of the invention, A is aryl.

In other embodiments, the compound is selected from the group consisting of:

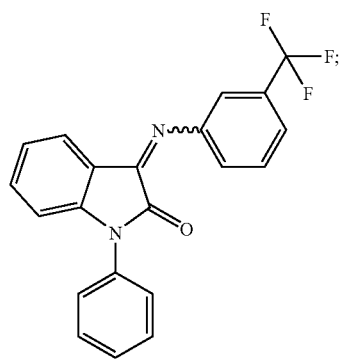

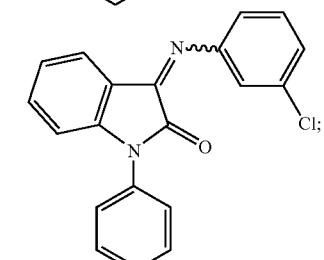

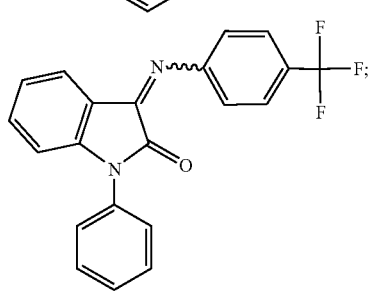

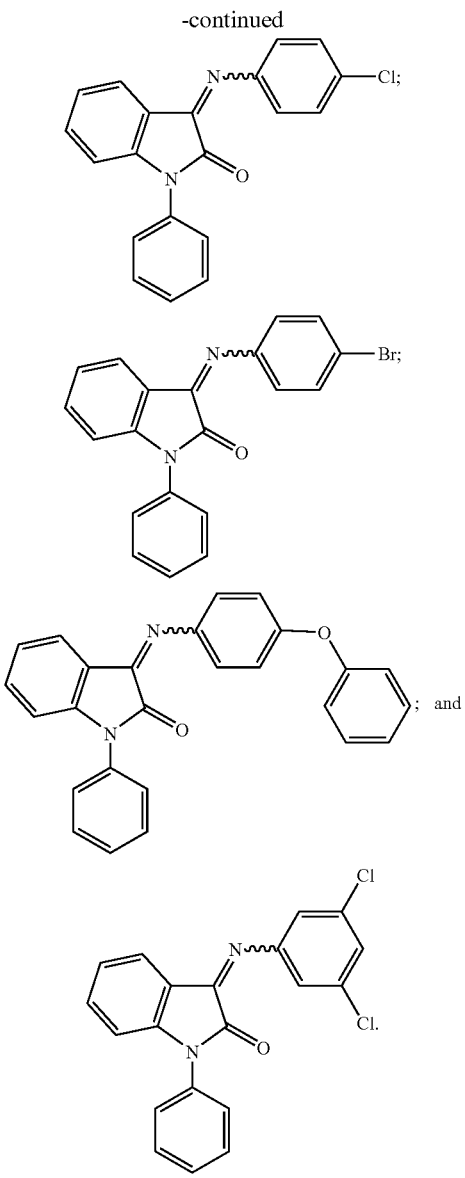

In still other embodiments, A is A' and A' is

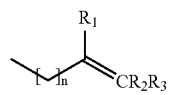

In one embodiment, the compound is:

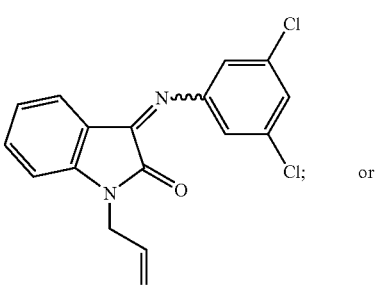

-continued

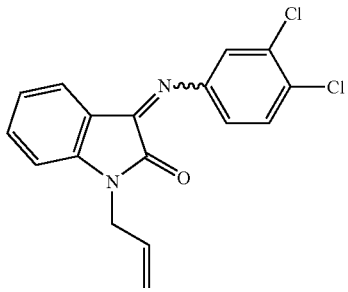

The invention provides a method of treating a subject suffering from an abnormality which comprises administering to the subject an amount of compound effective to treat the subject's abnormality wherein the compound has the structure:

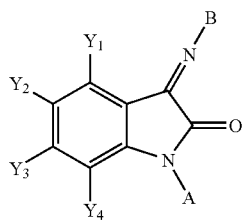

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$) alkyl;

wherein A is A', straight chained or branched $C_1$-$C_7$ alkyl, aryl, heteroaryl, aryl($C_1$-$C_6$)alkyl or heteroaryl ($C_1$-$C_6$) alkyl;

wherein A' is

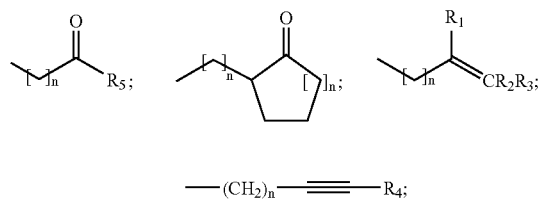

—(CH$_2$)$_n$—C≡C—R$_4$;

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$, aryl or heteroaryl;

wherein $R_5$ is straight chained or branched $C_1$-$C_7$ alkyl, —N(R$_4$)$_2$, —OR$_4$ or aryl;

wherein $R_6$ is straight chained or branched $C_1$-$C_7$ alkyl or aryl;

wherein B is aryl, pyridyl, pyridazinyl, pyrimidinyl, pyrazinyl, triazinyl, indolizinyl, indol-4-yl, indol-5-yl, indol-6-yl, indol-7-yl, isoindolyl, benzo[b]furan-4-yl, benzo[b]furan-5-yl, benzo[b]furan-6-yl, benzo[b]furan-7-yl, benzo[b]thiophen-4-yl, benzo[b]thiophen-5-yl, benzo[b]thiophen-6-yl, benzo[b]thiophen-7-yl, indazolyl, benzimidazolyl, benzo[b]thiazolyl, purinyl, imidazo[2,1-b]thiazolyl, quinolinyl, isoquinolinyl, quinazolinyl, 2,1,3-benzothiazolyl, furanyl, thienyl, pyrrolyl, oxazolyl, thiazolyl, imidazolyl, pyrazolyl, isoxazolyl, isothiazolyl, oxadiazolyl, triazolyl, thiadiazolyl, benzoxazolyl, benzisoxazolyl, cinnolinyl, quinoxalinyl, 1,8-napthyridinyl, pteridinyl, or phthalimidyl; provided however, that the carbon atom or carbon atoms ortho to the nitrogen atom of the imine bond may only be substituted with one or more of the following —F, —Cl, —Br, —I, —CN, methyl, ethyl or methoxy;

wherein n is an integer from 1 to 4 inclusive;

or a pharmaceutically acceptable salt thereof.

In one embodiment, the compound is A is aryl, heteroaryl, heteroaryl($C_1$-$C_6$) alkyl or —(CH$_2$)$_n$—CC—R$_4$; wherein the aryl is substituted with —OH;

In another embodiment, A is aryl, heteroaryl, or heteroaryl ($C_1$-$C_6$)alkyl; and wherein aryl is substituted with —F, —Cl, —Br, —I, —NO$_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —N(R$_4$)$_2$, —OR$_4$, —SR$_4$, —OCOR$_4$, —COR$_4$, —NCOR$_4$, —CO$_2$R$_4$, —CON(R$_4$)$_2$ or —(CH$_2$)$_n$O(CH$_2$)$_m$CH$_3$.

In one embodiment, the compound is an enantiomerically and diastereomerically pure compound.

In one embodiment, the compound is an enantiomerically or diastereomerically pure compound.

In some embodiments, the compound is a pure Z imine isomer or a pure Z alkene isomer of the compound.

In some embodiments, the compound is a pure E imine isomer or a pure E alkene isomer of the compound.

In other embodiments, A is A', straight chained or branched $C_1$-$C_7$ alkyl, aryl, heteroaryl, aryl($C_1$-$C_6$)alkyl or heteroaryl ($C_1$-$C_6$) alkyl; and A' is

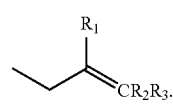

In some embodiments, each of $Y_1$, $Y_2$, $Y_3$, and $Y_4$ is independently —H; straight chained or branched $C_1$-$C_7$ alkyl, —CF$_3$, —F, —Cl, —Br, —I, —OR$_4$, —N(R$_4$)$_2$, or —CON(R$_4$)$_2$.

In other embodiments, A is aryl or aryl($C_1$-$C_6$)alkyl.

In still other embodiments, the compound is selected from the group consisting of:

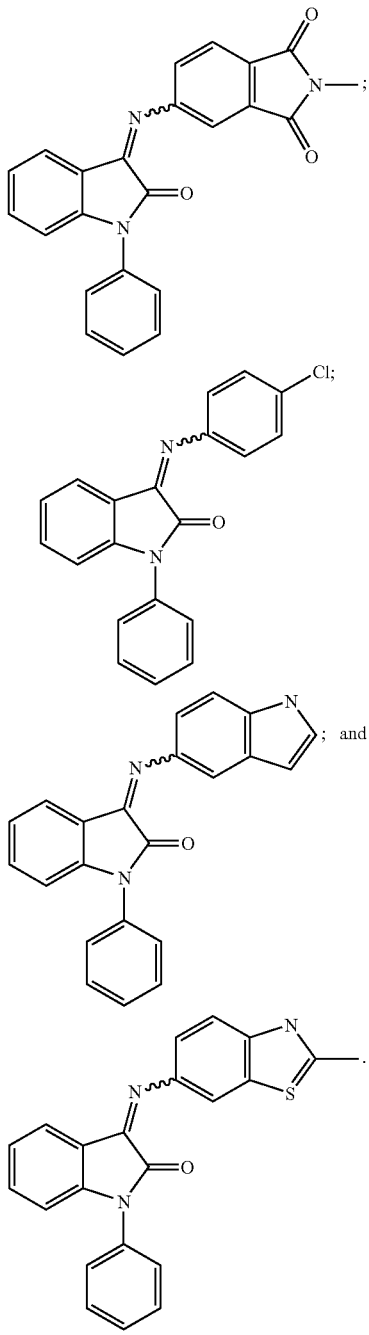

The invention provides a pharmaceutical composition comprising a therapeutically effective amount of any of the compounds described herein and a pharmaceutically acceptable carrier.

The invention provides a pharmaceutical composition made by combining a therapeutically effective amount of any of the compounds described herein and a pharmaceutically acceptable carrier.

The invention provides a process for making a pharmaceutical composition comprising combining a therapeutically effective amount of any of the compounds described herein and a pharmaceutically acceptable carrier.

The invention provides a method of treating a subject suffering from an abnormality which comprises administering to the subject an amount of any of the compounds described herein effective to treat the subject's abnormality.

In separate embodiments, the abnormality is a regulation of a steroid or pituitary hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder such as Alzheimer's disease, a learning disorder, a sleep disorder, a sensory modulation and transmission disorder, a motor coordination disorder, Huntington's disease, a sensory integration disorder, a motor integration disorder, a dopaminergic function disorder such as Parkinson's disease, a sensory transmission disorder, an olfaction disorder, a sympathetic innervation disorder, a stress-related disorder, a fluid-balance disorder, a seizure disorder, pain, inflammatory pain, chronic pain, psychotic behavior such as schizophrenia, morphine tolerance, drug addition particularly opiate addiction, migraine, an appetite disorder, such as obesity, or an eating/body weight disorders, such as bulimia or bulimia nervosa.

In preferred embodiments, the abnormality is Alzheimer's disease, obesity, diabetes, or pain, particularly neuropathic pain.

The invention provides a method of treating a subject suffering from pain which comprises administering to the subject an amount of any of the compounds described herein effective to treat the subject's pain.

The invention provides a method of treating a subject suffering from neuropathic pain which comprises administering to the subject an amount of any of the compounds described herein effective to treat the subject's neuropathic pain.

The invention provides for each pure stereoisomer of any of the compounds described herein. Such stereoisomers may include enantiomers, diastereomers, or E or Z alkene or imine isomers. The invention also provides for stereoisomeric mixtures, including racemic mixtures, diastereomeric mixtures, or E/Z isomeric mixtures. Stereoisomers can be synthesized in pure form (Nógrádi, M.; Stereoselective Synthesis, (1987) VCH Editor Ebel, H. and Asymmetric Synthesis, Volumes 3-5, (1983) Academic Press, Editor Morrison, J.) or they can be resolved by a variety of methods such as crystallization and chromatographic techniques (Jaques, J.; Collet, A.; Wilen, S.; Enantiomer, Racemates, and Resolutions, 1981, John Wiley and Sons and Asymmetric Synthesis, Vol. 2, 1983, Academic Press, Editor Morrison, J).

In addition the compounds of the present invention may be present as enantiomers, diasteriomers, isomers or two or more of the compounds may be present to form a racemic or diastereomeric mixture.

The compounds of the present invention are preferably 80% pure, more preferably 90% pure, and most preferably 95% pure.

Included in this invention are pharmaceutically acceptable salts and complexes of all of the compounds described herein. The acids and bases from which these salts are prepared include but are not limited to the acids and bases listed herein. The acids include, but are not limited to, the following inorganic acids: hydrochloric acid, hydrobromic acid, hydroiodic acid, sulfuric acid and boric acid. The acids include, but are not limited to, the following organic acids: acetic acid, malonic acid, succinic acid, fumaric acid, tartaric acid, maleic acid, citric acid, methanesulfonic acid, benzoic acid, glycolic acid, lactic acid and mandelic acid. The bases include, but are not limited to ammonia, methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound. Thus, in the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

Throughout the invention, the term "binding affinity" describes the concentration of a compound required to occupy one-half of the binding sites in a receptor population, as detectable by radioligand binding. Binding affinity concentration can be represented as $K_i$, inhibition constant, or $K_D$, dissociation constant.

The term "selectivity of binding affinity" refers to the ability of a chemical compound to discriminate one receptor from another. For example, a compound showing selectivity for receptor A versus receptor B will bind receptor A at lower concentrations than those required to bind receptor B.

Therefore, the statements of the form "binds to the GAL3 receptor with a binding affinity at least ten-fold higher than" a named receptor, indicates that the binding affinity at the GAL3 receptor is at least ten-fold greater than that for a named receptor, and binding affinity measurements (i.e. $K_i$ or $K_D$) for the compound are at least ten-fold lower in numerical value.

The present invention provides a method of treating an abnormality in a subject which comprises administering to the subject a composition comprising a pharmaceutically acceptable carrier and a therapeutically effective amount of a GAL3 receptor antagonist, wherein:
the GAL3 receptor antagonist binds to the human GAL3
  receptor with a binding affinity at least ten-fold higher
  than the binding affinity with which it binds to the human
  GAL1 receptor.

In some embodiments of this invention, the GAL3 receptor antagonist binds to the human GAL3 receptor with a binding affinity at least 30-fold higher than the binding affinity with which it binds to the human GAL1 receptor.

In further embodiments of the invention, the GAL3 receptor antagonist binds to the human GAL3 receptor with a binding affinity at least 50-fold higher than the binding affinity with which it binds to the human GAL1 receptor.

In other embodiments of the invention, the GAL3 receptor antagonist binds to the human GAL3 receptor with a binding affinity at least 100-fold higher than the binding affinity with which it binds to the human GAL1 receptor.

In still other embodiments of the invention, the GAL3 receptor antagonist binds to the human GAL3 receptor with a binding affinity at least 200-fold higher than the binding affinity with which it binds to the human GAL1 receptor.

For the purposes of this invention the term "pharmaceutically acceptable carrier" has been defined herein.

The term "antagonist" refers to a compound which binds to, and decreases the activity of, a receptor in the presence of an agonist. In the case of a G-protein coupled receptor, activation may be measured using an appropriate second messenger system which is coupled to the receptor in a cell or tissue in which the receptor is expressed. Some specific but by no means limiting examples of well-known second messenger systems are adenylate cyclase, intracellular calcium mobilization, ion channel activation, guanylate cyclase, inositol phospholipid hydrolysis, and MAP kinase activation. Conversely, the term "agonist" refers to a compound which binds to, and increases the activity of, a receptor as compared with the activity of the receptor in the absence of any agonist. Methods to perform second messenger assays are described in PCT International Publication No. 97/46250 and in PCT International Publication No. 98/15570, the contents of which are hereby incorporated by reference.

In the case that a receptor has activity in the absence of an agonist (constitutive receptor activity) the antagonist may act as an inverse agonist or an allosteric modulator, as opposed to a neutral antagonist, and suppress receptor signaling independent of the agonist (Lutz and Kenakin, 1999). The categories of "antagonist compounds" are therefore seen to include 1) neutral antagonists (which block agonist actions but do not affect constitutive activity); 2) inverse agonists (which block agonist actions as well as constitutive activity by stabilizing an inactive receptor conformation); 3) and allosteric modulators (which block agonist actions to a limited extent and which may also block constitutive activity through allosteric regulation). The probability that an antagonist is neutral and therefore of "zero efficacy" is relatively low, given that this would require identical affinities for different tertiary conformations of the receptor. Thus, Kenakin proposed in 1996 that, "with the development of sensitive test systems for the detection of inverse agonism will come a reclassification of many drugs. It might be observed that numerous previously classified neutral antagonists may be inverse agonists" (Kenakin, 1996). Indeed, there is now evidence from studies with known pharmacological agents to support the existence of inverse agonists for numerous receptors, including histamine, $5HT_{1A}$, $5HT_{2C}$, cannabinoid, dopamine, calcitonin and human formyl peptide receptors, among others (de Ligt, et al, 2000; Herrick-Davis, et al, 2000; Bakker, et al, 2000). In the case of the $5HT_{2C}$ receptor, clinically effective a typical antipsychotics drugs such as sertindole, clozapine, olanzapine, ziprasidone, risperidone, zotepine, tiospirone, fluperlapine and tenilapine displayed potent inverse activity whereas typical antipsychotic drugs such as chlorpromazine, thioridazine, spiperone and thiothixene were classified as neutral antagonists (Herrick-Davis et al, 2000). In the case of the histamine $H_1$ receptor, the therapeutically used anti-allergics cetirizine, loratadine and epinastine were found to be inverse agonists. These findings further extend the idea that many compounds previously thought of as neutral antagonists will be reclassified as inverse agonists when tested in a constitutively active receptor system (de Ligt et al, 2000).

The subject invention provides GAL3 antagonists which selectively bind to the GAL3 receptor. A GAL3 antagonist useful in the treatment of pain is one which selectively binds to the GAL3 receptor, and displays analgesic activity in an animal model which is predictive of the efficacy of analgesics to treat pain in humans. Animal models used to test potential analgesic agents are well known in the art.

In order to test compounds for selective binding to the human GAL3 receptor the cloned cDNAs encoding both the human and rat GAL1 and GAL2 receptors have been used. The cloning and assay methods for the human and rat GAL1 receptors may be found in PCT International Publication No. WO 95/22608, the contents of which are hereby incorporated by reference. The cloning and assay methods for the human and rat GAL2 receptors may be found in PCT International Publication No. WO 97/26853, the contents of which are hereby incorporated by reference.

The present invention provides for a method of determining the binding affinity of a GAL3 antagonist, wherein the GAL3 antagonist is dissolved in a "suitable solvent". A "suitable solvent" means one which permits the measurement of binding affinity of the GAL3 antagonist to the human GAL3 receptor at concentrations less than 1 µM, preferably less than 100 nM. Examples of solvents include, but are not limited to, DMSO, ethanol, N,N-dimethylacetamide, or water. For indolones, the preferred solvent is 3% DMSO (final concentration in the assay). For pyrimidines, the preferred solvent is 1% ethanol/0.09% polypuronic acid F-127 (final concentration in the assay). For any other type of compounds, the preferred solvent is the solvent which permits the measurement of binding affinity of a GAL3 antagonist at the lowest concentration. Once a suitable solvent is ascertained for the binding assay of the human GAL3 receptor, the same solvent is used in assays to determine the binding affinity for instance, at the GAL1 receptor.

In certain embodiments, the aforementioned GAL3 receptor antagonist additionally binds to the human GAL3 receptor with a binding affinity at least ten-fold higher than the binding affinity with which it binds to the human GAL2 receptor.

In other embodiments, the GAL3 receptor antagonist additionally binds to the human GAL3 receptor with a binding affinity at least 30-fold higher than the binding affinity with which it binds to the human GAL2 receptor.

In still other embodiments, the GAL3 receptor antagonist additionally binds to the human GAL3 receptor with a binding affinity at least 50-fold higher than the binding affinity with which it binds to the human GAL2 receptor.

In some embodiments, the GAL3 receptor antagonist additionally binds to the human GAL3 receptor with a binding affinity at least 100-fold higher than the binding affinity with which it binds to the human GAL2 receptor.

In further embodiments, the GAL3 receptor antagonist additionally binds to the human GAL3 receptor with a binding affinity at least 200-fold higher than the binding affinity with which it binds to the human GAL2 receptor.

In other embodiments, the receptor antagonist also binds to the human GAL3 receptor with a binding affinity at least ten-fold higher than the binding affinity with which it binds to each of the human $5HT_{1B}$, human $5HT_{1D}$, human. $5HT_{1E}$, human $5HT_{1F}$, human $5HT_{2A}$, rat $5HT_{2C}$, human $5HT_6$ and human $5HT_7$ receptors.

In still another embodiment, the receptor antagonist also binds to the human GAL3 receptor with a binding affinity at least ten-fold higher than the binding affinity with which it binds to the human histamine $H_1$ receptor.

In still another embodiment, the receptor antagonist also binds to the human GAL3 receptor with a binding affinity at least ten-fold higher than the binding affinity with which it binds to the human dopamine $D_1$, $D_2$, $D_3$, $D_4$ and $D_5$ receptors.

In a further embodiment, the receptor antagonist also binds to the human GAL3 receptor with a binding affinity at least ten-fold higher than the binding affinity with which it binds to the human $\alpha_{1A}$ adrenoceptor, the human $\alpha_{1B}$ adrenoceptor and the human $\alpha_{1D}$ adrenoceptor.

In another embodiment, the receptor antagonist also binds to the human GAL3 receptor with a binding affinity at least ten-fold higher than the binding affinity with which it binds to the human $\alpha_{2A}$ adrenoceptor, the human $\alpha_{2B}$ adrenoceptor and the human $\alpha_{2C}$ adrenoceptor.

The binding properties of compounds at different receptors were determined using cultured cell lines that selectively express the receptor of interest. Cell lines were prepared by transfecting the cloned cDNA or cloned genomic DNA or constructs containing both genomic DNA and cDNA encoding the receptors as further described in the Experimental Details herein below. Furthermore, the binding interactions of compounds at different transporters were determined using tissue preparations and specific assays as further described in the Experimental Details herein below.

In connection with this invention, a number of cloned receptors discussed herein, as stably transfected cell lines, have been made pursuant to, and in satisfaction of, the Budapest Treaty on the International Recognition of the Deposit of Microorganisms for the Purpose of Patent Procedure, and are made with the American Type Culture Collection, 10801 University Blvd., Manassas, Va. 20110-2209. Specifically, these deposits have been accorded ATCC Accession Numbers as follows:

ATCC Deposits:

| Designation | Receptor | ATCC Accession No. | Date of Deposit |
|---|---|---|---|
| (CHO) | human GAL1 | CRL-1650 | |
| hGalR2-264 | human GAL2 | CRL 12379 | Jul. 22, 1997 |
| L-hGalR3-228 | human GAL3 | CRL-12373 | Jul. 01, 1997 |
| 5HT1A-3 | human $5\text{-}HT_{1A}$ | CRL 11889 | May 11, 1995 |
| Ltk-11 | human $5\text{-}HT_{1B}$ (formerly human 5-HT1D2) | CRL 10422 | Apr.17, 1990 |
| Ltk-8-30-84 | human $5\text{-}HT_{1D}$ (formerly human 5-HT1D1) | CRL 10421 | Apr. 17, 1990 |
| $5HT_{1E}$-7 | human $5\text{-}HT_{1E}$ | CRL 10913 | Nov. 06, 1991 |
| L-5-$HT_{1F}$ | human $5\text{-}HT_{1F}$ | CRL 10957 | Dec. 27, 1991 |
| L-NGC-$5HT_2$ | human $5\text{-}HT_{2A}$ (formerly human 5-HT2) | CRL 10287 | Oct. 31, 1989 |
| pSr-1c | rat $5\text{-}HT_{2C}$ (formerly rat 5HT1C) | 67636 | |
| pBluescript-hS10 | human $5\text{-}HT_4$ | 75392 | Dec. 22, 1992 |
| L-5HT-4B | human $5\text{-}HT_7$ (formerly human 5-HT4B) | CRL 11166 | Oct. 20, 1992 |
| L-$\alpha_{1C}$ | human $\alpha_{1A}$ (formerly human α1C) | CRL11140 | Sep. 25, 1992 |
| L-$\alpha_{1B}$ | human $\alpha_{1B}$ | CRL11139 | Sep. 25, 1992 |
| L-$\alpha_{1A}$ | human $\alpha_{1D}$ (formerly hum α1A) | CRL11138 | Sep. 25, 1992 |
| L-$\alpha_{2A}$ | human $\alpha_{2A}$ | CRL11180 | Nov. 06, 1992 |
| L-NGC-$\alpha_{2B}$ | human $\alpha_{2B}$ | CRL10275 | Oct. 25, 1989 |
| L-$\alpha_{2C}$ | human $\alpha_{2C}$ | CRL11181 | Nov. 06, 1992 |

-continued

ATCC Deposits:

| Designation | Receptor | ATCC Accession No. | Date of Deposit |
|---|---|---|---|
| pDopD$_1$-GL-30 | human D$_5$ (formerly hum D1β) | 40839 | Jul. 10, 1990 |
| pCEXV-H$_1$ | human H$_1$ | 75346 | Nov. 06, 1992 |

The "5-HT$_{1C}$", "5-HT$_{1D1}$", "5-HT$_{1D2}$", "5-HT$_{4B}$", and "5-HT$_2$" receptors were renamed the "5-HT$_{2C}$", "5-HT$_{1D}$", "5-HT$_{1B}$", "5-HT$_7$", and "5-HT$_{2A}$" receptors, respectively, by the Serotonin Receptor Nomenclature Committee of the IUPHAR.
The "human α$_{1C}$", "human α$_{1A}$", and "human D$_{1β}$" were renamed the "human α$_{1A}$", "human α$_{1D}$", and "human D$_5$" respectively.

The following receptor sequences have been deposited with the GenBank DNA database, which is managed by the National Center for Biotechnology (Bethesda, Md.).

GENBANK DEPOSITS

| DESIGNATION | RECEPTOR | GENBANK No. |
|---|---|---|
| human mRNA for D-1 receptor | human D$_1$ (formerly human D$_{1α}$) | X58987 |
| human dopamine D2 receptor (DRD2) mRNA complete cds | human D$_2$ | M29066 |
| Rat mRNA for dopamine D3 receptor | rat D$_3$ | X53944 |
| *Homo sapiens* dopamine D4 receptor (DRD4) gene (D4.4) sequence | human D$_4$ | L12397 |

*The "human D$_{1α}$" receptor was renamed the "human D$_1$" receptor.

This invention further provides a Pharmaceutical composition comprising a therapeutically effective amount of the compound of the invention and a pharmaceutically acceptable carrier. In one embodiment, the amount of the compound is an amount from about 0.01 mg to about 800 mg. In another embodiment, the amount of the compound is an amount from about 0.01 mg to about 500 mg. In another embodiment, the amount of the compound is an amount from about 0.01 mg to about 250 mg. In another embodiment, the amount of the compound is an amount from about 0.1 mg to about 60 mg. In another embodiment, the amount of the compound is an amount from about 1 mg to about 20 mg. In a further embodiment, the carrier is a liquid and the composition is a solution. In another embodiment, the carrier is a solid and the composition is a powder or tablet. In a further embodiment, the carrier is a gel and the composition is a capsule or suppository.

This invention provides a pharmaceutical composition made by combining a therapeutically effective amount of the compound of this invention and a pharmaceutically acceptable carrier.

This invention provides a process for making a pharmaceutical composition comprising combining a therapeutically effective amount of the compound of this invention and a pharmaceutically acceptable carrier.

In the subject invention a "therapeutically effective amount" is any amount of a compound which, when administered to a subject suffering from a disease against which the compounds are effective, causes reduction, remission, or regression of the disease. In the subject application, a "subject" is a vertebrate, a mammal, or a human.

The present invention provides for the use of any of the chemical compounds disclosed herein for the preparation of a pharmaceutical composition for treating an abnormality. The invention also provides for the use of a chemical compound for the preparation of a pharmaceutical composition for treating an abnormality, wherein the abnormality is alleviated by decreasing the activity of a human GAL3 receptor. In one embodiment, the abnormality is pain. In another embodiment, the abnormality is neuropathic pain. In still another embodiment, the abnormality is Alzheimer's disease. In still another embodiment, the abnormality is obesity. In still another embodiment, the abnormality is diabetes.

In the present invention the term "pharmaceutically acceptable carrier" is any pharmaceutical carrier known to those of ordinary skill in the art as useful in formulating pharmaceutical compositions. On Dec. 24, 1997 the Food and Drug Administration of the United States Department of Health and Human Services published a guidance entitled "Q3C Impurities: Residual Solvent". The guidance recommends acceptable amounts of residual solvents in pharmaceuticals for the safety of the patient, and recommends the use of less toxic solvents in the manufacture of drug substances and dosage forms.

In an embodiment of the present invention, the pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch. In yet a further embodiment, the compound may be delivered to the subject by means of a spray or inhalant.

A solid carrier can include one or more substances which may also act as endogenous carriers (e.g. nutrient or micronutrient carriers), flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmoregulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate or isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

I. Synthesis of Chemical Compounds

The following examples are for the purpose of illustrating methods useful for making compounds of this invention.

General Methods: All reactions were performed under an Argon atmosphere and the reagents, neat or in appropriate solvents, were transferred to the reaction vessel via syringe and cannula techniques. Anhydrous solvents were purchased from the Aldrich Chemical Company and used as received. The examples described in the patent were named using the ACD/Name Program (version 4.01, Advanced Chemistry Development Inc., Toronto, Ontario, M5H2L3, Canada). The $^1$H NMR and $^{13}$C NMR spectra were recorded at either 300 MHz (GEQE Plus) or 400 MHz (Bruker Avance) in $CDCl_3$ as solvent and tetramethylsilane as the internal standard unless otherwise noted. Chemical shifts (δ) are expressed in ppm, coupling constants (J) are expressed in Hz, and splitting patterns are described as follows: s=singlet; d=doublet; t=triplet; q=quartet; quintet; sextet; septet; br=broad; m=mutiplet; dd=doublet of doublets; dt=doublet of triplets. Elemental analyses were performed by Robertson Microlit Laboratories, Inc. Unless otherwise, mass spectra were obtained using electrospray ionization (ESI, Micromass Platform II) and MH$^+$ is reported. Thin-layer Chromatography (TLC) was carried out on glass plates pre-coated with silica gel 60 $F_{254}$ (0.25 mm, EM Separations Tech.). Preparative TLC was carried out on glass sheets pre-coated with silica gel GF (2 mm, Analtech). Flash column chromatography was performed on Merck silica gel 60 (230-400 mesh). Melting points (mp) were determined in open capillary tubes on a Mel-Temp apparatus and are uncorrected.

The following additional abbreviations are used: HOAc, acetic acid; DIPEA, diisopropylethylamine; DMF, N,N-dimethylformamide; EtOAc, ethyl acetate; MeCH, methanol; TEA, triethylamine; THF, tetrahydrofuran; All solvent ratios are volume/volume unless stated otherwise.

A. General Procedures for Preparing Pyrimidines

The compounds of this invention were prepared by successively displacing the three chlorine atoms of a 2,4,6-trichloropyrimidine with amines. It was found that some amines (i.e. anilines) selectively displace the 2-position chlorine of 2,4,6-trichloropyrimidine, whereas other amines (e.g. piperidine) selectively displace the 4- or 6-position chlorine first (note that the 4- and 6-positions are chemically equivalent). Some amines react non-selectively at both the 2- and 4-positions of 2,4,6-trichloropyrimidine. It was also found that if the pyrimidine is substituted at the 4- or 6-position with an amine (mono- or di-substituted, or unsubstituted), then the next amine (mono- or di-substituted) undergoes substitution at the 2-position of the pyrimidine. Thus, several different Procedures were used to obtain the compounds described by this invention. The following Procedures are representative of the methods that are useful for making compounds of this invention.

Procedure A:

4,6-DICHLORO-N-PHENYL-2-PYRIMIDINAMINE

A solution of 2,4,6-trichloropyrimidine (5.5 g, 30 mmol) in tetrahydrofuran (15 mL) was added dropwise to a solution of aniline (2.8 mL, 1 equivalent) in tetrahydrofuran (25 mL). N,N-diisopropylethylamine (5.2 mL) was added and the solution was stirred at room temperature overnight. The solvent was removed and the crude material was purified by flash chromatography on silica gel. The column was eluted with 3% ethyl acetate in hexane, followed by 15% ethyl acetate in hexane. The eluent was removed, giving 4,6-dichloro-N-phenyl-2-pyrimidinamine (1.11 g, 4.6 mmol, 15%, $R_f$=0.4 in 3% ethyl acetate in hexane).

Procedure B:

4,6-DICHLORO-N-(3,4-DICHLOROPHENYL)-2-PYRIMIDINAMINE

A solution of 2,4,6-trichloropyrimidine (5.00 g), 3,4-dichloroaniline (4.45 g, 1 equivalent) in 1,4-dioxane (20 mL) and N,N-diisopropylethylamine (10 mL) was heated at reflux with stirring for 3 hours. The solvent was removed and the crude material was purified by flash chromatography on silica gel. The column was eluted with a gradient of cyclohexane to ethyl acetate/cyclohexane (1:9). The eluent was removed, giving 4,6-dichloro-N-(3,4-dichlorophenyl)-2-pyrimidinamine (1.83 g, 58%, $R_f$=0.39 in ethyl acetate/cyclohexane, 2:3).

Procedure C:

6-CHLORO-$N^4$,$N^4$-DIMETHYL-$N^2$-PHENYL-2,4-PYRIMIDINEDIAMINE

Dimethylamine in tetrahydrofuran (2M, 15 mL) was added to a solution of 4,6-dichloro-N-phenyl-2-pyrimidinamine (0.715 g, 2.97 mmol) in tetrahydrofuran (30 mL) and N,N-diisopropylethylamine (0.52 mL). The resulting mixture was stirred at room temperature overnight. The solvent was removed and the crude material was purified by flash chromatography on silica gel, eluting with ethyl acetate/hexane (1:9). The eluent was removed, giving 6-chloro-$N^4$,$N^4$-dimethyl-$N^2$-phenyl-2,4-pyrimidinediamine (0.592 g, 2.39 mmol, 80%, $R_f$=0.3).

Procedure D:

2,4-DICHLORO-6-(1-PIPERIDINYL)PYRIMIDINE

A mixture of 2,4,6-trichloropyrimidine (5.0 g, 27 mmol) and piperidine (2.3 g, 27 mmol) in tetrahydrofuran (50 mL) and N,N-diisopropylethylamine (3.5 g, 27 mmol) was stirred at room temperature for 24 hours. The solvent was removed and the crude material was purified by flash chromatography on silica gel. The column was eluted with a gradient of hexane to yield ethyl acetate/hexane (1:4). The eluent was removed, giving 2,4-dichloro-6-(1-piperidinyl)pyrimidine (3.67 g, 15.8 mmol, 59%, $R_f$=0.58 in ethyl acetate/hexane, 1:4).

Procedure E:

4-CHLORO-6-(1-PIPERIDINYL)-2-{4-[3-(TRIFLUOROMETHYL)-2-PYRIDINYL]-1-PIPERAZINYL}PYRIMIDINE

A mixture of 2,4-dichloro-6-(1-piperidinyl)pyrimidine (100 mg, 0.43 mmol) and 1-[3-(trifluoromethyl)pyrid-2-yl]piperazine (119 mg, 0.52 mmol) in chlorobenzene (1 mL) was heated at 140° C. in a sealed tube for 24 hours. The solvent was removed and the crude material was purified by preparative TLC, eluting with hexane/ethyl acetate (9:1). 4-chloro-6-(1-piperidinyl)-2-{4-[3-(trifluoromethyl)-2-pyridinyl]-1-piperazinyl}pyrimidine was obtained as a solid (79 mg, 0.19 mmol, 44%).

Procedure E:

N-(4-METHYLPHENYL)-6-(1-PIPERIDINYL)-2-{4-[3-(TRIFLUOROMETHYL)-2-PYRIDINYL]-1-PIPERZINYL}-4-PYRIMIDINAMINE

A mixture of 4-chloro-6-(1-piperidinyl)-2-{4-[3-(trifluoromethyl)-2-pyridinyl]-1-piperazinyl}pyrimidine (75.0 mg, 0.176 mmol), p-toluidine (23.1 mg, 0.216 mmol), 1,1'-(bisdiphenylphosphino)-1,1'-binaphthol (8.4 mg), tris (dibenzylidene acetone)dipalladium(0) (8.2 mg), and sodium tert-butoxide (86.4 mg) in dry toluene (1 mL) was heated at 90° C. in a sealed tube for 90 minutes. The solvent was removed and the crude material was purified by preparative TLC, eluting with hexane/ethyl acetate (4:1). N-(4-Methylphenyl)-6-(1-piperidinyl)-2-{4-[3-(trifluoromethyl)-2-pyridinyl]-1-piperazinyl}-4-pyrimidinamine was obtained, from the band at $R_f$=0.4, as a solid (59.5 mg, 0.119 mmol, 68%).

Procedure G:

$N^2$-ETHYL-$N^2$-[2-(1H-3-INDOLYL)ETHYL]-$N^4$-(4-METHYLPHENYL)-6-PIPERIDINO-2,4-PYRIMIDINEDIAMINE

A mixture of N-[4-chloro-6-(1-piperidinyl)-2-pyrimidinyl]-N-ethyl-N-[2-(1H-indol-3-yl)ethyl]amine (33.4 mg, 0.087 mmol) and p-toluidine (47 mg, 0.43 mmol) was heated neat under argon at 160° C. in a sealed tube for 12 hours. The crude material was purified by preparative TLC, eluting with hexane/ethyl acetate (4:1). $N^2$-Ethyl-$N^2$-[2-(1H-3-indolyl)ethyl]-$N^4$-(4-methylphenyl)-6-piperidino-2,4-pyrimidinediamine was obtained, from a band at $R_f$=0.37, as a solid (15 mg, 0.033 mmol, 38%).

Procedure H:

2,6-DICHLORO-N,N-DIMETHYL-4-PYRIMIDINAMINE

Sodium hydride (0.13 g, 0.79 mmol) was added to a solution of 2,6-dichloro-4-pyrimidinamine (0.40 g, 0.95 mmol) in dry tetrahydrofuran (5 mL) and stirred for 10 minutes, at which point gas evolution had ceased. Methyl iodide (0.06 mL, 0.95 mmol) was added and the resulting solution was stirred for 3 hours at room temperature. The solution was quenched with aqueous ammonium chloride/ammonium carbonate. The solution was extracted with ethyl acetate and the extracts were dried over sodium sulfate. The solvent was removed and the resulting crude product was purified by flash chromatography over silica gel, eluting with hexane/ethyl acetate (2:1). The desired product ($R_f$=0.55) was obtained as a white powder (70 mg, 0.36 mmol, 46%).

Procedure I:

N-ETHYL-2-(1H-INDOL-3-YL)ETHANAMINE

Step 1. Acetic anhydride (1.02 g) was added dropwise to a stirring solution of tryptamine (1.60 g) in tetrahydrofuran (5 mL) at 0° C. and then brought to room temperature. After 2 hours, the solvent was removed and the residue was taken up into ethyl acetate. The solution was filtered through a plug of silica gel and the solvent removed, giving N-[2-(1H-indol-3-yl)ethylacetyltryptamineacetamide (1.65 g, 100%).

Step 2. Lithium aluminum hydride in tetrahydrofuran (1M, 30 mL) was added dropwise to a stirring solution of N-[2-(1H-indol-3-yl)ethylacetyltryptamineacetamide (2.02 g) in tetrahydrofuran (10 mL) at 0° C. The solution was then heated at reflux overnight. The solution was cooled to 0° C. and water was very carefully added dropwise. The white solid was filtered and rinsed with ether/methanol (9:1, 2×25 mL). The solvent was removed from the filtrate, giving N-ethyl-2-(1H-indol-3-yl)ethanamine as a viscous pale yellow oil (1.75 g, 93%).

Procedure J:

4-CHLORO-N-[2-(1H-INDOL-3-YL)-1-METHYLETHYL]-6-(1-PIPERIDINYL)-2-PYRIMIDINAMINE

A mixture of 2,4-dichloro-6-(1-piperidinyl)pyrimidine (80 mg, 0.34 mmol), α-methyltryptamine (59 mg, 0.34 mmol), and potassium carbonate (47 mg, 0.34 mmol) in chlorobenzene (1 mL) was heated at 150° C. in a sealed tube for 16 hours. The solvent was removed and the crude material was purified by preparative TLC, eluting with cyclohexane/ethyl acetate (4:1). 4-Chloro-N-[2-(1H-indol-3-yl)-1-methylethyl]-6-(1-piperidinyl)-2-pyrimidinamine ($R_f$=0.19) was obtained as a solid (64.5 mg, 51%). $^1$H NMR (300 MHz, CDCl$_3$) δ 8.29 (br s, 1H), 7.68 (br d, 1H, J=7.5), 7.32 (d, 1H, J=7.8), 7.16 (t, 1H, J=7.8), 7.12 (t, 1H, J=7.8), 6.95 (d, 1H, J=2.1), 5.87 (s, 1H), 4.89 (br d, 1H, J=8.1), 4.36 (sextet, 1H, J=6.6), 3.58-3.50 (m, 4H), 3.07 (dd, 1H, J=14.4, 5.1), 2.83 (dd, 1H, J=14.1, 7.2), 1.70-1.55 (m, 6H), 1.16 (d, 3H, J=6.6).

Procedure K:

N-(4-METHYLPHENYL)-2-(1-PIPERAZINYL)-6-(1-PIPERIDINYL)-4-PYRIMIDINAMINE

A solution of 2-(4-benzyl-1-piperazinyl)-N-(4-methylphenyl)-6-(1-piperidinyl)-4-pyrimidinamine (0.40 g, 0.90 mmol) and ammonium formate (0.28 g, 4.5 mmol) in methanol over 10% palladium/charcoal was stirred at 70° C. for 3 hours. The solution was cooled and passed through celite. The solvent was removed, giving the desired product as a solid (0.21 g, 0.60 mmol, 66%).

Procedure L:

N-(4-METHYLPHENYL)-2-[4-(3-METHYL-2-PYRIDINYL)-1-PIPERAZINYL]-6-(1-PIPERIDINYL)-4-PYRIMIDINAMINE

A mixture of N-(4-methylphenyl)-2-(1-piperazinyl)-6-(1-piperidinyl)-4-pyrimidinamine (100 mg, 0.284 mmol), 2-bromo-3-methylpyridine (54 mg, 0.312 mmol), 1,1'-(bis-diphenylphosphino)-1,1'-binaphthol (13 mg), tris(dibenzylidene acetone)dipalladium(0) (13 mg), and sodium tert-butoxide (136 mg) in dry toluene (4 mL) was heated at 90° C. in a sealed tube for 2 hours. The reaction was quenched with water and the solution was extracted three times with ethyl acetate. The solvent was dried and removed. The crude material was purified by preparative TLC, eluting with hexane/ethyl acetate (2:1). N-(4-methylphenyl)-2-[4-(3-methyl-2-pyridinyl)-1-piperazinyl]-6-(1-piperidinyl)-4-pyrimidinamine was obtained, from the band at $R_f$=0.46, as a solid (17.1 mg, 0.0385 mmol, 14%).

Procedure M:

4,6-DICHLORO-2-{4-[3-(TRIFLUOROMETHYL)-2-PYRIDINYL]-1-PIPERZINYL}PYRIMIDINE and 2,4-DICHLORO-6-{4-[3-(TRIFLUOROMETHYL)-2-PYRIDINYL]-1-PIPERAZINYL}PYRIMIDINE A solution of 4-[3-(trifluoromethyl)-2-pyridinyl]-1-piperazine (127 mg, 0.66 mmol), 2,4,6-trichloropyrimidine (100 mg, 0.55 mmol) and N,N-diisopropylethylamine (95 μL) in tetrahydrofuran (1 mL) was stirred at 0° C. for 15 minutes. At this time, the starting material could no longer be detected by TLC. The solvent was removed and the crude material was purified by preparative TLC, eluting with ethyl acetate/hexane (1:4). Two bands were removed giving 4,6-dichloro-2-{4-[3-(trifluoromethyl)-2-pyridinyl]-1-piperazinyl}pyrimidine (41.7 mg, 0.110 mmol, 17%, $R_f$=0.41), and 2,4-dichloro-6-{4-[3-(trifluoromethyl)-2-pyridinyl]-1-piperazinyl}pyrimidine (162 mg, 0.429 mmol, 65%, $R_f$=0.10).

Procedure N:

4-{4-[4-CHLORO-6-(DIMETHYLAMINO)-2PYRIMIDINYL]-1-PIPERAZINYL}PHENOL

DIPEA (4.535 g, 0.0260 mol) was added to a stirred solution of 4-N,N-dimethylamino-2,6-dichloropyrimidine (2.00 g, 0.0104 mol) and 4-(1-piperazinyl)phenol (2.23 g, 0.0125 mol) in THF (50 mL) at room temperature under argon. The resulting mixture was refluxed for 48 h, cooled to room temperature, quenched with water (100 mL), concentrated under reduced pressure and the crude product was redissolved in EtOAc. The organic layer was separated and washed with water (2×100 mL), brine (2×100 mL) and purified by column chromatography on silica using EtOAc/Hexane (1:9), giving the desired product (2.77 g, 80%).

Procedure O:

A solution of p-toludine (0.2 g, 1.87 mmol) in THF (2 mL) was added to a stirred suspension of NaH (0.11 g, 2.79 mmol) in anhydrous THF (2 mL) at room temperature. The resulting mixture was heated at 40° C. for 15 minutes under argon and cooled to room temperature. 6-Chloropyrimidine (0.34 g, 1.03 mmol) in THF (25 mL) was added to the above mixture and the resulting mixture was heated at reflux for 15 h. The reaction mixture was then cooled to room temperature and quenched with saturated. NH$_4$Cl (2 drops). The crude product was concentrated under reduced pressure and redissolved in EtOAc. The organic layer was separated and washed with aqueous citric acid (2×100 mL), water (2×100 mL) and brine (2×100 mL). The crude product was purified by column chromatography on silica using EtOAc/hexanes (1:4), giving the desired product (0.23 g, 55%).

Procedure P:

2-{4-BENZYL-1-PIPERAZINYL)-$N^4$-(3,4-DICHLOROPHENYL)-$N^6$,$N^6$-DIMETHYL-4,6-PYRIMIDINEDIAMINE

Potassium tert-butoxide (1.6 mmol, 1 M in 2-methyl 2-propanol) was added to a solution of N-[2-(4-benzyl-1-piperazinyl)-6-chloro-4-pyrimidinyl]-N,N-dimethylamine (0.331 g, 0.997 mmol) and 3,4 dichloroaniline (0.178 g, 1.10 mmol) in dioxane (2 mL). Subsequently, tris(dibenzylidineacetone)dipalladium (40 mg, 0.04 mmol) and 2,2'-Bis(diphenylphosphino)-1,1'binapthyl (44 mg, 0.070 mmol) were added and the mixture was stirred for 7 h at 110° C. The resulting mixture was cooled to room temperature and concentrated under reduced pressure. The residue was treated with saturated NaHCO$_3$ (50 mL) and extracted with CH$_2$Cl$_2$ (3×50 mL). The organic layer was washed with brine (2×100 mL), dried over Na$_2$SO$_4$, concentrated in vacuo, and purified by preparative TLC using hexane/EtOAc to give the desired product (300 mg, 65%).

Procedure Q:

N-[2-(4-BENZYL-1-PIPERAZINYL)-6-CHLORO-4-PYRIMIDINYL]-N,N—

DIPEA (5.00 g, 40.0 mmol) was added dropwise to a solution of the N-(2,6-dichloro-4-pyrimidinyl)-N,N-dimethylamine (5.70 g, 29.6 mmol) and benzyl piperazine (6.00 g, 34.0 mmol) in m-xylene (15 mL) The mixture was stirred overnight at 130° C., cooled to room temperature, treated with saturated NaHCO$_3$ (50 mL) and then extracted with CH$_2$Cl$_2$ (3×50 mL). The organic layer was washed with brine (2×100 mL), dried over Na$_2$SO$_4$, and concentrated in vacuo. The crude product was purified by chromatography on silica using EtOAc/hexane (1:3), giving the desired product (6.8 g, 20 mmol, 67%).

Procedure R:

N$^4$,N$^4$-DIMETHYL-N$^6$-(4-METHYLPHENYL)-N$^2$-(2-PHENYLETHYL)-2,4,6-PYRIMIDINETRIAMINE

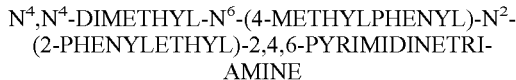

A mixture of N-[4-(dimethylamino)-6-(4-toluidino)-2-pyrimidinyl]-2-phenylacetamide (60 mg, 0.166 mmol), and LAH (1 mL, 1M in THF) in THF (10 mL) was refluxed for 3 h.

The crude product was concentrated in vacuo and treated with saturated NaHCO$_3$ (50 mL) and extracted with CH$_2$Cl$_2$ (3×50 mL). The organic layer was washed with brine (2×100 mL), dried over Na$_2$SO$_4$, filtered, and concentrated in vacuo. The crude product was purified by preparative TLC using hexane/EtOAc (1:3), giving the desired product (30 mg, 52%).

Procedure S:

N-[4-(DIMETHYLAMINO)-6-(4-TOLUIDINO)-2-PYRIMIDINYL]-2-PHENYLACETAMIDE

A mixture of N$^4$,N$^4$-dimethyl-N$^6$-(4-methylphenyl)-2,4,6-pyrimidinetriamine (122 mg, 0.50 mmol), phenylacetyl chloride (84 mg, 0.55 mmol), and triethylamine (100 mg, 1.00 mmol) in CH$_2$Cl$_2$ was stirred at room temperature for 16 h. The crude product was concentrated in vacuo and treated with saturated NaHCO$_3$ (50 mL) and extracted with CH$_2$Cl$_2$ (3×50 mL). The organic layer was washed with brine (2×100 mL), dried over Na$_2$SO$_4$, filtered, and concentrated in vacuo. The crude product was purified by preparative TLC using hexane/EtOAc (1:3), giving the desired product (60 mg, 33%).

Procedure T:

A mixture of N$^4$-(3-methoxyphenyl)-N$^6$,N$^6$-dimethyl-2-[4-(2-thienylcarbonyl)-1-piperazinyl]-4,6-pyrimidinediamine (28 mg, 0.06 mmol) and LAH (300 uL 1M, 0.3 mmol) in THF (10 mL) was refluxed for 16 h. The crude product was concentrated in vacuo and treated with saturated NaHCO$_3$ (50 mL) and extracted with EtOAc (3×50 mL). The organic layer was washed with brine (2×100 mL), dried over Na$_2$SO$_4$, filtered, and concentrated in vacuo. The crude product was purified by preparative TLC using hexane/EtOAc (1:3), giving the desired product (20 mg, 39%).

Procedure U:

2-[4-(3-METHOXYBENZYL)-1-PIPERAZINYL]-N$^4$-(3-METHOXYPHENYL)-N$^6$,N$^6$-DIMETHYL-4,6-PYRIMIDINEDIAMINE

A solution of N$^4$-(3-methoxyphenyl)-N$^6$,N$^6$-dimethyl-2-(1-piperazinyl)-4,6-pyrimidinediamine (36 mg, 0.1 mmol), DIPEA (52 mg, 0.4 mmol), and 1-(chloromethyl)-3-methoxybenzene (20 mg, 0.13 mmol) in 5 mL of dioxane was stirred at 100° C. for 16 h. The crude product was concentrated in vacuo and treated with saturated NaHCO$_3$ (50 mL) and extracted with CH$_2$Cl$_2$ (3×50 mL). The organic layer was washed with brine (2×100 mL), dried over Na$_2$SO$_4$, and concentrated in vacuo. The crude product was purified by chromatography on silica using hexane/EtOAc (1:3), giving the desired product (32 mg, 70%).

Procedure V:

6-CHLORO-N$^4$-(4-METHYLPHENYL)-2,4-PYRIMIDINEDIAMINE

A mixture of 4,6-dichloro-2-pyrimidinamine (1.64 g, 0.01 mol), p-toluidine (1.07 g, 0.01 mol) in dioxane (2 mL) was heated in a sealed tube for 30 minutes at 140° C. The crude product was treated with NaOH (50 ml, 2M) and extracted with CH$_2$Cl$_2$ (3×50 mL). The organic layer was washed with brine (2×100 mL), dried over Na$_2$SO$_4$, filtered, and concentrated in vacuo. The crude product was purified by chromatography on silica using hexane/EtOAc (1:3), giving the desired product (2 g, 78%).

Procedure W:

N$^4$-(3-METHOXYPHENYL)-N$^6$,N$^6$-DIMETHYL-2-[4-(2-THIENYLCARBONYL)-1-PIPERAZINYL]-4,6-PYRIMIDINEDIAMINE

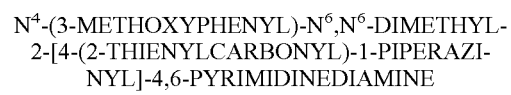

A mixture of 2-thiophenecarboxylic acid (15 mg, 0.12 mmol), DIPEA (129 mg, 1.00 mmol) and O-(7-azabenzotriazol-1-yl)N,N,N',N'-tetramethyluronium hexafluorophosphate (44 mg, 0.12 mmol) in DMF (5 mL) was stirred at room temperature for 30 minutes. N$^4$-(3-methoxyphenyl)-N$^6$,N$^6$-dimethyl-2-(1-piperazinyl)-4,6-pyrimidinediamine (36 mg, 0.10 mmol) was added to the above mixture and stirred at room temperature for 16 h. The crude product was treated with saturated NaHCO$_3$ (50 mL) and extracted with EtOAC (3×50 mL). The organic layer was washed with brine (2×100 mL), dried over Na$_2$SO$_4$, filtered, and concentrated in vacuo. The crude product was purified by chromatography on silica using hexane/EtOAc (1:3), giving the desired product (25 mg, 57%).

Procedure X:

2-(4-BENZYL-1-PIPERAZINYL)-N$^4$-(3-METHOXYPHENYL)-N$^6$,N$^6$-DIMETHYL-4,6-PYRIMIDINEDIAMINE

A mixture of N$^4$-(3-methoxyphenyl)-N$^6$,N$^6$-dimethyl-2-(1-piperazinyl)-4,6-pyrimidinediamine (36 mg, 0.10 mmol) and benzaldehyde (11 mg, 0.1 mmol) in a solution of methanol (5 mL) and acetic acid (0.5 mL) was stirred at room temperature for 1 h. Sodium cyanoborohydride (7 mg, 0.1 mmol) was added to the above solution and stirred at room temperature for 16 h. The crude product was treated with saturated NaHCO$_3$ (50 mL) and extracted with EtOAC (3×50 mL). The organic layer was washed with brine (2×50 mL), dried over Na$_2$SO$_4$, filtered, and concentrated in vacuo. The crude product was purified by chromatography on silica using hexane/EtOAc (1:3), giving the desired product (8 mg, 40%).

Procedure Y:

2-[4-(4-BROMOPHENYL)-1-PIPERAZINYL]-N$^4$-(3-METHOXYPHENYL)-N$^6$,N$^6$-DIMETHYL-4,6-PYRIMIDINEDIAMINE

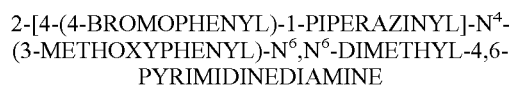

A mixture of N$^4$-(3-methoxyphenyl)-N$^6$,N$^6$-dimethyl-2-(1-piperazinyl)-4,6-pyrimidinediamine (36 mg, 0.1 mmol), 1-bromo-4-fluorobenzene (20 mg, 0.13 mmol) was heated at 100° C. for 1 h. The crude product was dissolved in CH$_2$Cl$_2$ (0.5 mL) and purified by preparative TLC using 5% methanol in EtOAc, giving the desired product (20 mg, 40%).

Procedure Z:

2-[4-(2-METHOXYBENZYL)-1-PIPERAZINYL]-N$^4$,N$^4$-DIMETHYL-N$^6$-(4-METHYLPHENYL)-4,6-PYRIMIDINEDIAMINE

A mixture of N$^4$,N$^4$-dimethyl-N$^6$-(4-methylphenyl)-2-(1-piperazinyl)-4,6-pyrimidinediamine (30 mg, 0.086 mmol), 1-(chloromethyl)-2-methoxybenzene (17 mg, 0.1 mmol) and triethylamine (200 mg, 2 mmol) in 1 DMF (1 mL) heated by microwave at 200° C. for 12 minutes. The crude product was treated with saturated NaHCO$_3$ (50 mL) and extracted with EtOAC (3×50 mL). The organic layer was washed with brine (2×100 mL), dried over Na$_2$SO$_4$, filtered, and concentrated in vacuo. The crude product was purified by chromatography on silica using hexane/EtOAc (1:3), giving the desired product (10 mg, 27%).

Procedure AA:

N$^4$-(3-METHOXYPHENYL)-N$^6$,N$^6$-DIMETHYL-2-[4-(2-THIENYLCARBONYL)-1-PIPERAZINYL]-4,6-PYRIMIDINEDIAMINE

A solution of N$^4$-(3-methoxyphenyl)-N$^6$,N$^6$-dimethyl-2-(1-piperazinyl)-4,6-pyrimidinediamine (33 mg, 0.1 mmol), 2-thiophenecarbonyl chloride (20 mg, 0.14 mmol), and triethylamine (40 mg, 0.4 mmol) in CH$_2$Cl$_2$ (5 mL) was stirred at room temperature for 16 h. The crude product was concentrated in vacuo and treated with saturated NaHCO$_3$ (50 mL) and extracted with CH$_2$Cl$_2$ (3×50 mL). The organic layer was washed with brine (2×100 mL), dried over Na$_2$SO$_4$, filtered, and concentrated in vacuo. The crude product was purified by chromatography on silica using hexane/EtOAc (1:3), giving the desired product as a pale red oil (35 mg, 80%).

Procedure BB:

N$^4$,N$^4$-DIMETHYL-N$^6$-(4-METHYLPHENYL)-2,4,6-PYRIMIDINETRIAMINE

A mixture of 6-chloro-N$^4$-(4-methylphenyl)-2,4-pyrimidinediamine (1.5 g, 6.4 mmol) and N,N-dimethylamine hydrochloride (0.56 g, 7 mmol) and triethylamine (1.4 g, 14 mmol) in DMF (2 mL), was heated at 170° C. for 16 h. The product was filtered out and the organic layer was treated with saturated NaHCO$_3$ (50 mL) and extracted with EtOAC (3×50 mL). The organic layer was washed with brine (2×100 mL), dried over Na$_2$SO$_4$, filtered, and concentrated in vacuo. The crude product was purified by chromatography on silica using hexane/EtOAc (1:3), giving the desired product (0.6 g, 40%).

Procedure CC:

N-(4-METHYLPHENYL)-2-[4-(1-OXIDO-2-PYRIDINYL)-1-PIPERAZINYL]-6-(1-PIPERIDINYL)-4-PYRIMIDINAMINE

A solution of 3-cholorperbenzoic acid (450 mg, 2.6 mmol), and 30% H$_2$O$_2$ (0.1 mL) in CH$_2$Cl$_2$ (2 mL) was added to a solution of N-(4-methylphenyl)-6-(1-piperidinyl)-2-[4-(2-pyridinyl)-1-piperazinyl]-4-pyrimidinamine (150 mg, 0.300 mmol) in CH$_2$Cl$_2$ at 0° C. The resulting mixture was gradually warmed to room temperature and stirred for 24 h, crude product was treated with saturated NaHCO$_3$ (50 mL) and extracted with EtOAC (3×50 mL). Combined organic layers were washed with brine (2×50 mL), dried over Na$_2$SO$_4$, filtered, concentrated in vacuo, and purified by chromatography on silica using hexane/EtOAc (1:3) to give the desired product.

Piperazines that were not commercially available were synthesized according to the method previously described (Ennis and Ghazal, 1992).

The following are examples to illustrate the compounds of this invention. Procedures A-BB as described above, were used and any modifications are noted in parentheses.

Example 1

N$^2$-CYCLOHEXYL-N$^2$-METHYL-N$^4$-(4-METHYLPHENYL)-6-(1-PIPERIDINYL)-2,4-PYRIMIDINEDIAMINE

Prepared by Procedures D, G (for substitution with cyclohexylamine), and G. $^1$H NMR (300 MHz, CDCl$_3$) δ 7.22 (d, 2H, J=7.8), 7.12 (d, 2H, J=7.8), 5.29 (s, 1H), 4.43 (br s, 1H), 3.55-3.44 (m, 5H), 3.01 (s, 3H), 2.33 (s, 3H), 2.00-1.05 (m, 16H).

Example 2

N$^2$-CYCLOHEXYL-N$^2$-(2-METHOXYETHYL)-N$^4$-(4-METHYLPHENYL)-6-(1-PIPERIDINYL)-2,4-PYRIMIDINEDIAMINE

Prepared by Procedures D, J (130° C.), and F (2 hours). $^1$H NMR (300 MHz, CDCl$_3$) δ 7.25 (d, 2H, J=8.1), 7.10 (d, 2H, J=8.1), 6.17 (br s, 1H), 5.31 (s, 1H), 4.58-4.43 (m, 1H), 3.61-3.57 (m, 4H), 3.52-3.48 (1,4H), 3.39 (s, 3H), 2.31 (s, 3H), 1.83-1.75 (m, 4H), 1.70-1.50 (m, 7H), 1.43-1.37 (m, 4H), 1.19-1.05 (m, 1H); ESI-MS m/z 424 (MH$^+$).

Example 3

N$^4$-(4-METHYLPHENYL)-N$^2$-PHENYL-6-(1-PIPERIDINYL)-2,4-PYRIMIDINEDIAMINE

Prepared by Procedures A, B (for substitution with aniline), and E (100° C., for substitution with piperidine). $^1$H NMR (300 MHz, CDCl$_3$) δ 7.58 (d, 2H, J=8.7), 7.26 (t, 2H, J=7.8), 7.19 (d, 2H, J=8.7), 7.15 (d, 2H, J=7.8), 6.95 (t, 1H, J=7.8), 6.82 (br s, 1H), 6.48 (br s, 1H), 5.49 (s, 1H), 3.56-3.46 (m, 4H), 2.34 (s, 3H), 1.67-1.52 (m, 6H); ESI-MS m/z 360 (MH$^+$).

Example 4

N$^2$,N$^4$-DI(4-METHYLPHENYL)-6-PIPERIDINO-2,4-PYRIMIDINEDIAMINE

Prepared by Procedures D and G (100° C., 12 hours, for substitution of D-toludine at C2 and C4 of the pyrimidine). $^1$H NMR (300 MHz, CDCl) δ 7.47 (d, 2H, J=8.3), 7.20 (d, 2H, J=7.8), 7.15 (d, 2H, J=8.3), 7.10 (d, 2H, J=8.3), 6.79 (br s, 1H), 6.46 (br s, 1H), 5.52 (s, 1H), 3.51 (t, 4H, J=4.6), 2.36 (s, 3H), 2.31 (s, 3H), 1.69-1.53 (m, 6H); ESI-MS m/z 374 (MH$^+$).

Example 5

N$^2$-(4-CHLOROPHENYL)-N$^4$-(4-METHYLPHENYL)-6-(1-PIPERIDINYL)-2,4-PYRIMIDINEDIAMINE

Prepared by Procedures D, G (for substitution with 4-chloroaniline), and G (3.5 hours). $^1$H NMR (300 MHz, CDCl$_3$) δ 8.79 (br s, 1H), 7.72 (br s, 1H), 7.54 (d, 2H, J=8.3), 7.28-7.17 (m, 6H), 5.36 (s, 1H), 3.61-3.46 (m, 4H), 2.36 (s, 3H); 1.76-1.53 (m, 6H); ESI-MS m/z 393 (MH$^+$ with $^{35}$Cl), 395(MH$^+$ with $^{37}$Cl).

Example 6

N$^2$-METHYL-N$^4$-(4-METHYLPHENYL)-N$^2$-PHENYL-6-(1-PIPERIDINyl)-2,4-PYRIMIDINEDIAMINE

Prepared by Procedures D, G (140° C., 90 minutes, for substitution with aniline), and G (3.5 hours). $^1$H NMR (300 MHz, CDCl$_3$) δ 7.42-7.33 (m, 4H), 7.18-7.14 (overlapping t at 7.16 & d at 7.15, 3H), 7.07 (d, 2H, 7=7.8), 6.25 (br s, 1H), 5.41 (s, 1H), 3.54 (s, 3H), 3.50-3.42 (m, 4H), 2.33 (s, 3H), 1.68-1.50 (m, 6H); ESI-MS m/z 374 (MH$^+$).

Example 7

N$^2$-METHYL-N$^2$,N$^4$-DI(4-METHYLPHENYL)-6-(1-PIPERIDINYL)-2,4-PYRIMIDINEDIAMINE

Prepared by Procedures D, G (180° C., 10 hours, for substitution with N-methyl-p-toluidine), and G (140° C.). $^1$H NMR (300 MHz, CDCl$_3$) δ 7.27-7.04 (m, 8H), 6.19 (br s, 1H), 5.38 (s, 1H), 3.52 (s, 3H), 3.48-3.41 (m, 4H), 2.38 (s, 3H), 2.31 (s, 3H), 1.67-1.49 (m, 6H); ESI-MS m/z 388 (MH$^+$).

Example 8

N$^2$-[2-(5-METHYL-1H-3-INDOLYL)ETHYL]-N$^4$-(4-METHYLPHENYL)-6-(1-PIPERIDINYL)-2,4-PYRIMIDINEDIAMINE

Prepared by Procedures D, J, and G (160° C., 12 hours). $^1$H NMR (300 MHz, CDCl$_3$) δ 8.05 (br s, 1H), 7.43 (s, 1H), 7.23 (d, 1H, J=8.4), 7.15 (d, 2H, J=8.4), 7.10 (d, 2H, J=8.4), 7.00 (d, 1H, J=8.4), 6.98 (s, 1H), 6.43 (br s, 1H), 5.37 (s, 1H), 4.86 (br t, 1H, J=7.1), 3.70 (q, 2H, L=7.1), 3.52-3.43 (m, 4H), 3.02 (t, 2H, J=7.1), 2.46 (s, 3H), 2.32 (s, 3H), 1.67-1.49 (m, 6H); ESI-MS m/z 441 (MH$^+$).

Example 9

N$^2$-[2-(5-METHOXY-1H-3-INDOLYL)ETHYL]-N$^4$-(4-METHYLPHENYL)-6-(1-PIPERIDINYL)-2,4-PYRIMIDINEDIAMINE

Prepared by Procedures D, E (160° C., 36 hours), and G. $^1$H NMR (300 MHz, CDCl$_3$) δ 8.00 (br s, 1H), 7.15 (d, 2H, J=8.4), 7.12 (d, 2H, J=8.4), 7.08-7.04 (m, 3H), 6.85 (dd, 1H, J=8.8, 2.6), 6.48 (br s, 1H), 5.36 (s, 1H), 4.96 (br s, 1H), 3.85 (s, 3), 3.72-3.67 (m, 2H), 3.55-3.45 (m, 4H), 3.02 (t, 2H, J=6.9), 2.32 (s, 3H), 1.68-1.49 (m, 6H); ESI-MS m/z 457 (MH$^+$).

Example 10

N$^2$-[2-(1H-3-INDOLYL)ETHYL]-N$^4$-(4-METHYLPHENYL)-6-(1-PIPERIDINYL)-2,4-PYRIMIDINEDIAMINE

Prepared by Procedures D, E (100° C.), and G (150° C.). $^1$H NMR (300 MHz, CDCl$_3$) δ 8.34 (br s, 1H), 7.63 (d, 1H, J=7.8), 7.31 (d, 1H, J=7.8), 7.23-7.09 (m, 6H), 6.94 (s, 1H), 6.60 (br s, 1H), 5.36 (s, 1H), 4.95 (t, 1H, J=6.3), 3.68 (dt, 2H, J=6.3, 6.9), 3.48-3.44 (m, 4H), 3.01 (t, 2H, J=6.9), 2.31 (s, 3H), 1.65-1.48 (m, 6H); ESI-MS m/z 427 (MH$^+$).

Example 11

N$^2$-[2-(1H-3-INDOLYL)ETHYL]-N$^2$-METHYL-N$^4$-(4-METHYLPHENYL)-6-(1-PIPERIDINYL)-2,4-PYRIMIDINEDIAMINE

Prepared by Procedures D, E (160° C., 4 hours), and F (12 hours). $^1$H NMR (300 MHz, CDCl$_3$) δ 8.02 (br s, 1H), 7.71 (d, 1H, J=7.8), 7.36 (d, 1H, J=7.8), 7.22 (d, 2H, J=7.8), 7.20 (t, 1H, J=7.8), 7.17-7.09 (m, 3H), 7.03 (s, 1H), 6.40 (br s, 1H), 5.35 (s, 1H), 3.91 (t, 2H, J=7.8), 3.56-3.46 (m, 4H), 3.16 (s, 3H), 3.09 (t, 2H, J=7.8), 2.33 (S, 3H), 1.70-1.52 (m, 6H); ESI-MS m/z 441 (MH$^+$).

Example 12

N$^2$-[2-(1H-INDOL-3-YL)ETHYL]-N$^2$-METHYL-N$^4$-PHENETHYL-6-(1-PIPERIDINYL)-2,4-PYRIMIDINEDIAMINE

Prepared by Procedures D, E (160° C., 12 hours), and G. $^1$H NMR (300 MHz, CDCl$_3$) δ 8.00 (br s, 1H), 7.71 (d, 1H, J=7.8), 7.34 (t, 2H, J=7.8), 7.24-7.15 (m, 5H), 7.08 (t, 1H, J=7.8), 6.98 (s, 1H), 4.95 (s, 1H), 4.39 (br s, 1H), 3.88 (t, 2H, J=7.8), 3.57-3.48 (m, 6H), 3.12 (s, 3H), 3.05 (t, 2H, J=7.8), 2.89 (t, 2H, J=7.8), 1.68-1.53 (m, 6H); ESI-MS m/z 455 (MH$^+$).

Example 13

N$^2$-[2-(1H-INDOL-3-YL)ETHYL]-N$^2$-METHYL-N$^4$-(2-NAPHTHYL)-6-(1-PIPERIDINYL)-2,4-PYRIMIDINEDIAMINE

Prepared by Procedures D, E (160° C., 12 hours, for substitution with N-methyltryptamine), and E (160° C., 12 hours). $^1$H NMR (300 MHz, CDCl$_3$) δ 7.95 (br s, 1H), 7.92 (s, 1H), 7.78-7.75 (m, 3H), 7.72 (d, 1H, J=8.1), 7.46-7.41 (m, 2H), 7.37 (d, 2H, J=8.4), 7.20 (t, 1H, J=7.8), 7.11 (t, 1H, J=7.8), 7.01 (s, 1H), 6.42 (br s, 1H), 5.45 (s, 1H), 3.95 (t, 2H, J=7.8), 3.56-3.49 (m, 4H), 3.19 (s, 3H), 3.11 (t, 2H, J=7.8), 1.62-1.59 (m, 6H); ESI-MS m/z 477 (MH$^+$).

Example 14

N$^4$-(3-FLUOROPHENYL)-N$^2$-[2-(1H-INDOL-3-YL)ETHYL]-N$^2$-METHYL-6-(1-PIPERIDINYL)-2,4-PYRIMIDINEDIAMINE

Prepared by Procedures D, E (160° C., 12 hours, for substitution with N-methyltryptamine), and G. $^1$H NMR (300 MHz, CDCl$_3$) δ 7.97 (br s, 1H), 7.71 (d, 1H, J=7.8), 7.41 (dt, 1H, J=9.5, 1.0), 7.34 (d, 1H, J=7.8), 7.22-7.06 (m, 4H), 7.02-7.00 (s at 7.02 & d at 7.01 overlapping, 2H), 7.01 (s, 1H), 6.33 (br s, 1H), 5.34 (s, 1H), 3.90 (t, 2H, J=7.8), 3.58-3.50 (m, 4H),3.16 (s, 3H), 3.08 (t, 2H, J=7.8), 1.70-1.54 (m, 6H); ESI-MS m/z 445 (MH$^+$).

Example 15

N$^4$-(3,4-DIFLUOROPHENYL)-N$^2$-[2-(1H-INDOL-3-YL)ETHYL]-N$^2$-METHYL-6-(1-PIPERIDINYL)-2,4-PYRIMIDINEDIAMINE

Prepared by Procedures D, E (160° C., 12 hours, for substitution with N-methyltryptamine), and G. $^1$H NMR (300 MHz, CDCl$_3$) δ 7.99 (br s, 1H), 7.68 (d, 1H, J=7.8), 7.51 (ddd, 1H, J=9.5, 7.8, 2.3), 7.35 (d, 1H, J=7.8), 7.19 (t, 1H, J=7.8), 7.11 (t, 1H, J=7.8), 7.07-6.90 (m, 3H), 7.01 (s, 1H), 6.22 (br s, 1H), 5.23 (s, 1H), 3.89 (t, 2H, J=7.8), 3.57-3.49 (m, 4H), 3.15 (s, 3H), 3.07 (t, 2H, J=7.8), 1.68-1.53 (m, 6H); ESI-MS m/z 463 (MH$^+$).

Example 16

N$^4$-(3-CHLORO-4-METHYLPHENYL)-N$^2$-[2-(1H-INDOL-3-YL)ETHYL]-N$^2$-METHYL-6-(1-PIPERIDINYL)-2,4-PYRIMIDINEDIAMINE

Prepared by Procedures D, E (160° C., 12 hours, for substitution with N-methyltryptamine), and G. $^1$H NMR (300 MHz, CDCl$_3$) δ 7.96 (br s, 1H), 7.69 (d, 1H, J=7.5), 7.51 (s, 1H), 7.36 (d, 1H, J=7.8), 7.19 (t, 1H, J=7.8), 7.14-7.06 (m, 3H), 7.01 (s, 1H), 6.18 (br s, 1H), 5.29 (s, 1H), 3.89 (t, 2H, J=7.8), 3.53-3.48 (m, 4H), 3.13 (s, 3H), 3.07 (t, 2H, J=7.8), 2.31 (s, 3H), 1.70-1.55 (m, 6H); ESI-MS m/z 475 (MH$^+$).

Example 17

N$^2$-[2-(1H-INDOL-3-YL)ETHYL]-N$^4$-(3-METHOXYPHENYL)-N$^2$-METHYL-6-(1-PIPERIDINYL)-2,4-PYRIMIDINEDIAMINE

Prepared by Procedures D, E (160° C., 12 hours, for substitution with N-methyltryptamine), and G. $^1$H NMR (300 MHz, CDCl$_3$) δ 8.02 (br s, 1H), 7.71 (d, 1H, J=7.8), 7.34 (d, 1H, J=8.3), 7.25-7.04 (m, 4H), 7.01 (s, 1H), 6.89 (d, 1H, J=7.8), 6.57 (dd, 1H, J=8.3, 2.4), 6.30 (br s, 1H), 5.42 (s, 1H), 3.91 (t, 2H, J=7.7), 3.76 (s, 3H), 3.57-3.49 (m, 4H), 3.16 (s, 3H), 3.08 (t, 2H, J=7.7), 1.70-1.53 (m, 6H); ESI-MS m/z 457 (MH$^+$).

Example 18

N$^2$-ETHYL-N$^2$-[2-(1H-INDOL-3-YL)ETHYL]-N$^4$-(4-METHYLPHENYL)-6-(1-PIPERIDINYL)-2,4-PYRIMIDINEDIAMINE

Prepared by Procedures D, E (160° C., 12 hours, for substitution with N-ethyltryptamine), and G. $^1$H NMR (300 MHz, CDCl$_3$) δ 7.97 (br s, 1H), 7.71 (d, 1H, J=7.8), 7.35 (d, 1H, J=7.8), 7.25-7.16 (overlapping d at 7.23 & t at 7.22, 3H), 7.14 (t, 1H, J=7.8), 7.08 (d, 2H, J=7.8), 7.02 (s, 1H), 6.19 (br s, 1H), 5.34 (s, 1H), 3.82 (t, 2H, J=7.9), 3.61 (q, 2H, J=7.1), 3.55-3.45 (m, 4H), 3.08 (t, 2H, J=7.9), 2.30 (s, 6H), 1.68-1.50 (m, 6H), 1.18 (t, 3H, J=7.1); ESI-MS m/z 455 (MH$^+$).

Example 19

N$^2$-[2-(1H-INDOL-3-YL)ETHYL]-N$^2$-(2-METHOXYETHYL)-N$^4$-(4-METHYLPHENYL)-6-(1-PIPERIDINYL)-2,4-PYRIMIDINEDIAMINE

Prepared by Procedures D, E (160° C., 12 hours, for substitution with N-methoxyethyltryptamine), and G. $^1$H NMR (300 MHz, CDCl$_3$ δ 7.96 (br s, 1H), 7.72 (d, 1H, J=7.5), 7.35 (d, 1H, J=7.8), 7.27-7.07 (m, 6H), 7.02 (s, 1H), 6.19 (br s, 1H), 5.35 (s, 1H), 3.88 (dd, 2H, J=9.9, 5.4), 3.74 (t, 2H, J=6.0), 3.60 (dd, 2H, J=10.5, 4.8), 3.57-3.46 (m, 4H), 3.34 (s, 3H), 3.12-3.07 (m, 2H), 2.32 (s, 6H), 1.70-1.58 (m, 6H); ESI-MS m/z 485 (MH$^+$).

Example 20

N$^2$-[2-(1H-3-INDOLYL)-1-METHYLETHYL]-N$^4$-(4-METHYLPHENYL)-6-(1-PIPERIDINYL)-2,4-PYRIMIDINEDIAMINE

Prepared by Procedures D, J, and G. $^1$H NMR (300 MHz, CDCl$_3$) δ 8.10 (br s, 1H), 7.70 (d, 1H, J=7.8), 7.36 (d, 1H, J=8.1), 7.19-6.98 (m, 7H), 6.60 (br s, 1H), 5.35 (s, 1H), 4.89 (br s, 1H), 4.44-4.36 (m, 1H), 3.55-3.45 (m, 4H), 3.14 (dd 1H, J=14.1, 5.1), 2.84 (dd, 1H, J=14.1, 7.5), 2.33 (s, 3H), 1.62-1.50 (m, 6H), 1.18 (d, 3H, J=6.6); ESI-MS m/z 441 (MH$^+$).

Example 21

N$^2$-[2-(1H-INDOL-3-YL)-1-METHYLETHYL]-N$^2$-METHYL-N$^4$-(4-METHYLPHENYL)-6-(1-PIPERIDINYL)-2,4-PYRIMIDINEDIAMINE

Prepared by Procedures D, E (160° C., 12 hours, for substitution with N,α-dimethyltryptamine), and G. $^1$H NMR (300 MHz, CDCl$_3$) δ 7.92 (br s, 1H), 7.73 (d, 1H, J=7.8), 7.34 (d, 1H, J=7.8), 7.19-7.09 (m, 6H), 7.03 (s, 1H), 6.17 (br s, 1H), 5.34 (s, 1H), 3.51-3.44 (m, 5H), 3.11-3.05 (m, 1H), 3.02 (s, 2H), 2.90 (dd, 1H, J=14.7, 7.5), 2.32 (s, 3H), 1.65-1.49 (m, 6H), 1.18 (d, 3H, J=6.6); ESI-MS m/z 455 (MH$^+$).

Example 22

N$^2$-METHYL-N$^4$-(4-METHYLPHENYL)-N$^2$-PHENETHYL-6-(1-PIPERIDINYL)-2,4-PYRIMIDINEDIAMINE

Prepared by Procedures D, E (160° C., 12 hours, for substitution at C2 of the pyrimidine), and G. ESI-MS m/z 402 (MH$^+$).

Example 23

2-(4-BENZYL-1-PIPERAZINYL)-N-(4-METHYLPHENYL)-6-(1-PIPERIDINYL)-4-PYRIMIDINAMINE

Prepared by Procedures D, I (140° C., overnight, for substitution with N-benzylpiperazine), and F (2 hours). $^1$H NMR (300 Mz, CDCl$_3$) δ 7.38-7.26 (m, 5H), 7.18 (d, 1H, J=7.8), 7.12 (d, 1H, J=7.8), 6.18 (br s, 1H), 5.34 (s, 1H), 3.93-3.87 (m, 4H), 3.77 (t, 4H, J=5.0), 3.55 (s, 2H), 3.48-3.42 (m, 4H), 2.49 (t, 4H, J=5.0), 2.31 (s, 3H), 1.66-1.49 (m, 6H); ESI-MS m/z 443 (MH$^+$).

Example 24

N-(4-METHYLPHENYL)-2-(4-PHENYL-1-PIPERIDINYL)-6-(1-PIPERIDINYL)-4-PYRIMIDINAMINE

Prepared by Procedures D, E (16 hours, for substitution with 4-phenylpiperidine), and F (1 hour). $^1$H NMR (300 MHz, CDCl$_3$) δ 7.34-7.24 (m, 5H), 7.19 (d, 2H, J=7.8), 7.12 (d, 2H, J=7.8), 6.22 (br s, 1H), 5.36 (s, 1H), 4.89 (d with fine splitting, 2H, J=13.0), 3.52-3.42 (m, 4H), 2.86 (dt, 2H, J=1.0, 13.0), 2.73 (tt, 1H, J=11.6, 1.5), 2.32 (s, 3H), 1.89 (d with fine splitting, 2H, 3=12.0), 1.74 (ddd, 2H, J=13.0, 12.0, 1.5), 1.67-1.52 (m, 6H); ESI-MS m/z 428 (MH$^+$).

Example 25

N-(4-METHYLPHENYL)-2-(4-PHENYLPIPERAZINYL)-6-(1-PIPERIDINYL)-4-PYRIMIDINAMINE

Prepared by Procedures D, G (180° C., 2.5 hours, for substitution with N-phenylpiperazine), and G (140° C., overnight). $^1$H NMR (300 MHz, CDCl$_3$) δ 7.28 (t, 2H, J=7.8), 7.19 (d, 2H, J=7.8), 7.13 (d, 2H, J=7.8), 6.99 (d, 2H, J=7.8), 6.89 (t, 1H, J=7.8), 6.23 (br s, 1H), 5.38 (s, 1H), 3.91 (t, 2H, J=4.6), 3.54-3.44 (m, 4H), 3.23 (t, 2H, J=4.6), 2.34 (s, 3H), 1.71-1.51 (m, 6H); ESI-MS m/z 429 (MH$^+$).

Example 26

2-[4-(2-ETHYLPHENYL)-1-PIPERAZINYL]-N-(4-METHYLPHENYL)-6-(1-PIPERIDINYL)-4-PYRIMIDINAMINE

Prepared by Procedures D, E (120° C.), and F. $^1$H NMR (300 MHz, CDCl$_3$) δ 7.28 (d, 1H, J=7.8), 7.24-7.08 (m, 7H), 6.37 (br s, 1H), 5.41 (s, 1H), 3.98-3.90 (m, 4H), 3.53-3.47 (m, 4H), 2.99-2.92 (m, 4H), 2.80 (q, 2H, J=8.3), 2.35 (s, 3H), 1.69-1.54 (m, 6H), 1.31 (t, 3H, J=8.3); ESI-MS m/z 457 (MH$^+$).

Example 27

2-[4-(2,6-DIMETHYLPHENYL)-1-PIPERAZINTYL]-N-(4-METHYLPHENYL)-6-(1-PIPERIDINYL)-4-PYRIMIDINAMINE

Prepared by Procedures D, E (120° C.), and F. $^1$H NMR (300 MHz, CDCl$_3$) δ 7.22 (d, 2H, J=7.8), 7.15 (d, 2H, J=7.8), 7.05-7.95 (m, 3H), 6.30 (br s, 1H), 5.39 (s, 1H), 3.88 (t, 4H, J=4.6), 3.53-3.47 (m, 4H), 3.15 (t, 4H, J=4.6), 2.37 (s, 6H), 2.34 (s, 3H), 1.68-1.53 (m, 6H); ESI-MS m/z 457 (MH$^+$).

Example 28

N-{2-[4-(2,4-DIMETHOXYPHENYL)PIPERAZINYL]-6-(1-PIPERIDINYL)-4-PYRIMIDINYL}-N-(4-METHYLPHENYL)AMINE

Prepared by Procedures D, E (150° C., 16 hours), and F (5 hours). $^1$H NMR (300 MHz, CDCl$_3$) δ 7.18 (d, 2H, J=8.1), 7.12 (d, 2H, J=8.1), 6.88 (d, 1H, J=9.0), 6.50 (d, 1H, J=2.4), 6.43 (dd, 1H, J=8.7, 2.4), 6.23 (br s, 1H), 5.36 (s, 1H), 3.94 (t, 4H, J=7.5), 3.87 (s, 3H), 3.79 (s, 3H), 3.52-3.44 (m, 4H), 3.03 (t, 4H, J=7.5), 2.33 (s, 3H), 1.65-1.52 (m, 6H); ESI-MS m/z 488 (MH$^+$).

Example 29

N-(4-METHYLPHENYL)-6-(1-PIPERIDINYL)-2-{4-[3-(TRIFLUOROMETHYL)PHENYL]-1-PIPERAZINYL}-4-PYRIMIDINAMINE

Prepared by Procedures D, E (120° C., 16 hours), and F. $^1$H NMR (300 MHz, CDCl$_3$) δ 7.36 (t, 1H, J=7.8), 7.20-7.09 (m, 7H), 6.25 (br s, 1H), 5.37 (s, 1H), 4.93 (t, 4H, J=4.6), 3.52-3.45 (m, 4H), 3.26 (t, 4H, J=4.6), 2.34 (s, 3H), 1.66-1.52 (m, 6H); ESI-MS m/z 497 (MH$^+$).

Example 30

N-(4-METHYLPHENYL)-6-(1-PIPERIDINYL)-2-[4-(2-PYRIDYL)-1-PIPERAZINYL]-4-PYRIMIDINAMINE

Prepared by Procedures D, G (120° C., 12 hours, for substitution with N-pyrid-2-ylpiperazine), and G (140° C.). $^1$H NMR (300 MHz, CDCl$_3$) δ 8.22 (dd, 1H, J=4.4, 1.5), 7.50 (dd, 1H, J=7.8, 1.5), 7.20 (d, 2H, J=8.1), 7.13 (, 2H, J=8.1), 6.69 (d, 1H, J=7.8), 6.63 (t, 1H, J=7.8), 6.26 (br s, 1H), 5.38 (s, 1H), 3.89 (t, 4H, J=4.3), 3.62 (t, 4H, J=4.8), 3.55-3.45 (m, 4H), 2.23 (s, 3H), 1.70-1.52 (m, 6H); ESI-MS m/z 430 (MH$^+$).

Example 31

N-(4-METHYLPHENYL)-2-[4-(3-METHYL-2-PYRIDINYL)-1-PIPERAZINYL]-6-(1-PIPERIDINYL)-4-PYRIMIDINAMINE

Prepared from 2-(4-benzyl-1-piperazinyl)-N-(4-methylphenyl)-6-(1-piperidinyl)-4-pyrimidinamine by Procedures K and L. $^1$H NMR (300 MHz, CDCl$_3$) δ 8.19 (dd, 1H, J=4.4, 2.2), 7.42 (dd, 1H, J=7.8, 2.2), 7.19 (d, 2H, J=8.1), 7.12 (d, 2H, J=8.1), 6.85 (dd, 1H, J=7.8, 4.4), 6.20 (br s, 1H), 5.38 (s, 1H), 3.93-3.87 (m, 4H), 3.53-3.48 (m, 4H), 3.24-3.18 (m, 4H), 2.33 (s, 3H), 1.67-1.53 (m, 6H); ESI-MS m/z 444 (MH$^+$).

Example 32

N-(4-METHYLPHENYL)-6-(1-PIPERIDINYL)-2-{4-[4-(TRIFLUOROMETHYL)-2-PYRIDINYL]-1-PIPERAZINYL}-4-PYRIMIDINAMINE

Prepared by Procedures D, E (16 hours), and F. ESI-MS m/z 498 (MH$^+$).

Example 33

N-(4-METHYLPHENYL)-6-(1-PIPERIDINYL)-2-{4-[6-(TRIFLUOROMETHYL)-2-PYRIDINYL]-1-PIPERAZINYL}-4-PYRIMIDINAMINE

Prepared by Procedures D, E (16 hours), and F. $^1$H NMR (300 MHz, CDCl$_3$) δ 7.56 (d, 1H, J=8.1), 7.19 (d, 2H, J=8.4), 7.14 (d, 2H, J=8.4), 6.94 (d, 1H, J=7.2), 6.80 (d, 1H, J=8.7), 6.23 (br s, 1H), 5.37 (s, 1H), 3.90-3.87 (m, 4H), 3.69-3.66 m, 4H), 3.50-4.46 (m, 4H), 2.34 (s, 3H), 1.67-1.53 (m, 6H); ESI-MS m/z 498 (MH$^+$).

Example 34

N-(4-METHYLPHENYL)-6-(1-PIPERIDINYL)-2-{4-[3-(TRIFLUOROMETHYL)-2-PYRIDINYL]-1-PIPERAZINYL}-4-PYRIMIDINAMINE

Prepared by Procedures D, E (16 hours), and F. $^1$H NMR (300 MHz, CDCl$_3$) δ 8.43 (dd, 1H, J=4.4, 2.2), 7.87 (dd, 1H, J=7.8, 2.2), 7.19 (d, 2H, J=8.1), 7.13 (d, 2H, J=8.1), 6.99 (dd, 1H, J=7.8-4.4), 6.23 (br s, 1H), 5.37 (s, 1H), 3.89 (t, 4H, J=4.8), 3.53-3.48 (m, 4H), 3.36 (t, 4H, J=4.8), 2.33 (s, 3H), 1.67-1.53 (m, 6H); ESI-MS m/z 498 (MH$^+$).

Example 35

N-CYCLOHEXYL-6-(1-PIPERIDINYL)-2-{4-[3-(TRIFLUOROMETHYL)-2-PYRIDINYL]-1-PIPERAZINYL}-4-PYRIMIDINAMINE

Prepared by Procedures M, E (120° C., for addition of piperidine), and F (3 hours). $^1$H NMR (300 MHz, CDCl$_3$) δ 8.43 (d, 1H, J=5.6), 7.84 (d, 1H, J=7.4), 6.95 (dd, 1H, J=7.4, 5.6), 4.95 (s, 1H), 4.34 (br s, 1H), 3.84 (t, 4H, J=5.1), 3.55-3.38 (m, 5H), 3.34 (t, 4H, J=5.1), 2.02 (dd, 2H, J=12.0, 1.4), 1.79-1.71 (m, 2H), 1.69-1.52 (m, 6H), 1.44-1.10 (m, 6H); ESI-MS m/z 490 (MH$^+$).

Example 36

N-BICYCLO[2.2.1]HEPT-2-YL-6-(1-PIPERIDINYL)-2-{4-[3-(TRIFLUOROMETHYL)-2-PYRIDINYL]-1-PIPERAZINYL}-4-PYRIMIDINAMINE

Prepared by Procedures M, E (120° C., for addition of piperidine), and F (3 hours). $^1$H NMR (300 MHz, CDCl$_3$) δ 8.42 (d, 1H, J=5.6), 7.86 (d, 1H, J=7.4), 6.95 (dd, 1H, J=7.4, 5.6), 4.95 (s, 1H), 4.37 (br s, 1H), 3.84 (t, 4H, J=5.1), 3.57-3.47 (m, 4H), 3.40-3.31 (m, 5H), 2.25 (br s, 2H), 1.78 (ddd, 2H, J=13.0, 4.6, 1.4), 1.67-1.42 (m, 9H), 1.25-1.12 (m, 4H); ESI-MS m/z 502 (MH$^+$).

Example 37

N-(4-METHYLPHENYL)-6-(1-PIPERIDINYL)-2-[4-(2-PYRIMIDINYL)-1-PIPERAZINYL]-4-PYRIMIDINAMINE

Prepared by Procedures D, G (120° C., 12 hours, for substitution with N-pyrimid-2-ylpiperazine), and G (150° C. 24 hours). $^1$H NMR (300 MHz, CDCl$_3$) δ 8.33 (d, 2H, J=4.9), 7.19 (d, 2H, J=0.8), 7.13 (d, 2H, J=7.8), 6.50 (t, 1H, J=7.8), 6.23 (br s, 1H), 5.37 (s, 1H), 3.97-3.82 (m, 8H), 3.56-3.44 (m, 4H), 2.34 (s, 3H), 1.70-1.53 (m, 6H); ESI-MS m/z 431 (MH$^+$).

Example 38

N-(4-METHYLPHENYL)-6-(1-PIPERIDINYL)-2-(1-PYRROLIDINYL)-4-PYRIMIDINAMINE

Prepared by Procedures D, G (120° C., 3 hours, for substitution with pyrrolidine), and G (140° C., 12 hours). $^1$H NMR (300 MHz, CDCl$_3$) δ 7.20 (d, 2H, J=7.8), 7.11 (d, 2H, J=7.8), 6.39 (br s, 1H), 5.34 (s, 1H), 3.56 (t, 4H, J=5.6), 3.53-3.44 (m, 4H), 2.33 (s, 3H), 1.91 (quintet, 4H, J=5.6), 1.67-1.50 (m, 6H); ESI-MS m/z 338 (MH$^+$).

Example 39

N-[2-(2,3-DIHYDRO-1H-INDOL-1-YL)-6-(1-PIPERIDINYL)-4-PYRIMIDINYL]-N-(4-METHYLPHENYL)AMINE

Prepared by Procedures D, E (16 hours), and F. $^1$H NMR (300 MHz, CDCl$_3$) δ 8.31 (d, 1H, J=7.8), 7.28-7.15 (m, 6H), 6.86 (t, 1H, J=7.8), 6.31 (br s, 1H), 5.49 (s, 1H), 4.22 (t, 4H, J=8.3), 3.59-3.53 (m, 4H), 3.13 (t, 4H, J=8.3), 2.35 (s, 3H), 1.70-1.55 (m, 6H); ESI-MS m/z 386 (MH$^+$).

Example 40

N-(4-METHYLPHENYL)-N-[6-(1-PIPERIDINYL)-2-(1,2,3,4-TETRAHYDRO-1-QUINOLINYL)-4-PYRIMIDINYL]AMINE

Prepared by Procedures D, G (180° C., 3 hours, for substitution with 1,2,3,4-tetrahydroquinoline), and G (140° C., 12 hours). $^1$H NMR (300 MHz, CDCl$_3$) δ 7.87 (d, 1H, J=7.8), 7.19 (d, 2H, J=7.8), 7.15-7.07 (m, 4H), 6.93 (t, 1H, J=7.8), 6.33 (br s, 1H), 5.49 (s, 1H), 4.04 (t, 2H, J=6.0), 3.54-3.44 (m, 4H), 2.79 (t, 2H, J=6.0), 2.34 (s, 3H), 1.98 (pentet, 2H, J=6.0), 1.69-1.52 (m, 6H); ESI-MS m/z 400 (MH$^+$).

Example 41

N-(4-METHYLPHENYL)-N-[6-(1-PIPERIDINYL)-2-(1,2,3,4-TETRAHYDRO-2-ISOQUINOLINYL)-4-PYRIMIDINYL]AMINE

Prepared by Procedures D, G (180° C., 3 hours, for substitution with 1,2,3,4-tetrahydroisoquinoline), and G (140° C., 12 hours). $^1$H NMR (300 MHz, CDCl$_3$) δ 7.56 (d, 1H, J=7.8), 7.26-7.06 (m, 7H), 6.37 (br s, 1H), 5.35 (s, 1H), 4.89 (s, 2H), 4.00 (t, 2H, J=6.0), 3.58-3.44 (m, 4H), 2.91 (t, 2H, J=6.0), 2.32 (s, 3H), 1.68-1.47 (m, 6H); ESI-MS m/z 400 (MH$^+$).

Example 42

N-[2-(6,7-DIMETHOXY-3,4-DIHYDRO-2(1H)-ISOQUINOLINYL)-6-(1-PIPERIDINYL)-4-PYRIMIDINYL]-N-(4-METHYLPHENYL)AMINE

Prepared by Procedures D, E (160° C., 12 hours), and F (5 hours). $^1$H NMR (300 MHz, CDCl$_3$) δ 7.19 (d, 2H, J=7.8), 7.13 (d, 2H, J=7.8), 6.70 (s, 1H), 6.64 (s, 1H), 6.25 (br s, 1H), 5.36 (s, 1H), 4.82 (s, 2H), 4.01 (t, 2H, J=5.9), 3.89 (s, 3H), 3.87 (s, 3H), 3.58-3.44 (m, 4H), 2.84 (t, 2H, J=5.9), 2.33 (s, 3H), 1.68-1.52 (m, 6H); ESI-MS m/z 460 (MH$^+$).

Example 43

N-[2-(2,3-DIHYDRO-1H-BENZO[DE]ISOQUINOLIN-2-YL)-6-(1-PIPERIDINYL)-4-PYRIMIDINYL]-N-(4-METHYLPHENYL)AMINE

Prepared by Procedures D, E (160° C., 12 hours), and G. ESI-MS m/z 436 (MH$^+$).

Example 44

4-PHENYL-1-[4-(1-PIPERIDINYL)-6-(4-TOLUIDINO)-2-PYRIMIDINYL]-4-PIPERIDINOL

Prepared by Procedures D, E (23 hours), and F. $^1$H NMR (300 MHz, CDCl$_3$) δ 7.51 (d, 2H, J=7.5), 7.36 (t, 2H, J=7.8), 7.26 (t, 1H+CHCl$_3$, J=7.8), 7.19 (d, 2H, J=8.4), 7.12 (d, 2H, J=8.4), 6.20 (br s, 1H), 5.36 (s, 1H), 4.67 (br d, 2H, J=13.5), 3.50-3.45 (m, 4H), 4.67 (br t, 2H, J=13.1), 2.33 (s, 3H), 2.10 (dt, 2H, J=4.2, 12.6), 1.78 (br d, 2H, J=13.5), 1.65-1.53 (m, 6H); ESI-MS m/z 444 (MH$^+$).

Example 45

$N^2,N^2$-BIS(2-METHOXYETHYL)-$N^4$-(4-METHYLPHENYL)-6-(1-PIPERIDINYL)-2,4 PYRIMIDINEDIAMINE

Prepared by Procedures D, G [140° C., 2 hours, for substitution with bis(methoxyethyl)amine], and G (140° C., 1.5 hours). $^1$H NMR (300 MHz, CDCl$_3$) δ 7.20 (d, 2H, J=7.8), 7.10 (d, 2H, J=7.8), 6.20 (br s, 1H), 5.33 (s, 1H), 3.77 (t, 4H, J=6.2), 3.59 (t, 4H, J=6.3), 3.47-3.40 (m, 4H), 3.36 (s, 6H), 1.64-1.49 (m, 6H); ESI-MS m/z 400 (MH$^+$).

Example 46

N-(4-METHYLPHENYL)-2-(3-PHENYL-4-MORPHOLINYL)-6-(1-PIPERIDINYL)-4-PYRIMIDINAMINE

Prepared by Procedures D, E (16 hours), and F (1 hour). $^1$H NMR (300 MHz, CDCl$_3$) δ 7.51 (d, 2H, J=7.8), 7.31 (t, 2H, J=7.8), 7.23 (t, 1H, J=7.8), 7.15 (d, 2H, J=7.8), 7.10 (d, 2H, J=7.8), 6.22 (br s, 1H), 5.84 (d, 1H, J=1.0), 5.36 (s, 1H), 4.51-4.42 (m, 2H), 3.94 (m, 2H), 3.66 (dt, 1H, J=1.0, 11.5), 3.49-3.43 (m, 4H), 3.24 (dt, 1H, J=1.5, 11.5), 2.32 (s, 3H), 1.64-1.47 (m, 6H); ESI-MS m/z 430 (MH$^+$).

Example 47

N-(4-METHYLPHENYL)-2-(2-PHENYL-4-MORPHOLINYL)-6-(1-PIPERIDINYL)-4-PYRIMIDINAMINE

Prepared by Procedures D, E (14 hours), and F (100° C., 2 hours). $^1$H NMR (300 MHz, CDCl$_3$) $^1$H NMR (300 MHz, CDCl$_3$) δ 7.46 (d, 2H, J=7.8), 7.38 (t, 2H, J=7.8), 7.34 (t, 1H, J=7.8), 7.18 (d, 2H, J=8.7), 7.13 (d, 2H, J=8.4), 6.19 (br s, 1H), 5.38 (s, 1H), 4.70 (br d, 1H, J=12.6), 4.58-4.51 (m, 1H), 4.11 (dd, 1H, J=10.2, 2.4), 3.80 (dt, 1H, J=2.7, 11.7), 3.50-3.43 (m, 4H), 3.10 (dt, 1H, J=2.1, 12.8), 2.89 (dd, 1H, J=13.2, 10.2), 2.33 (s, 3H), 1.66-1.50 (m, 6H); ESI-MS m/z 430 (MH$^+$).

Example 48

N-(4-METHYLPHENYL)-2-[(2S,3R)-3-METHYL-2-PHENYLMORPHOLINYL]-6-(1-PIPERIDINYL)-4-PYRIMIDINAMINE

Prepared by Procedures D, E (120° C.), and F (1 hour). $^1$H NMR (300 MHz, CDCl$_3$) δ 7.42 (d, 2H, J=7.8), 7.39 (t, 2H, J=7.8), 7.27 (t, 1H, J=7.8), 7.20 (d, 2H, J=7.8), 7.14 (d, 2H, J=7.8), 6.25 (br s, 1H), 5.39 (s, 1H), 4.99-4.90 (m, 1H), 4.77 (d, 1H, J=1.5), 4.39 (dd, 1H, J=13.0, 1.5), 4.15 (dd, 1H, J=8.3, 1.5), 3.80 (dt, 1H, J=3.7, 11.6), 3.53-3.45 (m, 4H), 3.26 (dt, 1H, J=3.7, 13.0), 2.33 (s, 3H), 1.68-1.52 (m, 6H), 0.90 (d, 3H, J=8.3); ESI-MS m/z 444 (MH$^+$).

Example 49

2-[(2R,3R)-3-(METHOXYMETHYL)-2-PHENYLMORPHOLINYL]-N-(4-METHYLPHENYL)-6-(1-PIPERIDINYL)-4-PYRIMIDINAMINE

Prepared by Procedures D, E, and F (3 hours). $^1$H NMR (300 MHz, CDCl$_3$) δ 7.56 (d, 2H, J=7.8), 7.31 (t, 2H, J=7.8), 7.27-7:20 (m, 3H), 7.13 (d, 2H, J=7.8), 6.31 (br s, 1H), 5.84 (d, 1H, J=1.0), 5.35 (dd, 1H, J=9.3, 2.7), 5.11 (s, 1H), 4.28 (d with splitting, 1H, J=13.0), 4.01 (t, 1H, J=9.0), 3.58-3.46 (m, 6H), 3.40 (s, 3H), 3.27-3.15 (m, 1H), 2.31 (s, 3H), 1.69-1.50 (m, 6H); ESI-MS m/z 473 (MH$^+$).

Example 50

$N^4,N^4$-DIMETHYL-$N^2,N^6$-DIPHENYL-2,4,6-PYRIMIDINETRIAMINE

Prepared by Procedures A, C, and G (140° C., overnight). $^1$H NMR (300 MHz, CDCl$_3$) δ 7.68 (d, 2H, J=7.8), 7.38-7.27 (m, 6H), 7.11-7.04 (m, 1H), 6.95 (t, 1H, J=7.8), 6.75 (br s, 1H), 6.38 (br s, 1H), 5.45 (s, 1H), 3.06 (s, 6H); ESI-MS m/z 306 (MH$^+$).

Example 51

$N^4,N^4$-DIMETHYL-$N^6$-(2-METHYLPHENYL)-$N^2$-PHENYL-2,4,6-PYRIMIDINETRIAMINE

Prepared by Procedures A, C, and G (140° C., overnight). $^1$H NMR (300 MHz, CDCl$_3$) δ 7.63 (d, 2H, J=7.5), 7.43 (d, 1H, J=7.5), 7.31-7.24 (m, 3H), 7.21 (d, 1H, J=7.8), 7.11 (t, 1H, J=7.4), 6.96 (t, 1H, J=7.7), 6.73 (br s, 1H), 6.12 (br s, 1H), 5.16 (s, 1H), 3.01 (s, 6H), 2.29 (s, 3H); ESI-MS m/z 320 (MH$^+$).

Example 52

$N^4,N^4$-DIMETHYL-$N^6$-(3-METHYLPHENYL)-$N^2$-PHENYL-2,4,6-PYRIMIDINETRIAMINE

Prepared by Procedures A, C, and G (140° C., overnight). $^1$H NMR (300 MHz; CDCl$_3$) δ 7.63 (d, 2H, J=7.8), 7.29 (t, 2H, J=7.8), 7.21 (d, 1H, J=8.1), 7.16-7.11 (m, 2H), 6.97 (d, 1H, J=8.1), 6.91 (d, 1H, J=7.5), 6.78 (br s, 1H), 6.38 (br s, 1H), 5.44 (s, 1H), 3.05 (s, 6H), 2.35 (s, 3H); ESI-MS m/z 320 (MH$^+$).

Example 53

$N^4,N^4$-DIMETHYL-$N^6$-(3-METHYLPHENYL)-$N^2$-(4-METHYLPHENYL)-2,4,6-PYRIMIDINETRIAMINE

Prepared by Procedures A, C, and G (overnight). $^1$H NMR (300 MHz, CDCl$_3$) δ 7.50 (d, 2H, J=7.8), 7.25-7.08 (m, 5H), 6.90 (d, 1H, J=7.5), 6.86 (br s, 1H), 6.54 (br s, 1H), 5.44 (s, 1H), 3.05 (s, 6H), 2.34 (s, 3H), 2.31 (s, 3H); ESI-MS m/z 334 (MH$^+$).

Example 54

$N^4,N^4$-DIMETHYL-$N^6$-(4-METHYLPHENYL)-$N^2$-PHENYL-2,4,6-PYRIMIDINETRIAMINE

Prepared by Procedures A, C, and G (140° C., overnight). $^1$H NMR (300 MHz, CDCl$_3$) δ 7.63 (d, 2H, J=7.8), 7.28 (t, 2H, J=7.5), 7.21 (d, 2H, J=7.8), 7.15 (d, 2H, J=8.1), 6.96 (t, 1H, J=7.5), 6.71 (br s, 1H), 6.29 (br s, 1H), 5.39 (s, 1H), 3.04 (s, 6H), 2.34 (s, 3H); ESI-MS m/z 320 (MH$^+$).

Example 55

N$^2$-(3,4-DICHLOROPHENYL)-N$^4$,N$^4$-DIMETHYL-N$^6$-(4-METHYLPHENYL)-2,4,6-PYRIMIDINETRIAMINE

Prepared by Procedures B, C, and G (180° C., 3 hours). $^1$H NMR (300 MHz, CDCl$_3$) δ 8.04 (d, 1H, J=2.1), 7.27 (d, 1H, J=7.8), 7.24 (dd, 1H, J=7.8, 2.1), 7.19 (d, 2H, J=8.7), 7.15 (d, 2H, J=8.7), 7.01 (br s, 1H), 6.59 (br s, 1H), 5.39 (s, 1H), 3.04 (s, 6H), 2.35 (s, 3H); ESI-MS m/z 388 (MH$^+$ with $^{35}$Cl, $^{35}$Cl), 390 (MH$^+$ with $^{35}$Cl, $^{37}$Cl), 392 (MH$^+$ with $^{37}$Cl).

Example 56

N$^4$,N$^4$-DIMETHYL-N$^2$,N$^6$-BIS (4-METHYLPHENYL)-2,4,6-PYRIMIDINETRIAMINE

Prepared by Procedures B, C, and G (180° C., 3 hours). $^1$H NMR (300 MHz, CDCl$_3$) δ 7.49 (d, 2H, J=8.7), 7.19 (d, 2H, J=8.4.), 7.14 (d, 2H, J=8.4.), 7.08 (d, 2H, J=8.4), 6.73 (br s, 1H), 6.39 (br s, 1H), 5.37 (s, 1H), 3.02 (s, 6H); ESI-MS m/z 334 (MH$^+$).

Example 57

N$^4$-(3-FLUOROPHENYL)-N$^6$,N$^6$-DIMETHYL-N$^2$-PHENYL-2,4,6-PYRIMIDINETRIAMINE

Prepared by Procedures A, C, and G (140° C., overnight). $^1$H NMR (300 MHz, CDCl$_3$) δ 7.62 (d, 2H, J=7.8), 7.34-7.23 (m, 5H), 7.01 (t, 1H, J=7.4), 6.77 (br s, 1H), 6.38 (br s, 1H), 5.43 (s, 1H), 3.07 (s, 6H); ESI-MS m/z 324 (MH$^+$).

Example 58

N$^2$-(4-CHLOROPHENYL)-N$^6$,N$^6$-DIMETHYL-N$^2$-PHENYL-2,4,6-PYRIMIDINETRIAMINE

Prepared by Procedures A, C, and G (150° C., overnight). $^1$H NMR (300 MHz, CDCl$_3$) δ 7.60 (d, 2H, J=7.5), 7.32-7.26 (m, 6H), 6.96 (t, 1H, J=7.5), 6.77 (br s, 1H), 6.34 (br s, 1H), 5.34 (s, 1H), 3.04 (s, 6H); ESI-MS m/z 340 (MH$^+$ with $^{37}$Cl), 342 (MH$^+$ with $^{37}$Cl).

Example 59

N$^4$-(4-BROMOPHENYL)-N$^6$,N$^6$-DIMETHYL-N$^2$-PHENYL-2,4,6-PYRIMIDINETRIAMINE

Prepared by Procedures A, C, and G (150° C., overnight). $^1$H NMR (300 MHz, CDCl$_3$) δ 7.59 (d, 2H, J=8.5), 7.42 (d, 2H, J=8.5), 7.31-7.22 (m, 4H), 6.98 (t, 1H, J=7.2), 6.92 (br s, 1H), 6.48 (br s, 1H), 5.35 (s, 1H). 3.05 (s, 6H); ESI-MS m/z 384 (MH$^+$ with $^{79}$Br), 386 (MH$^+$ with $^{81}$Br).

Example 60

N$^4$-(3,4-DICHLOROPHENYL)-N$^6$,N$^6$-DIMETHYL-N$^2$-PHENYL-2,4,6-PYRIMIDINETRIAMINE

Prepared by Procedures A, C, and G (0.5 mL diisopropylethylamine added, 150° C., overnight). $^1$H NMR (300 MHz, CDCl$_3$) δ 7.61 (d with s at the center, 3H, J=7.8), 7.34 (d, 2H, J=7.8), 7.29 (d, 1H, J=8.7), 7.17 (dd, 1H, J=8.7, 2.6), 6.98 (t, 1H, J=7.8), 6.80 (br s, 1H), 6.33 (br s, 1H), 5.33 (s, 1H), 3.07 (s, 6H); ESI-MS m/z 373 (MH$^+$).

Example 61

N$^4$-(4-CHLORO-3-METHYLPHENYL)-N$^6$,N$^6$-DIMETHYL-N$^2$-PHENYL-2,4,6-PYRIMIDINETRIAMINE

Prepared by Procedures A, C, and G (150° C., 1 hour). $^1$H NMR (300 MHz, CDCl$_3$) δ 7.61 (dd, 2H, J=7.4, 0.9), 7.30-7.25 (m, 3H), 7:19 (d, 1H, J=2.4), 7.12 (dd, 1H, J=8.5, 2.4), 6.97 (t, 1H, J=7.4), 6.88 (br s, 1H), 6.44 (br s, 1H), 5.35 (s, 1H), 3.05 (s, 6H), 2.35 (s, 3H); ESI-MS m/z 454 (MH$^+$ with $^{35}$Cl), 456 (MH$^+$ with $^{37}$Cl).

Example 62

N$^4$-(3-CHLORO-4-METHYLPHENYL)-N$^6$,N$^6$-DIMETHYL-N$^2$-PHENYL-2,4,6-PYRIMIDINETRIAMINE

Prepared by Procedures A, C, and F (100° C., 3 hours). $^1$H NMR (300 MHz, CDCl$_3$) δ 7.63 (d, 2H, J=7.8), 7.41 (d, 1H, J=1.8), 7.30 (t, 2H, J=7.8), 7.18 (d, 1H, J=7.8), 7.09 (dd, 1H, J=7.8, 1.8), 6.98 (t, 1H, J=7.8), 6.67 (br s, 2H), 5.35 (s, 1H), 3.07 (s, 6H), 2.37 (s, 3H); ESI-MS m/z 454 (MH$^+$ with $^{35}$Cl), 456 (MH$^+$ with $^{37}$Cl).

Example 63

N$^4$-(4-tert-BUTYLPHENYL)-N$^6$,N$^6$-DIMETHYL-N$^2$-PHENYL-2,4,6-PYRIMIDINETRIAMINE Prepared by Procedures A, C, and G (150° C., 5 hours). $^1$H NMR (300 MHz, CDCl$_3$) δ 7.62 (d, 2H, J=7.5), 7.36 (d, 2H, J=8.7), 7.29 (d, 2H, J=7.5), 7.25 (t, 2H, J=8.7), 6.95 (t, 1H, J=7.4), 6.69 (br s, 1H), 6.30 (br s, 1H), 5.44 (s, 1H), 3.05 (s, 6H), 1.33 (s, 9H); ESI-MS m/z 362 (MH$^+$).

Example 64

N$^4$,N$^4$-DIMETHYL-N$^6$-(4-PHENOXYPHENYL)-N$^2$-PHENYL-2,4,6-PYRIMIDINETRIAMINE

Prepared by Procedures A, C, and G (150° C., 2 hours). $^1$H NMR (300 MHz, CDCl$_3$) δ 7.61 (d, 2H, J=7.8), 7.35 (t, 2H, J=7.8), 7.31-7.24 (m, 3H), 7.12 (t, 2H, J=7.8), 7.08-7.04 (m, 3H), 6.98 (t, 1H, J=8.1), 6.74 (br s, 1H), 6.71 (dd, 1H, J=7.8, 2.0), 6.43 (br s, 1H), 5.41 (s, 1H), 3.03 (s, 6H); ESI-MS m/z 398 (MH$^+$).

Example 65

N$^4$,N$^4$-DIMETHYL-N$^6$-(2-NAPHTHYL)-N$^2$-PHENYL-2,4,6-PYRIMIDINETRIAMINE

Prepared by Procedures A, C, and G (150° C., 2 hours). $^1$H NMR (300 MHz, CDCl$_3$) δ 7.81 (s, 1H), 7.80 (d, 1H, J=7.5), 7.75 (d, 2H, J=7.8), 7.65 (d, 2H, J=7.5), 7.49-7.37 (m, 3H), 7.29 (t, 2H, J=7.5), 6.98 (t, 1H, J=8.1), 6.85 (br s, 1H), 6.59 (br s, 1H), 5.51 (s, 1H), 3.06 (s, 6H); ESI-MS m/z 356 (MH$^+$).

Example 66

N⁴-CYCLOHEXYL-N⁶,N⁶-DIMETHYL-N²-PHENYL-2,4,6-PYRIMIDINETRIAMINE

Prepared by Procedures A, C, and G (140° C., 2 days). ¹H NMR (300 MHz, CDCl₃) δ 7.62 (d, 2H, J=8.1), 7.26 (t, 2H, J=8.1), 6.92 (t, 1H, J=8.1), 6.64 (br s, 1H), 4.96 (s, 1H), 4.39 (br d, 1H, J=8.1), 3.53-3.44 (m, 1H), 3.05 (s, 6H), 2.09-1.99 (m, 2H), 1.80-1.55 (m, 4H), 1.44-1.11 (m, 4H); ESI-MS m/z 312 (MH⁺).

Example 67

N⁴,N⁴-DIMETHYL-N⁶-(4-METHYLCYCLOHEXYL)-N²-PHENYL-2,4,6-PYRIMIDINETRIAMINE

Prepared by Procedures A, C, and G (150° C., overnight). ESI-MS m/z 326 (MH⁺).

Example 68

N⁴-(4-tert-BUTYLCYCLOHEXYL)-N⁶,N⁶-DIMETHYL-N²-PHENYL-2,4,6-PYRIMIDINETRIAMINE

Prepared by Procedures A, C, and G (150° C., overnight). ¹H NMR (300 MHz, CDCl₃) δ 7.62 (d, 2H, J=8.4), 7.26 (t, 2H, J=7.7), 6.92 (t, 1H, J=7.1), 6.61 (br s, 1H), 4.96 (s, 1H), 4.32 (br d, 1H J=8.4), 3.46-3.37 (m, 1H), 3.06 (s, 6H), 1.88-1.80 ((m, 2H), 1.29-1.20 (m, 1H), 1.19-0,97 (m, 4H), 0.87 (s, 9H); ESI-MS m/z 368 (MH⁺).

Example 69

N⁴-BICYCLO[2.2.1]HEPT-2-YL-N⁶,N⁶-DIMETHYL-N²-PHENYL-2,4,6-PYRIMIDINETRIAMINE

Prepared by Procedures A, C, and G (140° C.). ¹H NMR (300 MHz, CDCl₃) δ 7.62 (d, 2H, J=7.8), 7.26 (t, 2H, J=8.0), 6.92 (t, 1H, J=7.2), 6.62 (br s, 1H), 4.94 (s, 1H), 4.42 (br d, 1H, J=5.4), 3.45-3.37 (m, 1H), 3.06 (S, 6H), 2.33-2.27 (m, 1H), 1.82 (dd, 1H, J=12.3, 6.0), 1.56-1.42 (m, 2H), 1.30-1.14 (m, 5H), 0.91-0.85 (m, 1H); ESI-MS m/z 324 (MH⁺).

Example 70

N⁴,N⁴-DIMETHYL-N²-PHENYL-N⁶-(1,7,7-TRIMETHYLBICYCLO[2.2.1]HEPT-2-YL)-2,4,6-PYRIMIDINETRIAMINE

Prepared b Procedures A, C, and G (overnight). ¹H NMR (300 MHz, CDCl₃) δ 7.62 (d, 2H, J=7.8), 7.26 (t, 2H, J=7.8), 6.93 (t, 1H, J=7.7), 6.87 (br s, 1H), 4.95 (s, 1H), 4.80 (br d, 1H, J=6.9), 3.94-3.84 (m, 1H), 3.06 (s, 6H), 2.45-2.34 (m, 1H), 1.82-1.62 (m, 3H), 1.46-1.32 (m, 1H), 1.29-1.16 (m, 2H), 0.99 (s, 3H), 0.90 (s, 3H), 0.89 (s, 3H); ESI-MS m/z 366 (MH⁺).

Example 71

N⁴,N⁴-DIMETHYL-N²-PHENYL-N⁶-[(2R,3S)-3,6,6-TRIMETHYLBICYCLO[3.1.1]HEPT-2-YL]-2,4,6-PYRIMIDINETRIAMINE

Prepared by Procedures A, C, and G (5 hours). ¹H NMR (300 MHz, CDCl₃) δ 7.64 (d, 2H, J=8.1), 7.26 (t, 2H, J=8.1), 6.92 (t, 1H, J=7.4), 6.72 (br s, 1H), 4.99 (s, 1H), 4.47 (br d, 1H, J=8.4), 4.05-3.91 (m, 1H), 3.06 (s, 6H), 2.72-2.62 (m, 1H), 2.46-2.36 (m, 1H), 2.00-1.45 (m, 5H), 1.25 (s, 3H), 1.16 (d, 3H, J=7.8), 1.10 (s, 3H); ESI-MS m/z 366 (MH⁺).

Example 72

N²,N⁴,N⁴-TRIMETHYL-N²,N⁶-BIS(4-METHYLPHENYL)-2,4,6-PYRIMIDINETRIAMINE

Prepared by Procedures D, E (150° C., 16 hours), and F (5 hours). ¹H NMR (300 MHz, CDCl₃) δ 7.26 (d, 2H, J=8.1), 7.15 (br d, 4H, J=8), 7.04 (d, 2H, J=8.1), 6.19 (br s, 1H), 5.29 (s, 1H), 3.50 (s, 3H), 2.94 (s, 6H), 2.36 (s, 3H), 2.29 (s, 3H); ESI-MS m/z 348 (MH⁺).

Example 73

N²-CYCLOHEXYL-N²,N⁴,N⁴-TRIMETHYL-N⁶-(4-METHYLPHENYL)-2,4,6-PYRIMIDINETRIAMINE

Prepared by Procedures D, E (150° C., 12 hours), and F (5 hours). ¹H NMR (300 MHz, CDCl₃) δ 7.25 (d, 2H, J=8.4), 7.10 (d, 2H, J=8.1), 6.26 (br s, 1H), 5.22 (s, 1H), 4.66-4.52 (m, 1H), 3.01 (s, 3H), 2.99 (s, 6H), 2.32 (s, 3H), 1.87-1.64 (m, 5H), 1.52-1.35 (m, 4H), 1.22-1.06 (m, 1H); ESI-MS m/z 340 (MH⁺).

Example 74

N²-CYCLOHEXYL-N²-(2-METHOXYETHYL)-N⁴,N⁴-DIMETHYL-N⁶-(4-METHYLPHENYL)-2,4,6-PYRIMIDINETRIAMINE

Prepared by Procedures H, J (overnight), and F (2 hours). ¹H NMR (300 MHz, CDCl₃) δ 7.28 (d, 2H, J=8.1), 7.11 (d, 2H, J=8.1), 6.19 (br s, 1H), 5.22 (s, 1H), 4.60-4.50 (m, 1H), 3.64-3.55 (m, 4H), 3.39 (s, 3H), 2.99 (s, 6H), 2.31 (s, 3H), 1.83-1.75 (m, 4H), 1.73-1.63 (m, 1H), 1.52-1.38 (m, 4H), 1.19-1.05 (m, 1H); ESI-MS m/z 384 (MH⁺).

Example 75

2-(2,3-DIHYDRO-1H-INDOL-1-YL)-N⁴,N⁴-DIMETHYL-N⁶-(4-METHYLPHENYL)-4,6-PYRIMIDINEDIAMINE

Prepared by Procedures H, E (150° C., 16 hours), and F (2 hours). ¹H NMR (300 MHz, CDCl₃) δ 8.37 (d, 1H, J=7.8), 7.26 (d, 2H, J=7.8), 7.20-7.11 (m, 4H), 6.86 (t, 1H, J=7.8), 6.31 (br s, 1H), 5.39 (s, 1H), 4.24 (t, 4H, J=8.3), 3.13 (t, 4H, J=8.3), 3.07 (s, 6H), 2.35 (s, 3H); ESI-MS m/z 346 (MH⁺).

Example 76

N²-[2-(1H-3-INDOLYL)ETHYL]-N⁴,N⁴-DIMETHYL-N⁶-(4-METHYLPHENYL)-2,4,6-PYRIMIDINETRIAMINE

Prepared by Procedures H, J, and G. ¹H NMR (300 MHz, CDCl₃) δ 8.19 (br s, 1H), 7.65 (d 1H, J=7.8), 7.36 (d, 1H, J=7.8), 7.21-7.09 (m, 6H), 7.04 (s, 1H), 6.52 (br s, 1H), 5.28 (s, H), 4.95 (br d, 1H, J=7.2), 3.72 (q, 2H, J=7.2), 3.06 (t, 2H, J=7.8), 2.99(s, 6H), 2.32 (s, 3H); ESI-MS m/z 387 (MH⁺).

Example 77

N²-[2-(1H-INDOL-3-YL)ETHYL]-N²,N⁴,N⁴-TRI-METHYL-N⁶-(4-METHYLPHENYL)-2,4,6-PYRIMIDINETRIAMINE

Prepared by Procedures H, J, and G or F. $^1$H NMR (300 MHz, CDCl$_3$) δ 8.14 (br s, 1H), 7.70 (d 1H, J=7.8), 7.32 (d, 1H, J=7.8), 7.22 (d, 2H, J=7.8), 7.17 (t, 1H, J=7.2), 7.12 (t, 1H, J=7.2), 7.08 (d, 2H, J=7.8), 6.98 (s, 1H), 6.36 (br s, 1H), 5.25 (s, 1H), 3.90 (t, 2H, J=7.8), 3.14 (s, 3H), 3.07 (t, 2H, J=7.8), 2.99(s, 6H), 2.30 (s, 3H); ESI-MS m/z 401 (MH$^+$).

Example 78

N⁴-(3,4-DICHLOROPHENYL)-N²-[2-(1H-3-INDOLYL)ETHYL]-N²,N⁶,N⁶-TRIMETHYL-2,4,6-PYRIMIDINETRIAMINE

Prepared by Procedures H, J, and G. $^1$H NMR (300 MHz, CDCl$_3$) δ 8.00 (br s, 1H), 7.75 (s, 1H), 7.68 (d 1H, J=7.8), 7.35 (d, 1H, J=7.8), 7.24-7.15 (m, 3H), 7.10 (t, 1H, J=7.2), 7.00 (s, 1H), 6.23 (br s, 1H), 5.15 (s, 1H), 3.90 (t, 2H, J=7.8); 3.14 (s, 3H), 3.08 (t, 2H, J=7.8), 3.03 (s, 6H); ESI-MS m/z 455 (MH$^+$ with $^{35}$Cl), 457 (MH$^+$ with $^{37}$Cl).

Example 79

N²-[2-(1H-INDOL-3-YL)ETHYL]-N²,N⁴,N⁴-TRI-METHYL-(2-NAPHTHYL)-6-(1-PIPERIDINYL)-2,4,6-PYRIMIDINETRIAMINE

Prepared by Procedures D, E (160° C., 28 hours), and G. $^1$H NMR (300 MHz, CDCl$_3$) δ 8.18 (br s, 1H), 7.92 (s, 1H), 7.90-7.03 (m, 10H), 6.95 (s, 1H), 6.84 (br s, 1H), 5.34 (s, 1H), 3.90 (t, 2H, J=7.8), 3.17 (s, 3H), 3.07 (t; 2H, J=7.8), 2.96 (s, 6H); ESI-MS m/z 437 (MH$^+$).

Example 80

1-[4-(DIMETHYLAMINO)-6-(4-TOLUIDINO)-2-PYRIMIDINYL]-4-PHENYL-4-PIPERIDINOL

Prepared by Procedures H, E (150° C., 10 hours), and F (3 hours). $^1$H NMR (300 MHz, CDCl$_3$) δ 7.43 (d, 2H, J=7.8), 7.35 (t, 2H, J=7.8), 7.27-7.21 (m, 3H), 7.14 (d, 2H, J=7.8), 6.24 (br s, 1H), 6.18 (br s, 1H), 5.28 (s, 1H), 4.43-4.37 (m, 2H), 4.03 (t, 2H, J=5.6), 3.06-2.97 (m with s at 3.03, 8H), 2.66-2.58 (m, 2H), 2.34 (s, 3H).

Example 81

N⁴,N⁴-DIMETHYL-N⁶-(4-METHYLPHENYL)-2-(4-PHENYL-1-PIPERIDINYL)-4,6-PYRIMIDINEDIAMINE

Prepared by Procedures H, E (150° C., 16 hours), and F (4 hours). $^1$H NMR (300 MHz, CDCl$_3$) δ 7.34-7.18 (m, 7H), 7.13 (d, 2H, J=7.8), 6.25 (br s, 1H), 5.28 (s, 1H), 4.94 (d with fine splitting, 2H, J=13.0), 3.01 (s, 6H), 2.87 (dt, 2H, J=1.0, 13.0), 2.74 (tt, 1H, J=11.6, 1.5), 2.32 (s, 3H), 1.90 (d with fine splitting, 2H, J=12.0), 1.72 (ddd, 2H, J=13.0, 12.0, 1.5); ESI-MS m/z 388 (MH$^+$).

Example 82

N⁴,N⁴-DIMETHYL-N⁶-(4-METHYLPHENYL)-2-(3-PHENYL-4-MORPHOLINYL)-4,6-PYRIMIDINEDIAMINE

Prepared by Procedures H, E (150° C., 20 hours), and F (3 hours). $^1$H NMR (300 MHz, CDCl$_3$) δ 7.51 (d, 2H, J=7.8), 7.32 (t, 2H, J=7.8), 7.23 (t, 1H, J=7.8), 7.17 (d, 2H, J=7.8), 7.09 (d, 2H, J=7.8), 6.25 (br s, 1H), 5.88 (d, 1H, J=1.0), 5.27 (s, 1H), 4.49 (t, 2H, J=13.2), 3.94 (m, 2H), 3.66 (dt, 1H, J=1.0, 11.5), 3.24 (dt, 1H, J=1.5, 11.5), 2.97 (s, 6H), 2.32 (s, 3H); ESI-MS m/z 390 (MH$^+$).

Example 83

N⁴,N⁴-DIMETHYL-N⁶-(4-METHYLPHENYL)-2-(2-PHENYL-4-MORPHOLINYL)-4,6-PYRIMIDINEDIAMINE

Prepared by Procedures H, E (150° C., 20 hours), and F (3 hours). $^1$H NMR (300 MHz, CDCl$_3$) δ 7.47 (d, 2H, J=7.8), 7.38 (t, 2H, J=7.8), 7.33 (t, 1H, J=7.8), 7.19 (d, 2H, J=7.8), 7.11 (d, 2H, J=7.8), 6.22 (br s, 1H), 5.29 (s, 1H), 4.74 (dd, 1H, J=13.2, 1.0), 4.59-4.51 (m, 2H), 4.16-4.08 (m, 1H), 3.80 (dt, 1H, J=1.0, 11.9), 3.11 (dt, 1H, J=1.5, 12.4), 2.98 (s, 6H), 2.90 (dd, 1H, J=10.6, 11.9), 2.33 (s, 3H); ESI-MS m/z 390 (MH$^+$).

Example 84

N⁴,N⁴-DIMETHYL-N-(4-METHYLPHENYL)-2-{4-[(4-METHYLPHENYL)SULFONYL]-1-PIPERAZINYL}-4,6-PYRIMIDINEDIAMINE

Prepared by Procedures H, E (150° C., overnight), and F (3 hours). $^1$H NMR (300 MHz, CDCl$_3$) δ 7.65 (d, 2H, J=8.3), 7.31 (d, 2H, J=8.3), 7.15 (d, 2H, J=8.4), 7.11 (d, 2H, J=7.2), 6.20 (br s, 1H), 5.22 (s, 1H), 3.87 (t, 4H, J=4.2), 3.02 (t, 4H, J=4.2), 2.95 (s, 6H), 2.43 (s, 3H), 2.33 (s, 3H); ESI-MS m/z 467 (MH$^+$).

Example 85

N⁴,N⁴-DIMETHYL-N⁶-(4-METHYLPHENYL)-2-[4-(2-METHYLPHENYL)-1-PIPERAZINYL]-4,6-PYRIMIDINEDIAMINE

Prepared by Procedures D, E (160° C., 12 hours), and F (12 hours). $^1$H NMR (300 MHz, CDCl$_3$) δ 7.23-7.10 (m, 6H), 7.02.-6.96 (m, 2H), 6.28 (br s, 1H), 5.28 (s, 1H), 3.95-3.86 (m, 4H), 2.99 (s, 6H), 2.96-2.92 (m, 4H), 2.36 (s, 3H), 2.32 (s, 3H); ESI-MS m/z 403 (MH$^+$).

Example 86

N⁴,N⁴-DIMETHYL-N⁶-(4-METHYLPHENYL)-2-[4-(3-METHYLPHENYL)-1-PIPERAZINYL]-4,6-PYRIMIDINEDIAMINE

Prepared by Procedures D, E (160° C., 12 hours), and F (12 hours). $^1$H NMR (300 MHz, CDCl$_3$) δ 7.19 (d, 2H, J=7.8), 7.17 (t, 1H, J=7.8), 7.11 (d, 2H, J=7.8), 6.91 (s, 1H), 6.89 (d, 1H, J=7.8), 6.69 (d, 1H, J=7.8), 6.33 (br s, 1H), 5.29 (s, 1H), 3.93 (t, 4H, J=5.1), 3.22 (t, 4H, J=5.1), 3.01 (s, 6H), 2.33 (s, 6H); ESI-MS m/z 403 (MH$^+$).

Example 87

N⁴,N⁴-DIMETHYL-N⁶-(4-METHYLPHENYL)-2-[4-(4-METHYLPHENYL)-1-PIPERAZINYL]-4,6-PYRIMIDINEDIAMINE

Prepared by Procedures D, E (160° C., 36 hours), and F (8 hours). $^1$H NMR (300 MHz, CDCl$_3$) δ 7.19 (d, 2H, J=9.0), 7.16 (d, 2H, J=8.7), 7.10 (d, 2H, J=9.0), 6.90 (d, 2H, J=8.4), 6.24 (br s, 1H), 5.27 (s, 1H), 3.93 (t, 4H, J=4.8), 3.18 (t, 4H, J=5.1), 3.00 (s, 6H), 2.33 (s, 3H), 2.28 (s, 3H); ESI-MS m/z 403 (MH⁺);

Example 88

N⁴,N⁴-DIMETHYL-N⁶-(4-METHYLPHENYL)-2-{4-[3-(TRIFLUOROMETHYL)-2-PYRIDINYL]-1-PIPERAZINYL}-4,6-PYRIMIDINEDIAMINE

Prepared by Procedures H, E (16 hours), and F. $^1$H NMR (300 MHz, CDCl$_3$) δ 8.57 (dd, 1H, J=4.4, 2.2), 7.87 (dd, 1H, J=7.8, 2.2), 7.20 (d, 2H, J=8.1), 7.13 (d, 2H, J=8.1), 6.98 (dd, 1H, J=7.8, 4.4), 6.24 (br s, 1H), 5.28 (s, 1H), 3.90 (t, 4H, J=4.8), 3.36 (t, 4H, J=4.8), 3.00 (s, 6H), 2.32 (s, 3H); ESI-MS m/z 458 (MH⁺).

Example 89

N-(4-METHYLPHENYL)-2-(1-PIPERIDINYL)-6-{4-[3-(TRIFLUOROMETHYL)-2-PYRIDINYL]-1-PIPERAZINYL}-4-PYRIMIDINAMINE

Prepared by Procedures M, E (120° C., for addition of piperidine), and F. $^1$H NMR (300 MHz, CDCl$_3$) δ 8.43 (dd, 1H, J=4.4, 2.2), 7.87 (dd, 1H, J=7.8, 2.2), 7.19 (d, 2H, J=8.1), 7.12 (d, 2H, J=8.1), 6.99 (dd, 1H, J=7.8, 4.4), 6.28 (br s, 1H), 5.35 (s, 1H), 3.77-3.72 (m, 4H), 3.62 (t, 4H, J=4.8), 3.33 (t, 4H, J=4.8), 2.33 (s, 3H), 1.69-1.52 (m, 6H); ESI-MS m/z 498 (MH⁺).

Example 90

6-[2-(METHOXYMETHYL)-1-PIPERIDINYL]-N-(4-METHYLPHENYL)-2-{4-[3-(TRIFLUOROMETHYL)-2-PYRIDINYL]-1-PIPERAZINYL}-4-PYRIMIDINAMINE

Prepared by Procedures D, J (90° C., overnight), and F (2 hours). $^1$H NMR (300 MHz, CDCl$_3$) δ 8.44 (dd, 1H, J=4.4, 2.2), 7.88 (dd, 1H, J=7.8, 2.2), 7.20 (d, 2H, J=8.1), 7.12 (d, 2H, J=8.1), 6.99 (dd, 1H, J=7.8, 4.4), 6.23 (br s, 1H), 5.38 (s, 1H), 4.68-4.54 (m, 1H), 4.15-4.03 (m, 1H), 3.90 (t, 4H, J=4.8), 3.57 (t, 1H, J=9.7), 3.44-3.35 (m, 5H), 3.34 (s, 3H), 2.81 (t, 1H, J=12.0); 2.33 (s, 3H), 1.93-1.86 (m, 1H), 1.72-1.41 (m, 3H), 1.29-1.25 (m, 1H), 0.91-0.86 (m, 1H); ESI-MS m/z 542 (MH⁺).

Example 115

N-4-[3-(BENZYLOXY)PHENYL]-N-6-,N-6-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.23-8.19 (m, 1H), 7.52 (dt, 1H, J=1.9, 7.2), 7.43-7.20 (m, 7H), 6.96 (s, 1H), 6.88 (d, 1H, J=8.0), 6.80 (d, 1H, J=8.1), 6.69-6.63 (m, 2H), 5.34 (s, 1H), 5.03 (s, 2H), 4.03-3.97 (m, 4H), 3.66 (t, 4H, J=5.2), 3.02 (s, 6H); ESI-MS m/z 482 (MH⁺).

Example 116

4-{4-[4-(DIMETHYLAMINO)-6-(4-TOLUIDINO)-2-PYRIMIDINYL]-1-PIPERAZINYL}PHENOL

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 10.04 (s, 1H), 7.19-7.14 (m, 4H), 6.85-6.79 (m, 4H), 5.31 (s, 1H), 5.22 (s, 1H), 3.96 (t, 4H, J=5.1), 3.05 (t, 4H, J=5.0), 3.03 (s, 6H), 2.34 (s, 3H); FIAMS m/z 405 (MH⁺).

Example 117

N⁴-[4-(BENZYLOXY)PHENYL]-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.21 (dd, 1H, J=1.9, 5.6), 7.55-7.27 (m, 7H), 7.24-7.16 (m, 2H), 7.04-6.91 (m, 2H), 6.69-6.64 (m, 2H), 5.06 (s, 2H), 5.05 (s, 1H), 4.08-3.97 (m, 4H), 3.69 (t, 4H, J=5.1), 3.03 (s, 6H); ESI-MS m/z 482 (MH⁺).

Example 118

N⁴-(1,3-BENZODIOXOL-5-YL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.24-8.18 (m, 1H), 7.48 (dt, 1H, J=1.9, 8.1), 6.92 (d, 1H, J=1.9), 6.75 (d, 1H, J=8.2), 6.74-6.54 (m, 3H), 6.41 (br s, 1H), 5.95 (s, 2H), 5.16 (s, 1H), 3.89 (t, 4H, J=5.1), 3.60 (t, 4H, J=5.3), 2.99 (s, 6H); ESI-MS m/z 420 (MH⁺).

Example 119

N⁴-(2,3-DIHYDRO-1,4-BENZODIOXIN-6-YL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl$_2$, Et$_3$N, Me$_2$NHHCl, stirred 3.5 h at −78° C., warmed to 0° C. and stirred 3 h), N, and O. $^1$H NMR (400 MHz, CDCl$_3$) δ 8.24-8.18 (m, 1H), 7.49 (dt, 1H, J=2.1, 7.1), 6.89 (d, 1H, J=2.2), 6.81, (d, 1H, J=8.6), 6.76 (d, 1H, J=2.4), 6.68 (d, 1H, J=8.5), 6.62 (dd, 1H, J=4.6, 7.0), 6.18 (br s, 1H), 5.21 (s, 1H), 4.33-4.15 (m, 4H), 3.89 (t, 4H, J=5.1), 3.61 (t, 4H, J=5.1), 3.00 (s, 6H); ESI-MS m/z 434 (MH⁺).

Example 120

N¹-(4-ISOQUINOLINYL)-N⁶,N⁶-DIMETHYL-2-[4-(2-PYRIDINYL)-1-PIPERAZINYL]-4,6-PYRIMIDINEDIAMINE

Prepared by Procedures A (CH$_2$Cl, Et$_3$N, Me$_2$NHHCl, stirred 3.5 h at −78° C., warmed to 0° C. and stirred 3 h), N, and O. ¹H NMR (400 MHz, CDCl₃) δ 8.93 (d, 1H, J=1.5), 8.31 (d, 1H, J=2.6), 8.27-8.19 (m, 1H), 8.01 (d, 1H, J=8.2), 7.70 (d, 1H, J=7.8), 7.59-7.52 (m, 1H), 7.51-7.45 (m, 2H), 6.78 (br s, 1H), 6.68 (d, 1H, J=8.6), 6.63 (dd, 1H, J=5.0, 7.1), 5.29 (s, 1H), 3.94 (t, 4H, J=5.0), 3.63 (t, 4H, J=5.3), 3.01 (s, 6H); ESI-MS m/z 427 (MH⁺).

Example 121

N⁴-(4-CYCLOHEXYLPHENYL)-N⁶,N⁶-DIMETHYL-2-[4-(2-PYRIDINYL)-1-PIPERAZINYL]-4,6-PYRIMIDINEDIAMINE

Prepared by Procedures A (CH₂Cl₂, Et₃N, Me₂NHHCl, stirred 3.5 h at −78° C., warmed to 0° C. and stirred 3 h), N, and O. ¹H NMR (400 MHz, CDCl₃) δ 8.25-8.19 (m, 1H), 7.49 (dt, 1H, J=2.0, 6.9), 7.22 (d, 2H, J=6.4), 7.16 (d, 2H, J=8.2), 6.68 (d, 1H, J=8.6), 6.66-6.60 (m, 1H), 6.21 (br s, 1H), 5.30 (s, 1H), 3.99-3.91 (m, 4H), 3.63 (t, 4H, J=5.2), 3.02 (s, 6H), 2.53-2.42 (m, 1H), 1.92-1.79 (m, 4H), 1.48-1.32 (m, 4H), 1.31-1.19 (m, 2H); ESI-MS m/z 458 (MH⁺).

Example 122

N⁴,N⁴-DIMETHYL-2-[4-(2-PYRIDINYL)-1-PIPERAZINYL]-N⁶-(5,6,7,8-TETRAHYDRO-1-NAPHTHALENYL)-4,6-PYRIMIDINEDIAMINE

Prepared by Procedures A (CH₂Cl₂, Et₃N, Me₂NHHCl, stirred 3.5 h at −78° C., warmed to 0° C. and stirred 3 h), N, and O. ¹H NMR (400 MHz, CDCl₃) δ 8.20 (dd, 1H, J=1.3, 4.9), 7.50 (dt, 1H, J=2.2, 6.8), 7.17 (d, 1H, J=7.5), 7.09 (t, 1H, J=7.6), 6.94 (d, 1H, J=7.7), 6.73-6.62 (m, 2H), 5.06 (s, 1H), 4.08-3.93 (m, 4H), 3.66 (t, 4H, J=5.3), 3.00 (s, 6H), 2.79 (t, 2H, J=6.0), 2.72 (t, 2H, J=5.9), 1.88-1.67 (m, 4H), NH (1H, unobserved); ESI-MS m/z 430 (MH⁺).

Example 123

N⁴-(2,3-DIHYDRO-1H-INDEN-5-YL)-N⁶,N⁶-DIMETHYL-2-[4-(2-PYRIDINYL)-1-PIPERAZINYL]-4,6-PYRIMIDINEDIAMINE

Prepared by Procedures A (CH₂Cl₂, Et₃N, Me₂NHHCl, stirred 3.5 h at −78° C., warmed to 0° C. and stirred 3 h), N, and O. ¹H NMR (400 MHz, CDCl₃) δ 8.20 (d, 1H, J=4.8), 7.51 (dt, 1H, J=1.8, 6.9), 7.19 (d, 1H, J=7.6), 7.14 (s, 1H), 7.04 (dd, 1H, J=1.7, 7.7), 6.73-6.61 (m, 2H), 5.23 (s, 1H), 4.09-3.94 (m, 4H), 3.68 (t, 4H, J=5.9), 3.04 (s, 6H), 2.89 (t, 4H, J=7.8), 2.16-2.01 (m, 2H), NH (1H, unobserved); ESI-MS m/z 416 (MH⁺).

Example 124

N⁴-(3,4-DICHLOROPHENYL)-N⁶,N⁶-DIMETHYL-2-[4-(2-PYRIDINYL)-1-PIPERAZINYL]-4,6-PYRIMIDINEDIAMINE

Prepared by Procedures A (CH₂Cl₂, Et₃N, Me₂NHHCl, stirred 3.5 h at −78° C., warmed to 0° C. and stirred 3 h), N, and O. ¹H NMR (400 MHz, CDCl₃) δ 8.31-8.20 (m, 1H), 7.79-7.69 (m, 1H), 7.61-7.44 (m, 1H), 7.42-7.28 (m, 1H), 7.25-7.11 (m, 1H), 6.79-6.61 (m, 2H), 6.42 (br s, 1H), 5.22 (s, 1H), 3.98-3.82 (m, 4H), 3.65-3.56 (m, 4H), 3.02 (s, 6H); ESI-MS m/z 444 (MH⁺ with ³⁵Cl, ³⁵Cl), 446 (MH⁺ with ³⁵Cl, ³⁷Cl), 448 (MH⁺ with ³⁷Cl, ³⁷Cl).

Example 125

N⁴,N⁴-DIMETHYL-2-[4-(2-PYRIDINYL)-1-PIPERAZINYL]-N⁶-[3-(TRIFLUOROMETHYL)PHENYL]-4,6-PYRIMIDINEDIAMINE

Prepared by Procedures A (CH₂Cl₂, Et₃N, Me₂NHHCl, stirred 3.5 h at −78° C., warmed to 0° C. and stirred 3 h), N, and O. ¹H NMR (400 MHz, CDCl₃) δ 8.59 (br s, 1H), 8.24-8.18 (m, 1H), 7.86 (s, 1H), 7.78-7.22 (m, 4H), 6.65 (t, 2H, J=5.0), 5.29 (s, 1H), 3.96 (t, 4H, J=5.5), 3.64 (t, 4H, J=5.2), 3.03 (s, 6H); ESI-MS m/z 444 (MH⁺).

Example 126

2-(4-BENZYL-1-PIPERAZINYL)-N⁴-[3-(DIMETHYLAMINO)PHENYL]-N⁶,N⁶-DIMETHYL-4,6-PYRIMIDINEDIAMINE

Prepared by Procedures P (toluene, 95° C., 16 h), Q (dioxane, 120° C.), and A. ¹H NMR (400 MHz, CDCl₃) δ 7.52-7.37 (m, 7H), 7.25 (t, 1H, J=2.0), 7.14 (dd, 1H, J=1.5, 8.2), 7.05 (dd, 1H, J=2.5, 8.2), 4.36 (s, 2H), 3.98 (br s, 4H), 3.36 (s, 4H), 3.11 (s, 6H), 3.05 (s, 6H), 2.60 (s, 1H); ESI-MS m/z 432 (MH⁺).

Example 127

2-(4-BENZYL-1-PIPERAZINYL)-N⁴,N⁴-DIMETHYL-N⁶-(2-METHYL-1,3-BENZOTHIAZOL-5-YL)-4,6-PYRIMIDINEDIAMINE

Prepared by Procedures P (130° C., 13 h), Q, and A. ¹H NMR (400 MHz, CDCl₃) δ 8.12 (s, 1H), 7.87 (d, 1H, J=8.8), 7.52-7.38 (m, 6H), 5.58 (s, 1H), 4.58 (s, 1H), 4.30 (s, 2H), 3.79-3.42 (m, 4H), 3.22-2.91 (m, 4H), 3;09 (s, 6H), 2.98 (s, 3H); ESI-MS m/z 460 (MH⁺).

Example 128

2-(4-BENZYL-1-PIPERAZINYL)-N⁴-CYCLOHEPTYL-N⁶,N⁶-DIMETHYL-4,6-PYRIMIDINEDIAMINE

Prepared by Procedures P (140° C., toluene, 6 h), Q, and A. ¹H NMR (400 MHz, CDCl₃) δ 7.20-7.09 (m, 5H), 4.78 (s, 1H), 4.18 (br s, 1H), 3.74 (t, 4H, J=5.2), 3.52 (s, 2H), 2.99 (s, 6H), 2.46 (t, 4H, J=5.1), 2.03-1.92 (m, 2H), 1.87-1.68 (m, 11H); ESI-MS m/z 409 (MH⁺).

Example 129

4-{[2-(4-BENZYL-1-PIPERAZINYL)-6-(DIMETHYLAMINO)-4-PYRIMIDINYL]AMINO}-2-CHLOROBENZONITRILE

Prepared by Procedures P (toluene, 95° C., 16 h), Q (dioxane, 120° C.), and A. ¹H NMR (400 MHz, CDCl₃) δ 7.88 (d, 1H, J=3.1), 7.48 (d, 1H, J=8.5), 7.42-7.22 (m, 6H), 6.45 (s, 1H), 5.20 (s, 1H), 3.79 (t, 4H, J=5.2), 3.55 (s, 2H), 3.02 (s, 6H), 2.51 (t, 4H, J=5.0); ESI-MS m/z 448 (MH⁺ with ³⁵Cl), 450 (M^H+ with ³⁷Cl).

Example 130

2-(4-BENZYL-1-PIPERAZINYL)-N$^4$,N$^4$-DIMETHYL-N$^6$-(1,3,3-TRIMETHYLBICYCLO[2.2.1]HEPT-2-YL)-4,6-PYRIMIDINEDIAMINE

Prepared by procedures P (toluene, 95° C., 16 h), Q (dioxane, 120° C.), and A. $^1$H NMR (400 MHz, CDCl$_3$) δ 7.38-7.21 (m, 6H), 4.87 (s, 1H), 3.79-3.69 (m, 4H), 3.53 (s, 2H), 3.46 (s, 1H), 2.98 (s, 6H), 2.46 (t, 4H, J=5.1), 1.71 (S, 1H), 1.69-1.62 (m, 2H), 1.48-1.35 (m, 2H), 1.20 (d, 1H, J=10.2), 1.19-1.02 (m, 1H), 1.14 (s, 3H), 1.07 (s, 3H), 0.79 (s, 3H); ESI-MS m/z 449 (MH$^+$).

Example 131

2-{4-[3-(BENZYLOXY)PHENYL]-1-PIPERAZINYL}-N$^4$,N$^4$-DIMETHYL-N$^6$-(4-METHYLPHENYL)-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 M4 Hz, CDCl$_3$) δ 7.44 (d, 2H, J=7.1), 7.36 (t, 2H, J=7.0), 7.29 (d, 1H, J=7.1), 7.22-7.04 (m, 5H), 6.58-6.52 (m, 2H), 6.48 (d, 1H, J=7.2), 5.29 (s, 1H), 5.21 (s, 1H), 5.03 (s, 2H), 3.89-3.80 (m, 4H), 3.28-3.15 (m, 4H), 3.00 (s, 6H), 2.30 (s, 3H); ESI-MS m/z 495 (MH$^+$).

Example 132

N$^4$,N$^4$-DIMETHYL-2-[4-(2-PYRIDINYL)-1-PIPERAZINYL]-N$^6$-(3-QUINOLINYL)-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.93 (d, 1H, J=2.6), 8.31 (d, 1H, J=2.5), 8.26-8.18 (m, 1H), 8.02 (d, 1H, J=8.2), 7.71 (d, 1H, J=7.7), 7.57 (dt, 1H, J=1.5, 5.3), 7.53-7.46 (m, 2H), 6.68 (d, 1H, J=8.6), 6.64 (dd, 1H, J=4.9, 7.1), 5.30 (d, 2H, J=3.7), 3.94 (t, 4H, J=4.9), 3.64 (t, 4H, J=5.4), 3.03 (s, 6H); ESI-MS m/z 427 (MH$^+$).

Example 133

N$^4$-[4-BROMO-3-(TRIFLUOROMETHYL)PHENYL]-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.23-8.19 (m, 1H), 8.17 (d, 1H, J=2.3), 7.57 (d, 1H, J=8.7), 7.53-7.47 (m, 1H), 7.39 (d, 1H, J=5.2), 6.69 (d, 1H, J=8.7), 6.64 (t, 1H, J=5.0), 6.27 (s, 1H), 5.19 (s, 1H), 3.94-3.87 (m, 4H), 3.65-3.59 (m, 4H), 3.04 (s, 6H); ESI-MS m/z 522 (MH$^+$ with $^{79}$Br), 524 (MH$^+$ with $^{81}$Br).

Example 134

N$^4$-{3-CHLORO-4-[(TRIFLUOROMETHYL)SULFANYL]PHENYL}-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.23-8.19 (m, 1H), 7.91 (d, 1H, J=2.3), 7.61 (d, 1H, J=8.5), 7.50 (dt, 1H, J=2.1, 8.5), 7.30-7.20 (m, 1H), 6.70 (d, 1H, J=9.1), 6.64 (dd, 1H, J=4.7, 7.1), 6.35 (br s, 1H), 5.26 (s, 1H), 3.92 (t, 4H, J=5.6), 3.64 (t, 4H, J=5.0), 3.06 (s, 6H); ESI-MS m/z 510 (MH$^+$ with $^{35}$Cl), 512 (MH$^+$ with $^{37}$Cl).

Example 135

N$^4$-(3-ETHOXYPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.28-8.19 (m, 1H), 7.50 (dt, 1H, J=2.1, 6.9), 7.19 (t, 1H, J=8.1), 6.96 (t, 1H, J=2.1), 6.85 (d, 1H, J=8.2), 6.68 (d, 1H, J=8.6), 6.63-6.56 (m, 1H), 6.35 (br s, 1H), 5.36 (s, 1H), 4.09-3.98 (m, 2H), 3.91 (t, 4H, J=5.3), 3.61 (t, 4H, J=5.1), 3.02 (s, 6H), 1.39 (t, 3H, J=5.7); ESI-MS m/z 420 (MH$^+$).

Example 136

N$^4$-[2-CHLORO-4-(TRIFLUOROMETHYL)PHENYL]-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.23-8.15 (m, 1H), 8.15 (d, 1H, J=2.1), 7.50 (dt, 1H, J=2.0, 8.8), 7.42-7.33 (m, 2H), 6.69 (d, 1H, J=8.6), 6.64 (dd, 1H, J=4.8, 6.3), 6.28 (s, 1H), 5.18 (s, 1H), 3.91 (t, 4H, J=5.0), 3.62 (t, 4H, J=5.1), 3.04 (s, 6H); ESI-MS m/z 478 (MH$^+$ with $^{35}$Cl), 480 (MH$^+$ with $^{37}$Cl).

Example 137

N-4-(2-ADAMANTYL)-2-(4-BENZYL-1-PIPERAZINYL)-N$^6$-N$^6$-DIMETHYL-4,6-PYRIMIDINEDIAMINE

Prepared by Procedures P (toluene, 90° C.), Q, and A. $^1$H NMR (400 MHz, CDCl$_3$) δ 7.39-7.21 (m, 5H), 4.83 (s, 1H), 4.72 (br s, 1H), 3.74 (m, 3H), 3.52 (s, 2H), 2.98 (s, 6H), 2.46 (t, 4H, J=5.3), 2.05-1.53 (m, 13H); ESI-MS m/z: 433 (MH$^+$).

Example 138

N-4-(1-NORADAMANTYL)-2-(4-BENZYL-1-PIPERAZINYL)-N-6-N-6-DIMETHYL-4,6-PYRIMIDINEDIAMINE

Prepared by Procedures P (toluene, 90° C.), Q, and A. $^1$H NMR (400 MHz, CDCl$_3$) δ 7.38-7.20 (m, 5H), 4.97 (s, 1H), 4.67 (br s, 1H), 3.74 (s, 4H), 3.52 (s, 2H), 2.99 (s, 6H), 2.46 (t, 4H, J=5.2), 2.32-1.51 (m, 15H); ESI-MS m/z: 447 (MH$^+$).

Example 139

2-(4-BENZYL-1-PIPERAZINYL)-N$^4$,N$^4$-DIMETHYL-N$^6$-[(1S,2R,3R,5S)-2,6,6-TRIMETHYLBICYCLO[3.1.1]HEPT-3-YL]-4,6-PYRIMIDINEDIAMINE

Prepared by Procedures P (toluene, 150° C., 4 h), Q (neat, 130° C.), and A. $^1$H NMR (400 MHz, CDCl$_3$) δ 7.38-7.21 (m, 5H), 4.86 (s, 1H), 4.35 (br s, 1H), 3.75 (t, 4H, J=4.6), 3.53 (s, 2H), 2.99 (s, 6H), 2.66-2.56 (m, 1H), 2.47 (t, 4H, J=4.5), 2.41-2.33 (m, 1H), 1.98-1.92 (m, 1H), 1.83 (t, 1H, J=5.8), 1.68-1.60 (m, 2H), 1.23 (s, 3H), 1.14 (d, 3H, J=7.3), 1.05 (s, 3H), 0.92 (d, 2H); ESI-MS m/z: 449 (MH$^+$).

Example 140

2-[4-(5-BROMO-2-PYRIDINYL)-1-PIPERAZINYL]-N$^4$,N$^4$-DIMETHYL-N$^6$-(4-METHYLPHENYL)-4,6-PYRIMIDINEDIAMINE

Prepared using Procedure Y (DMF). $^1$H NMR (400 MHz, CDCl$_3$) δ 8.21 (d, 1H, J=2.6), 7.53 (dd, 1H, J=2.6, 8.8), 7.19 (d, 2H, J=8.5), 7.12 (d, 2H, J=8.5), 6.21 (s, 1H), 5.28 (s, 1H), 3.88 (t, 4H, J=5.0), 3.58 (t, 4H, J=5.2), 3.00 (s, 6H), 2.33 (s, 3H); ESI-MS m/z: 468 (MH$^+$ with $^{79}$Br), 470 (MH$^+$ with $^{81}$Br).

Example 141

6-{4-[4-(DIMETHYLAMINO)-6-(4-TOLUDINO)-2-PYRIMIDINYL]-1-PIPERAZINYL}NICOTINAMIDE

Prepared by Procedure Y (DMF). $^1$H NMR (400 MHz, CDCl$_3$) δ 8.13 (s, 1H), 7.30-7.25 (m, 4H), 7.17 (d, 2H, J=8.5), 7.13 (d, 2H, J=8.6), 6.18 (br s, 1H), 5.28 (s, 1H), 3.82 (t, 2H, J=5.1), 3.79 (t, 2H, J=5.3), 3.60 (t, 2H, J=5.1), 3.41 (t, 2H, J=5.3), 2.99 (s, 6H), 2.33 (s, 3H); ESI-MS m/z: 433 (MH$^+$).

Example 142

2-[4-(3-METHOXYBENZYL)-1-PIPERAZINYL]-N$^4$,N$^4$-DIMETHYL-N$^6$-(4-METHYLPHENYL)-4,6-PYRIMIDINEDIAMINE

Prepared by Procedure Z (DIEA). $^1$H NMR (400 MHz, CDCl$_3$) δ 7.22 (d, 1H, J=6.8), 7.17 (d, 2H, J=8.3), 7.10 (d, 2H, J=8.2), 6.93 (d, 1H, J=2.3), 6.92 (d, 1H, J=2.4), 6.80 (dd, 1H, J=2.0, 7.6), 6.18 (br s, 1H), 5.25 (s, 1H), 3.82 (s, 3H), 3.78 (t, 4H, J=5.1), 3.52 (s, 2H), 2.97 (s, 6H), 2.49 (t, 4H, J=5.1), 2.31 (s, 3H); ESI-MS m/z: 433 (MH$^+$).

Example 143

2-[4-(5-BROMO-2-PYRIDINYL)-1-PIPERAZINYL]-N$^4$-(3-METHOXYPHENYL)-N$^6$,N$^6$-DIMETHYL-4,6-PYRIMIDINEDIAMINE

Prepared by Procedure Y. $^1$H NMR (400 MHz, CDCl$_3$) δ 8.21 (d, 1H, J=2.4), 7.53 (dd, 1H, J=2.5, 9.2), 7.20 (t, 1H, J=8.1), 7.00 (t, 1H, J=2.0), 6.85 (dd, 1H, J=2.0, 8.0), 6.62-6.54 (m, 2H), 6.29 (s, 1H), 5.36 (s, 1H), 3.89 (t, 4H, J=5.1), 3.80 (s, 3H), 3.58 (t, 4H, J=4.9), 3.02 (s, 6H); ESI-MS m/z: 484 (MH$^+$ with $^{79}$Br), 486 (MH$^+$ with $^{81}$Br).

Example 144

N$^4$-(3-METHOXYPHENYL)-N$^6$,N$^6$-DIMETHYL-2-[4-(2-PYRIDINYLMETHYL)-1-PIPERAZINYL]-4,6-PYRIMIDINEDIAMINE

Prepared by Procedure X. $^1$H NMR (400 MHz, CDCl$_3$) δ 8.61-8.54 (m, 1H), 7.66 (dt, 1H, J=1.8, 7.8), 7.45 (d, 1H, J=7.8), 7.23-7.14 (m, 2H), 7.00 (t, 1H, J=2.5), 6.87-6.78 (m, 1H), 6.61-6.54 (m, 1H), 6.26 (br s, 1H), 5.33 (s, 1H), 3.82 (t, 4H, J=5.0), 3.78 (s, 3H), 3.70 (s, 2H), 2.99 (s, 6H), 2.56 (t, 4H, J=5.0); ESI-MS m/z: 420 (MH$^+$).

Example 145

2-[4-(CYCLOHEXYLMETHYL)-1-PIPERAZINYL]-N$^4$-(3-METHOXYPHENYL)-N$^6$,N$^6$-DIMETHYL-4,6-PYRIMIDINEDIAMINE

Prepared by Procedure T. $^1$H NMR (400 MHz, CDCl$_3$) δ 7.21 (t, 1H, J=8.2), 7.00-6.95 (m, 1H), 6.85 (d, 1H, J=8.2), 6.59 (d, 1H, J=7.7), 6.32 (s, 1H), 5.36 (s, 1H), 3.82-3.71 (m, 4H), 3.79 (s, 3H), 3.69-3.62 (m, 2H), 3.58-3.50 (m, 2H), 3.01 (s, 6H), 2.54-2.45 (m, 1H), 1.87-1.48 (m, 8H), 1.45-1.29 (m, 4H); ESI-MS m/z: 425 (MH$^+$).

Example 146

N$^4$-(3-METHOXYPHENYL)-N$^6$,N$^6$-DIMETHYL-2-[4-(3-THIENYLMETHYL)-1-PIPERAZINYL]-4,6-PYRIMIDINEDIAMINE

Prepared by Procedures T (reduction 4 h) and W. $^1$H NMR (400 MHz, CDCl$_3$) δ 7.27 (dd, 1H, J=3.2, 5.1), 7.19 (t, 1H, J=8.0), 7.16-7.11 (m, 1H), 7.08 (dd, 1H, J=1.3, 4.9), 7.00 (t, 1H, J=2.3), 6.82 (dd, 1H, J=2.0, 8.3), 6.57 (dd, 1H, J=2.5, 8.2), 6.25 (s, 1H), 5.33 (s, 1H), 3.79 (t, 4H, J=5.5), 3.78 (s, 3H), 3.57 (s, 2H), 2.99 (s, 6H), 2.48 (t, 4H, J=5.2); ESI-MS m/z: 425 (MH$^+$).

Example 147

N$^4$-(3-METHOXYPHENYL)-N$^6$,N$^6$-DIMETHYL-2-[4-(4-PYRIDINYLMETHYL)-1-PIPERAZINYL]-4,6-PYRIMIDINEDIAMINE

Prepared by Procedure T (acylation with DIPEA). $^1$H NMR (400 MHz, CDCl$_3$) δ 8.55 (dd, 2H, J=1.5, 5.8), 7.31 (d, 2H, J=6.0), 7.19 (t, 1H, J=8.3), 6.99 (t, 1H, J=2.1), 6.83 (dd, 1H, J=1.5, 7.8), 6.58 (dd, 1H, J=2.0, 7.8), 6.28 (br s, 1H), 5.34 (s, 1H), 3.80 (t, 4H, J=5.2), 3.78 (s, 3H), 3.54 (s, 2H), 3.00 (s, 6H), 2.49 (t, 4H, J=5.3; ESI-MS m/z: 420 (MH$^+$).

Example 148

2-[4-(3-METHOXYBENZYL)-1-PIPERAZINYL]-N$^4$-(3-METHOXYPHENYL)-N$^6$,N$^6$-DIMETHYL-4,6-PYRIMIDINEDIAMINE

Prepared by Procedure S. $^1$H NMR (400 MHz, CDCl$_3$) δ 7.22 (d, 1H, J=7.9), 7.17 (t, 1H, J=8.2), 6.99 (t, 1H, J=2.1), 6.95-6.84 (m, 2H), 6.86-6.78 (m, 2H), 6.59-6.55 (m, 1H), 6.29 (br s, 1H), 5.32 (s, 1H), 3.82 (s, 3H), 3.79 (t, 4H, J=5.1), 3.77 (s, 3H), 3.52 (s, 2H), 2.99 (s, 6H), 2.49 (t, 4H, J=5.1); ESI-MS m/z: 449 (MH$^+$).

Example 149

N$^2$-[2-(3-METHOXYPHENYL)ETHYL]-N$^4$,N$^4$-DIMETHYL-N$^6$-(4-METHYLPHENYL)-2,4,6-PYRIMIDINETRIAMINE

Prepared by Procedure F (dioxane, potassium tert-butoxide, 120° C., 16 h), Q (toluene, TEA, 120° C.), A (CH$_2$Cl$_2$, Δ, TEA). $^1$H NMR (400 MHz, CDCl$_3$) δ 7.22 (t, 1H, J=7.9), 7.18 (d, 2H, J=8.4), 7.12 (d, 2H, J=8.3), 6.84 (d, 1H, J=7.6), 6.82-6.74 (m, 2H), 6.28 (br s, 1H), 5.28 (s, 1H), 4.77 (s, 1H), 3.80 (s, 3H), 3.63 (q, 2H, J=6.7), 2.99 (s, 6H), 2.89 (t, 2H, J=7.4), 2.32 (s, 3H); ESI-MS m/z: 378 (MH$^+$).

Example 150

N²-[2-(2-METHOXYPHENYL)ETHYL]-N⁴,N⁴-DIMETHYL-N⁶-(4-METHYLPHENYL)-2,4,6-PYRIMIDINETRIAMINE

Prepared by Procedures F (dioxane, potassium tert-butoxide, 140° C., 16 h), Q (toluene), and A (CH₂Cl₂, Δ, TEA). ¹H NMR (400 MHz, CDCl₃) δ 7.23-7.12 (m, 4H), 7.12 (d, 2H, J=8.1), 6.89 (d, 1H, J=7.8), 6.86 (d, 1H, J=7.6), 6.61 (d, 1H, J=8.0), 6.50 (br s, 1H), 5.25 (s, 1H), 3.84 (s, 3H), 3.60 (q, 2H, J=7.1), 3.00 (s, 6H), 2.93 (t, 2H, J=7.6), 2.33 (s, 3H); ESI-MS m/z: 378 (MH⁺).

Example 151

2-(4-BENZYL-1-PIPERAZINYL)-N⁴-(3,4-DICHLOROPHENYL)-N⁶,N⁶-DIMETHYL-4,6-PYRIMIDINEDIAMINE

Prepared by Procedures P (toluene, 140° C., 6 h), Q (dioxane, 120° C.), and A. ¹H NMR (400 MHz, CDCl₃) δ 7.65 (d, 1H, J=2.5), 7.35-7.30 (m, 4H), 7.29-7.22 (m, 2H), 7.13 (dd, 1H, J=1.5, 8.5), 6.19 (br s, 1H), 5.21 (s, 1H), 3.78 (t, 4H, J=5.0), 3.55 (s, 2H), 3.00 (s, 6H), 2.49 (t, 4H, J=5.0); ESI-MS m/z: 457 (MH⁺ with ³⁵Cl, ³⁵Cl), 459 (MH⁺ with ³⁵Cl, ³⁷Cl), 461 (MH⁺ with ³⁷ Cl, ³⁷Cl).

Example 152

N⁴-[4-(BENZYLOXY)CYCLOHEXYL]-2-(4-BENZYL-1-PIPERAZINYL)-N⁶,N⁶-DIMETHYL-4,6-PYRIMIDINEDIAMINE

Prepared by Procedures P (16 h), Q, and A. ¹H NMR (400 MHz, CDCl₃) δ 7.42-7.18 (m, 10H), 4.94 (s, 1H), 4.61 (d, 1H, J=11.8), 4.51 (d, 1H, J=11.8), 4.39 (br s, 1H), 3.75 (t, 4H, J=5.0), 3.53 (s, 2H), 3.31 (dt, 1H, J=5.3, 8.3), 2.95 (s, 6H), 2.46 (t, 4H, J=5.0), 2.19-2.11 (m, 1H), 2.07-1.98 (m, 1H), 1.79-1.56 (m, 3H), 1.53-1.41 (m, 1H), 1.40-1.21 (m, 3H); ESI-MS m/z: 501 (MH⁺).

Example 153

2-(4-BENZYL-1-PIPERAZINYL)-N⁴,N⁴-DIMETHYL-N⁶-[(1R,2R,4R)-1,7,7-TRIMETHYLBICYCLO[2.2.1]HEPT-2-YL]-4,6-PYRIMIDINEDIAMINE

Prepared by Procedures P (90° C., 16 h), Q, and A. ¹H NMR (400 MHz, CDCl₃) δ 7.44-7.22 (m, 6H), 4.81 (s, 1H), 4.36 (d, 1H, J=7.0), 3.74 (s, 4H), 3.53 (s, 2H), 2.98 (s, 6H), 2.46 (t, 4H, J=5.1), 1.84 (dd, 1H, J=8.9, 12.9), 1.78-1.52 (m, 4H), 1.29-1.11 (m, 2H), 0.97 (s, 3H), 0.89 (s, 3H), 0.83 (s, 3H); ESI-MS m/z: 449 (MH⁺).

Example 154

N⁴,N⁴-DIMETHYL-N⁶-(4-METHYLPHENYL)-2-[4-(TETRAHYDRO-2-FURANYLMETHYL)-1-PIPERAZINYL]-4,6-PYRIMIDINEDIAMINE

Prepared by Procedures A, P (16 h), and Q (dioxane, 120° C.). ¹H NMR (400 MHz, CDCl₃) δ 7.17 (d, 2H, J=8.4), 7.11 (d, 2H, J=8.0), 6.22 (br s, 1H), 5.29 (s, 1H), 4.12-4.03 (m, 1H), 3.91 (q, 1H, J=6.7), 3.80 (t, 4H, J=5.1), 3.76 (q, 1H, J=7.5), 2.98 (s, 6H), 2.57 (t, 4H, J=5.0), 2.56-2.40 (m, 2H), 2.32 (s, 3H), 2.05-1.96 (m, 1H), 1.94-1.80 (m, 2H), 1.57-1.45 (m, 1H); ESI-MS m/z: 397 (MH⁺).

Example 155

3-{[2-(4-BENZYL-1-PIPERAZINYL)-6-(DIMETHYLAMINO)-4-PYRIMIDINYL]AMINO}PHENOL

Prepared By Procedures P (Toluene, 120° C., 40 H), Q (dioxane, 120° C.), AND A. ¹H NMR (400 MHz, CDCl₃) δ 7.38-7.29 (m, 4H), 7.28-7.26 (m, 1H), 7.13 (t, 1H, J=8.0), 6.84 (t, 1H, J=2.8), 6.80 (ddd, 1H, J=0.7, 2.0, 7.9), 6.48 (ddd, 1H, J=0.7, 2.1, 8.0), 6.32 (br s, 1H), 5.32 (s, 1H), 3.79 (t, 4H, J=5.0), 3.55 (s, 2H), 3.49 (s, 1H), 2.99 (s, 6H), 2.50 (t, 4H, J=5.0); ESI-MS m/z: 405 (MH⁺).

Example 156

2-(4-BENZYL-1-PIPERAZINYL)-N⁴-(4-FLUOROPHENYL)-N⁶,N⁶-DIMETHYL-4,6-PYRIMIDINEDIAMINE

Prepared by Procedures P (toluene, sodium tert-butoxide, 120° C., 16 h), Q (dioxane, 120° C.), and A. ¹H NMR (400 MHz, CDCl₃) δ 7.37-7.30 (m, 4H), 7.29-7.21 (m, 3H), 6.99 (t, 2H, J=8.6), 6.14 (br s, 1H), 5.13 (s, 1H), 3.77 (t, 4H, J=4.9), 3.54 (s, 2H), 2.97 (s, 6H), 2.48 (t, 4H, J=4.9); ESI-MS m/z: 407 (MH⁺).

Example 157

2-(4-BENZYL-1-PIPERAZINYL)-N⁴,N⁴-DIMETHYL-N⁶-(4-METHYLCYCLOHEXYL)-4,6-PYRIMIDINEDIAMINE

Prepared by Procedures P (sodium tert-butoxide, toluene, 120° C., 16 h), Q (dioxane, 120° C.), and A. ¹H NMR (400 MHz, CDCl₃) δ 7.35-7.10 (m, 6H), 4.82 (d, 1H, J=4.9), 3.81-3.61 (m, 5H), 3.53 (s, 2H), 2.99 (s, 6H), 2.46 (t, 4H, J=4.5), 1.79-1.46 (m, 7H), 1.29-0.98 (m, 2H), 0.90 (d, 3H, J=6.6); ESI-MS m/z: 409 (MH⁺).

Example 158

2-(4-BENZYL-1-PIPERAZINYL)-N⁴-[4-(DIMETHYLAMINO)PHENYL]-N⁶,N⁶-DIMETHYL-4,6-PYRIMIDINEDIAMINE

Prepared by Procedures P (sodium tert-butoxide, toluene, 120° C., 16 h), Q (neat, 130° C.) and A. ¹H NMR (400 MHz, CDCl₃) δ 7.39-7.22 (m, 5H), 7.14 (d, 2H, J=8.4), 6.71 (d, 2H, J=8.8), 6.04 (br s, 1H), 5.08 (s, 1H), 3.85-3.74 (m, 4H), 3.54 (s, 2H), 2.94 (s, 6H), 2.93 (s, 6H), 2.48 (t, 4H, J=5.1); ESI-MS m/z: 432 (MH⁺).

Example 159

N⁴,N⁴-DIMETHYL-N⁶-(4-METHYLPHENYL)-2-[4-(2-PHENYLETHYL)-1-PIPERAZINYL]-4,6-PYRIMIDINEDIAMINE

Prepared by Procedure S (toluene, 120° C.). ¹H NMR (400 MHz, CDCl₃) δ 7.34-7.20 (m, 5H), 7.18 (d, 2H, J=8.5), 7.12 (d, 2H, J=8.5), 6.21 (br s, 1H), 5.26 (s, 1H), 3.88-3.79 (m, 4H), 2.99 (s, 6H), 2.90-2.83 (m, 2H), 2.68-2.63 (m, 2H), 2.60 (t, 4H, J=4.4), 2.32 (s, 3H); ESI-MS m/z: 417 (MH⁺).

Example 160

2-(4-BENZYL-1-PIPERAZINYL)-N$^4$-(3-CHLOROPHENYL)-N$^6$,N$^6$-DIMETHYL-4,6-PYRIMIDINEDIAMINE

Prepared by Procedures P (toluene, sodium tert-butoxide, 120° C., 40 h), Q (dioxane, 120° C.), and A. $^1$H NMR (400 MHz, CDCl$_3$) δ 7.48 (t, 1H, J=1.9), 7.38-7.23 (m, 5H), 7.20-7.11 (m, 2H), 6.95 (ddd, 1H, J=1.2, 1.9, 7.6), 6.28 (br s, 1H), 5.24 (s, 1H), 3.79 (t, 4H, J=5.0), 3.54 (s, 2H), 3.00 (s, 6H), 2.49 (t, 4H, J=5.0); ESI-MS m/z: 423 (MH$^+$ with $^{35}$Cl), 425 (MH$^+$ with $^{37}$Cl).

Example 161

N$^2$,N$^4$,N$^4$-TRIMETHYL-N$^6$-(4-METHYLPHENYL)-N$^2$-[2-(2-PYRIDINYL)ETHYL]-2,4,6-PYRIMIDINETRIAMINE

Prepared by Procedures F (dioxane, potassium tert-butoxide, 140° C., 16 h), Q, and A (CH$_2$Cl$_2$, Δ, TEA). $^1$H NMR (400 MHz, CDCl$_3$) δ 8.54 (ddd, 1H, J=1.2, 2.1, 5.3), 7.57 (dt, 1H, J=1.7, 7.6), 7.23 (d, 2H, J=8.6), 7.18 (d, 1H, J=7.7), 7.14-7.09 (m, 1H), 7.10 (d, 2H, J=7.7), 6.29 (br s, 1H), 5.24 (s, 1H), 3.93. (dd, 2H, J=5.9, 7.8), 3.11 (dd, 2H, J=6.0, 7.7), 3.08 (s, 3H), 3.00 (s, 6H), 2.32 (s, 3H); ESI-MS m/z: 363 (MH$^+$).

Example 162

N$^4$,N$^4$-DIMETHYL-N$^6$-(4-METHYLPHENYL)-N$^2$-(3-PHENYLPROPYL)-2,4,6-PYRIMIDINETRIAMINE

Prepared using Procedures R, S, and V. $^1$H NMR (400 MHz, CDCl$_3$) δ 7.25 (d, 2H, J=7.7), 7.22-7.14 (m, 5H), 7.11 (d, 2H, J=8.1), 6.41 (br s, 1H), 5.27 (s, 1H), 4.76 (t, 1H, J=5.7), 3.41 (dd, 2H, J=7.0, 12.9), 2.96 (s, 6H), 2.70 (t, 2H, J=7.7), 2.31 (s, 3H), 1.91 (t, 2H, J=7.5); ESI-MS m/z: 362 (MH$^+$).

Example 163

2-(4-CYCLOHEXYL-1-PIPERAZINYL)-N$^4$-(3-METHOXYPHENYL)-N$^6$,N$^6$-DIMETHYL-4,6-PYRIMIDINEDIAMINE

Prepared using Procedures P (16 h), Q (dioxane, 120° C.), and A. $^1$H NMR (400 MHz, CDCl$_3$) δ 7.11 (t, 1H, J=8.3), 6.92 (t, 1H, J=2.4), 6.78-6.73 (m, 1H), 6.53-6.48 (m, 1H), 6.39 (br s, 1H), 5.27 (s, 1H), 3.72 (t, 4H, J=5.0), 3.71 (s, 3H), 2.92 (s, 6H), 2.55 (t, 4H, J=5.1), 2.28-2.18 (m, 1H), 1.87-1.79 (m, 2H), 1.77-1.68 (m, 2H), 1.56 (d, 1H, J=12.4), 1.24-1.08 (m, 4H), 1.08-0.97 (m, 1H); ESI-MS m/z: 411 (MH$^+$).

Example 164

2-(4-BENZYL-1-PIPERAZINYL)-N$^4$-(3-FLUOROPHENYL)-N$^6$,N$^6$-DIMETHYL-4,6-PYRIMIDINEDIAMINE

Prepared by Procedures P (140° C., 4 h), Q (neat, 130° C.), and A. $^1$H NMR (400 MHz, CDCl$_3$) δ 7.37-7.31 (m, 5H), 7.28-7.17 (m, 2H), 6.98. (ddd, 1H, J=0.7, 2.0, 8.1), 6.67 (ddt, 1H, J=0.9, 2.0, 8.3), 6.30 (br s, 1H), 5.27 (s, 1H), 3.79 (t, 4H, J=5.1), 3.55 (s, 2H), 3.00 (s, 6H), 2.50 (t, 4H, J=5.0); ESI-MS m/z: 407 (MH$^+$).

Example 165

N$^4$-(3-METHOXYPHENYL)-N$^6$,N$^6$-DIMETHYL-2-[4-(2-THIENYLMETHYL)-1-PIPERAZINYL]-4,6-PYRIMIDINEDIAMINE

Prepared by Procedure T. $^1$H NMR (400 MHz, CDCl$_3$) δ 7.24 (dd, 1H, J=1.2, 5.2), 7.19 (t, 1H, J=8.1), 6.99 (t, 1H, J=2.0), 6.96-6.91 (m, 2H), 6.83 (ddd, 1H, J=0.8, 1.7, 7.9), 6.57 (dd, 1H, J=2.0, 8.2), 6.25 (br s, 1H), 5.33 (s, 1H), 3.81 (t, 4H, J=5.2), 3.78 (s, 3H), 3.76 (s, 2H), 2.99 (s, 6H), 2.53 (t, 4H, J=5.1); ESI-MS m/z: 425 (MH$^+$).

Example 166

2-[4-(2-METHOXYBENZYL)-1-PIPERAZINYL]-N$^4$-(3-METHOXYPHENYL)-N$^6$,N$^6$-DIMETHYL-4,6-PYRIMIDINEDIAMINE

Prepared by Procedure T (reduction 3 h). $^1$H NMR (400 MHz, CDCl$_3$) δ 7.40 (dd, 1H, J=1.6, 7.6), 7.23 (dd, 1H, J=1.2, 7.6), 7.19 (t, 1H, J=8.3), 7.01 (t, 1H, J=1.9), 6.95 (dt, 1H, J=1.0, 7.3), 6.87 (dd, 1H, J=1.1, 8.3), 6.82 (ddd, 1H, J=1.0, 2.0, 8.2), 6.57 (ddd, 1H, J=0.7, 2.5, 8.2), 6.26 (br s, 1H), 5.32 (s, 1H), 3.82 (s, 3H), 3.81 (t, 4H, J=5.1), 3.78 (s, 3H), 3.62 (s, 2H), 2.99 (s, 6H), 2.55 (t, 4H, J=5.0); ESI-MS m/z: 449 (MH$^+$).

Example 167

2-(4-BENZYL-1-PIPERAZINYL)-N$^4$,N$^4$-DIMETHYL-N$^6$-[(1R,2S)-1,7,7-TRIMETHYLBICYCLO[2.2.1]HEPT-2-YL]-4,6-PYRIMIDINEDIAMINE

Prepared by Procedures P (toluene, 120° C., 16 h), Q (neat, 130° C.), and A. $^1$H NMR (400 MHz, CDCl$_3$) δ 7.37-7.22 (m, 5H), 4.82 (s, 1H), 4.51 (br s, 1H), 3.74 (m, 4H), 3.53 (s, 2H), 2.97 (s, 6H), 2.47 (t, 4H, J=4.7), 2.39-2.30 (m, 1H), 1.76-1.68 (m, 4H), 1.66 (t, 1H, J=4.7), 1.41-1.31 (m. 2H), 0.96 (s, 3H), 0.88 (s, 3H), 0.86 (s, 3H); ESI-MS m/z: 449 (MH$^+$).

Example 168

N$^4$-(2-ADAMANTYL)-2-(4-BENZYL-1-PIPERAZINYL)-N$^6$,N$^6$-DIMETHYL-4,6-PYRIMIDINEDIAMINE

Prepared by Procedures P (90° C., toluene), Q, and A. $^1$H NMR (400 MHz, CDCl$_3$) δ 7.39-7.21 (m, 5H), 4.83 (s, 1H), 4.72 (br s, 1H), 3.74 (m, 5H), 3.52 (s, 2H), 2.98 (s, 6H), 2.46 (t, 4H, J=5.3), 2.05-1.53 (m, 14H); ESI-MS m/z: 447 (MH$^+$).

Example 169

2-(4-BENZYL-1-PIPERAZINYL)-N$^4$-(4-TERT-BUTYLCYCLOHEXYL)-N$^6$,N$^6$-DIMETHYL-4,6-PYRIMIDINEDIAMINE

Prepared by Procedures P (toluene, 16 h), Q (neat, 130° C.), and A. $^1$H NMR (400 MHz, CDCl$_3$) δ 7.36-7.22 (m, 5H), 4.82 (s, 1H), 3.74 (t, 4H, J=4.7), 3.53 (s, 2H), 3.33 (s, 1H), 2.98 (s, 6H), 2.46 (t, 4H, J=4.7), 1.15-0.91 (m, 9H), 0.86 (s, 9H); ESI-MS m/z: 451 (MH+).

Example 170

2-(4-BENZYL-1-PIPERAZINYL)-$N^4$-CYCLOOCTYL-$N^6$,$N^6$-DIMETHYL-4,6-PYRIMIDINEDIAMINE

Prepared by Procedures P (16 h), Q, and A. $^1$H NMR (400 MHz, CDCl$_3$) δ 7.39-7.21 (m, 5H), 4.79 (s, 1H), 4.34 (s, 1H), 3.74 (t, 4H, J=4.7), 3.53 (s, 2H), 2.99 (s, 6H), 2.40 (t, 4H, J=4.6), 1.93-1.49 (m, 15H); ESI-MS m/z: 423 (MH+).

Example 171

2-(4-BENZYL-1-PIPERAZINYL)-$N^4$-(4-CHLOROPHENYL)-$N^6$,$N^6$-DIMETHYL-4,6-PYRIMIDINEDIAMINE

Prepared by Procedures P (140° C., Q (neat, 130° C.), and A. $^1$H NMR (400 MHz, CDCl$_3$) δ 7.38-7.22 (m, 9H), 6.31 (br s, 1H), 5.21 (s, 1H), 3.78 (t, 4H, J=5.1 Hz), 3.55 (s, 2H), 2.99 (s, 6H), 2.49 (t, 4H, J=5.1); ESI-MS m/z: 423 (MH+ with $^{35}$Cl), 425 (MH+ with $^{37}$Cl).

Example 172

2-(4-BENZYL-1-PIPERAZINYL)-$N^4$-(3-CHLORO-4-METHYLPHENYL)-$N^6$,$N^6$-DIMETHYL-4,6-PYRIMIDINEDIAMINE

Prepared by Procedures P (toluene, 120° C., 16 h), Q (neat, 130° C.), and A. $^1$H NMR (400 MHz, CDCl$_3$) δ 7.43-(d, 1H, J=2.1), 7.38-7.09 (m, 5H), 7.07 (d, 1H, J=2.1), 7.05 (d, 1H, J=2.6), 6.02 (s, 1H), 5.21 (s, 1H), 3.78 (t, 4H, J=5.6), 3.54 (s, 2H), 2.99 (s, 6H), 2.49 (t, 4H, J=5.0), 2.31 (s, 3H); ESI-MS m/z: 437 (MH+ with $^{35}$Cl), 439 (MH+ with $^{37}$Cl).

Example 173

2-(4-BENZYL-1-PIPERAZINYL)-$N^4$,$N^4$-DIMETHYL-$N^6$-(1,2,3,4-TETRAHYDRO-2-NAPHTHALENYL)-4,6-PYRIMIDINEDIAMINE

Prepared by Procedures P (16 h), Q, and A. $^1$H NMR (400 MHz, CDCl$_3$) δ 7.41-7.04 (m, 9H), 4.99 (s, 1H), 4.91 (s, 1H), 3.74 (m, 4H), 3.53 (s, 2H), 3.47 (m, 1H), 2.99 (s, 6H), 2.90-2.69 (m, 2H), 2.49 (m, 4H), 2.09-1.71 (m, 4H); ESI-MS m/z: 443 (MH+).

Example 174

$N^4$,$N^4$-DIMETHYL-$N^6$-(4-METHYLPHENYL)-2-[4-(2-THIENYLMETHYL)-1-PIPERAZINYL]-4,6-PYRIMIDINEDIAMINE

Prepared by Procedure X (NaBH(OAc)$_3$, CH$_2$Cl$_2$, molecular sieves). $^1$H NMR (400 MHz, CDCl$_3$) δ 7.17 (d, 2H, J=8.3), 7.15-7.09 (m, 2H), 7.03-6.94 (m, 3H), 5.22 (br s, 1H), 4.85 (s, 1H), 3.86-3.79 (m, 4H), 3.77 (s, 2H), 2.98 (s, 6H), 2.62-2.53 (m, 4H), 2.32 (s, 3H); ESI-MS m/z: 409 (MH+).

Example 175

2-[4-(2-METHOXYBENZYL)-1-PIPERAZINYL]-$N^4$,$N^4$-DIMETHYL-$N^6$-(4-METHYLPHENYL)-4,6-PYRIMIDINEDIAMINE

Prepared by Procedure Z. $^1$H NMR (400 MHz, CDCl$_3$) δ 7.40 (dd, 1H, J=1.6, 7.5), 7.23 (dt, 1H, J=1.4, 7.6), 7.17 (d, 2H, J=8.4), 7.10 (d, 2H, J=8.3), 6.94 (t, 1H, J=7.5), 6.87 (d, 1H, J=7.6), 6.17 (br s, 1H), 5.24 (s, 1H), 3.82 (s, 3H), 3.79 (t, 4H, J=5.0), 3.62 (s, 2H), 2.97 (s, 6H), 2.55 (t, 4H, J=5.0), 2.31 (s, 3H); ESI-MS m/z: 433 (MH+).

Example 176

$N^2$-(2-ANILINOETHYL)-$N^4$,$N^4$-DIMETHYL-$N^6$-(4-METHYLPHENYL)-2,4,6-PYRIMIDINETRIAMINE

Prepared by Procedures A, Q (toluene, 100° C.), and F (potassium tert-butoxide, 110° C., 16 h). $^1$H NMR (400 MHz, CDCl$_3$) δ 7.19-7.10 (m, 6H), 6.67 (dt, 1H, J=0.8, 7.3), 6.59 (dd, 2H, J=0.8, 8.4), 6.31 (br s, 1H), 5.28 (s, 1H), 4.99 (s, 1H), 3.66 (q, 2H, J=6.0), 3.49 (s, 1H), 3.37 (t, 2H, J=6.0), 3.00 (s, 6H), 2.33 (s, 3H); ESI-MS m/z: 363 (MH+).

Example 177

$N^4$-(3-METHOXYPHENYL)-$N^2$,$N^6$,$N^6$-TRIMETHYL-$N^2$-[2-(2-PYRIDINYL)ETHYL]-2,4,6-PYRIMIDINETRIAMINE

Prepared by Procedures F (dioxane, 140° C., 15 h), A (CH$_2$Cl$_2$, Δ, TEA), and Q (toluene, TEA, A, 40 h). $^1$H NMR (400 MHz, CDCl$_3$) δ 8.55 (d, 1H, J=4.7), 7.58 (t, 1H, J=7.4), 7.25-7.16 (m, 2H), 7.15-7.06 (m, 2H), 6.89 (d, 1H, J=8.1), 6.57 (d, 1H, J=6.7), 6.30 (br s, 1H), 5.31 (s, 1H), 3.95 (t, 2H, J=6.4), 3.78 (s, 3H), 3.18-3.06 (m, 5H), 3.02 (s, 6H); ESI-MS m/z: 379 (MH+).

Example 178

$N^4$-(4-CYCLOHEXYLPHENYL)-$N^6$,$N^6$-DIMETHYL-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3h), N, and O. $^1$H NMR (400 MHz, CDCl$_3$) δ 9.90 (br s, 1H), 8.19-8.16 (m, 1H), 8.09-8.06 (m, 1H), 7.89-7.85 (m, 1H), 7.20-7.18 (m, 4H), 5.28 (s, 1H), 3.99 (t, 4H, J=5.3), 3.73 (t, 4H, J=5.3), 3.04 (s, 6H), 2.53-2.44 (m, 1H), 1.91-1.71 (m, 4H), 1.46-1.71 (m, 6H); ESI-MS m/z: 459 (MH+).

Example 179

$N^4$-[3-(BENZYLOXY)PHENYL]-$N^6$,$N^6$-DIMETHYL-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3 h), N, and O. $^1$H NMR (400 MHz, CDCl$_3$) δ 9.82 (br s, 1H), 8.17-8.15 (m, 1H), 8.09-8.06 (m. 1H), 7.89 (d, 1H, J=2.8), 7.45-7.29 (m, 9H), 5.32 (s, 1H), 5.05 (s, 2H), 4.03 (t, 4H, J=5.6), 3.74 (t, 4H, J=5.0), 3.05 (s, 6H); ESI-MS m/z: 483 (MH+).

Example 180

$N^4$-(2,3-DIHYDRO-1H-INDEN-5-YL)-$N^6$,$N^6$-DIMETHYL-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3 h), N, and O. $^1$H NMR (400 MHz, CDCl$_3$) δ 10.01 (br s, 1H), 8.16 (s, 1H), 8.10-8.97 (m, 1H), 7.91-7.87 (m, 1H), 7.19 (d, 1H, J=6.3), 7.1-3 (s, 1H), 7.04 (d, 1H, J=7.6), 5.23 (s, 1H), 4.03 (t, 4H, J=5.2), 3.74 (t, 4H, J=5.1), 3.05 (s, 6H), 2.89 (t, 2H, J=6.9), 2.14-2.04 (m, 4H); ESI-MS m/z: 417 (MH$^+$).

Example 181

$N^4$,$N^4$-DIMETHYL-$N^6$-(4-METHYLPHENYL)-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3 h), N, and O. $^1$H NMR (400 MHz, CDCl$_3$) δ 10.01 (s, 1H), 8.17 (s, 1H), 8.12-8.09 (m, 1H), 7.90 (d, 1H, J=2.6), 7.18 (d, 2H, J=8.6), 7.16 (d, 2H, J=8.1), 5.19 (s, 1H), 4.18-4.02 (m, 4H), 3.77 (t, 4H, J=5.1), 3.20 (br s, 3H), 2.99 (br s, 3H), 2.35 (s, 3H); ESI-MS m/z: 391 (MH$^+$).

Example 183

$N^4$-(3,4-DIMETHYLPHENYL)-$N^6$,$N^6$-DIMETHYL-2-[4-(2-PYRAZINYL)-1-PIPERAZINYL]-4,6-PYRIMIDINEDIAMINE

Prepared by Procedures A (CH$_2$Cl$_2$, Et$_3$N, Me$_2$NHHCl, −78° C. for 3.5 h, warmed from −78° C. to 0° C. and stirred for 3 h), N, and O. $^1$H NMR (400 MHz, CDCl$_3$) δ 8.75 (br s, 1H), 8.16 (d, 1H, J=1.3), 8.08 (dd, 1H, J=1.5, 2.8), 7.88 (d, 1H, J=2.5), 7.10 (d, 1H, J=7.8), 7.08-7.00 (m, 2H), 5.26 (s, 1H), 4.00 (t, 4H, J=5.1), 3.72 (t, 4H, J=5.0), 3.03 (s, 6H), 2.24 (s, 6H); ESI-MS m/z: 405 (MH$^+$).

Example 184

1-[2-(4-BENZYL-1-PIPERAZINYL)-6-(4-TOLUIDINO)-4-PYRIMIDINYL]-4-PIPERIDINONE

Prepared by Procedures a (Ch$_2$cl$_2$, −78° C., 4H), N (24H), and O. $^1$H NMR (400 MHz, CDCl$_3$) δ 7.38-7.30 (m, 5H), 7.19-7.10 (m, 4H), 6.24 (s, 1H), 5.40 (s, 1H), 3.84-3.75 (m, 8H), 3.56 (s, 2H), 2.54-2.43 (m, 8H), 2.32 (s, 3H); ESI-MS m/z: 457 (MH$^+$).

Example 185

$N^4$,$N^4$-dimethyl-$N^6$-(2-propylphenyl)-2-[4-(2-pyridinyl)-1-piperazinyl]-4,6-pyrimidinediamine:

Prepared by Procedures A (Ch$_2$cl$_2$, Tea, 3-4 H at −78° C., then 3-4 H at 0° C.), N, and O. $^1$H NMR (400 MHz, CDCl$_3$) δ 8.22-8.18 (m, 1H), 7.56-7.40 (m, 2H), 7.25-7.07 (m, 3H), 6.75-6.60 (m, 2H), 6.04 (s, 1H), 5.04 (s, 1H), 3.91 (m, 4H), 3.62 (m, 4H), 2.96 (s, 6H), 2.60 (t, 2H, J=7.5), 1.62 (m, 2H), 0.96 (t, 3H, J=8.8); ESI-MS M/Z: 418 (MH$^+$).

Example 186

$N^4$-(2-BENZYLPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$CL$_2$, TEA, 3-4 H at −78° C., then 3-4 H at 0° C.), N, AND O. $^1$H NMR (400 MHZ, CDCL$_3$) δ 8.20-8.18 (M, 1H), 7.54-7.45 (M, 1H), 7.34-7.04 (M, 9H), 6.73-6.59 (M, 2H), 5.99 (BR S, 1H), 5.01 (S, 1H), 3.99 (S, 2H), 3.93-3.83 (M, 4H), 3.66-3.57 (M, 4H), 2.96 (S, 6H); ESI-MS M/Z: 466 (MH$^+$).

Example 187

$N^4$-(4-HEXYLPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 460 (MH$^+$).

Example 188

$N^4$-(4-BENZYLPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.22-8.18 (m, 1H), 7.52-7.45 (m, 1H), 7.32-7.09 (m, 9H), 6.78 (d, 1H, J=9.2), 6.65-6.59 (m, 1H), 6.24 (br s, 1H), 5.29 (s, 1H), 3.96 (s, 2H), 3.91-3.83 (m, 4H), 3.63-3.55 (m, 4H), 3.00 (s, 6H); ESI-MS m/z: 466 (MH$^+$).

Example 189

$N^4$-(4-HEPTYLPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.25-8.18 (m, 1H), 7.57-7.44 (m, 1H), 7.38-7.08 (m, 4H), 6.75-6.57 (m, 2H), 6.26 (br s, 1H), 5.29 (s, 1H), 3.95-3.85 (m, 4H), 3.71-3.56 (m, 4H), 3.00 (s, 6H), 2.57 (t, 2H, J=5.2), 1.84-1.51 (m, 4H), 1.40-1.16 (m, 6H), 0.93-0.82 (m, 3H); ESI-MS m/z: 474 (MH$^+$).

Example 190

$N^4$-(3,4-DIMETHYLPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.25-8.19 (m, 1H), 7.55-7.44 (m, 1H), 7.31-7.23 (m, 1H), 7.14-7.02 (m, 2H), 6.73-6.59 (m, 2H), 6.18 (br s, 1H), 5.29 (s, 1H), 3.95-3.85 (m, 4H), 3.67-3.55 (m, 4H), 3.00 (s, 6H), 2.24 (s, 3H), 2.23 (s, 3H); ESI-MS m/z: 404 (MH$^+$).

Example 191

N$^4$-(3-ISOPROPYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.25-8.19 (m, 1H), 7.54-7.45 (m, 1H), 7.31-7.21 (m, 2H), 7.13-7.08 (m, 1H), 6.95-6.88 (m, 1H), 6.74-6.60 (m, 2H), 6.29 (br s, 1H), 5.37-5.34 (m, 1H), 3.96-3.87 (m, 4H), 3.68-3.57 (m, 4H), 3.30 (s, 6H), 2.95-2.85 (m, 1H), 1.36-1.19 (m, 6H); ESI-MS m/z: 418 (MH$^+$).

Example 192

N$^4$,N$^4$-DIMETHYL-N$^6$-(4-OCTYLPHENYL)-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.22 (s, 1H), 7.55-7.44 (m, 1H), 7.37-7.07 (m, 4H), 6.76-6.59 (m, 2H), 6.28 (br s, 1H), 5.29 (s, 1H), 3.96-3.86 (m, 4H), 3.69-3.56 (m, 4H), 3.00 (s, 6H), 2.57 (t, 2H, J=5.1), 1.74-1.51 (m, 4H), 1.41-1.08 (m, 8H), 0.93-0.82 (m, 3H); ESI-MS m/z: 488 (MH$^+$).

Example 193

N$^4$-(3-IODOPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.29-8.18 (m, 1H), 8.01-7.93 (m, 1H), 7.56-7.45 (m, 1H), 7.39-7.29 (m, 1H), 7.11-6.95 (m, 2H), 6.78-6.56), (m, 2H), 6.42-6.25 (m, 1H), 5.34 (s, 1H), 3.95-3.85 (m, 4H), 3.65-3.56 (m, 4H), 3.00 (s, 6H); ESI-MS m/z: 502 (MH$^+$).

Example 194

N$^4$-(4-CHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.) N, and O. $^1$H NMR (400 MHz, CDCl$_3$) δ 8.28 (s, 1H), 7.53-7.42 (m, 1H), 7.35-7.24 (m, 2H), 7.11-6.95 (m, 2H), 6.76-6.57 (m, 2H), 6.21 (s, 1H), 5.29 (s, 1H), 3.97-3.86 (m, 4H), 3.67-3.57 (m, 4H), 3.00 (s, 6H); ESI-MS m/z: 410 (MH$^+$).

Example 195

N$^5$-(2-CHLOROPHENYL)-N$^4$,N$^4$-DIMETHYL-2-[4-(2-PYRIDINYL)-1-PIPERAZINYL]-4,5-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.50-8.10 (m, 2H), 7.55-7.12 (m, 4H), 7.05-6.90 (m, 2H), 6.61 (s, 1H), 5.31 (s, 1H), 3.95-3.85 (m, 4H), 3.65-3.54 (m, 4H), 3.00 (s, 6H); ESI-MS m/z: 410 (MH$^+$).

Example 196

N$^4$-(3,4-DIFLUOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H N$^4$R (400 MHz, CDCl$_3$) δ 8.31 (,s, 1H), 7.59-6.95 (m, 4H), 6.68-6.54 (m, 2H), 6.29 (s, 1H), 5.27 (s, 1H), 3.94-3.82 (m, 4H), 3.63-3.51 (m, 4H), 3.01 (s, 6H); ESI-MS m/z: 412 (MH$^+$).

Example 197

N$^4$-[3-METHOXY-5-(TRIFLUOROMETHYL)PHENYL]-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.26-8.18 (m, 1H), 7.58-7.11 (m, 3H), 6.77-6.38 (m, 3H), 6.34 (s, 1H), 5.25 (s, 1H), 3.96-3.88 (m, 4H), 3.85 (s, 3H), 3.69-3.55 (m, 4H), 3.00 (s, 6H); ESI-MS m/z: 474 (MH$^+$).

Example 198

N$^4$,N$^4$-DIMETHYL-2-[4-(2-PYRIDINYL)-1-PIPERAZINYL]-N$^6$-(2,3,4-TRIFLUOROPHENYL)-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.26-8.18 (m, 1H), 7.58-7.11 (m, 3H), 6.77-6.38 (m, 2H), 6.34 (s, 1H), 5.25 (s, 1H), 3.96-3.88 (m, 4H), 3.85 (s, 3H), 3.69-3.55 (m, 4H), 3.00 (s, 6H); ESI-MS m/z: 430 (MH$^+$).

Example 199

N$^4$-(4-BROMO-2-FLUOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.27-8.17 (m, 1H), 7.61-7.01 (m, 4H), 6.75-6.57 (m, 2H), 6.34 (br s, 1H), 5.23 (s, 1H), 3.95-3.85 (m, 4H), 3.68-3.59 (m, 4H), 3.00 (s, 6H); ESI-MS m/z: 472 (MH$^+$).

Example 200

N$^4$-(4-FLUORO-3-METHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.27-8.17 (m, 1H), 7.56-7.47 (m, 1H), 7.21-6.89 (m, 3H), 6.75-6.58 (m, 2H), 6.24 (br s, 1H), 5.18 (s, 1H), 3.95-3.84 (m, 4H), 3.69-3.55 (m, 4H), 3.00 (s, 6H), 2.25 (s, 3H); ESI-MS m/z: 408 (MH$^+$).

Example 201

$N^4$-(2,5-DIMETHOXYPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.27-8.16 (m, 1H). 7.96-7.86 (m, 1H), 7.56-7.43 (m, 1H), 6.93-6.42 (m, 5H), 5.31 (s, 1H), 4.01-3.90 (m, 4H), 3.84 (s, 3H), 3.79 (s, 3H), 3.70-3.54 (m, 4H), 3.04(s, 6H); ESI-MS m/z: 436 (MH$^+$).

Example 202

$N^4$-(3,5-DIMETHOXYPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.26-8.17 (m, 1H), 7.55-7.44 (, 1H), 6.73-6.58 (m, 2H), 6.59-6.53(m, 2H), 6.23 (br s, 1H), 5.37 (s, 1H), 3.98-3.88 (m, 4H), 3.77 (s, 6H), 3.62-3.58 (m, 4H), 3.01 (s, 6H); ESI-MS m/z: 436 (MH$^+$).

Example 203

$N^4$-[3-(BENZYLOXY)PHENYL]-2-[4-(3-BROMOPHENYL)-1-PIPERAZINYL]-$N^6$,$N^6$-DIMETHYL-4,6-PYRIMIDINEDIAMINE

Prepared by Procedures A (CH$_2$Cl$_2$, TEA, 3-4 h at −78° C., then 3-4 h at 0° C.), N (TEA), and O. $^1$H NMR (400 MHz, CDCl$_3$) δ 7.55-6.26 (m, 14H), 5.29 (s, 1H), 5.06 (s, 2H), 3.97-3.82 (m, 4H), 3.21-3.14 (m, 4H), 3.01 (s, 6H); ESI-MS m/z: 560 (MH$^+$).

Example 204

$N^4$-(2-BROMO-4-METHYLPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.26-8.16 (m, 1H), 7.81 (d, 1H, J=8.8), 7.52-7.44 (m, 1H), 7.38 (d, 1H, J=8.5), 7.08 (d, 1H, J=8.5), 6.72 (m, 2H), 6.47 (br s, 1H), 5.24 (s, 1H), 3.90 (t, 4H, J=6.3), 3.61 (t, 4H, J=6.4), 3.01 (s, 6H), 2.28 (s, 3H); ESI-MS m/z: 468 (MH$^+$).

Example 205

$N^4$-(2,4-DICHLOROPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.) N, and O. $^1$H NMR (400 MHz, CDCl$_3$) δ 8.25-8.17 (m, 1H), 8.21 (d, 1H, J=9.2), 7.49 (t, 1H, J=9.0), 7.38-7.16 (m, 2H), 6.71-6.59 (m, 2H), 6.57 (br s, 1H), 5.25 (s, 1H), 3.93-3.85 (m, 4H), 3.65-3.55 (m, 4H), 3.03 (s, 6H); ESI-MS m/z: 444 (MH$^+$).

Example 206

$N^4$-(3-FLUOROPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. $^1$H NMR (400 MHz, CDCl$_3$) δ 8.25-6.39 (m, 9H), 5.30 (s, 1H), 3.97-3.85 (m, 4H), 3.74-3.58 (m, 4H), 3.01 (s, 6H); ESI-MS m/z: 394 (MH$^+$).

Example 207

$N^4$,$N^4$-DIMETHYL-2-[4-(2-PYRIDINYL)-1-PIPERAZINYL]-$N^6$[3-(TRIFLUOROMETHOXY)PHENYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 460 (MH$^+$).

Example 208

$N^4$-(2,5-DICHLOROPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 445 (MH$^+$).

Example 209

$N^4$,$N^4$-DIMETHYL-$N^6$-(4-PROPYLPHENYL)-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 418 (MH$^+$).

Example 210

$N^4$,$N^4$-DIMETHYL-$N^6$-(4-PENTYLPHENYL)-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 446 (MH$^+$).

Example 211

$N^4$-(4-SEC-BUTYLPHENYL)-$N^6$,$N^6$-DIMETHYL-2-[4 (2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 432 (MH$^+$).

Example 212

$N^4$-(2-TERT-BUTYLPHENYL)-$N^6$,$N^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 432 (MH$^+$).

Example 213

N$^4$-(2,5-DIMETHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 404 (MH$^+$).

Example 214

N$^4$-(3,5-DIMETHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 434 (MH$^+$).

Example 215

N$^4$-(2,3-DIMETHYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 404 (MH$^+$).

Example 216

N$^4$-(3-BENZYLPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 466 (MH$^+$).

Example 217

N$^4$-(4-BROMO-2-CHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 489 (MH$^+$).

Example 218

N$^4$-(2,3-DICHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 445 (MH$^+$).

Example 219

N$^4$,N$^4$-DIMETHYL-2-[4-(2-PYRIDINYL)-1-PIPERAZINYL]-N$^6$-(2,4,5-TRIFLUOROPHENYL)-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 430 (MH$^+$).

Example 220

N$^4$-(5-CHLORO-2-METHOXYPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 440 (MH$^+$).

Example 221

N$^4$,N$^4$-DIMETHYL-2-[4-(2-PYRIDINYL)-1-PIPERAZINYL]-N$^6$-(3,4,5-TRIFLUOROPHENYL)-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 430 (MH$^+$).

Example 222

N$^4$-(2-CHLORO-5-FLUOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 428 (MH$^+$).

Example 223

N$^4$-(2-CHLORO-4-METHYLPHENYL)-N$^6$,N$^6$-DIMETHYL-2-[4-(2-PYRIDINYL)-1-PIPERAZINYL-1,-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 424 (MH$^+$).

Example 224

N$^4$-(3-CHLOROPHENYL)-N$^6$,N$^6$-DIMETHYL-2-[4-(2-PYRIDINYL)-1-PIPERAZINYL]-4,6-PYRIMIDINEDIAMINE

Prepared by Procedures A (CH$_2$Cl$_2$, TEA, 3-4 h at −78° C., then 3-4 h at 0° C.), N, and O. ESI-MS m/z: 410 (MH$^+$).

Example 225

2-(4-BENZYL-1-PIPERAZINYL)-N$^4$-[3-METHOXY-5-(TRIFLUOROMETHYL)PHENYL]-N$^6$,N$^6$-DIMETHYL-4,6-PYRIMIDINEDIAMINE

Prepared by Procedures O (toluene, 75° C.), Q (toluene, 120° C.), and A. ESI-MS m/z: 487 (MH$^+$).

Example 226

2-(4-BENZYL-1-PIPERAZINYL)-N$^4$-[2-METHOXY-5-(TRIFLUOROMETHYL)PHENYL]-N$^6$,N$^6$-DIMETHYL-4,6-PYRIMIDINEDIAMINE

Prepared by Procedures O, Q (dioxane, 120° C.), and A. ESI-MS m/z: 487 (MH$^+$).

Example 227

2-(4-BENZYL-1-PIPERAZINYL)-N$^4$-(2,5-DIMETHOXYPHENYL)-N$^6$,N$^6$-DIMETHYL-4,6-PYRIMIDINEDIAMINE

Prepared by Procedures O, Q (dioxane, 120° C.), and A. ESI-MS m/z: 449 (MH$^+$).

Example 228

N$^4$-[3-(BENZYLOXY)PHENYL]-2-(4-BENZYL-1-PIPERAZINYL)-N$^6$,N$^6$-DIMETHYL-4,6-PYRIMIDINEDIAMINE

Prepared by Procedures O, Q (toluene, 120° C.), and A. ESI-MS m/z: 495 (MH$^+$).

Example 229

2-(4-BENZYL-1-PIPERAZINYL)-$N^4$,$N^4$-DIMETHYL-$N^6$-[4-(TRIFLUOROMETHYL)PHENYL]-4,6-PYRIMIDINEDIAMINE

Prepared by Procedures P (toluene, 105° C.), Q (toluene, 120° C.), and A. ESI-MS m/z: 457 (MH$^+$).

Example 230

2-(4-BENZYL-1-PIPERAZINYL)-$N^4$,$N^4$-DIMETHYL-$N^6$-(2,3,4-TRICHLOROPHENYL)-4,6-PYRIMIDINEDIAMINE

Prepared by Procedures O (60° C.), Q (toluene, 120° C.), and A. ESI-MS m/z: 492 (MH$^+$).

Example 231

2-[4-(2-FURYLMETHYL)-1-PIPERAZINYL]-$N^4$,$N^4$-DIMETHYL-$N^6$-(4-METHYLPHENYL)-4,6-PYRIMIDINEDIAMINE

Prepared by Procedures R (16 h), P (sodium tert-butoxide, toluene, 120° C.), N (TEA, toluene reflux), and A. ESI-MS m/z: 393 (MH$^+$).

Example 232

$N^2$-[2-(4-METHOXYPHENYL)ETHYL]-$N^4$,$N^4$-DIMETHYL-$N^6$-(4-METHYLPHENYL)-2,4,6-PYRIMIDINETRIAMINE

Prepared by Procedures V, R, and S (DIEA, DMAP). ESI-MS m/z: 378 (MH$^+$).

Example 233

$N^4$-(3-METHOXYPHENYL)-$N^6$,$N^6$-DIMETHYL-2-[4-(TETRAHYDRO-2-FURANYLMETHYL)-1-PIPERAZINYL]-4,6-PYRIMIDINEDIAMINE

Prepared by Procedures A, P (16 h), and Q (dioxane, 120° C.). ESI-MS m/z: 413 (MH$^+$).

Example 235

2-[4-(4-METHOXYBENZYL)-1-PIPERAZINYL]-$N^4$,$N^4$-DIMETHYL-$N^6$-(4-METHYLPHENYL)-4,6-PYRIMIDINEDIAMINE

Prepared by Procedure Z. ESI-MS m/z: 433 (MH$^+$).

Example 237

$N^4$,$N^4$-DIMETHYL-1-(4-METHYLPHENYL)-$N^2$-[2-(2-THIENYL)ETHYL]-2,4,6-PYRIMIDINETRIAMINE

Prepared by Procedures R, S, and V. ESI-MS m/z: 354 (MH$^+$).

Example 238

$N^4$,$N^4$-DIMETHYL-$N^6$-(4-METHYLPHENYL)-2-[4-(3-THIENYLMETHYL)-1-PIPERAZINYL]-4,6-PYRIMIDINEDIAMINE

Prepared by Procedures AA, T (2 h), and W. ESI-MS m/z: 409 (MH$^+$).

Example 239

2-(4-BENZYL-1-PIPERAZINYL)-$N^4$-[4-CHLORO-2-(TRIFLUOROMETHYL)PHENYL]-$N^6$,$N^6$-DIMETHYL-4,6-PYRIMIDINEDIAMINE

Prepared by Procedures O (100° C., 40 h), Q (toluene, 120° C.), and A. ESI-MS m/z: 491 (MH$^+$).

Example 240

$N^4$-(3-BROMO-4-METHYLPHENYL)-$N^6$,$N^6$-DIMETHYL-2-[4-(2-PYRIDINYL)-1-PIPERAZINYL]-4,6-PYRIMIDINEDIAMINE

Prepared by Procedures O (80° C.), Q (toluene, 120° C.), and A. ESI-MS m/z: 469 (MH$^+$).

Example 241

2-{4-[4-(DIMETHYLAMINO)-6-(4-TOLUIDINO)-2-PYRIMIDINYL]-1-PIPERAZINYL}NICOTINONITRILE

Prepared by Procedures O, Q (toluene, 120° C.), and A. ESI-MS m/z: 415 (MH$^+$).

Example 242

$N^4$,$N^4$-DIMETHYL-$N^6$-[4-METHYL-3-(2-PYRIDINYLAMINO)PHENYL]-2-(4-(2-PYRIDINYL)-1-PIPERAZINYL]-4,6-PYRIMIDINEDIAMINE

Prepared by Procedures P (toluene), Q (toluene, 120° C.), and A. ESI-MS m/z: 482 (MH$^+$).

Example 243

$N^4$-(3-BROMOPHENYL)-$N^6$,$N^6$-DIMETHYL-2-[4-(2-PYRIDINYL)-1-PIPERAZINYL]-4,6-PYRIMIDINEDIAMINE

Prepared by Procedures O (85° C.), Q (toluene, 120° C.), and A. ESI-MS m/z: 455 (MH$^+$).

Example 244

2-(4-BENZYL-1-PIPERAZINYL)-$N^4$-[2-CHLORO-4-(TRIFLUOROMETHYL)PHENYL]-$N^6$,$N^6$-DIMETHYL-4,6-PYRIMIDINEDIAMINE

Prepared by Procedures P (16 h, toluene), Q (toluene, 120° C.), and A. ESI-MS m/z: 491 (MH$^+$).

Example 245

$N^4$-(3-METHOXYPHENYL)-$N^6$,$N^6$-DIMETHYL-2-[4-(2-PYRIDINYL)-1-PIPERAZINYL]-4,6-PYRIMIDINEDIAMINE

Prepared by Procedures A, N, and P. ESI-MS m/z: 406 (MH$^+$).

Example 246

N⁴-(3-METHOXYPHENYL)-N⁶,N⁶-DIMETHYL-2-{4-[2-(TRIFLUOROMETHYL)PHENYL]-1-PIPERAZINYL}-4,6-PYRIMIDINEDIAMINE

Prepared by Procedures A, N, and P. ESI-MS m/z: 473 (MH⁺).

Example 247

N⁴-(3-METHOXYPHENYL)-N⁶,N⁶-DIMETHYL-N²-(2-PHENYLETHYL)-2,4,6-PYRIMIDINETRIAMINE

Prepared by Procedures A, N, and P. ESI-MS m/z: 364 (MH⁺).

Example 248

N²,N⁴,N⁴-TRIMETHYL-N⁶-(4-METHYLPHENYL)-N²-(2-PHENYLETHYL)-2,4,6-PYRIMIDINETRIAMINE

Prepared by Procedures A, N, and P. ESI-MS m/z: 362 (MH⁺).

Example 249

N-(4-METHYLPHENYL)-2-(4-[1-OXIDO-3-(TRIFLUOROMETHYL)-2-PYRIDINYL]-1-PIPERAZINYL}-6-(1-PIPERIDINYL)-4-PYRIMIDINAMINE

Prepared by Procedure CC. ESI-MS m/z: 514 (MH⁺).

Example 250

N⁴,N⁴-DIMETHYL-N⁶-(4-METHYLPHENYL)-N²-(2-PHENYLETHYL)-2,4,6-PYRIMIDINETRIAMINE

Prepared by Procedures R and S. ESI-MS m/z: 348 (MH⁺).

Example 251

N⁴-(3-METHOXYPHENYL)-N²,N⁶,N⁶-TRIMETHYL-N²-(2-PHENYLETHYL)-2,4,6-PYRIMIDINETRIAMINE

Prepared by Procedures A, N, and P. ESI-MS m/z: 378 (MH⁺).

Example 252

2-(4-BENZYL-1-PIPERAZINYL)-N⁴-(3-METHOXYPHENYL)-N⁶,N⁶-DIMETHYL-4,6-PYRIMIDINEDIAMINE

Prepared by Procedures A, N, and P. ESI-MS m/z: 419 (MH⁺).

Example 253

2-(4-BENZYL-1-PIPERAZINYL)-N⁴,N⁴-DIMETHYL-N⁶-(4-METHYLPHENYL)-4,6-PYRIMIDINEDIAMINE

Prepared by Procedures A, N, and P. ESI-MS m/z: 403 (MH⁺).

Examples 1-90 and 115-253 as described above are merely illustrative of the methods used to synthesize pyrimidine derivatives. Further derivatives may be obtained utilizing methods shown in Schemes 1-5b. The substituents in Schemes 1-5b are described in the Detailed Description.

It may be necessary to incorporate protection and deprotection strategies for substituents such as amino, amido, carboxylic acid, and hydroxyl groups in the synthetic methods described above to form pyrimidine derivatives. Methods for protection and deprotection of such groups are well-known in the art, and may be found, for example in Green, T. W. and Wuts, P. G. M. (1991) Protection Groups in Organic Synthesis, 2nd Edition John Wiley & Sons, New York.

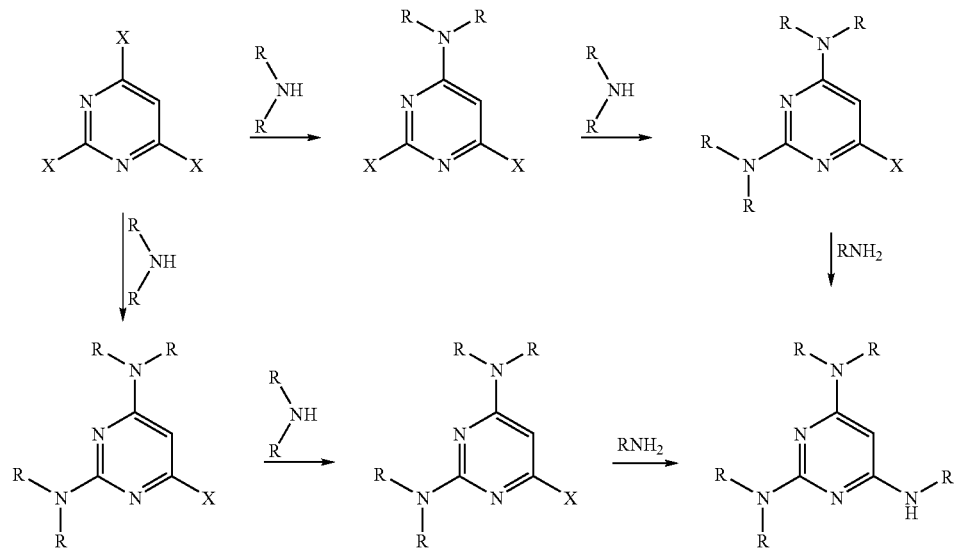

Scheme 1. Synthesis of Substituted Triaminopyrimidines

X = leaving group such halogen OTf or OTs

Scheme 2. Alternate Synthesis of Substituted Triaminopyrimidines

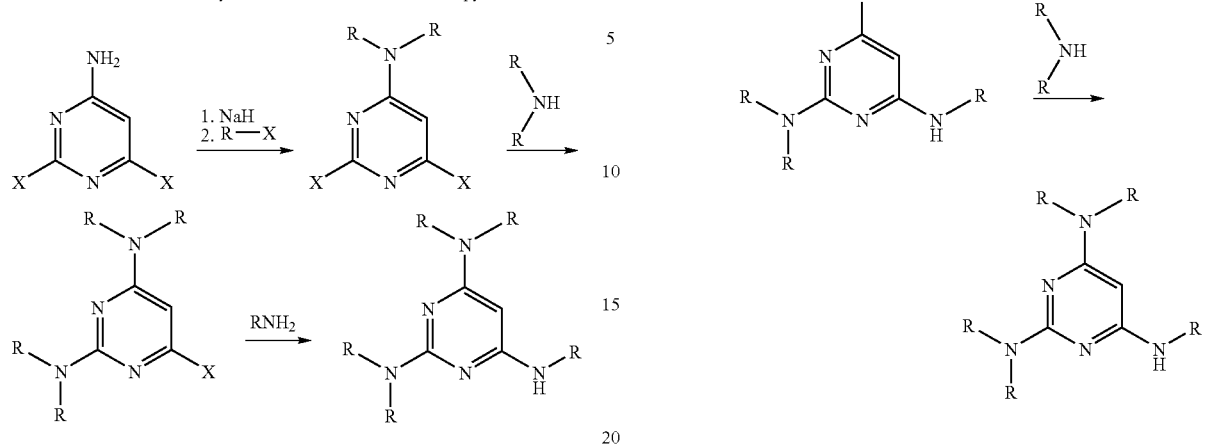

X = leaving group such halogen OTf or OTs

Scheme 3. Alternate Synthesis of Substituted Triaminopyrimidines

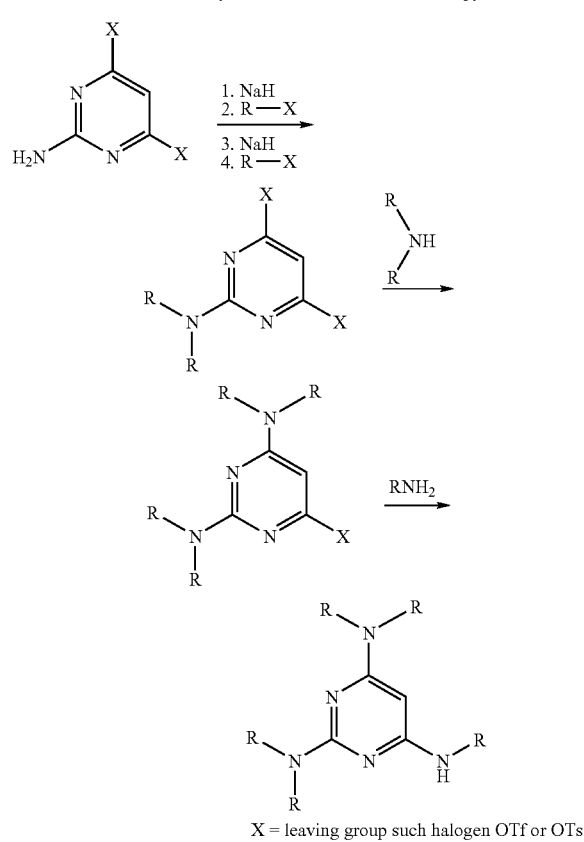

X = leaving group such halogen OTf or OTs

Alternatively,

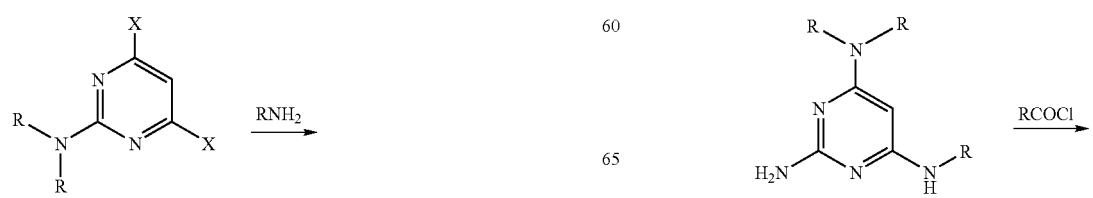

-continued

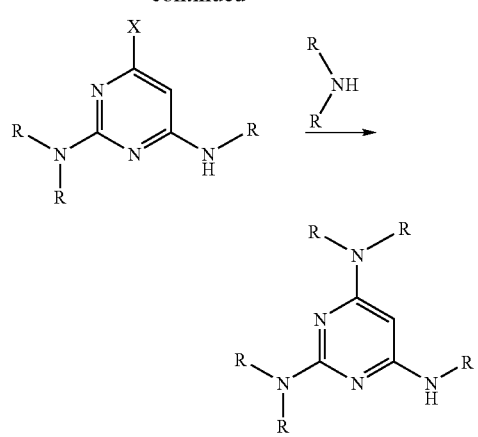

Scheme 4. Synthesis of Morpholine Intermediates

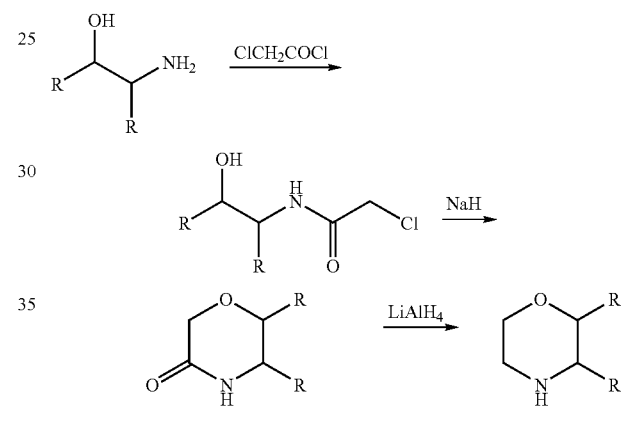

Scheme 5. Synthesis of N-Alkylamine Intermediates

Scheme 5a. Synthesis of Triaminopyrimidines from 2-Amidopyrimidines

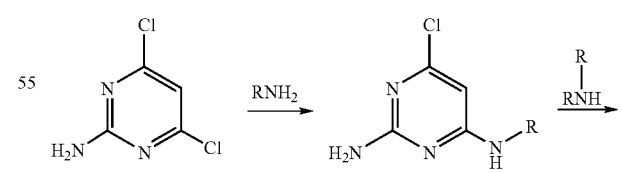

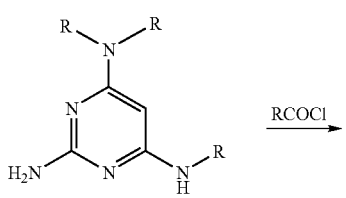

-continued

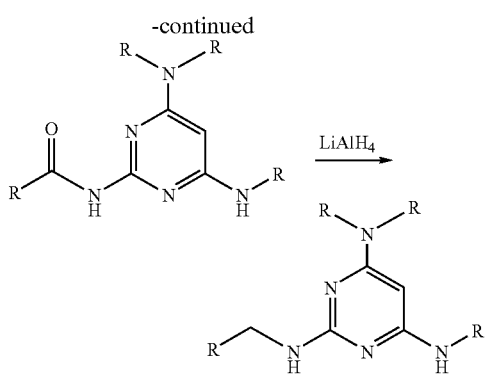

Radioligand Binding of Pyrimidines at Cloned Galanin Receptors

The binding properties of the pyrimidines of the present invention were evaluated at the cloned human galanin receptors, GAL1, GAL2, and GAL3, using protocols described herein.

Radioligand Binding Assay Results

The pyrimidines described in Examples 1-90 and 115-253 were assayed using cloned human galanin receptors. The compounds were found to be selective for the GAL3 receptor. The binding affinities of the compounds of Examples 1-90 and 115-253 are illustrated in Tables 1-3a.

Scheme 5b. Substitution on the Piperazine Moiety of 2-(Piperazin-1-yl)pyrimidines

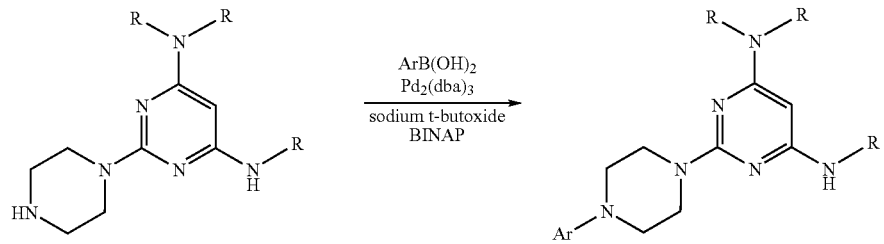

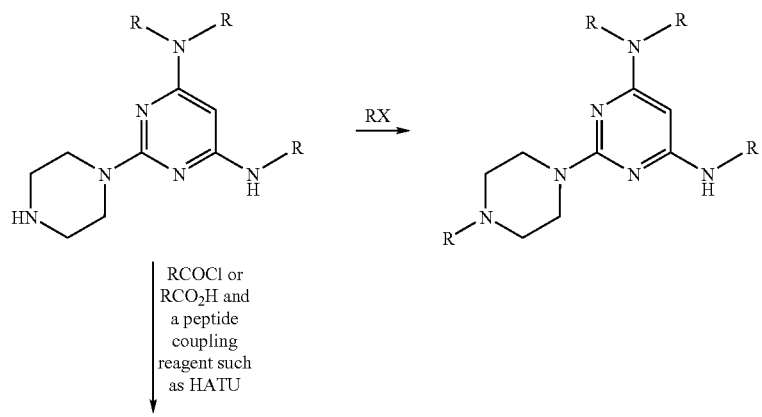

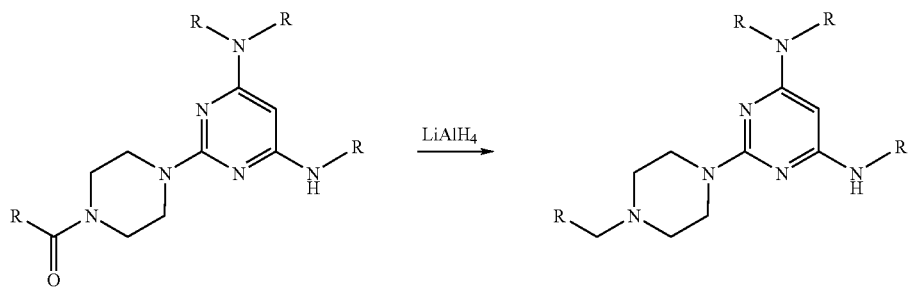

X is a leaving group such as a halogen or tosylate; HATU is 0-(7-azabenzenzotriazol-1-yl)- N,N,N', N'-tetramethyluronium hexafluorophosphate; dba is dibenzylideneacetone; BINAP is a 2,2'-bis (diphen-ylphosphino)-1,1'-binaphthyl.

TABLE 1
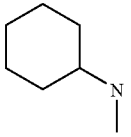
| | substitution | | Ki (nM) | | |
|---|---|---|---|---|---|
| Example | R1 | R2 | GalR1 | GalR2 | GalR3 |
| 1 | 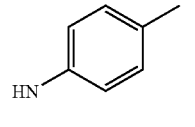 | 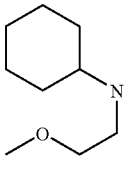 | 668 | 188 | 35 |
| 2 | 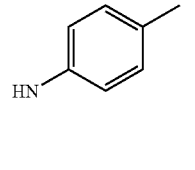 | 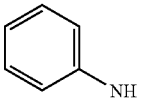 | 2818 | 562 | 26 |
| 3 | 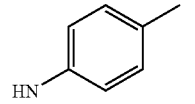 | 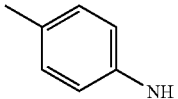 | >5000 | >5000 | 163 |
| 4 | 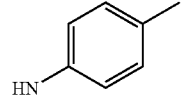 | 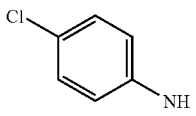 | >5000 | >5000 | 627 |
| 5 | 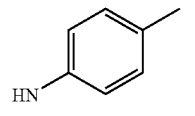 | 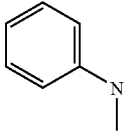 | >5000 | >5000 | 345 |
| 6 | 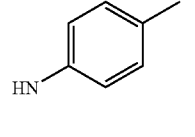 | 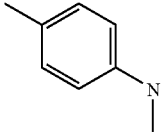 | >5000 | 2157 | 248 |
| 7 | 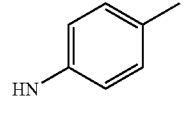 | 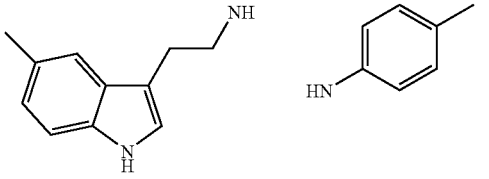 | 1107 | 775 | 177 |
| 8 | 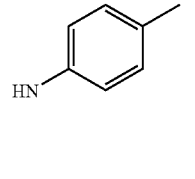 | 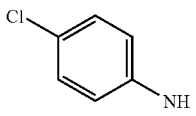 | >5000 | 795 | 264 |

TABLE 1-continued
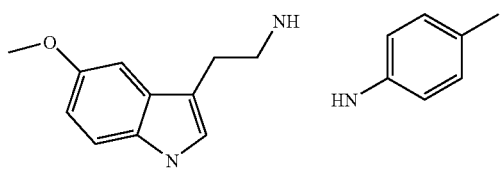
| | substitution | | Ki (nM) | | |
|---|---|---|---|---|---|
| Example | R1 | R2 | GalR1 | GalR2 | GalR3 |
| 9 | 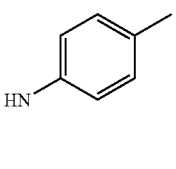 | 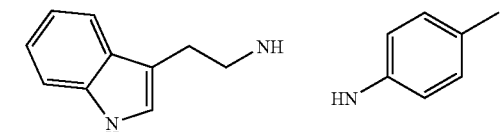 | >5000 | 2110 | 568 |
| 10 | 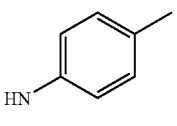 | 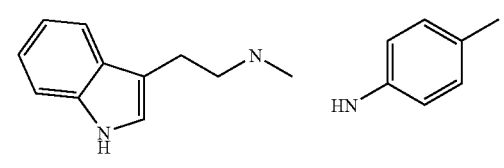 | >5000 | 865 | 100 |
| 11 | 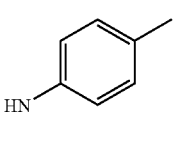 | 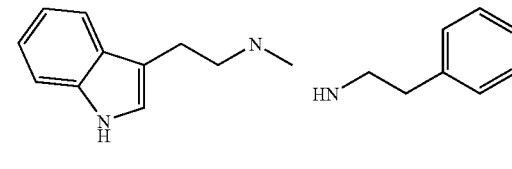 | >5000 | 681 | 91 |
| 12 | 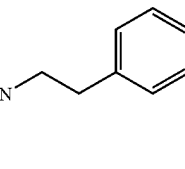 | 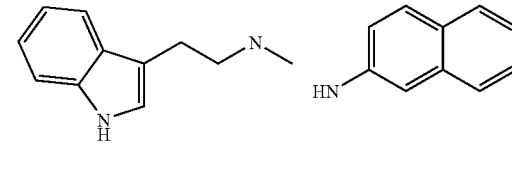 | >5000 | 1995 | 322 |
| 13 | 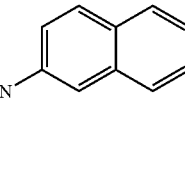 | 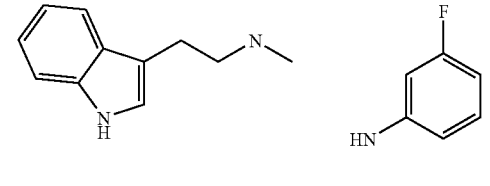 | 2065 | 1413 | 81 |
| 14 | 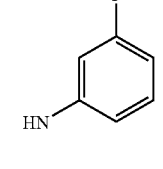 | 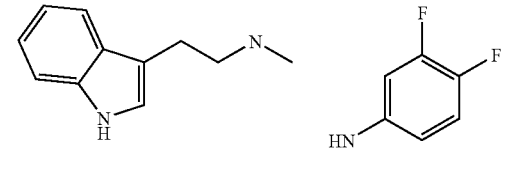 | >5000 | 1336 | 54 |
| 15 | 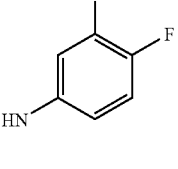 | | 2427 | 624 | 73 |

TABLE 1-continued
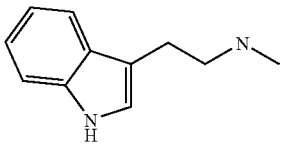
| Example | substitution | | Ki (nM) | | |
|---|---|---|---|---|---|
| | R1 | R2 | GalR1 | GalR2 | GalR3 |
| 16 | 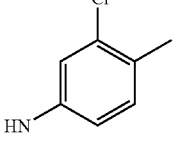 | 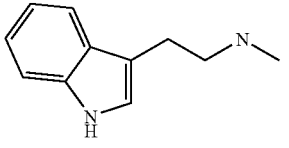 | >5000 | >5000 | 33 |
| 17 | 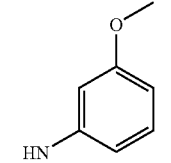 | 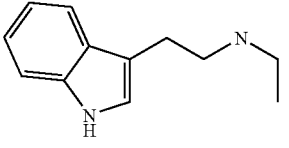 | >5000 | 2089 | 87 |
| 18 | 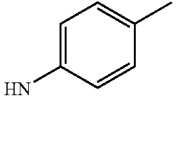 | 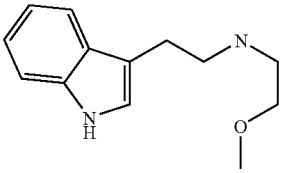 | 3589 | 543 | 40 |
| 19 | 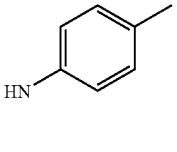 | 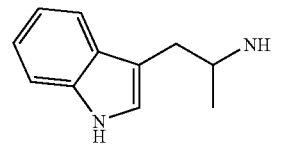 | >5000 | 1771 | 79 |
| 20 | 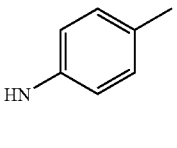 | 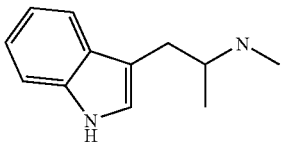 | >5000 | >5000 | 164 |
| 21 | 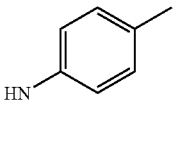 | 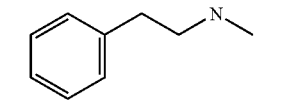 | 4786 | 1096 | 49 |
| 22 | 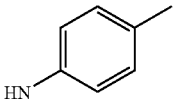 | 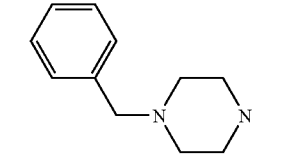 | 442 | 176 | 28 |
| 23 | 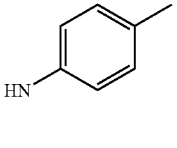 | | >5000 | >5000 | 60 |

TABLE 1-continued
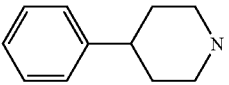
| Example | substitution | | Ki (nM) | | |
| --- | --- | --- | --- | --- | --- |
| | R1 | R2 | GalR1 | GalR2 | GalR3 |
| 24 | 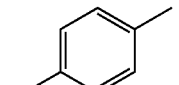 | 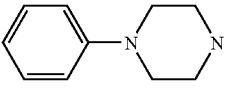 | >5000 | 3961 | 210 |
| 25 | 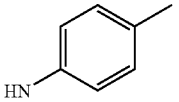 | 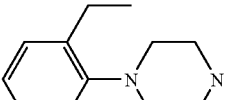 | >5000 | 1497 | 548 |
| 26 | 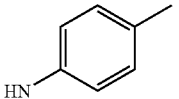 | 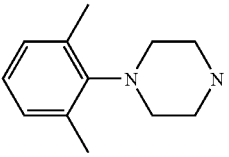 | >5000 | 4049 | 85 |
| 27 | 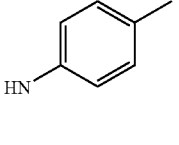 | 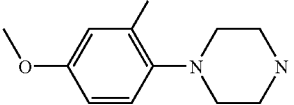 | 2692 | 272 | 63 |
| 28 | 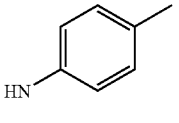 | 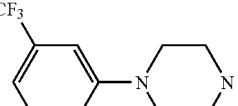 | >5000 | >5000 | 270 |
| 29 | 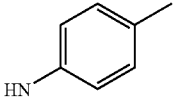 | 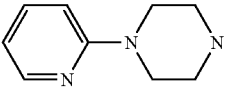 | 716 | 359 | 46 |
| 30 | 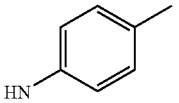 | 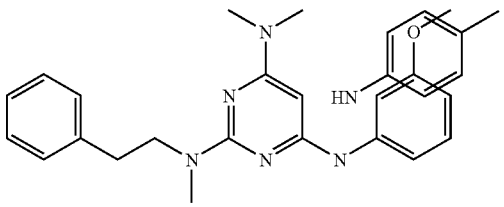 | >5000 | 2613 | 197 |
| 31 |  | | >5000 | 3402 | 174 |

TABLE 1-continued
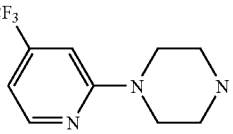
| Example | substitution | | Ki (nM) | | |
| --- | --- | --- | --- | --- | --- |
| | R1 | R2 | GalR1 | GalR2 | GalR3 |
| 32 | 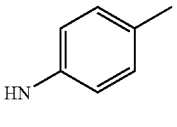 | 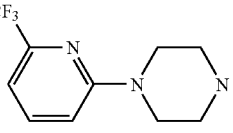 | >5000 | 1860 | 145 |
| 33 | 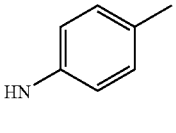 | 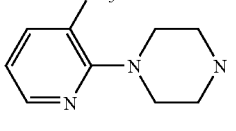 | >5000 | >5000 | 181 |
| 34 | 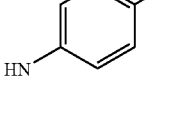 | 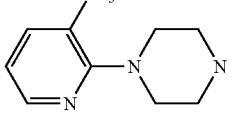 | 912 | 168 | 23 |
| 35 | 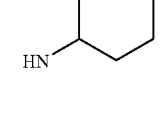 | 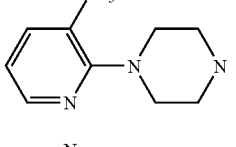 | | | 111 |
| 36 | 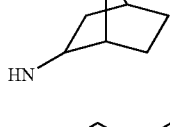 | 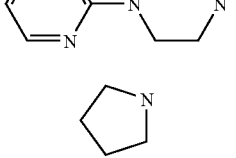 | 442 | 90 | 93 |
| 37 | 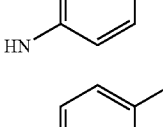 |  | >5000 | 903 | 343 |
| 38 | 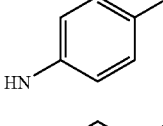 | 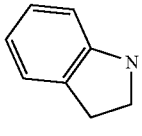 | 2901 | 516 | 320 |
| 39 | 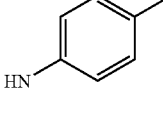 | 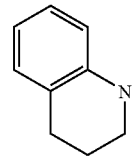 | >5000 | >5000 | 128 |
| 40 | 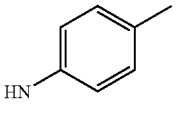 | | >5000 | 2623 | 164 |

TABLE 1-continued
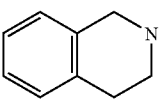
| Example | substitution | | Ki (nM) | | |
| --- | --- | --- | --- | --- | --- |
| | R1 | R2 | GalR1 | GalR2 | GalR3 |
| 41 | 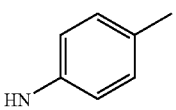 | 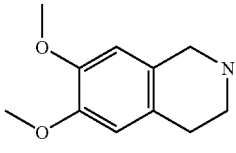 | 2131 | 840 | 151 |
| 42 | 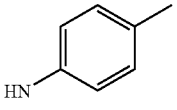 | 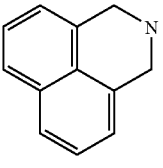 | >5000 | 1137 | 275 |
| 43 | 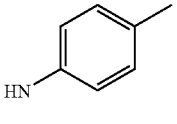 | 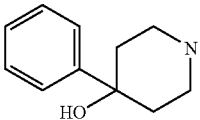 | >5000 | >5000 | 107 |
| 44 | 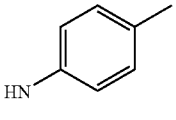 | 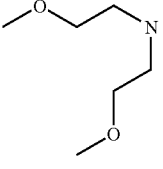 | >5000 | 1023 | 133 |
| 45 | 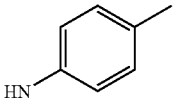 | 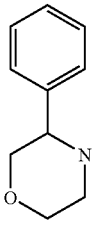 | >5000 | >5000 | 505 |
| 46 | 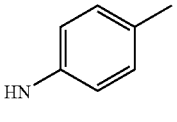 | 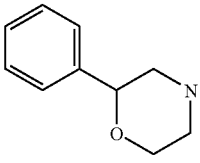 | >5000 | >5000 | 577 |
| 47 | 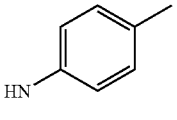 | | >5000 | 3012 | 115 |

TABLE 1-continued
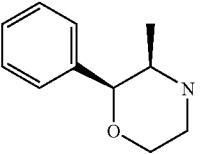
| | substitution | | Ki (nM) | | |
|---|---|---|---|---|---|
| Example | R1 | R2 | GalR1 | GalR2 | GalR3 |
| 48 | 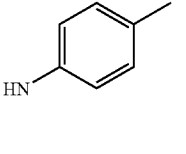 | 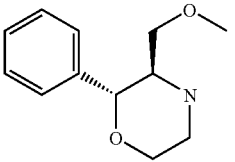 | >5000 | 4233 | 120 |
| 49 | 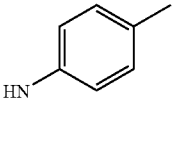 | 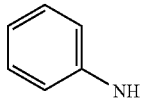 | >5000 | 3273 | 211 |
TABLE 2
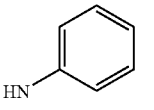
| | substitution | | Ki (nM) | | |
|---|---|---|---|---|---|
| Example | R1 | R2 | GalR1 | GalR2 | GalR3 |
| 50 | 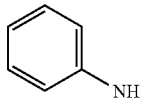 | 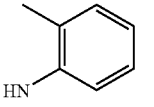 | >5000 | >5000 | 699 |
| 51 | 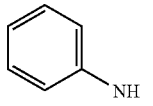 | 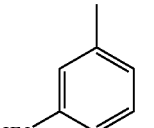 | >5000 | >5000 | 987 |
| 52 | 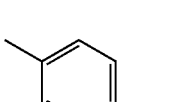 | 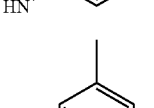 | >5000 | >5000 | 570 |
| 53 |  |  | >5000 | >5000 | 980 |

TABLE 2-continued

Structure: pyrimidine with N(CH3)2 at 4-position, R1 at 2-position, R2 at 6-position

| Example | R1 | R2 | GalR1 | GalR2 | GalR3 |
|---------|----|----|-------|-------|-------|
| 54 | phenyl-NH | 4-methylphenyl-NH | >5000 | >5000 | 132 |
| 55 | 3,4-dichlorophenyl-NH | 4-methylphenyl-NH | >5000 | >5000 | 48 |
| 56 | 4-methylphenyl-NH | 4-methylphenyl-NH | >5000 | >5000 | 794 |
| 57 | phenyl-NH | 3-fluorophenyl-NH | >5000 | >5000 | 360 |
| 58 | phenyl-NH | 4-chlorophenyl-NH | >5000 | >5000 | 783 |
| 59 | phenyl-NH | 4-bromophenyl-NH | >5000 | >5000 | 566 |
| 60 | phenyl-NH | 3,4-dichlorophenyl-NH | >5000 | >5000 | 86 |
| 61 | phenyl-NH | 4-chloro-3-methylphenyl-NH | >5000 | >5000 | 753 |
| 62 | phenyl-NH | 3-chloro-4-methylphenyl-NH | >5000 | >5000 | 736 |
| 63 | phenyl-NH | 4-tert-butylphenyl-NH | >5000 | >5000 | 731 |
| 64 | phenyl-NH | 4-phenoxyphenyl-NH | >5000 | >5000 | 572 |

TABLE 2-continued

Structure: pyrimidine with N(CH3)2 at position 4, R1 at position 2, R2 at position 6

| Example | R1 | R2 | Ki (nM) GalR1 | Ki (nM) GalR2 | Ki (nM) GalR3 |
|---|---|---|---|---|---|
| 65 | phenyl-NH | 2-naphthyl-NH | >5000 | >5000 | 329 |
| 66 | phenyl-NH | cyclohexyl-NH | >5000 | >5000 | 699 |
| 67 | phenyl-NH | 4-methylcyclohexyl-NH | >5000 | >5000 | 752 |
| 68 | phenyl-NH | 4-tert-butylcyclohexyl-NH | >5000 | 2155 | 164 |
| 69 | phenyl-NH | norbornyl-NH | >5000 | >5000 | 417 |
| 70 | phenyl-NH | bornyl-NH | >5000 | 944 | 476 |
| 71 | phenyl-NH | pinanyl-NH | >5000 | 944 | 72 |
| 72 | 4-methylphenyl-N(CH3) | 4-methylphenyl-NH | >5000 | 2083 | 132 |
| 73 | cyclohexyl-N(CH3) | 4-methylphenyl-NH | >5000 | 1550 | 124 |

TABLE 2-continued
| | substitution | | Ki (nM) | | |
|---|---|---|---|---|---|
| Example | R1 | R2 | GalR1 | GalR2 | GalR3 |
| 74 | 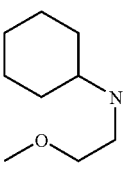 | 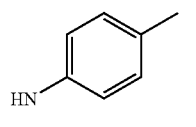 | 2291 | 468 | 47 |
| 75 | 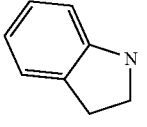 | 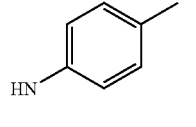 | 1462 | 2458 | 144 |
| 76 | 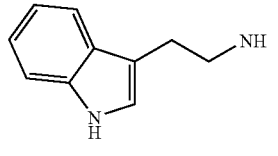 | 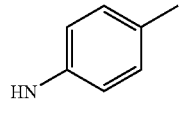 | 3802 | 1657 | 392 |
| 77 | 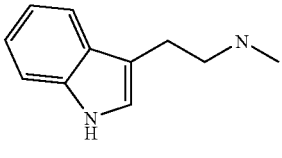 | 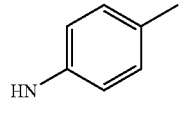 | 3802 | 709 | 79 |
| 78 | 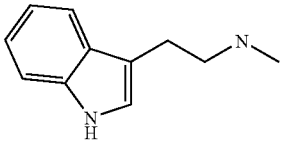 | 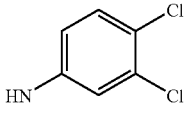 | 4942 | 1862 | 41 |
| 79 | 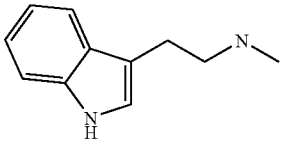 | 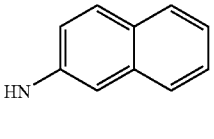 | 3802 | 1656 | 190 |
| 80 | 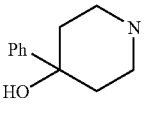 | 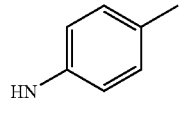 | >5000 | 2478 | 615 |
| 81 | 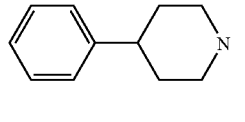 | 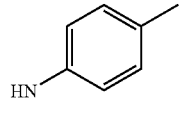 | >5000 | 4789 | 160 |
| 82 | 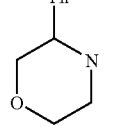 | 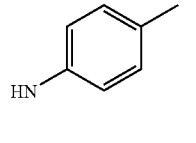 | >5000 | >5000 | 232 |

TABLE 2-continued
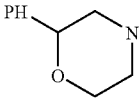
| | substitution | | Ki (nM) | | |
|---|---|---|---|---|---|
| Example | R1 | R2 | GalR1 | GalR2 | GalR3 |
| 83 | 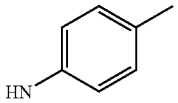 | 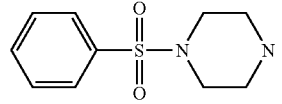 | >5000 | >5000 | 160 |
| 84 | 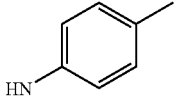 | 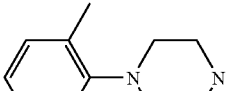 | >5000 | >5000 | 261 |
| 85 | 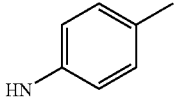 | 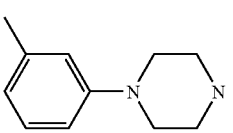 | >5000 | 4228 | 72 |
| 86 | 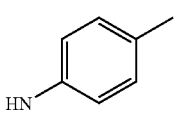 | 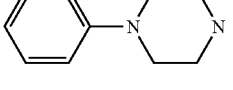 | >5000 | >5000 | 227 |
| 87 | 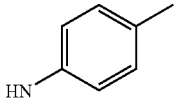 | 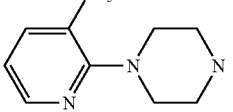 | >5000 | 4617 | 157 |
| 88 | 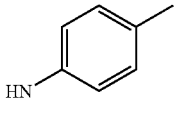 |  | 2188 | 355 | 39 |
Key: Ph = Phenyl
TABLE 3
| | | substitution | | | Ki (nM) | | |
|---|---|---|---|---|---|---|---|
| Example | X | R1 | R2 | R3 | GalR1 | GalR2 | GalR3 |
| 89 | H |  | | | 1122 | 1274 | 105 |

TABLE 3-continued

| | | substitution | | | Ki (nM) | | |
|---|---|---|---|---|---|---|---|
| Example | X | R1 | R2 | R3 | GalR1 | GalR2 | GalR3 |
| 90 | H | 3-CF₃-pyridin-2-yl piperazine | 3-(piperidin-1-yl) | CH₂-O-NH-(4-methylphenyl) | >5000 | 2460 | 105 |

TABLE 3a

| Example | Structure | Ki (nM) Gal3 |
|---|---|---|
| 115 | 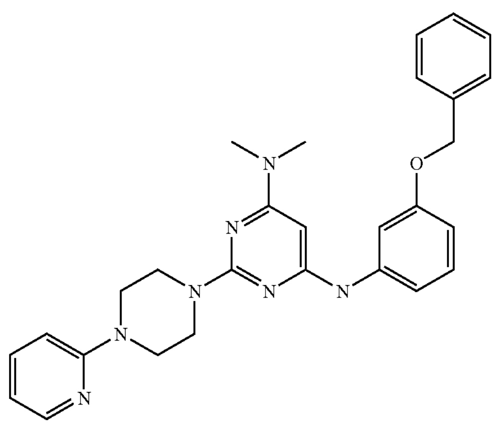 | 13 |
| 116 | 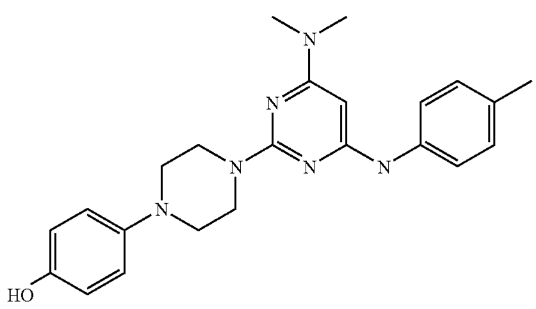 | 479 |
| 117 | 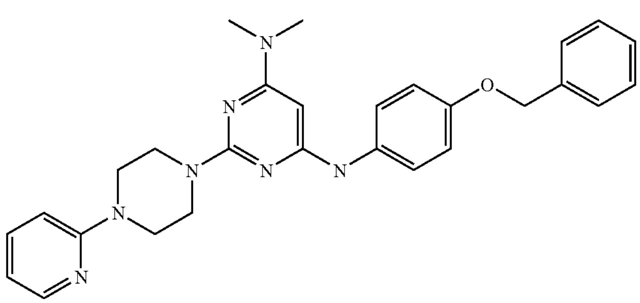 | 61 |

TABLE 3a-continued

| Example | Structure | Ki (nM) Gal3 |
|---|---|---|
| 118 | 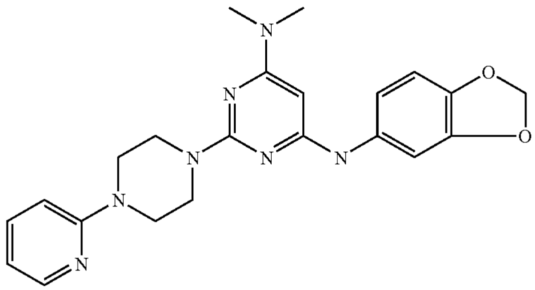 | 508 |
| 119 | 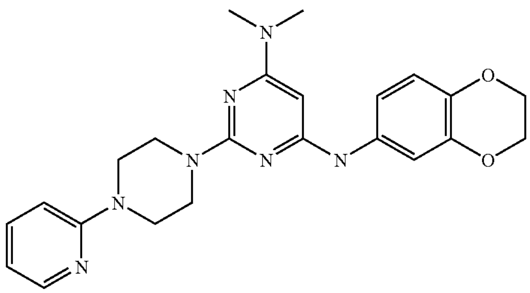 | 540 |
| 120 | 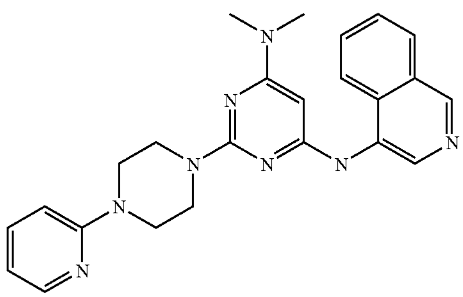 | 664 |
| 121 | 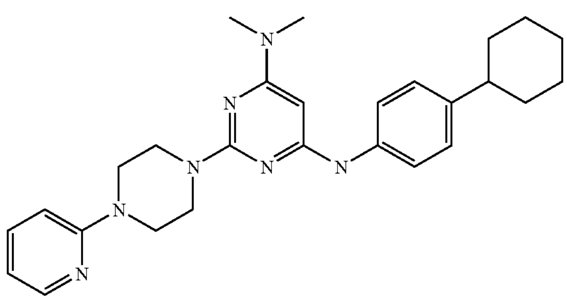 | 21 |
| 122 | 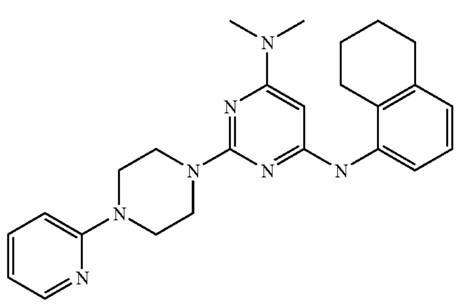 | 65 |

TABLE 3a-continued
| Example | Structure | Ki (nM) Gal3 |
|---|---|---|
| 123 | 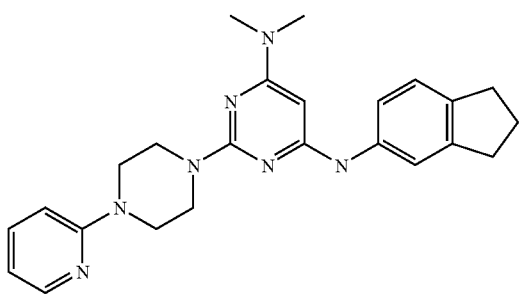 | 61 |
| 124 | 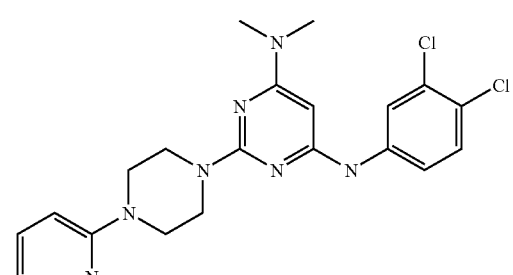 | 36 |
| 125 | 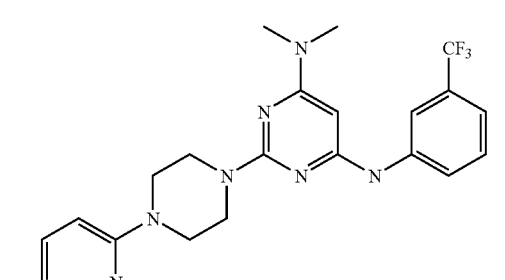 | 75 |
| 126 | 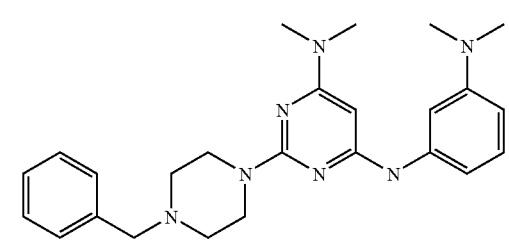 | 99 |
| 127 | 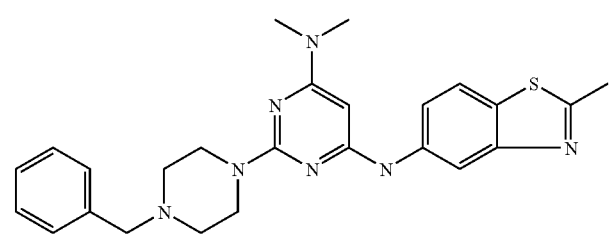 | 255 |

TABLE 3a-continued
| Example | Structure | Ki (nM) Gal3 |
|---|---|---|
| 128 | 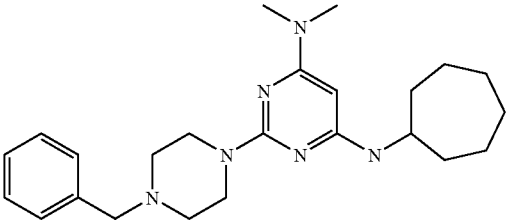 | 249 |
| 129 | 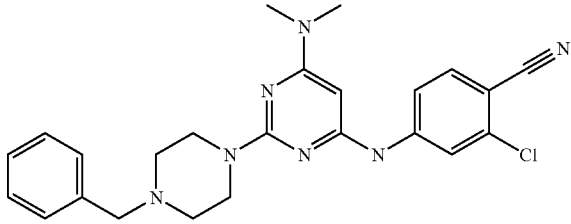 | 405 |
| 130 | 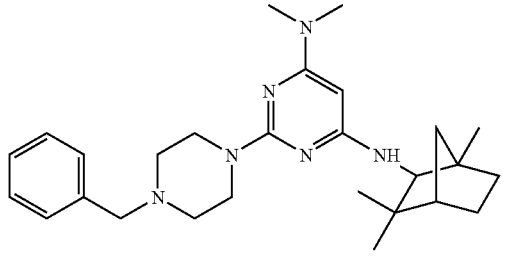 | 100 |
| 131 | 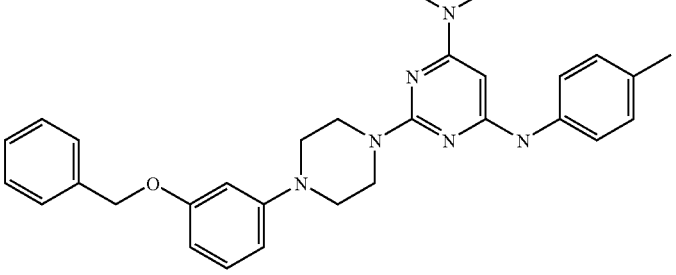 | 20 |
| 132 | 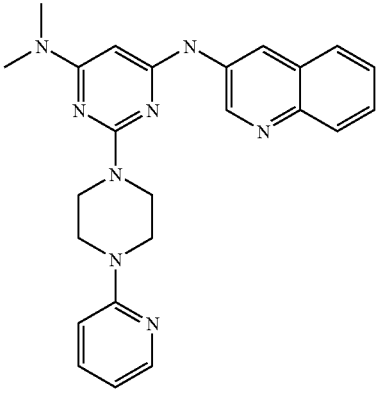 | 618 |

TABLE 3a-continued
| Example | Structure | Ki (nM) Gal3 |
|---|---|---|
| 133 | 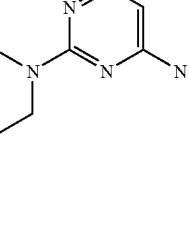 | 60 |
| 134 | 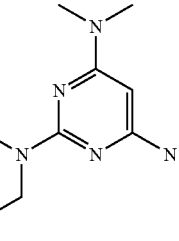 | 25 |
| 135 | 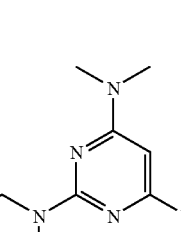 | 100 |
| 136 | 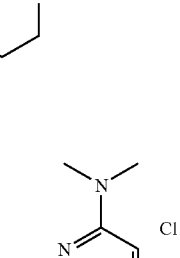 | 25 |
| 137 | 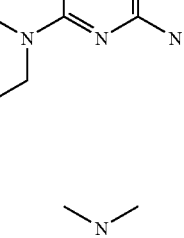 | 124 |

TABLE 3a-continued

| Example | Structure | Ki (nM) Gal3 |
|---|---|---|
| 138 | 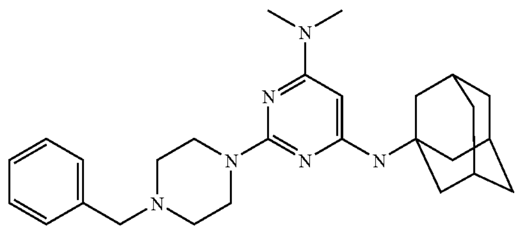 | 52 |
| 139 | 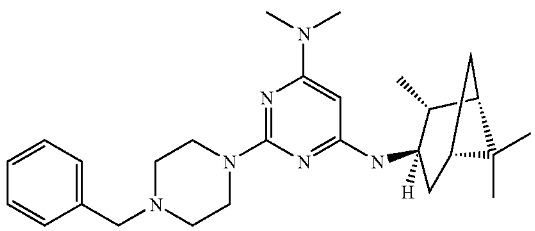 | 47 |
| 140 | 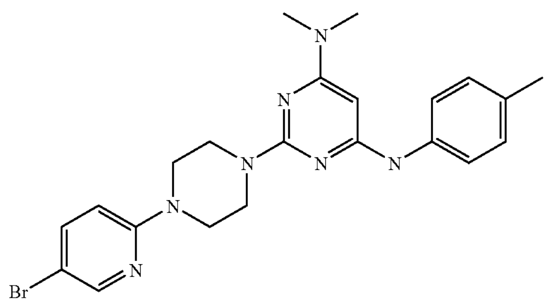 | 169 |
| 141 | 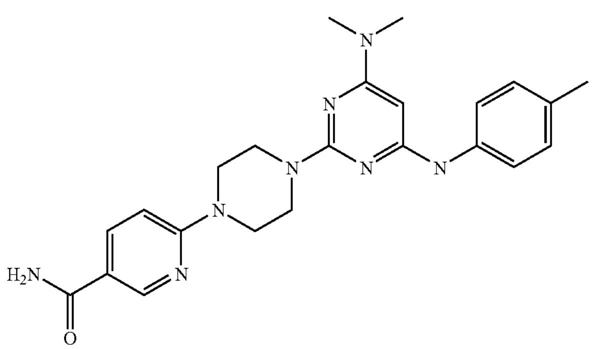 | 509 |
| 142 | 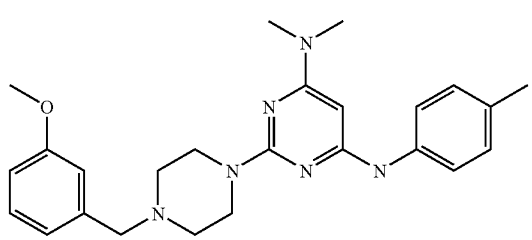 | 28 |

TABLE 3a-continued

| Example | Structure | Ki (nM) Gal3 |
|---|---|---|
| 143 | 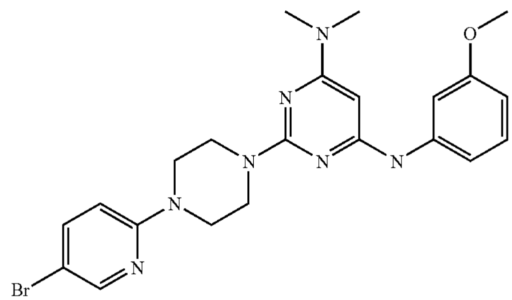 | 144 |
| 144 | 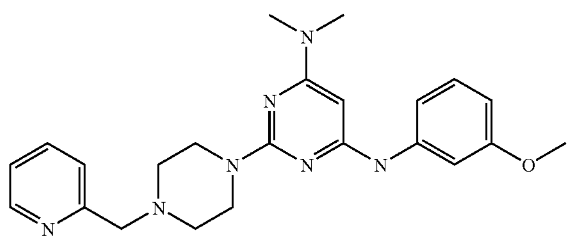 | 529 |
| 145 | 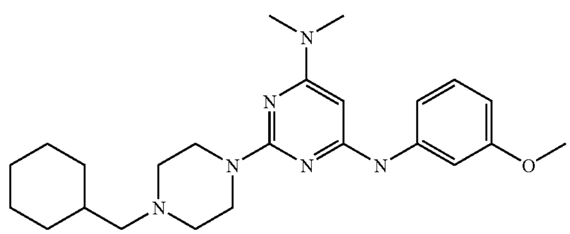 | 155 |
| 146 | 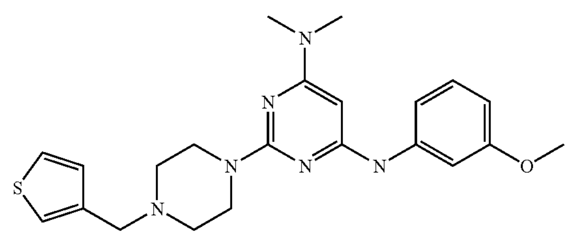 | 72 |
| 147 | 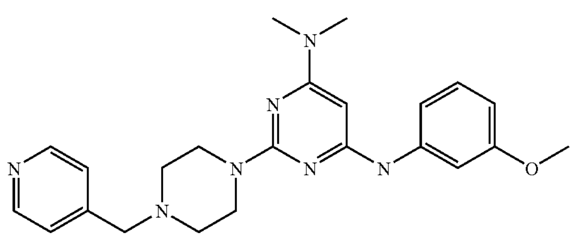 | 640 |
| 148 | 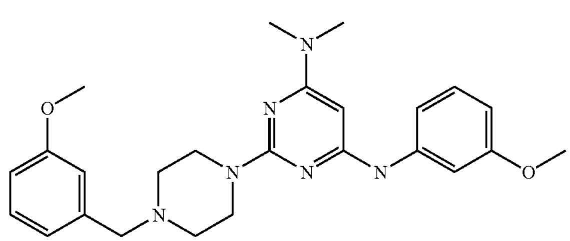 | 276 |

TABLE 3a-continued

| Example | Structure | Ki (nM) Gal3 |
|---|---|---|
| 149 | 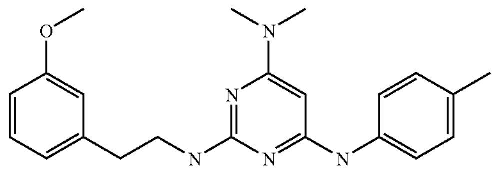 | 138* |
| 150 | 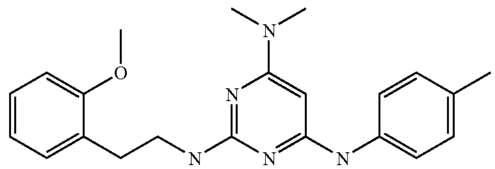 | 180 |
| 151 | 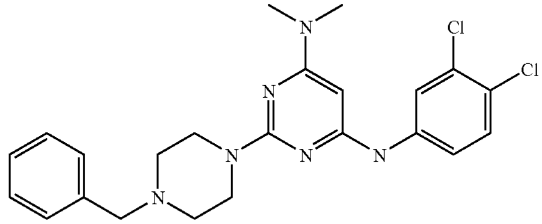 | 11 |
| 152 | 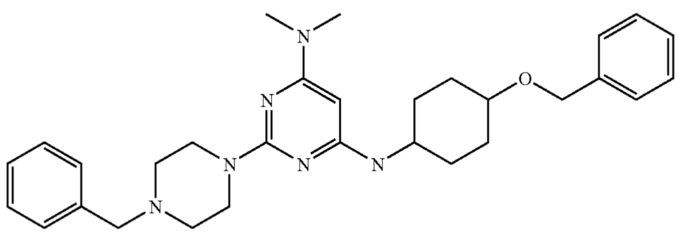 | 172 |
| 153 | 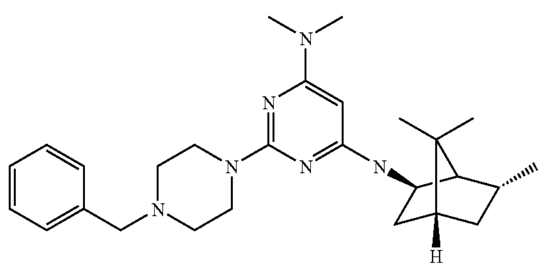 | 55 |
| 154 | 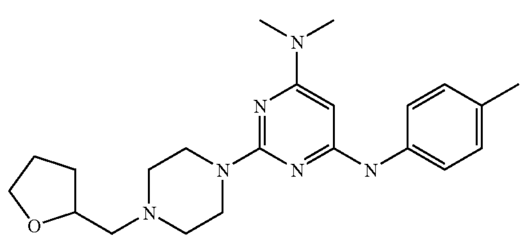 | 441 |
| 155 | 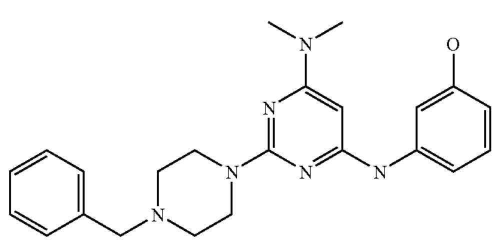 | 316 |

TABLE 3a-continued

| Example | Structure | Ki (nM) Gal3 |
|---|---|---|
| 156 | 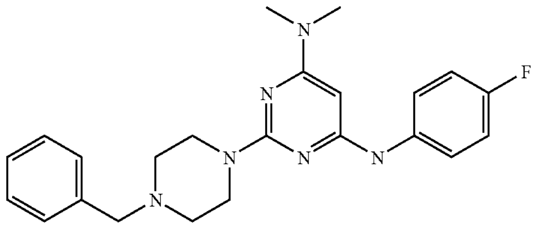 | 61 |
| 157 | 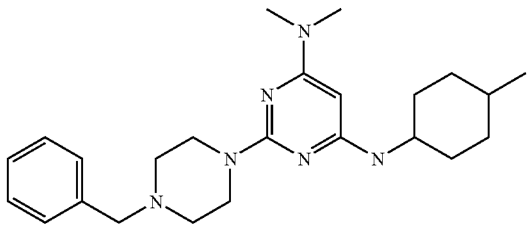 | 273 |
| 158 | 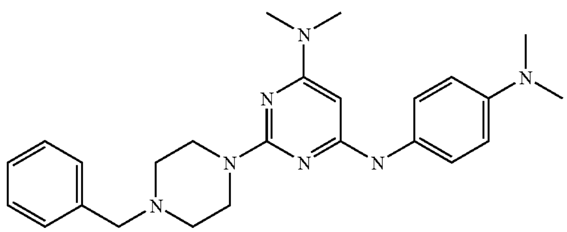 | 941 |
| 159 | 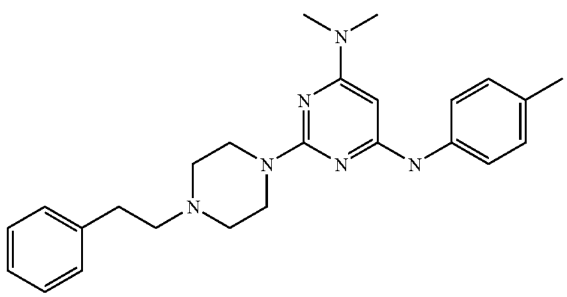 | 180 |
| 160 | 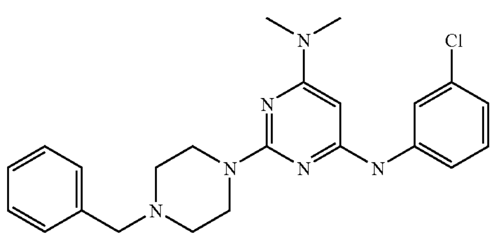 | 26 |
| 161 | 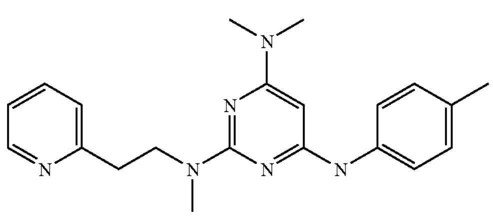 | 114 |

TABLE 3a-continued

| Example | Structure | Ki (nM) Gal3 |
|---|---|---|
| 162 | 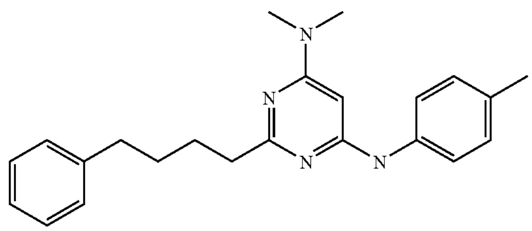 | 42 |
| 163 | 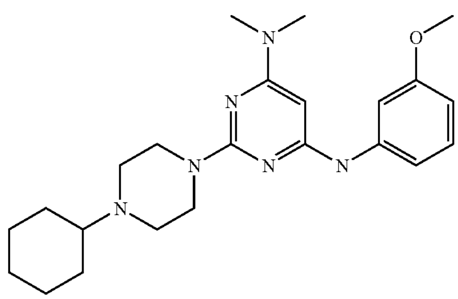 | 500 |
| 164 | 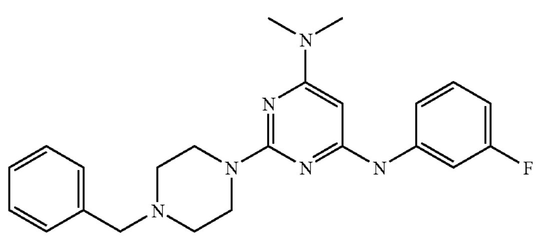 | 60 |
| 165 | 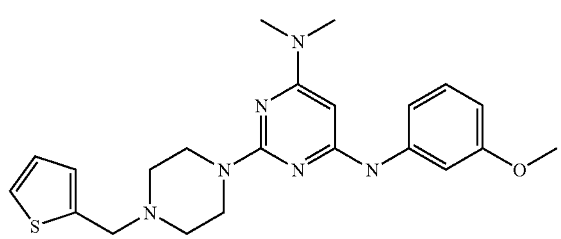 | 139* |
| 166 | 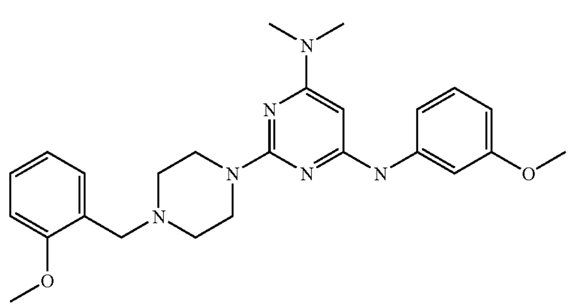 | 263 |

TABLE 3a-continued

| Example | Structure | Ki (nM) Gal3 |
|---------|-----------|--------------|
| 167 | 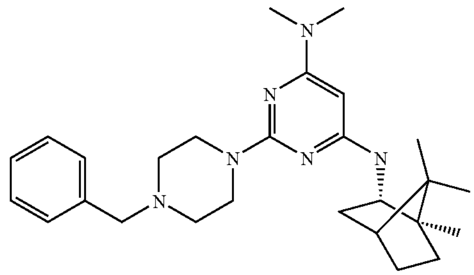 | 50 |
| 168 | 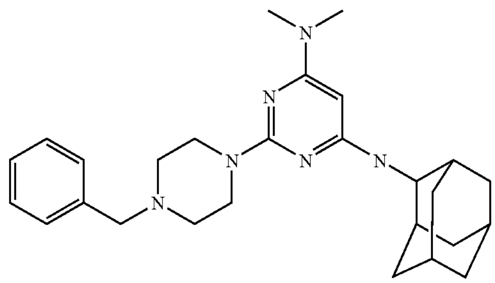 | 50 |
| 169 | 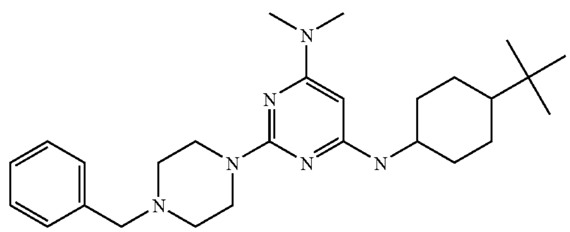 | 77 |
| 170 | 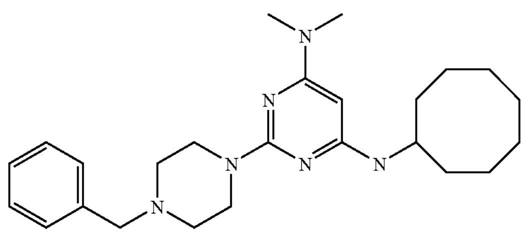 | 91 |
| 171 | 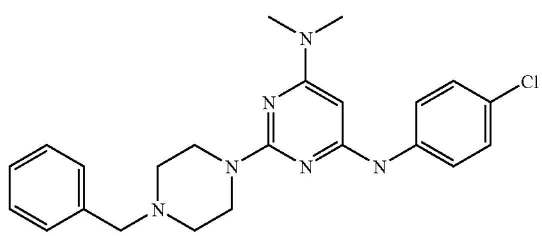 | 25 |
| 172 | 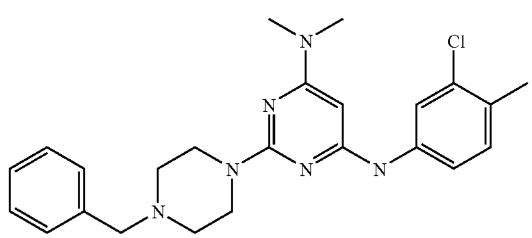 | 20 |

TABLE 3a-continued

| Example | Structure | Ki (nM) Gal3 |
|---|---|---|
| 173 | 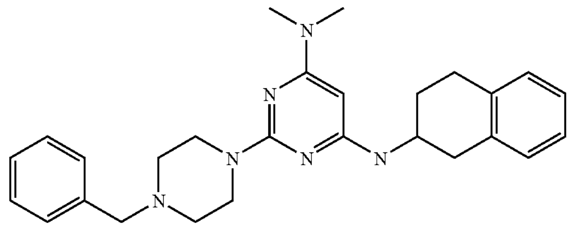 | 117 |
| 174 | 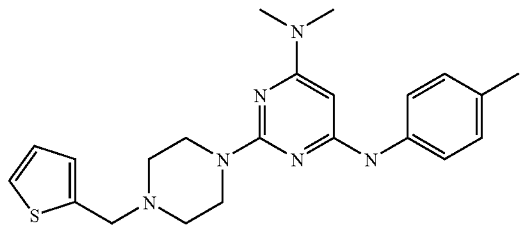 | 325* |
| 175 | 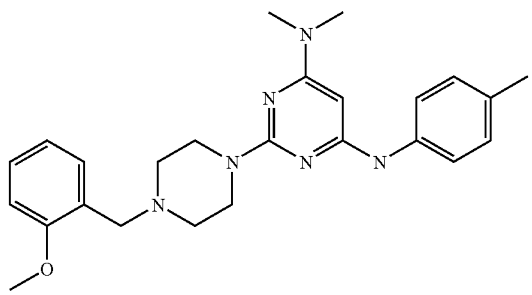 | 56 |
| 176 | 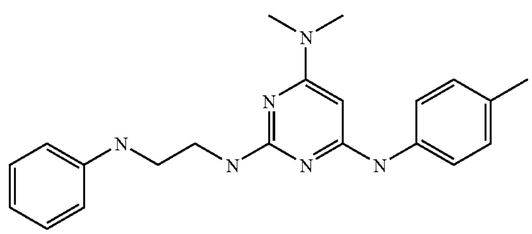 | 608 |
| 177 | 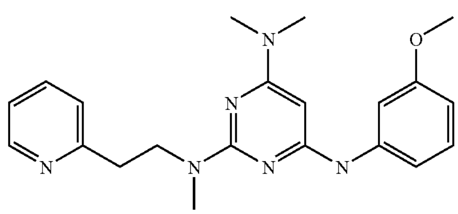 | 142 |
| 178 | 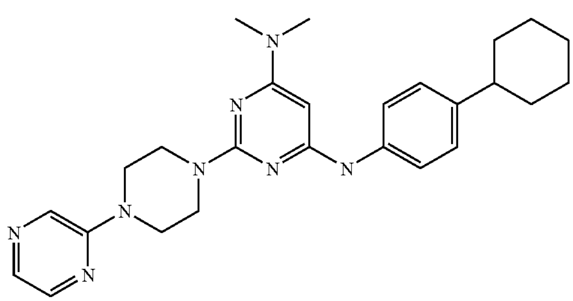 | 26 |

TABLE 3a-continued

| Example | Structure | Ki (nM) Gal3 |
|---|---|---|
| 179 | 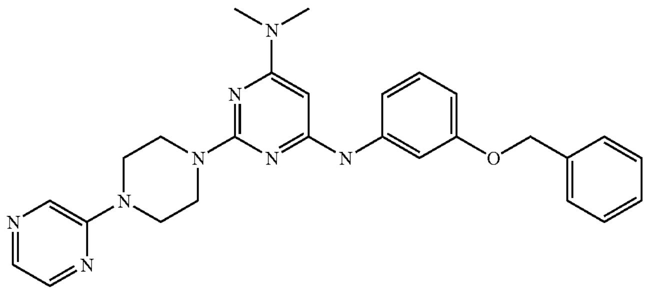 | 15 |
| 180 | 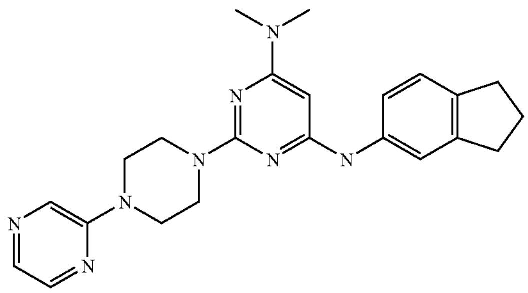 | 151 |
| 181 | 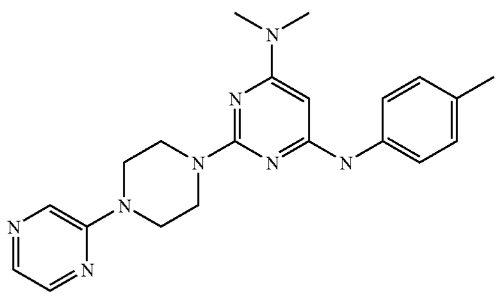 | 750 |
| 183 | 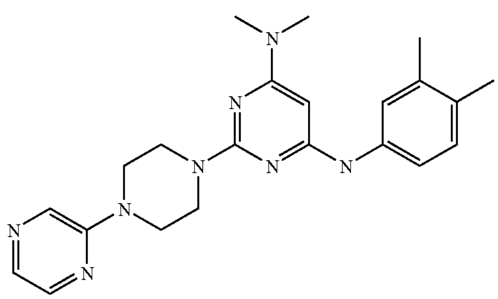 | 66 |
| 184 | 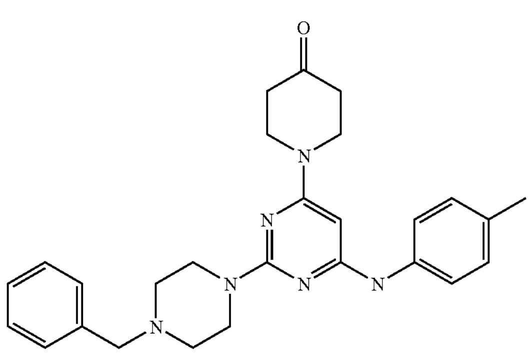 | 163 |

TABLE 3a-continued

| Example | Structure | Ki (nM) Gal3 |
|---|---|---|
| 185 | 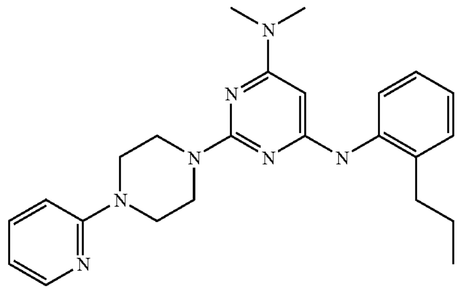 | 365 |
| 186 | 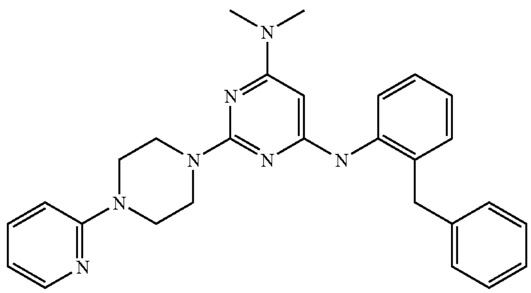 | 69 |
| 187 | 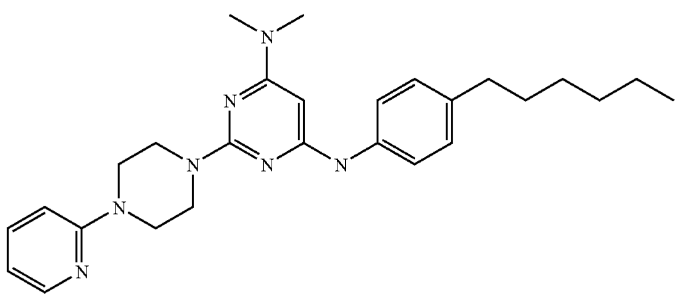 | 19 |
| 188 | 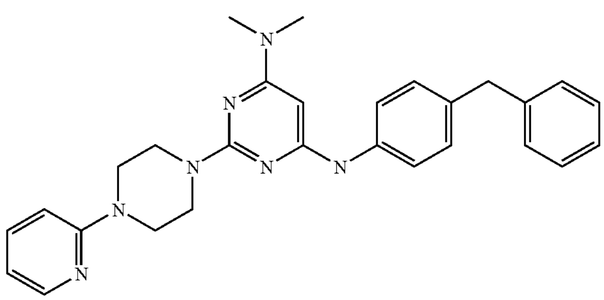 | 27 |
| 189 | 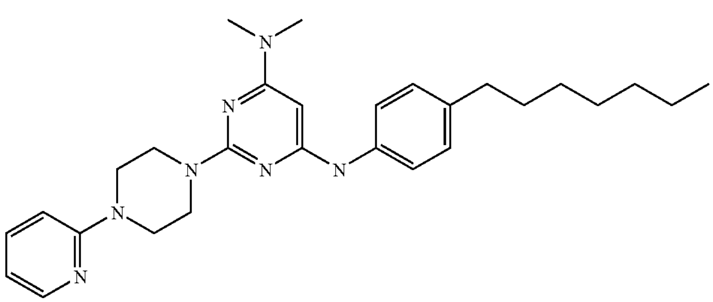 | 26 |

TABLE 3a-continued

| Example | Structure | Ki (nM) Gal3 |
|---|---|---|
| 190 | 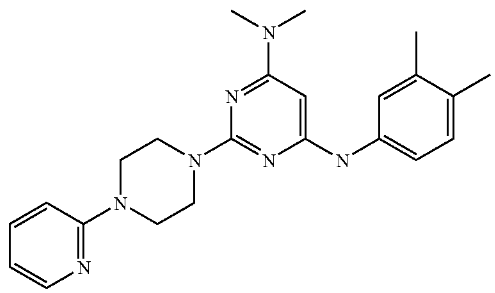 | 153 |
| 191 | 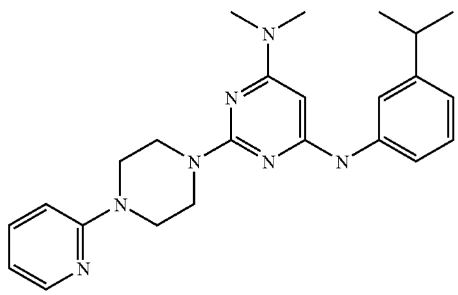 | 75 |
| 192 | 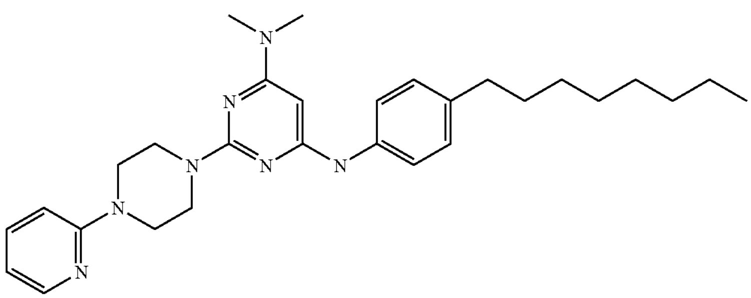 | 18 |
| 193 | 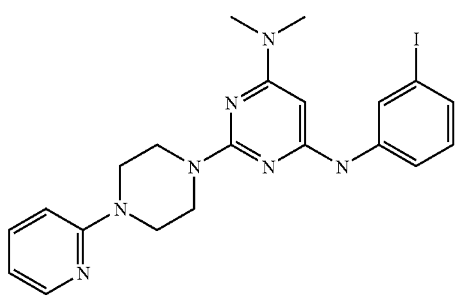 | 244 |
| 194 | 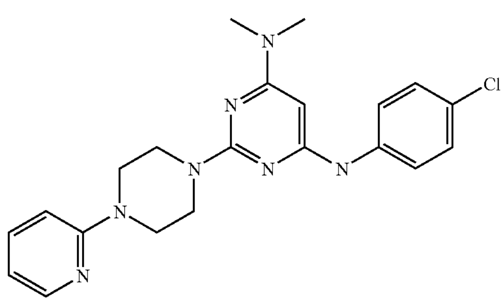 | 248 |

TABLE 3a-continued

| Example | Structure | Ki (nM) Gal3 |
|---|---|---|
| 195 | 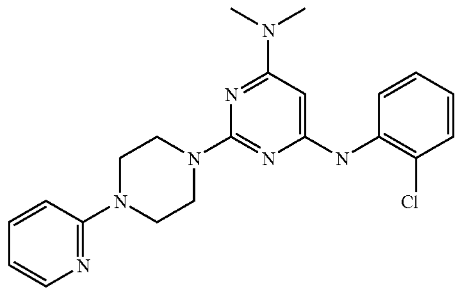 | 388 |
| 196 | 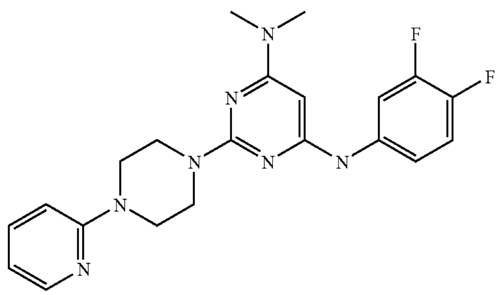 | 443 |
| 197 | 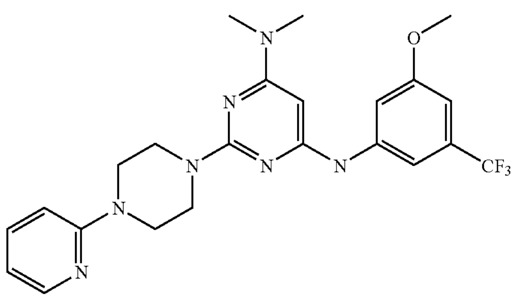 | 666 |
| 198 | 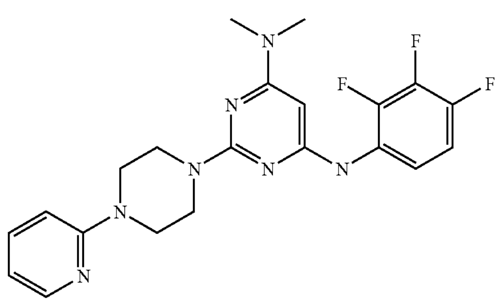 | 560 |
| 199 | 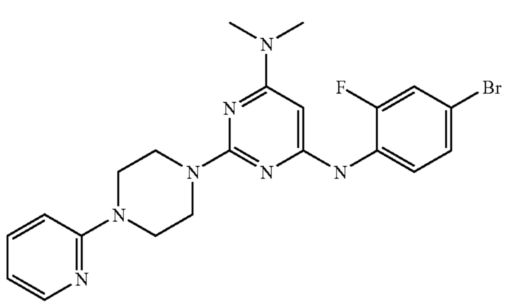 | 199 |

TABLE 3a-continued

| Example | Structure | Ki (nM) Gal3 |
|---|---|---|
| 200 | 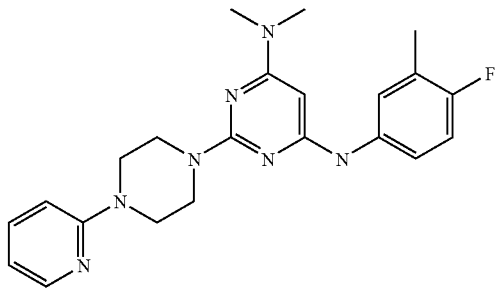 | 311 |
| 201 | 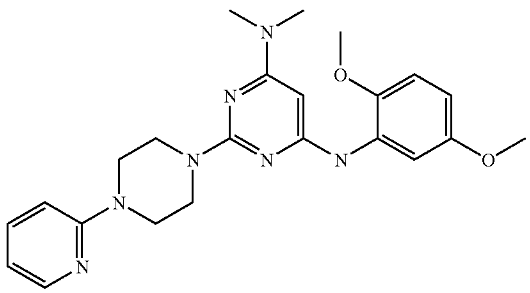 | 566 |
| 202 | 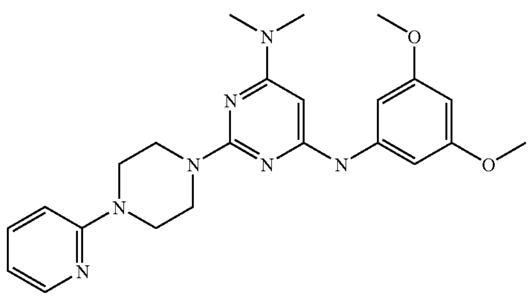 | 740 |
| 203 | 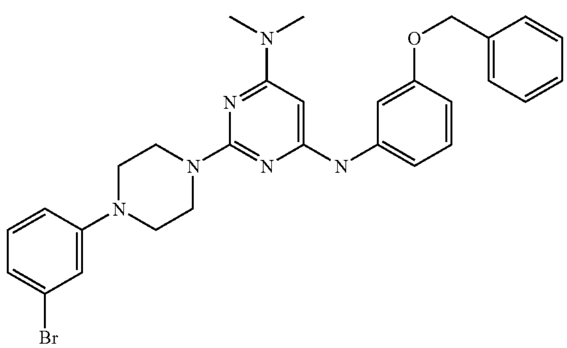 | 52 |
| 204 | 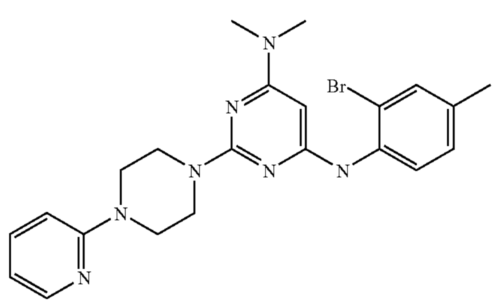 | 269 |

TABLE 3a-continued

| Example | Structure | Ki (nM) Gal3 |
|---|---|---|
| 205 | 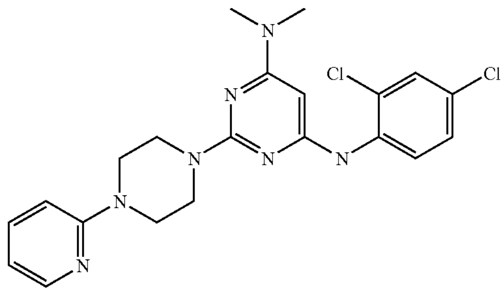 | 193 |
| 206 | 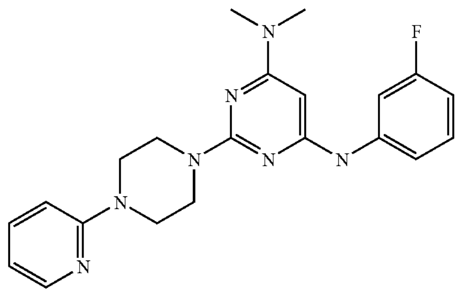 | 454 |
| 207 | 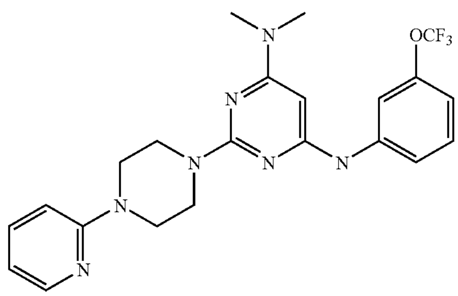 | 58 |
| 208 | 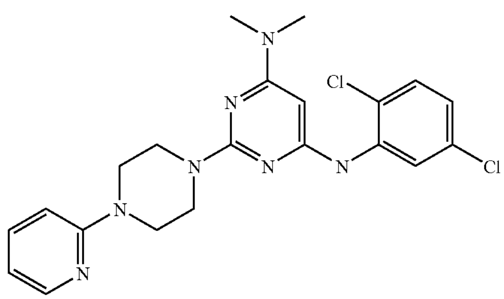 | 120 |
| 209 | 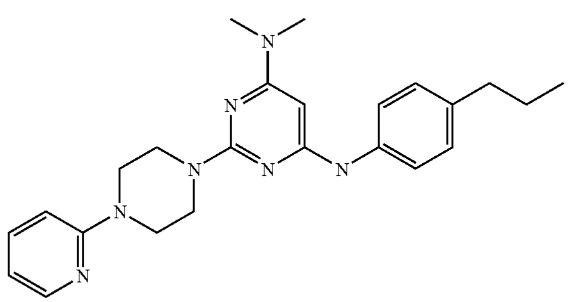 | 205 |

TABLE 3a-continued
| Example | Structure | Ki (nM) Gal3 |
|---|---|---|
| 210 | 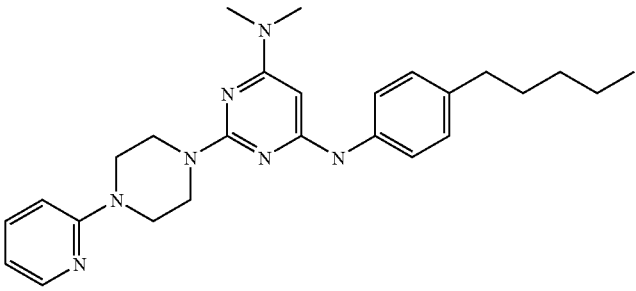 | 58 |
| 211 | 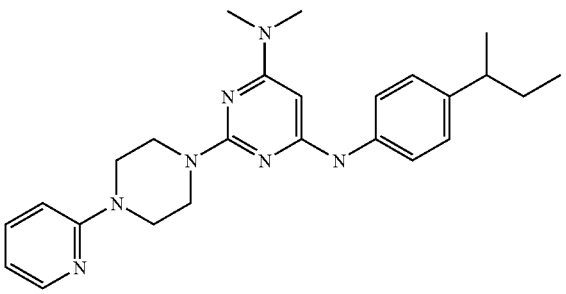 | 58 |
| 212 | 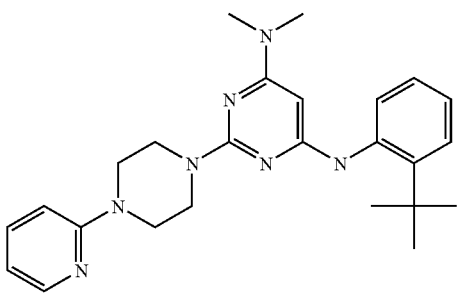 | 231 |
| 213 | 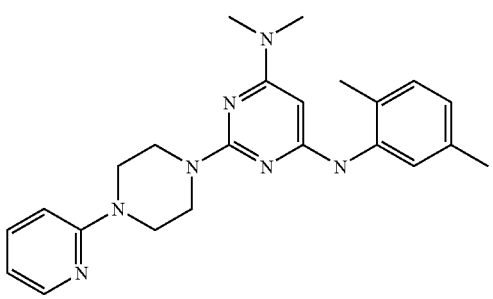 | 165 |
| 214 | 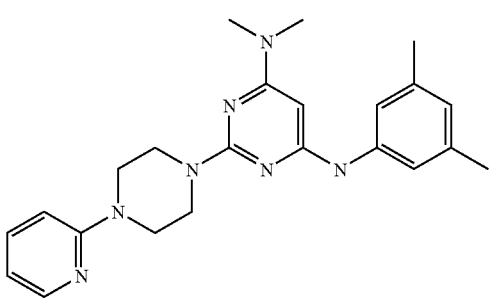 | 676 |

TABLE 3a-continued

| Example | Structure | Ki (nM) Gal3 |
|---|---|---|
| 215 | 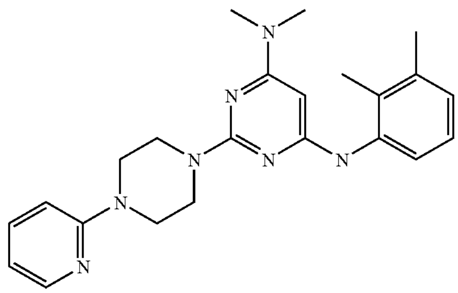 | 450 |
| 216 | 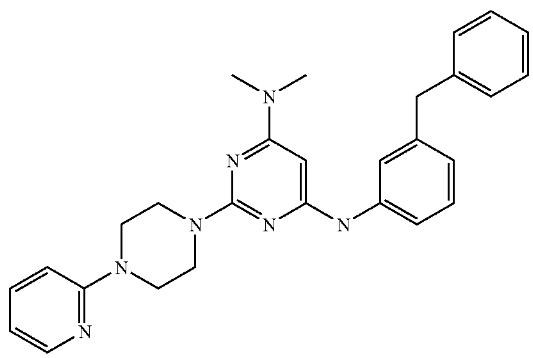 | 50 |
| 217 | 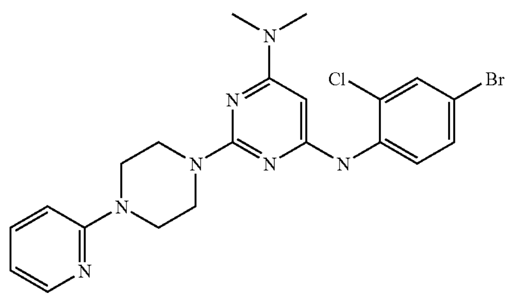 | 190 |
| 218 | 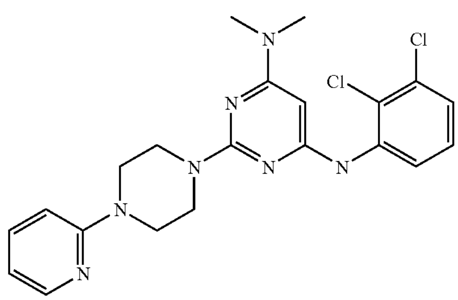 | 616 |
| 219 | 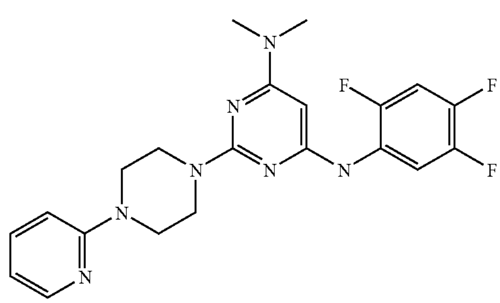 | 558 |

TABLE 3a-continued

| Example | Structure | Ki (nM) Gal3 |
|---|---|---|
| 220 | 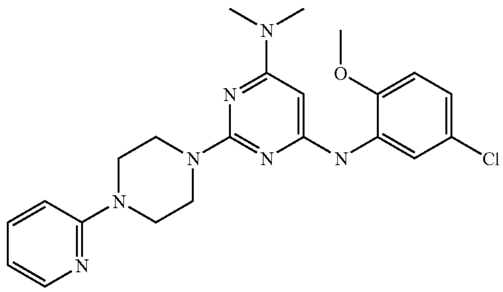 | 708 |
| 221 | 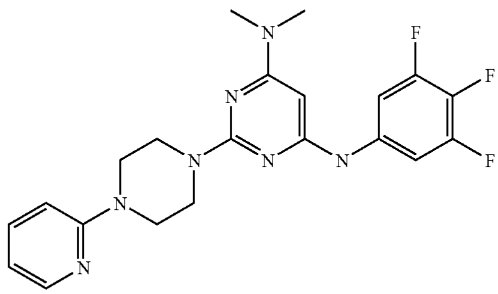 | 213 |
| 222 | 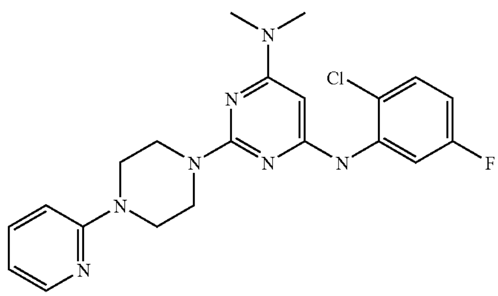 | 847 |
| 223 | 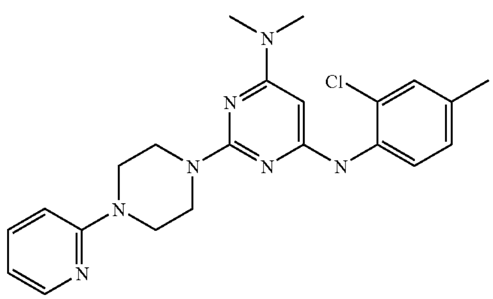 | 559 |
| 224 | 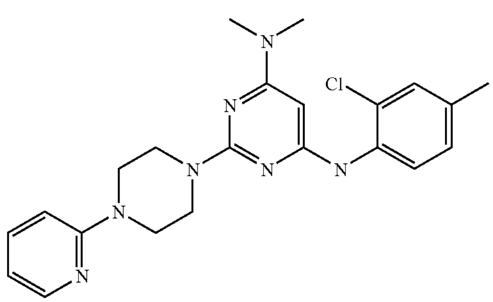 | 218 |

TABLE 3a-continued
| Example | Structure | Ki (nM) Gal3 |
|---|---|---|
| 225 | 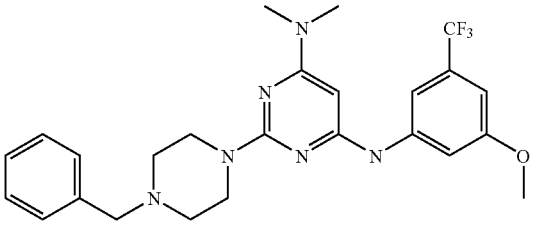 | 66 |
| 226 | 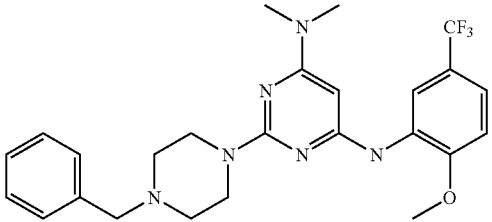 | 72 |
| 227 | 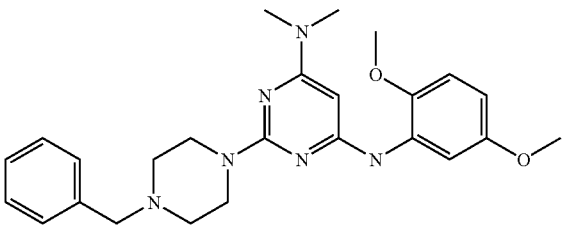 | 600 |
| 228 | 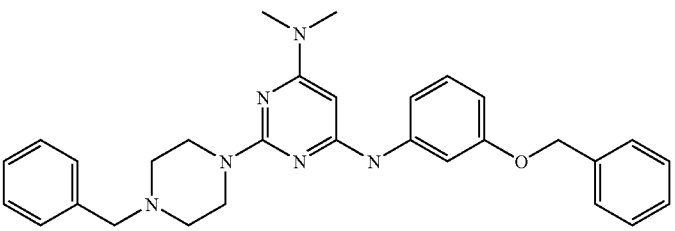 | 32 |
| 229 | 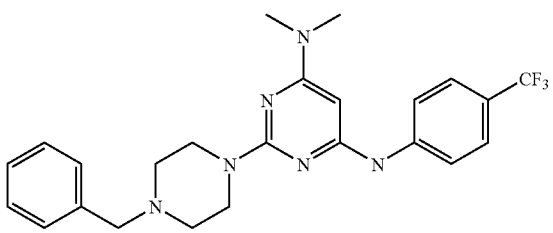 | 37 |
| 230 | 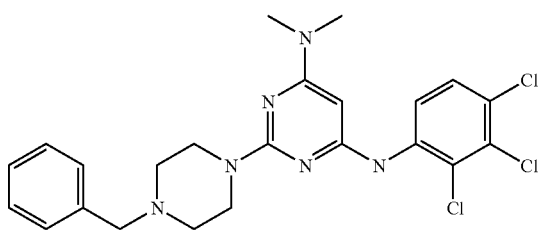 | 52 |

TABLE 3a-continued

| Example | Structure | Ki (nM) Gal3 |
|---------|-----------|--------------|
| 231 | 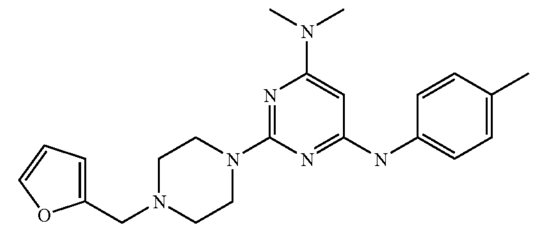 | 136 |
| 232 | 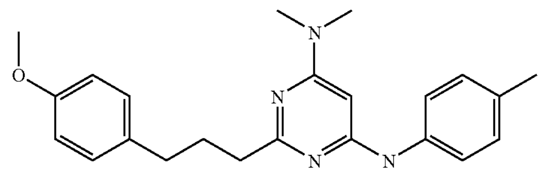 | 155* |
| 233 | 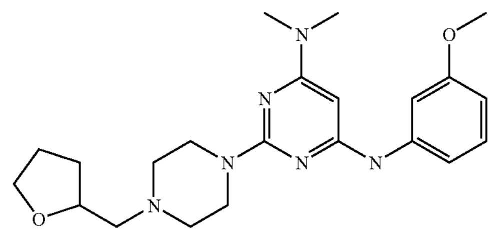 | 869 |
| 235 | 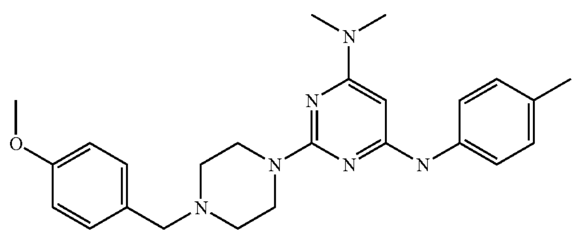 | 114* |
| 237 | 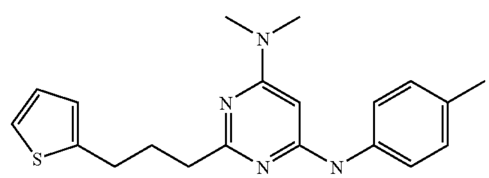 | 404* |
| 238 | 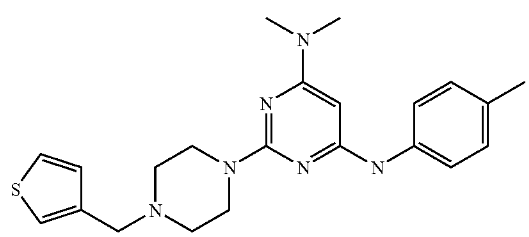 | 331* |
| 239 | 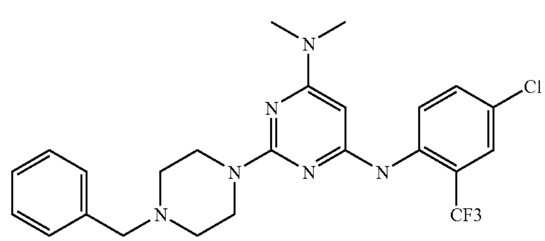 | 59 |

TABLE 3a-continued
| Example | Structure | Ki (nM) Gal3 |
|---|---|---|
| 240 | 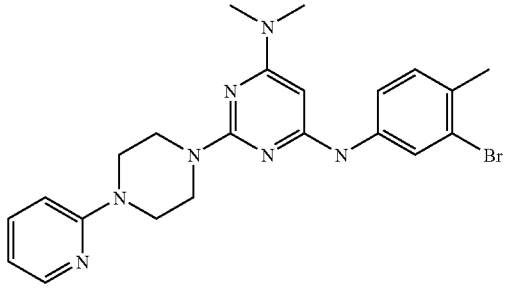 | 77 |
| 241 | 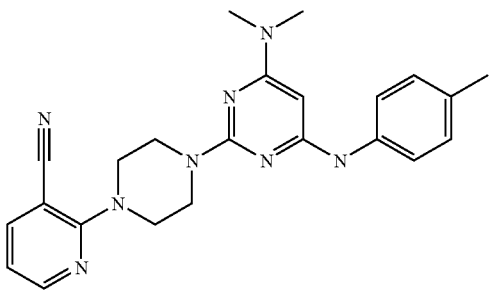 | 261 |
| 242 | 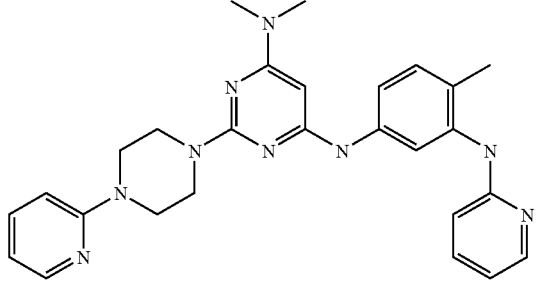 | 166 |
| 243 | 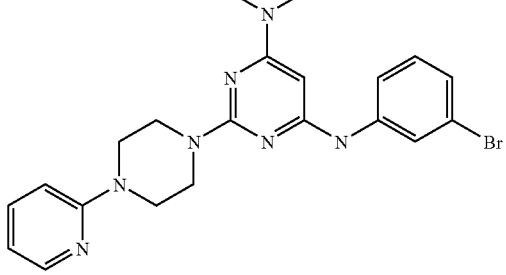 | 46 |
| 244 | 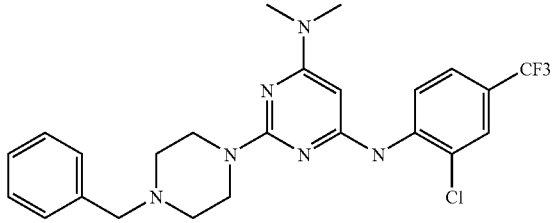 | 55 |

TABLE 3a-continued

| Example | Structure | Ki (nM) Gal3 |
|---|---|---|
| 245 | 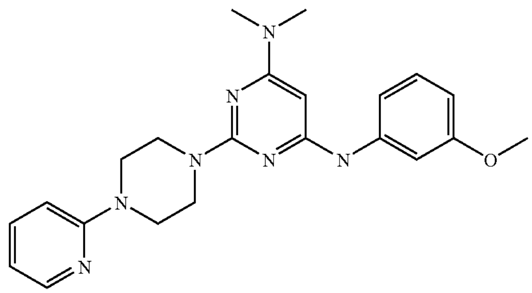 | 537 |
| 246 | 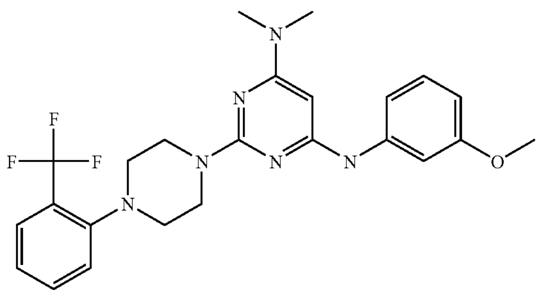 | 270 |
| 247 | 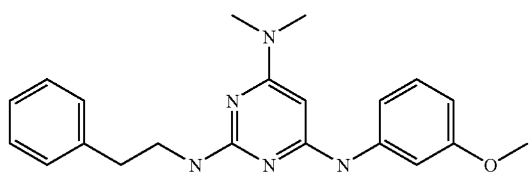 | 195 |
| 248 | 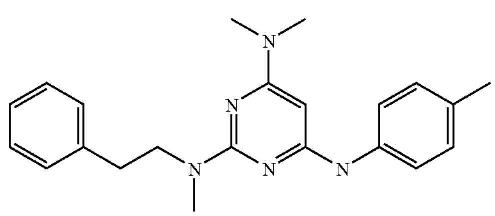 | 33 |
| 249 | 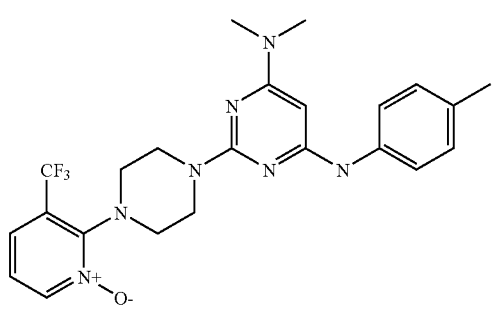 | 386 |
| 250 | 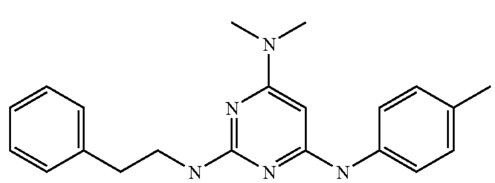 | 119 |

TABLE 3a-continued

| Example | Structure | Ki (nM) Gal3 |
|---------|-----------|--------------|
| 251 | 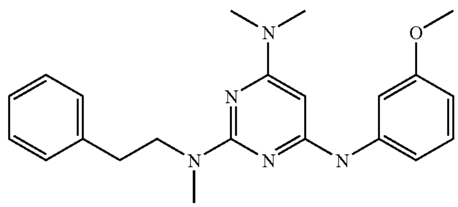 | 54 |
| 252 | 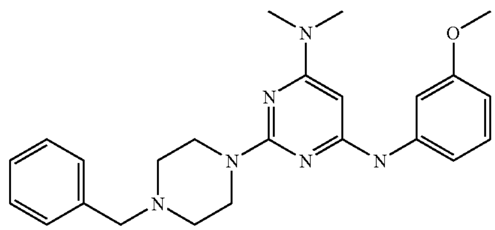 | 88 |
| 253 | 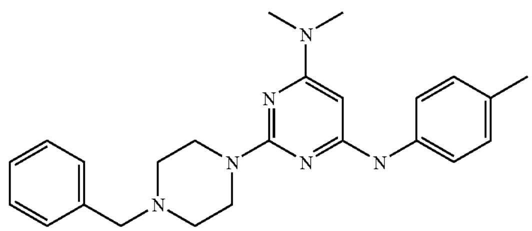 | 49 |

*The binding assay normally used for the indolone compounds was used to test this compound.

B. General Procedure for Preparing Indolones

General Procedure for Synthesis of Iminoisatins. The appropriately substituted isatin (10 mg-10 g) was placed in a flask and the appropriate aniline (1.0-1.1 equivalents) was added and the mixture was stirred to homogeneity. The mixture was then heated to 110° C. for 2-7 hours and then cooled. Solids were crystallized from hot methanol and filtered, giving the desired products (usually as an inseparable interconverting mixture of E/Z isomers).

Procedure A:

1-(3-THIENYL)-1H-INDOLE-2,3-DIONE

Triethylamine (56.9 mL, 0.408 mol), was added to a mixture of 1H-indole-2,3-dione (15.0 g, 0.102 mol), copper (II) acetate (46.0 g, 0.255 mol), and 3-thienylboronic acid (19.6 g, 0.153 mol) in $CH_2Cl_2$ (500 mL). The reaction mixture was stirred overnight, filtered through Celite, rinsed with EtOAc/hexane (1:1, 300 mL), and concentrated in vacuo. The crude product was purified by column chromatography on silica using Hexane/EtOAc (1:1), giving the desired product (1.1 g, 50%).

Procedure B:

(3E)-3-[(4-METHYLPHENYL)IMINO]-1-(3-THIENYL)-1,3-DIHYDRO-2H-INDOL-2-ONE

A solution of 1-(3-Thienyl)-1H-indole-2,3-dione (20 mg, 0.087 mmol) in 1% HOAc/MeOH (8 mL) was added to a solution of p-toluidine (19 mg, 0.18 mmol) in 1% HOAc/MeOH (8 mL). The reaction mixture was stirred for 12 h at room temperature, heated at 50° C. for 1 h, and concentrated in vacuo. The residue was purified by preparative TLC or silica using EtOAc/hexanes (3:7, 0.1% TEA) giving the desired product (14 mg, 50%).

Procedure C:

(3Z)-1-PHENYL-3-{[4-(3-THIENYL)PHENYL]IMINO}-1,3-DIHYDRO-2H-INDOL-2-ONE

A mixture of (3Z)-3-[(4-bromophenyl)imino]-1-phenyl-1,3-dihydro-2H-indol-2-one (50.0 mg, 0.133 mmol), thiophene-3-boronic acid (26.0 mg, 0.199 mmol), tetrakis(triphenylphosphine)palladium(0) (31.0 mg, 0.0268 mmol in THF (5 mL), and aqueous $Na_2CO_3$ (2M, 100 µL) was heated at 67° C. for 24 h. The crude product was concentrated in vacuo and the residue was extracted with $CH_2Cl_2$ (3×1 ml), and concentrated. The crude product was purified by preparative TLC using 10% methanol in $CHCl_3$, giving the desired product (18 mg, 35%).

Procedure D:

(3Z)-5-BROMO-3-{[3-(TRIFLUOROMETHYL)PHENYL]IMINO}-1,3-DIHYDRO-2H-INDOL-2-ONE

A mixture of 5-bromo-1H-indole-2,3-dione (1.0 g, 0.442 mmol) and 3-trifluoromethylaniline (0.993 g, 6.2 mmol) in a solution of 1% acetic acid in methanol was stirred at 50° C. for 12 h. The crude product was concentrated in vacuo, giving the desired crude product (640 mg, 40%).

Procedure E:

(3Z)-5-BROMO-1-PHENYL-3-{[3-(TRIFLUO-ROMETHYL)PHENYL]IMINO}-1,3-DIHYDRO-2H-INDOL-2-ONE

A mixture of (3z)-5-bromo-3-{[3-(trifluoromethyl)phenyl]imino}-1,3-dihydro-2h-indol-2-one (100 mg, 0.272 mmol), copper (II) acetate (54 mg, 0.33 mmol), triethylamine (82.8 mg, 0.817 mmol), and benzene boronic acid (40 mg, 0.325 mmol) in 5 mL of $CH_2Cl_2$ was stirred at room temperature for 12 h. The crude mixture was concentrated in vacuo and purified by preparative TLC using EtOAc:hexane (3:7, 1% triethylamine), giving the desired product (22 mg, 20%).

Procedure F:

(3Z)-1,5-DIPHENYL-3-{[3-(TRIFLUOROMETHYL)PHENYL]IMINO}-1,3-DIHYDRO-2H-INDOL-2-ONE

A mixture of (3z)-5-bromo-1-phenyl-3-{[3-(trifluoromethyl)phenyl]imino}-1,3-dihydro-2H-indol-2-one (22 mg, 0.05 mmol), tetrakis(triphenylphosphine)palladium(0) (12.0 mg, 0.01 mmol), benzene boronic acid (10 mg, 0.08 mmol) in THF (5 mL), and aqueous $Na_2CO_3$ (2M, 10C µL) was heated at 67° C. for 24 h. The crude product was concentrated in vacuo and the residue was extracted with $CH_2Cl_2$ (3×1 ml), concentrated, and purified by preparative TLC using 10% methanol in $CHCl_3$, giving the desired product (4 mg, 18%).

Procedure G:

ETHYL 5-[(2,3-DIOXO-2,3-DIHYDRO-1H-INDOL-1-YL)METHYL]-2-FUROATE

A mixture of ethyl 5-(chloromethyl)-2-furoate (148 mg, 1.01 mmol) in dioxane (15 ml) was added to a mixture of NaH (48 mg, 1.20 mmol) in dioxane (10 mL) under argon at 0° C. The mixture was stirred for 1 h at room temperature, refluxed under argon for 16 h, cooled to room temperature, and then concentrated in vacuo. The residue was purified by preparative TLC using EtOAc/hexane (3:7), giving the desired product (56 mg, 19%).

Procedure H:

ETHYL 5-[((3Z)-2-OXO-3-{[3-(TRIFLUOROMETHYL)PHENYL]IMINO}-2,3-DIHYDRO-1H-INDOL-1-YL)METHYL]-2-FUROATE

A mixture of ethyl 5-[(2,3-dioxo-2,3-dihydro-1H-indol-1-yl)methyl]-2-furoate (60 mg, 0.200 mmol) and 3-trifluoromethylaniline (32 mg, 0.200 mmol) was heated at 140° C. for 2 h. The residue was dissolved in $CHCl_3$ (1 mL) and purified by preparative TLC using EtOAc/hexane (6:4), giving the desired product (20 mg, 23%).

Procedure I:

6-METHOXY-1-PHENYL-1H-INDOLE-2,3-DIONE

A solution of N-(3-methoxyphenyl)-N-phenylamine (1.14 g, 5.72 in ether (3 mL) was added to a solution of oxylyl chloride (728 g, 5.75 mmol) and heated at reflux for 1 h. The resulting mixture was cooled to room temperature, concentrated to dryness, and redissolved in nitrobenzene (35 mL). The solution was added to a solution of $AlCl_3$ in nitrobenzene (0.762 g, 5.72 mmol), and the resulting mixture was heated at 70° C. for 16 h. The crude product was concentrated in vacuo and purified by column chromatography using EtOAc/hexane (1:1), giving the desired product 60, mg, 50%).

Procedure J:

(3Z)-1-(4-BROMOPHENYL)-3-{[3-(TRIFLUOROMETHYL)PHENYL]IMINO}-1,3-DIHYDRO-2H-INDOL-2-ONE

A solution of (3Z)-3-{[3-(trifluoromethyl)phenyl]imino}-1,3-dihydro-2H-indol-2-one (100 mg, 0.344 mmol), copper (II) acetate (93 mg, 0.516 mmol), triethylamine (105 mg, 1.03 mmol), and 4-bromobenzene boronic acid (104 mg, 0.516 mmol) in 5 mL of $CH_2Cl_2$ was stirred at room temperature for 12 h. The crude mixture was concentrated in vacuo and purified by preparative TLC using EtOAc:hexane (3:7, 1% triethylamine), giving the desired product (65 mg, 42%).

Procedure K:

A solution of (3Z)-1-(4-bromophenyl)-3-{[3-(trifluoromethyl)phenyl]imino}-1,3-dihydro-2H-indol-2-one (30 mg, 0.068), tetrakis(triphenylphosphine)palladium(0) (16.0 mg, 0.014 mmol), benzene boronic acid (13 mg, 0.101 mmol) in THF (5 mL), and aqueous $Na_2CO_3$ (0.45 M, 300 µL) was heated at 67° C. for 40 h. The crude product was concentrated in vacuo and the residue was extracted with $CH_2Cl_2$ (3×1 ml), concentrated, and purified by preparative TLC using 10% methanol in $CHCl_3$, giving the desired product (5 mg, 16%).

The compounds of Examples 92-107, inclusive, were purchased from Bionet Research Ltd., 3 Highfield Industrial Estate, Camelford, Cornwall PL32 9QZ, UK. These compounds can also be synthesized using the procedure described above.

Example 91

3-[(2-METHOXYPHENYL)IMINO]-1-PHENYL-1,3-DIHYDRO-2H-INDOL-2-ONE

Example 92

1-PHENYL-3-[[3-(TRIFLUOROMETHYL)PHENYL]IMINO]-1,3-DIHYDRO-2H-INDOL-2-ONE

Example 93

3-[(3-METHYLPHENYL)IMINO]-1-PHENYL-1,3-DIHYDRO-2H-INDOL-2-ONE

Example 94

3-[(3-CHLOROPHENYL)IMINO]-1-PHENYL-1,3-DIHYDRO-2H-INDOL-2-ONE

Example 95

1-PHENYL-3-[[4-(TRIFLUOROMETHYL)PHENYL]IMINO]-1,3-DIHYDRO-2H-INDOL-2-ONE

Example 96

3-[(4-METHYLPHENYL)IMINO]-1-PHENYL-1,3-DIHYDRO-2H-INDOL-2-ONE

Example 97

3-[(4-CHLOROPHENYL)IMINO]-1-PHENYL-1,3-DIHYDRO-2H-INDOL-2-ONE

Example 98

3-[(4-BROMOPHENYL)IMINO]-1-PHENYL-1,3-DIHYDRO-2H-INDOL-2-ONE

Example 99

3-[(4-FLUOROPHENYL)IMINO]-1-PHENYL-1,3-DIHYDRO-2H-INDOL-2-ONE

Example 100

3-[(4-PHENOXYPHENYL)IMINO]-1-PHENYL-1,3-DIHYDRO-2H-INDOL-2-ONE

Example 101

3-[(4-ETHOXYPHENYL)IMINO]-1-PHENYL-1,3-DIHYDRO-2H-INDOL-2-ONE

Example 102

3-[(4-METHOXYPHENYL)IMINO]-1-PHENYL-1,3-DIHYDRO-2H-INDOL-2-ONE

Example 103

3-[(3,5-DICHLOROPHENYL)IMINO]-1-PHENYL-1,3-DIHYDRO-2H-INDOL-2-ONE

Example 104

3-[(3,5-DIMETHYLPHENYL)IMINO]-1-PHENYL-1,3-DIHYDRO-2H-INDOL-2-ONE

Example 105

1-ALLYL-3-[(3,4-DICHLOROPHENYL)IMINO]-1,3-DIHYDRO-2H-INDOL-2-ONE

Example 106

1-ALLYL-3-[(3,5-DICHLOROPHENYL)IMINO]-1,3-DIHYDRO-2H-INDOL-2-ONE

Example 107

3-[(4-BROMOPHENYL)IMINO]-1-ISOPROPYL-1,3-DIHYDRO-2H-INDOL-2-ONE

The methods that follow demonstrate procedures useful for synthesizing compounds of this invention (illustrated in Schemes 6 and 7). Substituted isatins useful for synthesizing compounds of this invention can alternatively be obtained using the procedures described in the following references: Garden, S. J.; Da Silva, L. E.; Pinto, A. C.; Synthetic Communications, 1998, 28, 1679-1689.

Coppola, G. M.; Journal of Heterocyclic Chemistry, 1987, 24, 1249.

Hess, B. A. Jr; Corbino, S., Journal of Heterocyclic Chemistry, 1971, 8, 161.

Bryant, W. M. III; Huhn, G. F.; Jensen, J. H.; Pierce, M. E.; Stammbach, C.; Synthetic Communications, 1993, 23, 1617-1625.

Example 108

1-[(5-CHLORO-2-THIENYL)METHYL]-3-{[3-(TRIFLUOROMETHYL)PHENYL]IMINO}-1,3-DIHYDRO-2H-INDOL-2-ONE

A mixture of 1-[(5-chloro-2-thienyl)methyl]-2H-indole-2,3-dione (25 mg, 0.09 mmol) (prepared as described below) and 3-trifluoromethylaniline (11.3 µL, 0.09 mmol) was heated neat at 140° C. for 2 h. The crude material was purified by preparative TLC using a mixture of 3:7 ethyl acetate in hexane as the eluent, giving the desired product (23 mg 0.05 mmol, 61%). $^1$H NMR (400 MHz): δ (major isomer) 7.57 (t, J=7.7, 1H), 7.53 (t, J=7.8, 1H), 7.33 (t, J=7.8, 1H), 7.28 (s, 1H), 7.19 (d, J=7.6, 2H), 6.24-6.72 (m, 4H), 6.56 (d, J=7.7, 1H), 5.02 (s, 2H); ESI-MS m/z found 421 (MH$^+$).

1-[(5-CHLORO-2-THIENYL)METHYL]-2H-INDOLE-2,3-DIONE

A solution of isatin (125 mg, 0.85 mmol) in anhydrous dioxane (10 mL) was added dropwise to a solution of sodium hydride (60% dispersion in mineral oil, 24 mg, 0.62 mmol) in anhydrous dioxane (10 mL) at 0° C. under argon. The mixture was allowed to stir for 5 minutes and then 2-chloro-5-(chloromethyl)thiophene (0.12 mL, 1.02 mmol) in dioxane (10 mL) was added dropwise to the resulting mixture. The reaction mixture was heated at reflux under argon for 16 h and concentrated in vacuo. The crude material was purified preparative TLC using 1:24 methanol in chloroform as the eluent, giving the desired product as a yellow solid (53 mg, 0.19 mmol, 22%). $^1$H NMR (400 MHz): δ 7.62 (d, J=7.4, 1H), 7.56 (t, J=7.8, 1H), 7.14 (t, J=7.7, 1H), 6.94 (d, J=8.0, 1H), 6.90 (d, J=3.2, 1H), 6.78 (d, J=3.7, 1H), 4.90 (s, 2H).

Example 109

1-(3-THIENYL)-3-{[3-(TRIFLUOROMETHYL)PHENYL]IMINO}-1,3-DIHYDRO-2H-INDOL-2-ONE

A mixture of 1-(3-thienyl)-2H-indole-2,3-dione (25 mg, 0.11 mmol) (prepared as described below) and 3-trifluoromethylaniline (14 µL, 0.11 mmol) was heated neat at 140° C. for 2 h. The crude material was purified by preparative TLC using a mixture of 3:7 ethyl acetate and hexane as the eluent, giving the desired product as a yellow solid (7.3 mg, 0.02 mmol, 22%). $^1$H NMR (400 MHz) δ 7.62-7.19 (m, 9H), 6.94 (d, J=8.0, 1H), 6.76 (t, J=7.6, 1H); ESI-MS m/z found 373 (MH$^+$).

1-(3-THIENYL)-2H-INDOLE-2,3-DIONE

Copper(II) acetate monohydrate (4.25 g, 23.4 mmol) was heated at reflux in acetic anhydride (30 mL) for 2 h. The mixture was filtered and washed with anhydrous ether (500 mL). The solid was dried in vacuo at 55° C. for 16 h. Dichloromethane (1 mL) was added to a mixture of copper (II) acetate (62 mg, 0.34 mmol), isatin (50 mg, 0.34 mmol), and thiophene-3-boronic acid (87 mg, 0.68 mmol), followed by triethylamine (0.10 mL, 0.68 mmol) under argon. The resulting solution was stirred for 16 h at room temperature. The reaction mixture was then recharged with 0.10 mmol copper(II) acetate, 0.10 mmol of 3-thiophene boronic acid, and 1 drop of triethylamine, and the mixture was heated at 50° C. for 6 h. The crude material was purified by preparative TLC using 3:97 methanol in chloroform as the eluent, giving the desired product as a yellow solid (25 mg, 0.11 mmol, 33%). $^1$H NMR (400 kHz): δ 7.70 (d, J=7.5, 1H), 7.58 (t, J=7.8, 1H), 7.50 (d, J=5.1, 1H), 7.48 (s, 1H), 7.24 (d, J=5.1, 1H), 7.18 (t, J=7.51, 1H), 7.05 (d, J=8.0, 1H).

Example 110

2-METHYL-5-[(2-OXO-1-PHENYL-1,2-DIHYDRO-3H-INDOL-3-YLIDENE)AMINO]-2H-ISOINDOLE-1,3(2H)-DIONE

A mixture of 1-phenylisatin (50 mg, 0.22 mmol) and 4-amino-N-methylpthalimide (40 mg, 0.22 mmol) was heated neat at 215° C. for 2 h. The crude material was purified by preparative TLC using a mixture of 3:7 ethyl acetate and hexane as the eluent, giving the desired product as a yellow solid (8 mg, 0.02 mmol, 10%). $^1$H NMR (400 MHz): δ 7.88 (d, J=7.8, 1H), 7.83-7.80 (m, 1H), 7.51 (t, J=7.5, 1H), 7.47-7.18 (m, 6H), 7.02 (t, J=8.0, 1H), 6.91-6.79 (m, 2H), 6.58 (d, J=7.5, 1H), 3.22 (s, 3H); ESI-MS m/z found 382 (MH$^+$).

Example 111

1-[(5-CHLORO-1-BENZOTHIEN-3-YL)METHYL]-3-{[3-(TRIFLUOROMETHYL)PHENYL]IMINO}-1,3-DIHYDRO-2H-INDOL-2-ONE

A mixture of 1-[(5-chloro-1-benzothien-3-yl)methyl]-2H-indole-2,3-dione (50 ma, 0.15 mmol) (prepared as described below) and 3-trifluoromethylaniline (0.020 mL, 0.15 mmol) was heated neat at 140° C. for 2 h. The crude material was purified by preparative TLC using a mixture of 1:3 ethyl acetate and hexane as the eluent giving the desired product as a yellow solid (13 mg, 0.030 mmol, 18%). $^1$H NMR (400 MHz): δ 7.98 (d, J=2.0, 1H), 7.80 (d, J=8.6, 1H), 7.58 (t, J=7.7, 1H), 7.52 (d, J=8.1, 1H), 7.43 (s, 1H), 7.38 (dd, J=8.6, 1.9, 1H), 7.31 (overlapping singlet and dt, J=1.2, 7.8, 2H), 7.24 (d, J=7.8, 1H), 6.87 (d, J=7.9, 1H), 6.77 (t, J=7.7, 1H), 6.59 (d, J=7.7, 1H), 5.20 (s, 2H). ESI-MS m/z found 471 (MH$^+$ with $^{35}$Cl), 473 (MH$^+$ with $^{37}$Cl).

1-[(5-CHLORO-1-BENZOTHIEN-3-YL)METHYL]-2H-INDOLE-2,3-dione

A solution of isatin (125 mg, 0.85 mmol) in anhydrous dioxane (10 mL) was added dropwise to a solution of sodium hydride (60% dispersion in mineral oil, 25 mg, 0.62 mmol) in anhydrous dioxane (10 mL) at 0° C. under argon. The mixture was allowed to stir for 5 minutes and then a solution of 3-(bromomethyl)-5-chlorobenzo[b]thiophene (267 mg, 1.02 mmol) in dioxane (10 mL) was added dropwise to the reaction mixture. The reaction mixture was heated at reflux under argon for 16 h and concentrated in vacuo. The crude material was purified by preparative TLC using 1:24 methanol in chloroform as the eluent, giving the desired product as a yellow solid (125 mg, 0.38 mmol, 45%). $^1$H NMR (400 MHz): δ 7.89 (s, 1H), 7.79 (d, J=8.5, 1H), 7.65 (d, J=7.5, 1H), 7.54 (t, J=8.0, 1H), 7.42 (s, 1H), 7.38 (d, J=8.5, 1H), 7.14 (t, J=7.5, 1H), 6.88 (d, J=7.8, 1H), 5.13 (s, 2H).

Example 112

3-(1H-INDOL-5-YLIMINO)-1-PHENYL-1,3-DIHYDRO-2H-INDOL-2-ONE 1-phenylisatin (51.8 mg, 0.23 mmol) and 5-aminoindole (31 mg, 0.23 mmol) were mixed and heated at 140° C. for 2 h. The resulting crude product was purified by preparative TLC using ethyl acetate/hexane (6:4) as the eluent, giving the desired product as a yellow solid (10.8 mg, 14%). $^1$H NMR (400 MHz): δ 8.28 (s, 1H), 7.57 (t, J=7.7, 2H), 7.49-7.40 (m, 6H), 7.29-7.23 (m, 1H), 7.03 (dd, J=8.5, 1.7, 1H), 6.98 (d, J=7.6, 1H), 6.83 (d, J=8.0, 1H), 6.74, J=7.6, 1H), 6.59 (s, 1H); ESI-MS m/z found 338 (MH$^+$).

Example 113

3-[(6-CHLORO-3-PYRIDINYL)IMINO]-1-PHENYL-1,3-DIHYDRO-2H-INDOL-2-ONE 1-phenylisatin. (23.0 mg, 0.10 mmol) and 5-amino-2-chloropyridine (12.8 mg, 0.10 mmol) were mixed and heated at 140° C. for 7 h. The resulting crude product was purified by preparative TLC using hexane/ethyl acetate (8:2) as the eluent, giving the desired product as a yellow solid (19.7 mg, 59%). $^1$H NMR (400 MHz) δ 8.15 (d, J=8, 1H), 7.6-7.2 (m, 9H), 6.85-6.75 (m, 2H); ESI-MS m/z found 334 (MH$^+$).

Example 114

3-[(2-METHYL-1,3-BENZOTHIAZOL-5-YL)IMINO]-1-PHENYL-1,3-DIHYDRO-2H-INDOL-2-ONE 5-amino-2-methylbenzothiazole (52.2 mg, 0.31 mmol) was mixed with 1-phenylisatin (69.7 mg, 0.31 mmol) and heated at 140° C. for 3 h. The resulting crude product was purified by preparative TLC using ethyl acetate/hexane (6:4) as the eluent to give the desired product as a yellow solid (36.9 ma, 32.3%). $^1$H NMR Data: δ 7.9-6.7 (m, 12H), 2.9 (s, 3H). ESI-MS m/z found 370 (MH$^+$).

Example 254

(3Z)-3-[(3,4-DICHLOROPHENYL)IMINO]-1-(2-PYRIDINYLMETHYL)-1,3-DIHYDRO-2H-INDOL-2-ONE

Prepared by Procedures H and K (for substitution of 2-picolyl chloride). $^1$H NMR (400 MHz, CDCl$_3$) δ 8.51-8.46 (m, 1H), 7.87-7.78 (m, 1H), 7.64 (d, 1H, J=7.1), 7.53-7.31 (m, 5H), 7.28 (d, 1H, J=4.1), 7.12 (d, 1H, J=8.1), 6.58-6.53 (m, 1H), 5.51 (s, 2H); ESI-MS m/z 381 (MH$^+$).

Example 255

(3Z)-3-[(3,4-DICHLOROPHENYL)IMINO]-1-[(3,5-DIMETHYL-4-ISOXAZOLYL)METHYL]-1,3-DIHYDRO-2H-INDOL-2-ONE

Prepared by Procedure B (microwave heating). $^1$H NMR (400 MHz, CDCl$_3$) δ 7.63 (d, 1H, J=9.1), 7.46 (dt, 1H, J=8.1, 2.0), 7.28 (d, 1H, J=2.1), 7.02 (d, 1H, J=2.0), 6.88 (dt, 1H, J=8.0, 2.1), 6.74-6.72 (m, 1H), 6.72-6.70 (m, 1H), 5.53 (s, 2H), 2.50 (s, 3H), 2.24 (s, 3H); ESI-MS m/z 399 (MH⁺).

Example 256

(3Z)-3-[(3,4-DICHLOROPHENYL)IMINO-1-[3-(TRIFLUOROMETHYL)PHENYL]-1,3-DIHYDRO-2H-INDOL-2-ONE

Prepared by Procedures A and B. ¹H NMR (400 MHz, CDCl₃) δ 7.90-7.87 (m, 1H), 7.83-7.79 (m, 1H), 7.67 (d, 1H, J=8), 7.46-7.40 (m, 1H), 7.33 (d, 1H, J=2), 7.08-7.05 (m, 1H), 6.96-6.80 (m, 5H); ESI-MS m/z 435 (MH⁺).

Example 257

(3Z)-1-(3,5-DICHLOROPHENYL)-3-[(3,4-DICHLOROPHENYL)IMINO]-1,3-DIHYDRO-2H-INDOL-2-ONE

Prepared by Procedures A and B. ¹H NMR (400 MHz, CDCl₃) δ 7.93 (d, 1H, J=8.1), 7.79 (d, 1H, J=6.0), 7.72-7.68 (m, 1H), 7.59-7.45 (m, 1H), 7.46 (d, 1H, J=8.1), 7.32 (dt, 1H, J=8.0, 2.1), 7.23 (d, 1H, J=2.5), 6.97 (dd, 1H, J=8.0, 2.1), 6.92-6.87 (m, 1H), 6.85-6.81 (m, 1H); ESI-MS m/z 435 (MH⁺).

Example 258

(3Z)-3-[(3,4-DICHLOROPHENYL)IMINO]-6-METHOXY-1-PHENYL-1,3-DIHYDRO-2H-INDOL-2-ONE

Prepared by Procedures K, L, and B. ¹H NMR (400 MHz, CDCl₃) δ 7.69-7.54 (m, 1H), 7.53-7.38 (m, 3H), 7.29 (d, 1H, J=2.0), 7.17 (d, 1H, J=8.1), 7.12 (d, 1H, J=8.0), 6.84 (d, 1H, J=2.5), 6.78 (d, 1H, J=8), 6.6 (dd, 2H, J=8.0, 2.0), 6.55 (dd, 2H, J=8.1, 2.5); ESI-MS m/z (398 MH⁺).

Example 259

(3Z)-3-[(4-CHLORO-3-METHYLPHENYL)IMINO]-1-(3-THIENYL)-1,3-DIHYDRO-2H-INDOL-2-ONE

Prepared by Procedures A and B (80° C.). ¹H NMR (400 MHz, CDCl₃) δ 7.69-7.62 (m, 2H), 7.49 (s, 1H), 7.47 (s, 1H), 7.41 (dt, 1H, J=7.1, 1.6), 7.3 (dd, 1H, J=5.0, 1.6), 7.05-6.97 (m, 1H, 6.93-6.86 (m, 1H), 6.77 (m, 1H), 6.56 (m, 1H), 2.53 (s, 3H); ESI-MS m/z 353 (MH⁺).

Example 260

(3Z)-3-(2-NAPHTHYLIMINO)-1-(3-THIENYL)-1,3-DIHYDRO-2H-INDOL-2-ONE

Prepared by Procedures A and B (80° C.). ¹H NMR (400 MHz, CDCl₃) δ 8.15 (d, 1H, J=9.1), 8.06-7.99 (m, 1H), 7.89-7.80 (m, 1H), 7.78-7.71 (m, 1H), 7.71-7.47 (m, 4H), 7.41-7.35 (m, 1H), 7.33 (d, 1H, J=5.2), 7.28 (d, 1H, J=6.8.1), 7.00 (d, 1H, J=8.0), 6.76 (t, 1H, J=7.8), 6.67 (d, 1H, J=7.9); ESI-MS m/z 355 (MH⁺).

Example 261

(3Z)-3-[(4-CHLOROPHENYL)IMINO]-1-(3-THIENYL)-1,3-DIHYDRO-2H-INDOL-2-ONE

Prepared by Procedures A and B (80° C.). ¹H NMR (400 MHz, CDCl₃) δ 7.69-7.56 (m, 2H), 7.54-7.48 (m, 1H), 7.41 (dt, 1H, J=8, 2), 7.32-7.28 (m, 1H), 7.11-6.99 (m, 3H), 6.89 (dt, 1H, J=8), 6.77-6.73 (m, 1H), 6.66-6.33 (m, 1H); ESI-MS m/z 339 (MH⁺).

Example 262

(3Z)-3-[(4-IODOPHENYL)IMINO]-1-(3-THIENYL)-1,3-DIHYDRO-2H-INDOL-2-ONE

Prepared by Procedures A and B (1% HOAc, in MeOH). ¹H NMR (400 MHz, CDCl₃) δ 7.79-7.74 (m, 2H), 7.53-7.48 (m, 2H), 7.35 (dt, 1H, J=8.0, 1.2), 7.29-7.24 (m, 1H), 6.98 (d, 1H, J=8.0), 6.89-6.75 (m, 4H.); ESI-MS m/z 431 (MH⁺).

Example 263

(3Z)-3-[(4-METHYLPHENYL)IMINO]-1-(3-THIENYL)-1,3-DIHYDRO-2H-INDOL-2-ONE

Prepared by Procedures A and B (1% HOAc in MeOH). ¹H NMR (400 MHz, CDCl₃) δ 7.52-7.44 (m, 2H), 7.35-7.22 (m, 4H), 6.99-6.93 (m, 3H), 6.87-6.78 (m, 2H), 2.42 (s, 3H); ESI-MS m/z 319 (MH⁺).

Example 264

(3Z)-3-((3,5-DIFLUOROPHENYL)IMINO]-1-(3-THIENYL)-1,3-DIHYDRO-2H-INDOL-2-ONE

Prepared by Procedures A and B (1% HOAc in MeOH). ¹H NMR (400 MHz, CDCl₃) δ 7.54-7.16 (m, 4H), 6.99 (dt, 1H, J=8.2, 0.8), 6.89 (dt, 1H, J=7.7, 1.1), 6.76 (d, 1H, J=7.5), 6.71 (tt, 1H, J=9.3, 2.3), 6.64-6.57 (m, 2H); ESI-MS m/z 341 (MH⁺).

Example 265

(3Z)-3-([1,1'-BIPHENYL]-4-YLIMINO)-1-(3-THIENYL)-1,3-DIHYDRO-2H-INDOL-2-ONE

Prepared by Procedures A and B (1% HOAc in MeOH). ¹H NMR (400 MHz, CDCl₃) δ 7.73-7.12 (m, 13H), 6.99 (d, 1H, J=8.0), 6.89 (d, 1H, J=8.0), 6.82 (dt, 1H, J=7.6, 1.0); ESI-MS m/z 381 (MH⁺).

Example 266

ETHYL 3-{[(3Z)-2-OXO-1-(3-THIENYL)-1,2-DIHYDRO-3H-INDOL-3-YLIDENE]AMINO}BENZOATE

Prepared by Procedures A and B (1% HOAc in MeOH). ¹H NMR (400 MHz, CDCl₃) δ 7.96 (d, 1H, J=7.4), 7.75-7.17 (m, 6H), 6.98 (d, 1H, J=8.0), 6.87-6.78 (m, 2H), 6.63 (d, 1H, J=7.8), 4.45-4.32 (m, 2H), 1.43-1.33 (m, H); ESI-MS m/z 377 (MH⁺).

Example 267

(3Z)-3-[(6-CHLORO-3-PYRIDINYL)IMINO]-1-(3-THIENYL)-1,3-DIHYDRO-2H-INDOL-2-ONE

Prepared by Procedures A and B (1% HOAc in MeOH). $^1$H NMR (400 MHz, CDCl$_3$) δ 8.21-6.81 (m, 10H); ESI-MS m/z 340.13 (MH$^+$).

Example 268

3Z)-3-[(4-PHENOXYPHENYL)IMINO]-1-(3-THIENYL)-1,3-DIHYDRO-2H-INDOL-2-ONE

Prepared by Procedures A and B (1% HOAc in MeOH). $^1$H NMR (400 MHz, CDCl$_3$) δ 7.85-6.70 (m, 16H); ESI-MS m/z 397 (MH$^+$).

Example 269

(3Z)-3-[(4-BROMOPHENYL)IMINO]-1-(3-THIENYL)-1,3-DIHYDRO-2H-INDOL-2-ONE

Prepared by Procedures A and H. $^1$H NMR (400 MHz, CDCl$_3$) δ 7.82-6.55 (m, 11H); ESI-MS m/z 383 (MH$^+$).

Example 270

(3Z)-3-[(3-CHLOROPHENYL)IMINO]-1-(3-THIENYL)-1,3-DIHYDRO-2H-INDOL-2-ONE

Prepared by Procedures A and H. $^1$H NMR (400 MHz, CDCl$_3$) δ 7.55-6.50 (m, 11H); ESI-MS m/z 339 (MH$^+$).

Example 271

(3Z)-3-[(3-METHYLPHENYL)IMINO]-1-(3-THIENYL)-1,3-DIHYDRO-2H-INDOL-2-ONE

Prepared by Procedures A and B (1% HOAc in MeOH). $^1$H N (400 MHz, CDCl$_3$) δ 7.67-6.78 (m, 11H), 2.39 (s, 3H); ESI-MS m/z 319 (MH$^+$).

Example 272

(3Z)-3-[(3,4-DICHLOROPHENYL)IMINO]-1-(3-THIENYL)-1,3-DIHYDRO-2H-INDOL-2-ONE

Prepared, by Procedures A and B (1% HOAc in MeOH). $^1$H NMR (400 MHz, CDCl$_3$) δ 7.82-6.80 (m, 10H); ESI-MS m/z 373 (MH$^+$).

Example 273

(3Z)-1-(2-PYRIDINYLMETHYL)-3-{[3-(TRIFLUOROMETHYL)PHENYL]IMINO}-1,3-DIHYDRO-2H-INDOL-2-ONE

Prepared by Procedure B. ESI-MS m/z 382 (MH$^+$).

Example 274

(3Z)-3-[(3,5-DICHLOROPHENYL)IMINO]-1-(2-PYRIDINYLMETHYL)-1,3-DIHYDRO-2H-INDOL-2-ONE

Prepared by Procedure B. ESI-MS m/z 382 (MH$^+$).

Example 275

(3Z)-1-[(3,5-DIMETHYL-4-ISOXAZOLYL)METHYL]-3-{[3-(TRIFLUOROMETHYL)PHENYL]IMINO}-1,3-DIHYDRO-2H-INDOL-2-ONE

Prepared by Procedure B. ESI-MS m/z 400 (MH$^+$).

Example 276

(3Z)-3-[(3,4-DIFLUOROPHENYL)IMINO]-1-(3-PYRIDINYLMETHYL)-1,3-DIHYDRO-2H-INDOL-2-ONE

Prepared by Procedure B. ESI-MS m/z 350 (MH$^+$).

Example 277

(3Z)-1-(3-PYRIDINYLMETHYL)-3-{[3-(TRIFLUOROMETHYL)PHENYL]IMINO}-1,3-DIHYDRO-2H-INDOL-2-ONE

Prepared by Procedure B. ESI-MS m/z 382 ((MH$^+$).

Example 278

(3Z)-3-[(3,4-DIFLUOROPHENYL)IMINO]-1-(2-PYRIDINYLMETHYL)-1,3-DIHYDRO-2H-INDOL-2-ONE

Prepared by Procedure B. ESI-MS m/z 350 (MH$^+$).

Example 279

(3Z)-3-[(3,5-DICHLOROPHENYL)IMINO]-1-(3-PYRIDINYLMETHYL)-1,3-DIHYDRO-2H-INDOL-2-ONE

Prepared by Procedure B. ESI-MS m/z 384 (MH$^+$).

Example 280

(3Z)-3-[(3,5-DICHLOROPHENYL)IMINO]-1-[(3,5-DIMETHYL-4-ISOXAZOLYL)METHYL]-1,3-DIHYDRO-2H-INDOL-2-ONE

Prepared by Procedure B. ESI-MS m/z 402 (MH$^+$).

Example 281

(3Z)-3-[(9-ETHYL-9H-CARBAZOL-3-YL)IMINO]-1-PHENYL-1,3-DIHYDRO-2H-INDOL-2-ONE

Prepared by Procedure H. $^1$H NMR (400 MHz, CDCl$_3$) δ 8.28-6.66 (m, 16H), 4.47-4.35 (m, 2H), 1.55-1.44 (m, 3H); ESI-MS m/z 416 (MH$^+$).

Example 282

(3Z)-1-PHENYL-3-(5-QUINOLINYLIMINO)-1,3-DIHYDRO-2H-INDOL-2-ONE

Prepared by Procedure H. $^1$H NMR (400 MHz, CDCl$_3$) δ 9.38-9.32 (m, 1H), 8.55-8.50 (m, 1H), 8.01-6.62 (m, 12H), 6.43-6.35 (m, 1H); ESI-MS m/z 350 (MH$^+$).

Example 283

(3Z)-3-[(4-IODOPHENYL)IMINO]-1-PHENYL-1,3-DIHYDRO-2H-INDOL-2-ONE

Prepared by Procedure B (0.1% HOAc, 80° C., 92 h, 4 eq $RNH_2$, 3 Å molecular sieves). ESI-MS m/z 425 ($MH^+$).

Example 285

(3Z)-3-[(3,4-DIFLUOROPHENYL)IMINO]-1-PHENYL-1,3-DIHYDRO-2H-INDOL-2-ONE

Prepared by Procedure B (0.1% HOAc, 80° C., 92 h, 4 eq $RNH_2$, 3 Å molecular sieves). ESI-MS m/z 335 ($MH^+$).

Example 286

(3Z)-3-[(2-CHLORO-4-METHYLPHENYL)IMINO]-1-PHENYL-1,3-DIHYDRO-2H-INDOL-2-ONE

Prepared by Procedure B (0.1% HOAc, 80° C., 92 h, 4 eq $RNH_2$, 3 Å molecular sieves). ESI-MS m/z 347 ($MH^+$ with $^{35}Cl$), 349 ($MH^+$ with $^{37}Cl$).

Example 287

(3Z)-3-[(2,4-DIMETHOXYPHENYL)IMINO]-1-PHENYL-1,3-DIHYDRO-2H-INDOL-2-ONE

Prepared by Procedure B (0.1% HOAc, 80° C., 92 h, 4 eq $RNH_2$, 3 Å molecular sieves). ESI-MS m/z 359 ($MH^+$).

Example 288

3-{[(3Z)-2-OXO-1-PHENYL-1,2-DIHYDRO-3H-INDOL-3-YLIDENE]AMINO}BENZONITRILE

Prepared by Procedure B (0.1% HOAc, 80° C., 92 h, 4 eq $RNH_2$, 3 Å molecular sieves). ESI-MS m/z 324 ($MH^+$).

Example 289

(3Z)-3-{[2-METHYL-5-(TRIFLUOROMETHYL)PHENYL]IMINO}-1-PHENYL-1,3-DIHYDRO-2H-INDOL-2-ONE

Prepared by Procedure B (0.1% HOAc, 80° C., 92 h, 4 eq $RNH_2$, 3 Å molecular sieves). ESI-MS m/z 381 ($MH^+$).

Example 290

(3Z)-3-[(4-CHLORO-3-METHYLPHENYL)IMINO]-1-(3-THIENYL)-1,3-DIHYDRO-2H-INDOL-2-ONE

Prepared by Procedures A and B (80° C.). ESI-MS m/z 353 ($MH^+$).

Example 291

(3Z)-3-(6-QUINOLINYLIMINO)-1-(3-THIENYL)-1,3-DIHYDRO-2H-INDOL-2-ONE

Prepared by Procedures A and B (80° C.). ESI-MS m/z 356 ($MH^+$).

Example 292

(3Z)-3-[(4-CHLOROPHENYL)IMINO]-1-(3-THIENYL)-1,3-DIHYDRO-2H-INDOL-2-ONE

Prepared by Procedures A and B (80° C.). ESI-MS m/z 339 ($MH^+$).

Example 295

(3Z)-3-[(3-ISOPROPYLPHENYL)IMINO]-1-(3-THIENYL)-1,3-DIHYDRO-2H-INDOL-2-ONE

Prepared by Procedures A and B (80° C.). ESI-MS m/z 347 ($MH^+$).

Example 296

(3Z)-3-[(4-CYCLOHEXYLPHENYL)IMINO]-1-(3-THIENYL)-1,3-DIHYDRO-2H-INDOL-2-ONE

Prepared by Procedures A and B (80° C.). ESI-MS m/z 387 ($MH^+$).

Example 297

(4-{[(3Z)-2-OXO-1-PHENYL-1,2-DIHYDRO-3H-INDOL-3-YLIDENE]AMINO}PHENYL)ACETONITRILE

Prepared by Procedure B (0.1% HOAc, 80° C., 92 h, 4 eq $RNH_2$, 3 Å molecular sieves). ESI-MS m/z 339 ($MH^+$).

Example 298

(3Z)-3-[(2,2-DIFLUORO-1,3-BENZODIOXOL-5-YL)IMINO]-1-PHENYL-1,3-DIHYDRO-2H-INDOL-2-ONE

Prepared by Procedure B (0.1% HOAc, 80° C., 92 h, 4 eq $RNH_2$, 3 Å molecular sieves). ESI-MS m/z 379 ($MH^+$).

Example 299

(3Z)-3-(1,3-BENZOTHIAZOL-6-YLIMINO)-1-PHENYL-1,3-DIHYDRO-2H-INDOL-2-ONE

Prepared by Procedure H. ESI-MS m/z 356($MH^+$).

Example 300

(3Z)-1-TETRAHYDRO-2H-PYRAN-4-YL-3-{[3-(TRIFLUOROMETHYL)PHENYL]IMINO}-1,3-DIHYDRO-2H-INDOL-2-ONE

Prepared by Procedures G and H. ESI-MS m/z 375 ($MH^+$).

Example 301

(3Z)-3-(1H-INDAZOL-6-YLIMINO)-1-PHENYL-1,3-DIHYDRO-2H-INDOL-2-ONE

Prepared by Procedure H. ESI-MS m/z 339 ($MH^+$).

Example 302

(3Z)-3-[(3-CHLOROPHENYL)IMINO]-6-METHOXY-1-PHENYL-1,3-DIHYDRO-2H-INDOL-2-ONE

Prepared by Procedures I and H. ESI-MS m/z 363 (MH⁺).

Example 303

(3Z)-6-METHOXY-1-PHENYL-3-{[3-(TRIFLUOROMETHYL)PHENYL]IMINO}-1,3-DIHYDRO-2H-INDOL-2-ONE

Prepared by Procedures I and H. ESI-MS m/z 397 (MH⁺).

Example 304

(3Z)-1-PHENYL-3-{[4-(3-THIENYL)PHENYL]IMINO}-1,3-DIHYDRO-2H-INDOL-2-ONE

Prepared by Procedures H and C. ESI-MS m/z 381 (MH⁺).

Example 305

(3Z)-1-PHENYL-3-{[3'-(TRIFLUOROMETHYL)[1,1'-BIPHENYL]-4-YL]IMINO}-1,3-DIHYDRO-2H-INDOL-2-ONE

Prepared by Procedures H and C. ESI-MS m/z 443 (MH⁺).

Example 306

(3Z)-1-PHENYL-3-{[4-(3-PYRIDINYL)PHENYL]IMINO}-1,3-DIHYDRO-2H-INDOL-2-ONE

Prepared by Procedures H and C. ESI-MS m/z 376 (MH⁺).

Example 307

(3Z)-3-[(3-BROMOPHENYL)IMINO]-1-PHENYL-1,3-DIHYDRO-2H-INDOL-2-ONE

Prepared by Procedure B. ESI-MS m/z 378 (MH⁺).

Example 308

(3Z)-1,5-DIPHENYL-3-{[3-(TRIFLUOROMETHYL)PHENYL]IMINO}-1,3-DIHYDRO-2H-INDOL-2-ONE

Prepared by Procedures D, E, and F. ESI-MS m/z 443 (MH⁺).

Example 309

(3Z)-1-[1,1'-BIPHENYL]-4-YL-3-{[3-(TRIFLUOROMETHYL)PHENYL]IMINO}-1,3-DIHYDRO-2H-INDOL-2-ONE

Prepared by Procedures H (6 eq of aniline), J, and K. ESI-MS m/z 443 (MH⁺).

Example 310

(3Z)-1-(4-HYDROXYPHENYL)-3-{[3-(TRIFLUOROMETHYL)PHENYL]IMINO}-1,3-DIHYDRO-2H-INDOL-2-ONE

Prepared by Procedures H (6 eq of aniline) and E. ESI-MS m/z 383 (MH⁺).

Example 311

(3Z)-3-[(3,4-DICHLOROPHENYL)IMINO]-1-(3-PYRIDINYLMETHYL)-1,3-DIHYDRO-2H-INDOL-2-ONE

Prepared by Procedures H (75° C., 2 h), K (3-picolyl chloride), and B. ESI-MS m/z 383 (MH⁺).

Examples 91-114 and 254-311 as described above are merely illustrative of the methods used to synthesize indolone derivatives. Further derivatives may be obtained utilizing methods shown in Schemes 6a, 7a and 8-10. The substituents in Schemes 6a, 7a and 8-10 are described in the Detailed Description.

It may be necessary to incorporate protection and deprotection strategies for substituents such as amino, amido, carboxylic acid, and hydroxyl groups in the synthetic methods described above to form indolone derivatives. Methods for protection and deprotection of such groups are well-known in the art, and may be found, for example in Green, T. W. and Wuts, P. G. M. (1991) Protection Groups in Organic Synthesis, 2nd Edition John Wiley & Sons, New York.

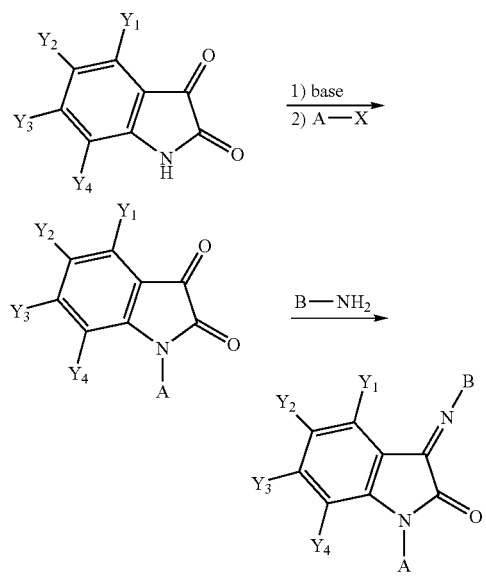

Scheme 6ª

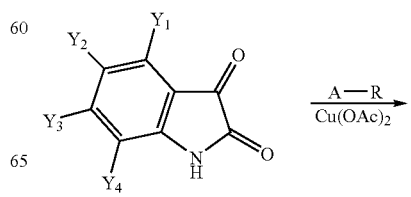

Scheme 7ª

-continued

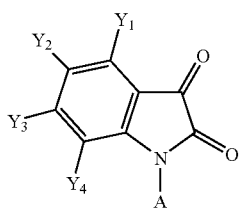

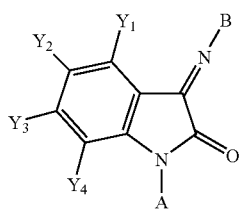

$^a$Y$_1$, Y$_2$, Y$_3$, Y$_4$, A and B are defined as described in the specification. X is a leaving group such as Cl, Br, I, or OTs. R is boric acid or a dialkylborate group.

Scheme 8$^a$. Synthesis of Isatins

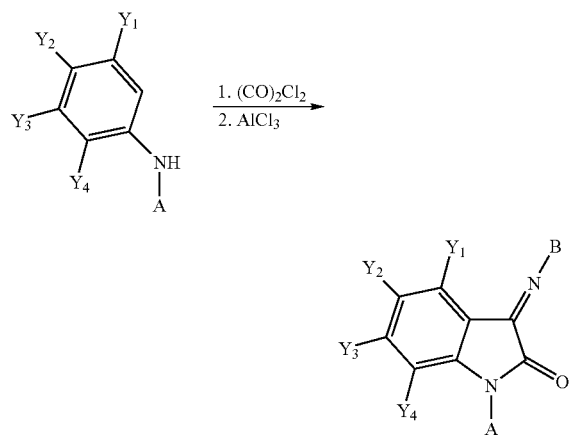

$^a$Y$_1$, Y$_2$, Y$_3$, Y$_4$, A and B are defined as described in the specification. X is a leaving group such as Cl, Br, I, or OTs. R is boric acid or a dialkylborate group.

Scheme 9$^a$. Synthesis of Substituted Iminoindolones

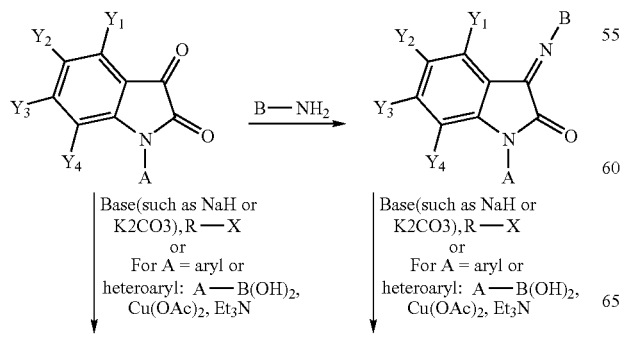

-continued

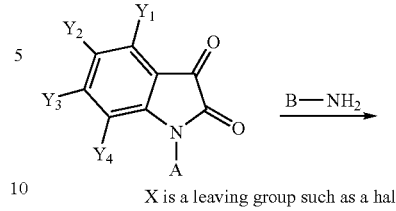

X is a leaving group such as a halogen or tosylate $^a$Y$_1$, Y$_2$, Y$_3$, Y$_4$, A and B are defined as described in the specification. X is a leaving group such as Cl, Br, I, or OTs. R is boric acid or a dialkylborate group.

Scheme 10$^a$. Synthesis of Aryl or Heteroaryl-Substituted Iminoindolones

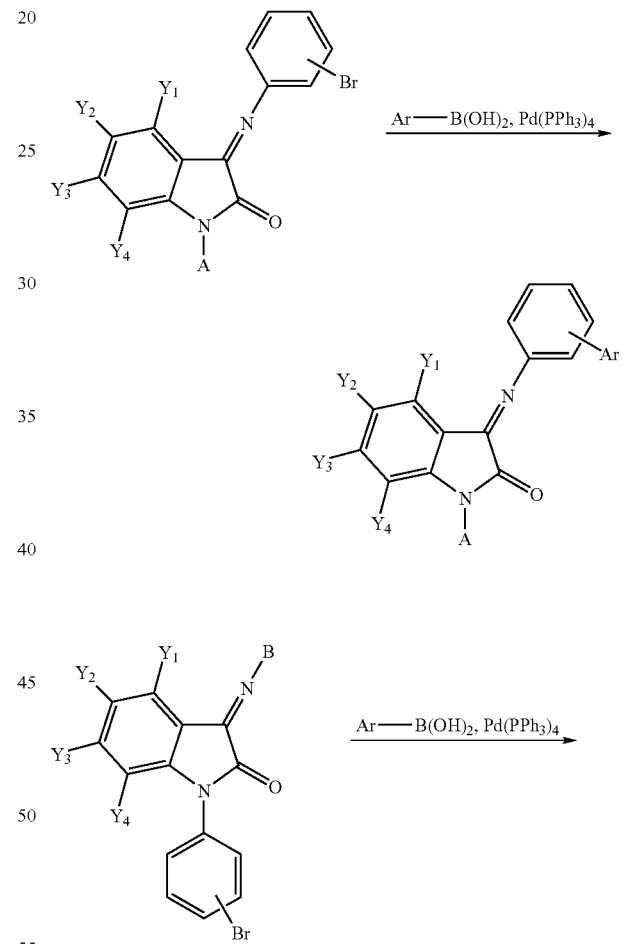

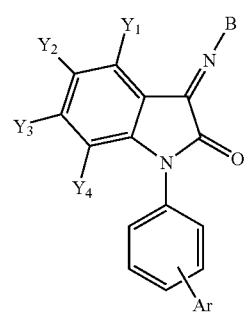

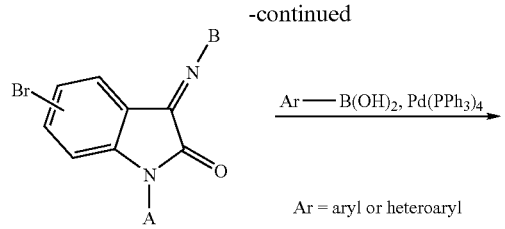

Ar = aryl or heteroaryl

[a]$Y_1$, $Y_2$, $Y_3$, $Y_4$, A and B are defined as described in the specification. X is a leaving group such as Cl, Br, I, or OTs. R is boric acid or a dialkylborate group.

Radioligand Binding of Indolones at Cloned Galanin Receptors

The binding properties of the indolones of the present invention were evaluated at the cloned human galanin receptors, GAL1, GAL2, and GAL3, using protocols described herein.

Radioligand Binding Assay Results

The indolones described in Examples 91-114 and 254-311 were assayed using cloned human galanin receptors. The compounds were found to be selective for the GAL3 receptor The binding affinities of the compounds of Examples 91-114 and 254-311 are illustrated in Tables 4 and 4a.

TABLE 4

| Example | R1 | R2 | R3 | R4 | R5 | GalR 1 | GalR 2 | GalR3 |
|---|---|---|---|---|---|---|---|---|
| 91 | Ph | OMe | H | H | H | * | * | 527 |
| 92 | Ph | H | CF3 | H | H | * | * | |
| 93 | Ph | H | Me | H | H | * | * | 171 |
| 94 | Ph | H | Cl | H | H | * | * | 49 |
| 95 | Ph | H | H | CF3 | H | * | * | 29 |
| 96 | Ph | H | H | Me | H | * | * | 111 |
| 97 | Ph | H | H | Cl | H | * | * | 51 |
| 98 | Ph | H | H | Br | H | * | * | 38 |
| 99 | Ph | H | H | F | H | * | * | 229 |
| 100 | Ph | H | H | OPh | H | * | * | |
| 101 | Ph | H | H | OEt | H | * | * | 305 |
| 102 | Ph | H | H | OMe | H | * | * | 429 |
| 103 | Ph | H | Cl | H | Cl | * | * | 68 |
| 104 | Ph | H | Me | H | Me | * | * | 143 |
| 105 | allyl | H | Cl | Cl | H | * | * | 97 |
| 106 | allyl | H | Cl | H | Cl | * | * | 62 |
| 107 | isopropyl | H | H | Br | H | * | * | 126 |

Key:
* = >10000
OMe = Methoxy
Ph = Phenyl
OPh = Phenoxy
Me = Methyl
OEt = Ethoxy TABLE 4a

| Example | Structure | Ki (nM) Gal3 |
|---|---|---|
| 108 | 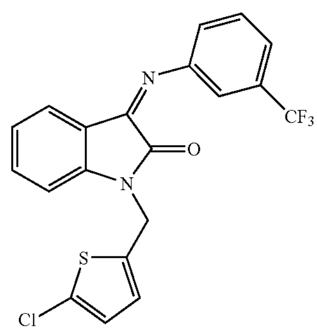 | 84 |
| 109 | 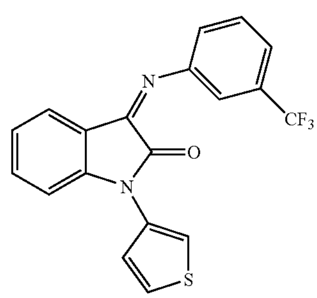 | 103 |

TABLE 4a-continued
| Example | Structure | Ki (nM) Gal3 |
|---------|-----------|--------------|
| 110 | 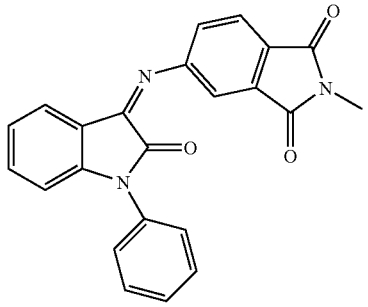 | 138 |
| 111 | 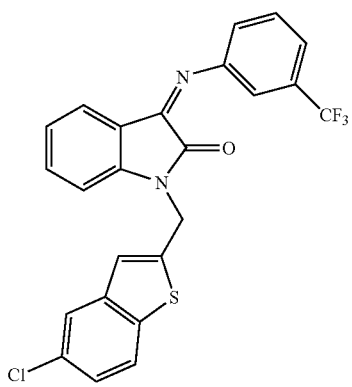 | 1178 |
| 112 | 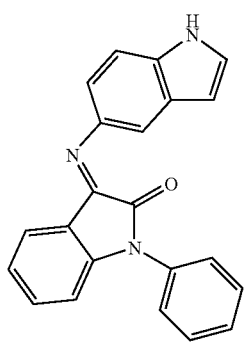 | 2324 |
| 113 | 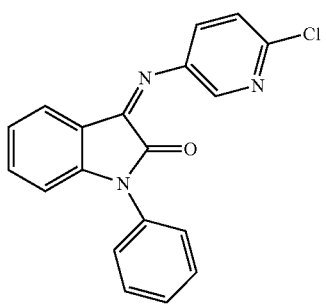 | 136 |

TABLE 4a-continued

| Example | Structure | Ki (nM) Gal3 |
|---|---|---|
| 114 | 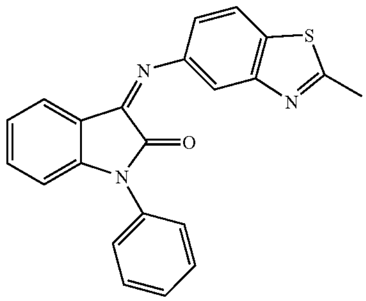 | 569 |
| 254 | 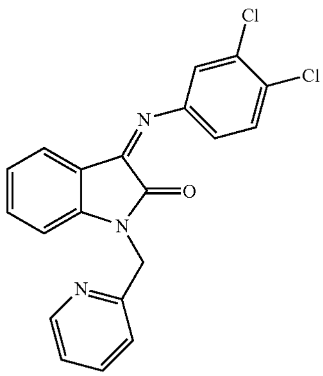 | 64 |
| 255 | 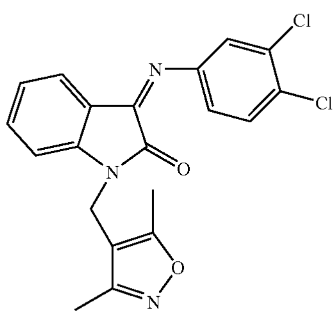 | 49 |
| 256 | 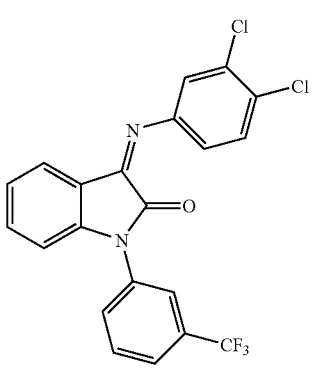 | 18 |

TABLE 4a-continued

| Example | Structure | Ki (nM) Gal3 |
| --- | --- | --- |
| 257 | 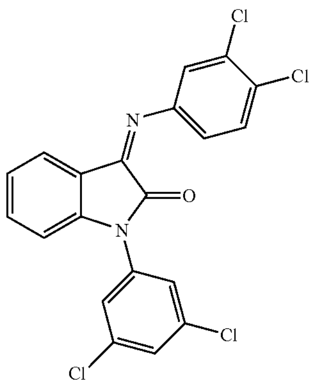 | 33 |
| 258 | 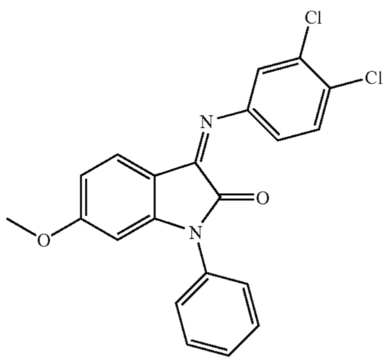 | 67 |
| 259 | 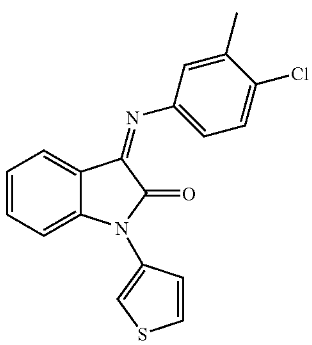 | 55 |
| 260 | 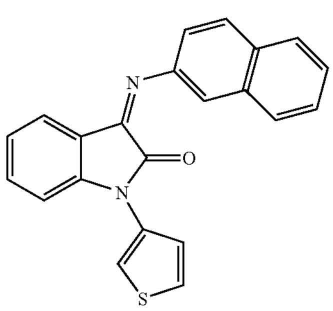 | 60 |

TABLE 4a-continued
| Example | Structure | Ki (nM) Gal3 |
|---|---|---|
| 261 | 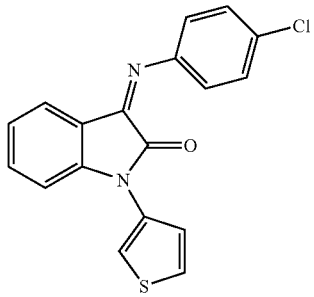 | 34 |
| 262 | 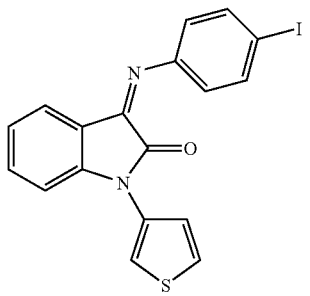 | 46 |
| 263 | 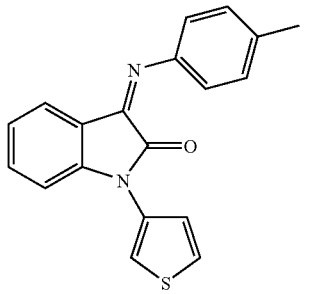 | 136 |
| 264 | 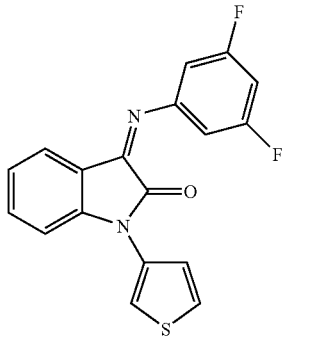 | 27 |
| 265 | 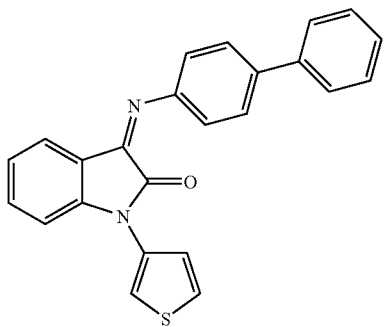 | 80 |

TABLE 4a-continued

| Example | Structure | Ki (nM) Gal3 |
|---------|-----------|--------------|
| 266 | 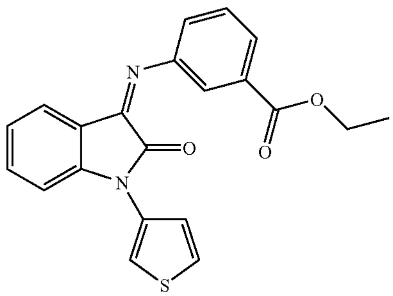 | 236 |
| 267 | 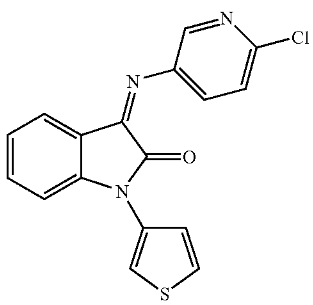 | 234 |
| 268 | 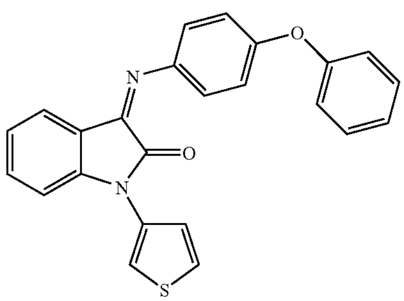 | 57 |
| 269 | 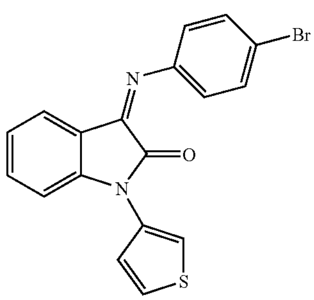 | 46 |
| 270 | 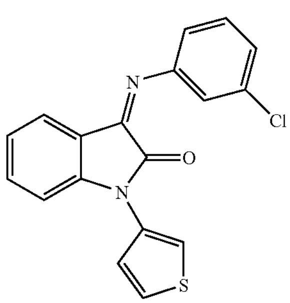 | 42 |

TABLE 4a-continued

| Example | Structure | Ki (nM) Gal3 |
|---|---|---|
| 271 | 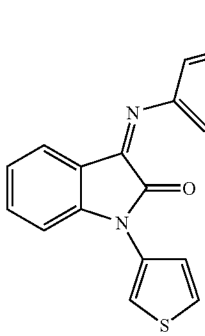 | 114 |
| 272 | 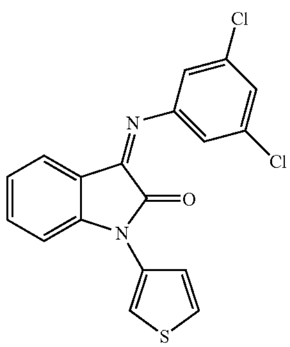 | 26 |
| 273 | 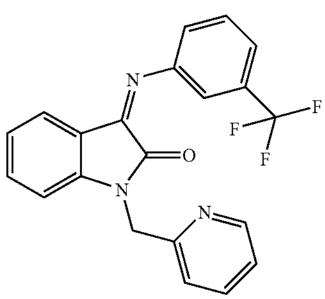 | 202 |
| 274 | 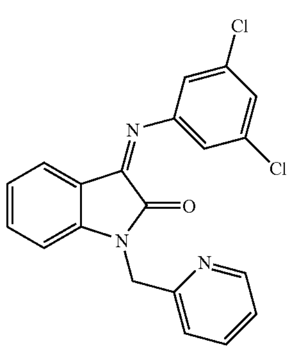 | 174 |

TABLE 4a-continued

| Example | Structure | Ki (nM) Gal3 |
|---|---|---|
| 275 | 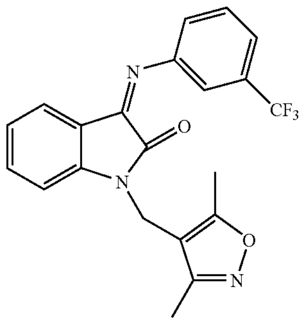 | 595 |
| 276 | 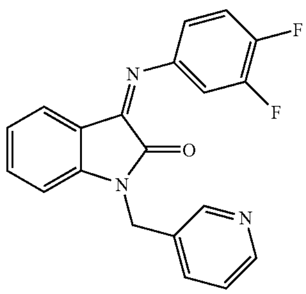 | 192 |
| 277 | 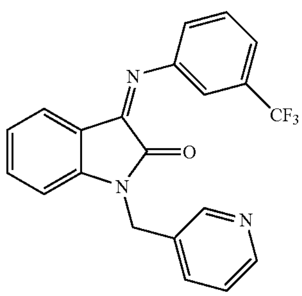 | 198 |
| 278 | 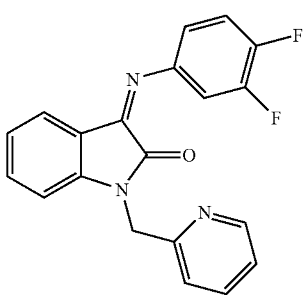 | 340 |
| 279 | 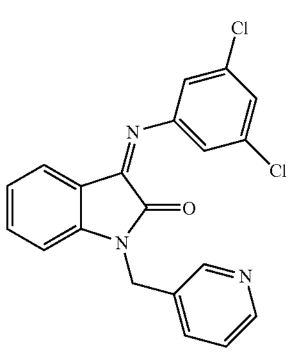 | 81 |

TABLE 4a-continued

| Example | Structure | Ki (nM) Gal3 |
| --- | --- | --- |
| 280 | (3-imino-1-((3,5-dimethylisoxazol-4-yl)methyl)indolin-2-one with 3,5-dichlorophenyl) | 521 |
| 281 | (3-((9-ethyl-9H-carbazol-3-yl)imino)-1-phenylindolin-2-one) | 150 |
| 282 | (3-(quinolin-5-ylimino)-1-phenylindolin-2-one) | 333 |
| 283 | (3-((4-iodophenyl)imino)-1-phenylindolin-2-one) | 33 |
| 285 | (3-((3,4-difluorophenyl)imino)-1-phenylindolin-2-one) | 26 |

TABLE 4a-continued

| Example | Structure | Ki (nM) Gal3 |
|---|---|---|
| 286 | (2-chloro-4-methylphenyl)imino-1-phenylindolin-2-one | 38 |
| 287 | (2,4-dimethoxyphenyl)imino-1-phenylindolin-2-one | 260 |
| 288 | (3-cyanophenyl)imino-1-phenylindolin-2-one | 39 |
| 289 | (2-methyl-5-trifluoromethylphenyl)imino-1-phenylindolin-2-one | 59 |

TABLE 4a-continued

| Example | Structure | Ki (nM) Gal3 |
|---|---|---|
| 290 | 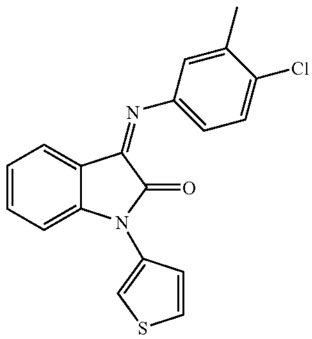 | 55 |
| 291 | 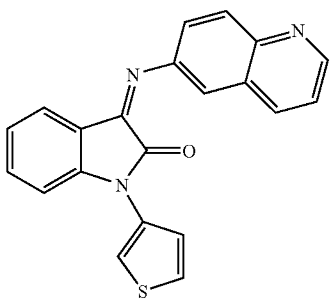 | 271 |
| 292 | 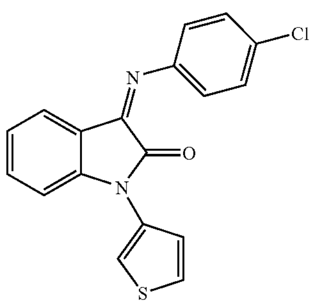 | 34 |
| 295 | 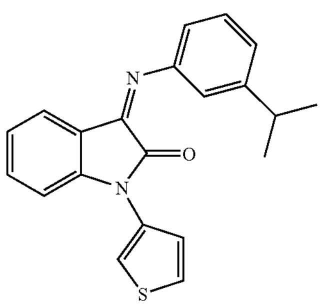 | 242 |
| 296 | 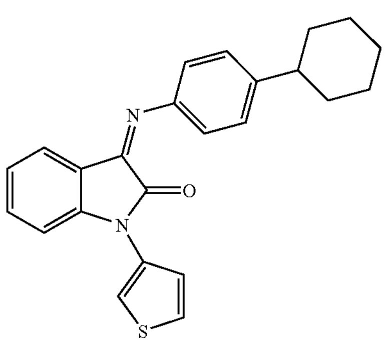 | 82 |

TABLE 4a-continued

| Example | Structure | Ki (nM) Gal3 |
|---------|-----------|--------------|
| 297 | 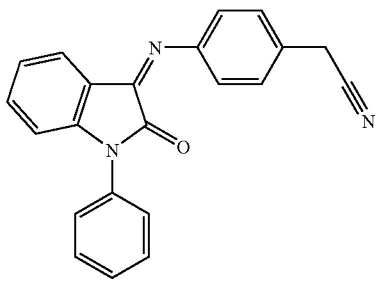 | 226 |
| 298 | 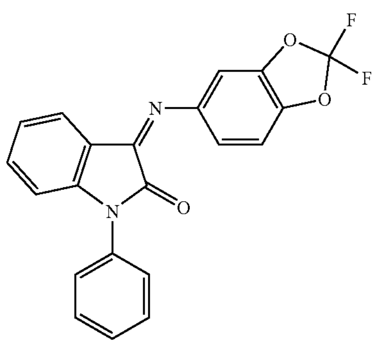 | 22 |
| 299 | 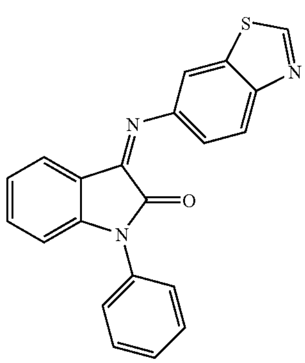 | 377 |
| 300 | 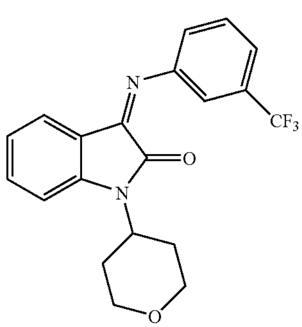 | 742 |

TABLE 4a-continued

| Example | Structure | Ki (nM) Gal3 |
|---------|-----------|--------------|
| 301 | 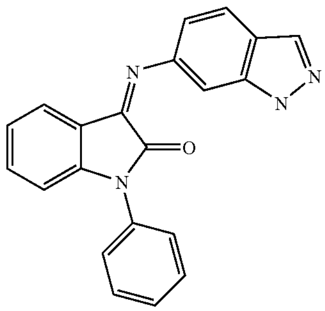 | 875 |
| 302 | 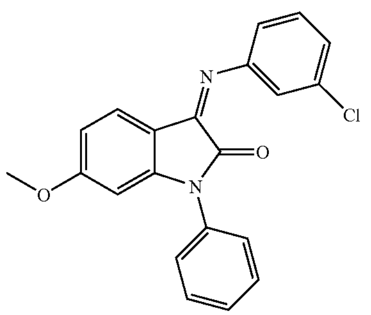 | 150 |
| 303 | 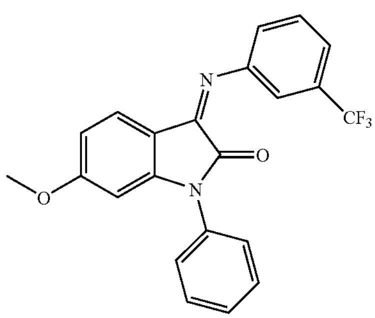 | 214 |
| 304 | 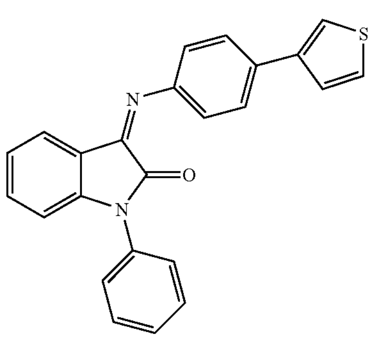 | 728 |

TABLE 4a-continued
| Example | Structure | Ki (nM) Gal3 |
|---------|-----------|--------------|
| 305 | 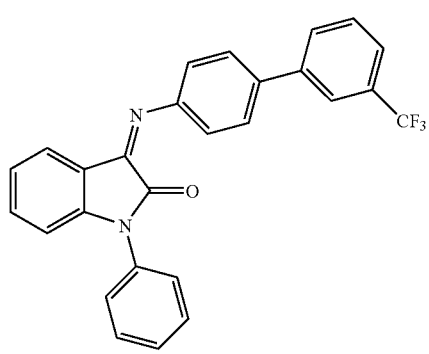 | 638 |
| 306 | 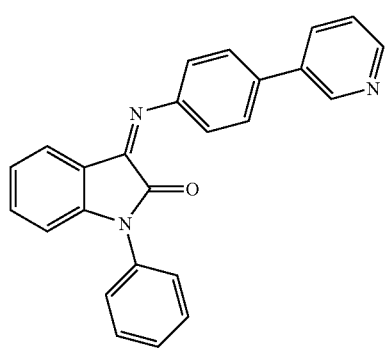 | 160 |
| 307 | 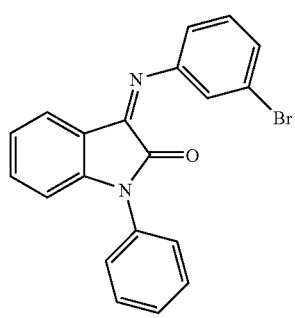 | 41 |
| 308 | 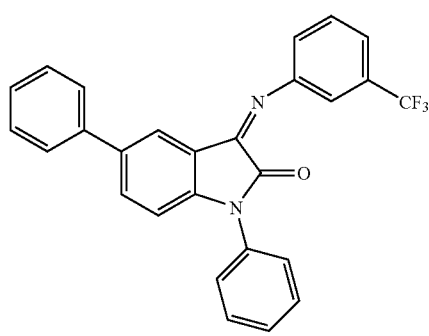 | 98 |

TABLE 4a-continued

| Example | Structure | Ki (nM) Gal3 |
|---------|-----------|--------------|
| 309 | (3-CF3-phenyl imine of 1-(biphenyl-4-yl)-indolin-2-one) | 224 |
| 310 | (3-CF3-phenyl imine of 1-(4-hydroxyphenyl)-indolin-2-one) | 126 |
| 311 | (3,4-dichlorophenyl imine of 1-(pyridin-3-ylmethyl)-indolin-2-one) | 32 |

Oral Compositions

As a specific embodiment of an oral composition of a compound of this invention, 100 mg of one of the compounds described herein is formulated with sufficient finely divided lactose to provide a total amount of 580 to 590 mg to fill a size 0 hard gel capsule.

Binding Properties of Compounds at Cloned Receptors

A. Materials and Methods

The binding properties of the compounds of the present invention were evaluated at one or more cloned receptors or native, tissue-derived transporters, using protocols described below.

Cell Culture

COS-7 cells were grown on 150 mm plates in D-MEM with supplements (Dulbecco's Modified Eagle Medium with 10% bovine calf serum, 4 mM glutamine, 100 units/ml penicillin, 100 µg/ml streptomycin) at 37° C. with 5% $CO_2$. Stock plates of COS-7 cells were trypsinized and split 1:6 every 3-4 days. Human embryonic kidney 293 cells were grown on 150 mm plates in D-MEM with supplements (minimal essential medium) with Hanks' salts and supplements (Dulbecco's Modified Eagle Medium with 10% bovine calf serum, 4 mM glutamine, 100 units/ml penicillin, 100 µg/ml streptomycin) at 37° C. with 5% $CO_2$. Stock plates of 293 cells were trypsinized and split 1:6 every 3-4 days. Mouse fibroblast LM(tk−) cells were grown on 150 mm plates in D-MEM with supplements (Dulbecco's Modified Eagle Medium with 10% bovine calf serum, 4 mM glutamine, 100 units/mL penicillin, 100 µg/mL streptomycin) at 37° C. with 5% $CO_2$. Stock plates of LM(tk−) cells were trypsinized and split 1:10 every 3-4 days. Chinese Hamster Ovary (CHO) cells were grown on 150 mm plates in HAM's F12 medium with (HAM's F-12 with 10% bovine calf serum, 4 mM glutamine, 100 units/mL penicillin, 100 μg/mL streptomycin) at 37° C. with 5% $CO_2$. Stock plates of CHO cells were trypsinized and split 1:8 every 3-4 days.

LM(tk–) cells were stably transfected with the human GAL1 or GAL3 receptor. CHO cells were stably transfected with the human GAL2 receptor.

Stable Transfection cDNAs for the human and rat GAL1, and human and rat GAL3 receptors were transfected with a G-418 resistant gene into the mouse fibroblast LM(tk–) cell line by a calcium phosphate transfection method (Cullen, 1987). Stably transfected cells were selected with G-418. Human and rat GAL2 receptors were similarly transfected into CHO cells.

Membrane Harvest

Membranes were harvested from stably transfected LM(tk–) cells. Adherent cells were washed twice in ice-cold phosphate buffered saline (138 mM NaCl, 8.1 mM Na2HPO4, 2.5 nM KCl, 1.2 mM $KH_2PO_4$, 0.9 mM CaCl2, 0.5 mM MgCl2, pH 7.4) and lysed by sonication in ice-cold sonication buffer (20 mM Tris-HCl, 5 mM EDTA, pH 7.7). Large particles and debris were cleared by low speed centrifugation (200×g, 5 min, 4° C.). Membranes were collected from the supernatant fraction by centrifugation (32,000×g, 18 min, 4° C.), washed with ice-cold hypotonic buffer, and collected again by centrifugation (32,000×g, 18 min, 4° C.). The final membrane pellet was resuspended by sonication into a small volume of ice-cold binding buffer (~1 ml for every 5 plates: 10 mM NaCl, 20 my HEPES, 0.22 mM $KH_2PO_4$, 1.26 mM Cal2, 0.81 mM MgSO4, pH 7.4). Protein concentration was measured by the Bradford method (Bradford, 1976) using Pio-Rad Reagent, with bovine serum albumin as a standard. Membranes were held on ice for up to one hour and used fresh, or flash frozen and stored in liquid nitrogen. Membranes were prepared similarly from CHO cells.

The evidence presented in this invention suggests that GPCR-targeted molecules that bind to and antagonize the GAL3 receptor may be used for the treatment of pain, specifically neuropathic pain, and other disorders. The design of such compounds may be optimized by determining their binding affinity at the recombinant GAL3, GAL1, and other known GPCR and transporter targets.

Additionally, the GAL3 antagonist(s) optimally may not bind at the following receptors due to possible side effects: human GAL2; human $H_1$ histamine; human $\alpha_{1A}$ adrenergic, human $\alpha_{1B}$ adrenergic, human $\alpha_{1D}$ adrenergic, human $\alpha_{2A}$ adrenergic, human $\alpha_{2B}$ adrenergic, and human $\alpha_{2C}$ adrenergic; human dopamine $D_1$, $D_2$, $D_3$, $D_4$, and $D_5$; and the human $5HT_{1B}$, human $5HT_{1D}$, human $5HT_{1E}$, human $5HT_{1F}$, human $5HT_{2A}$, rat $5HT_{2C}$, human $5HT_6$, and human $5HT_7$ receptors.

Radioligand Binding Assays and Enzymatic Assays

The methods to obtain the cDNA of the receptors, express said receptors in heterologous systems, and carry out assays to determine binding affinity are described as follows.

Galanin Receptors: Binding assays were performed according to the following published methods: human GAL3 (PCT International Publication No. WO 98/15570), human GAL1 (PCT International Publication No. WO 95/2260), human GAL2 (PCT International Publication No. WO 97/26853).

Human $5HT_{1B}$, $5HT_{1D}$, $5HT_{1E}$, $5HT_{1F}$, and $5HT_7$ Receptors: The cell lysates of LM(tk–) clonal cell line stably transfected with the genes encoding each of these 5HT receptor-subtypes were prepared as described above. Cell membranes were suspended in 50 mM Tris-HCl buffer (pH 7.4 at 37° C.) containing 10 mM MgCl2, 0.2 mM EDTA, 10 M pargyline, and 0.1% ascorbate. The affinities of compounds were determined in equilibrium competition binding assays by incubation for 30 minutes at 37° C. in the presence of 5 nM [$^3$H]-serotonin. Nonspecific binding was determined in the presence of 10 μM serotonin. The bound radioligand was separated by filtration through GF/B filters using a cell harvester.

Human $5HT_{2A}$ Receptor: The coding sequence of the human $5HT_{2A}$ receptor was obtained from a human brain cortex cDNA library, and cloned into the cloning site of pCEXV-3 eukaryotic expression vector. This construct was transfected into COS-7 cells by the DEAE-dextran method (Cullen, 1987). Cells were harvested after 72 hours and lysed by sonication in 5 mM Tris-HCl, 5 mM EDTA, pH 7.5. The cell lysates were subjected to centrifugation at 1000 rpm for 5 minutes at 4° C., and the supernatant was subjected to centrifugation at 30,000×g for. 20 minutes at 4° C. The pellet was suspended in 50 mM Tris-HCl buffer (pH 7.7 at room temperature) containing 10 mM MgSO4, 0.5 mM EDTA, and 0.1% ascorbate. The affinity of compounds at $5HT_{2A}$ receptors were determined in equilibrium competition binding assays using [$^3$H]ketanserin (1 nM). Nonspecific binding was defined by the addition of 10 μM mianserin. The bound radioligand was separated by filtration through GF/B filters using a cell harvester.

$5-HT_{1A}$ Receptor: The cDNA corresponding to the $5-HT_{1A}$ receptor open reading frames and variable non-coding 5'- and 3'-regions, was cloned into the eukaryotic expression vector pCEXV-3. These constructs were transfected transiently into COS-7 cells by the DEAE-dextran method (Cullen, 1987), and harvested after 72 hours. Radioligand binding assays were performed as described above for the $5-HT_{2A}$ receptor, except that $^3$H-8-OH-DPAT was used as the radioligand and nonspecific binding was determined by the addition of 10 μM mianserin.

Other 5-HT Receptors: Other serotonin receptor binding assays were performed according to published methods: rat $5HT_{2C}$ receptor (Julius et al., 1988); and $5-HT_6$ (Monsma, et al., 1993). The binding assays using the $5-HT_4$ receptor were performed according to the procedures described in U.S. Pat. No. 5,766,879, the disclosure of which is hereby incorporated by reference in its entirety into this application.

Other receptors: Cell membranes expressing human dopamine $D_1$, $D_2$, $D_4$ and rat $D_3$ receptors were purchased through BioSignal, Inc. (Montreal, Canada). Binding assays using the histamine H, receptor; dopamine receptors; and $\alpha_{1A}$, $\alpha_{1B}$, and $\alpha_2$ adrenergic receptors may be carried out according to the procedures described in U.S. Pat. No. 5,780,485, the disclosure of which is hereby incorporated by reference in its entirety into this application. Binding assays using the dopamine $D_5$ receptor may be carried out according to the procedures described in U.S. Pat. No. 5,882,855, the disclosure of which is hereby incorporated by reference in its entirety into this application. Binding assays for the human $\alpha_{1D}$ adrenergic receptor may be carried out according to the procedures described in U.S. Pat. No. 6,156,518, the disclosure of which is hereby incorporated by reference in its entirety into this application.

The methods to determine binding affinity at native transporters are described in the following publications: 5HT transporter and NE transporter (Owens et al., 1997), and DA transporter (Javitch et al, 1984).

Materials

Cell culture media and supplements were from Specialty Media (Lavallette, N.J.). Cell culture plates (150 mm and 96-well microtiter) were from Corning (Corning, N.Y.). Polypropylene 96-well microtiter plates were from Co-star (Cambridge, Mass.). Bovine serum albumin (ultra-fat free, A-7511) was from Sigma (St. Louis, Mo.). All radioligands were from New England Nuclear (Boston, Mass.). Commercially available peptides and peptide analogs were either from Bachem Calif. (Torrance, Calif.) or Peninsula (Belmont, Calif.). All other materials were reagent grade.

Data Analysis

Binding data were analyzed using nonlinear regression and statistical techniques available in the GraphPAD Prism package (San, Diego, Calif.). Enzymatic assay data were derived from a standard curve of reference compound data.

The selectivity ratios for compounds of the claimed invention were calculated from the binding data presented in Tables 1-4, Table 7 and Table 9 of the subject application. More specifically, these ratios were calculated by dividing (a) the binding affinity ($K_i$ value) of said compound to a particular receptor or transporter by (b) the binding affinity ($K_i$ value) of said compound to the human GAL3 receptor. The data presented in Table 8 and Table 10, hereinafter, were calculated using the above described method.

For example, the GAL3/GAL1 selectivity ratio of 10-fold recited in claim 110 of the subject application is characteristic of Example 34. This binding ratio was calculated by dividing (a) the $K_i$ value of 912 for the binding of Example 34 to the GALL receptor (see Table 1) by (b) the $K_i$ value of 23 for the binding of Example 34. to the human GAL3 receptor, thus obtaining the result of 39. Therefore the GAL3/GAL1 binding ratio for Example 34 was determined to be greater than 10-fold.

B. Results

The compounds described in the claimed invention were assayed using a panel of cloned receptors and native transporters. The preferred compounds were found to be selective GAL3 antagonists. The binding affinities and selectivity ratios of several compounds are illustrated in Tables 7-10.

TABLE 7

Antagonist binding affinity (Ki) at the human GAL3 receptor vs. serotonin receptors and several transporters.

| Example | hGAL3 Ki (nM) | h5HT$_{1A}$ Ki (nM) | h5HT$_{1B}$ Ki (nM) | h5HT$_{1D}$ Ki (nM) | h5HT$_{1E}$ Ki (nM) | h5HT$_{1F}$ Ki (nM) | h5HT$_{2A}$ Ki (nM) | r5HT$_{2c}$ Ki (nM) | h5HT$_4$ Ki (nM) | h5HT$_6$ Ki (nM) | h5HT$_7$ Ki (nM) | r5HT Uptk Ki (nM) | rNE Uptk Ki (nM) | rDA Uptk Ki (nM) |
|---|---|---|---|---|---|---|---|---|---|---|---|---|---|---|
| 11 | 91 | 4682 | 101 | 102 | 9174 | 1780 | 6708 | 802 | 1308 | 800 | 1012 | 1595 | * | 5430 |
| 15 | 73 | 5098 | 487 | 1272 | 11038 | 4192 | 11270 | 572 | 2301 | 1457 | 2527 | 1737 | * | 24500 |
| 17 | 87 | 3477 | 407 | 1032 | 33523 | 10271 | 7157 | 562 | 2606 | 711 | 1797 | 719 | 18325 | 27200 |
| 22 | 28 | 9714 | 1981 | 1852 | 13230 | 5773 | 20689 | 1717 | 2457 | 2264 | 2672 | 8483 | 13085 | 7480 |
| 34 | 23 | * | 1059 | 2976 | 28282 | 4803 | * | 2076 | 20762 | 38921 | 4439 | 37462 | * | 3900 |
| 49 | 211 | 29187 | 8447 | 16872 | 23886 | 8894 | * | 6687 | 13230 | 13 | 12268 | 40666 | 37585 | 2010 |
| 60 | 86 | 33666 | 5461 | 9198 | 1180 | 2124 | 26118 | 1781 | 1180 | 47536 | 3235 | 25274 | 46108 | 14500 |
| 77 | 79 | 5472 | 365 | 716 | 5888 | 3237 | 2242 | 456 | 1324 | 503 | 1547 | 821 | 28083 | 2790 |
| 92 | 38 | * | 11323 | 32139 | 18934 | 5290 | * | ND | 72 | * | ND | 45111 | 33879 | 17800 |
| 94 | 49 | * | 3349 | 10764 | 25227 | 5683 | * | 4099 | 4120 | 3647 | 8018 | 12961 | 4876 | 2200 |
| 95 | 29 | 28288 | 5226 | 16018 | 27211 | 4446 | * | 3471 | 3031 | 21507 | 11638 | * | 6101 | 12000 |
| 97 | 51 | * | 5057 | 14235 | 22692 | 4157 | * | 1950 | 2550 | 29131 | 11283 | 36308 | 4412 | 8440 |
| 98 | 38 | 24576 | 2419 | 9118 | 16240 | 3359 | * | 2260 | 1210 | 14018 | 8464 | 36329 | 5496 | 7430 |

* = >50000
ND = Not determined

TABLE 8

Antagonist selectivity ratios determined for the human GAL3 receptor vs. serotonin receptors and several transporters.

| Example | hGAL3 | h5HT$_{1A}$ | h5HT$_{1B}$ | h5HT$_{1D}$ | h5HT$_{1E}$ | h5HT$_{1F}$ | h5HT$_{2A}$ | r5HT$_{2c}$ | h5HT$_4$ | h5HT$_6$ | h5HT$_7$ | r5HT Uptk | rNE Uptk | rDA Uptk |
|---|---|---|---|---|---|---|---|---|---|---|---|---|---|---|
| 11 | 1 | >30 | 1 | 1 | >100 | 20 | >30 | 9 | 14 | 9 | 11 | 18 | >100 | >30 |
| 15 | 1 | >30 | 7 | 17 | >100 | >30 | >100 | 8 | >30 | 20 | >30 | 24 | >100 | >100 |
| 17 | 1 | >30 | 5 | 12 | >100 | >100 | >30 | 6 | 30 | 8 | 21 | 8 | >100 | >100 |
| 22 | 1 | >100 | >30 | >30 | >100 | >100 | >100 | >30 | >30 | >30 | >30 | >100 | >100 | >100 |
| 34 | 1 | >100 | >30 | >100 | >100 | >100 | >100 | >30 | >100 | >100 | >100 | >100 | >100 | >100 |
| 49 | 1 | >100 | >30 | >30 | >100 | >30 | >100 | >30 | >30 | 0 | >30 | >100 | >100 | 10 |
| 60 | 1 | >100 | >30 | >100 | 14 | 25 | >100 | 21 | 14 | >100 | >30 | >100 | >100 | >100 |
| 77 | 1 | >30 | 5 | 9 | >30 | >30 | 28 | 6 | 17 | 6 | 20 | 10 | >100 | >30 |
| 92 | 1 | >100 | >100 | >100 | >100 | >100 | >100 | ND | 2 | >100 | ND | >100 | >100 | >100 |
| 94 | 1 | >100 | >30 | >100 | >100 | >100 | >100 | >30 | >30 | >30 | >100 | >100 | >30 | >130 |
| 95 | 1 | >100 | >100 | >100 | >100 | >100 | >100 | >100 | >100 | >100 | >100 | >100 | >100 | >100 |
| 97 | 1 | >100 | >30 | >100 | >100 | >30 | >100 | >30 | >30 | >100 | >100 | >100 | >30 | >100 |
| 98 | 1 | >100 | >30 | >100 | >100 | >30 | >100 | >30 | >30 | >100 | >100 | >100 | >100 | >100 |

ND = Not determined

TABLE 9

Antagonist binding affinity (Ki) at the human GAL3 receptor vs. alpha-adrenergic, dopamine, and histamine receptors.

| Example | hGAL3 Ki (nM) | $h\alpha_{1A}$ Ki (nM) | $h\alpha_{1B}$ Ki (nM) | $h\alpha_{1D}$ Ki (nM) | $h\alpha_{2A}$ Ki (nM) | $h\alpha_{2B}$ Ki (nM) | $h\alpha_{2C}$ Ki (nM) | $hD_1$ Ki (nM) | $hD_2$ Ki (nM) | $rD_3$ Ki (nM) | $hD_4$ Ki (nM) | $hD_5$ Ki (nM) | $hH_1$ Ki (nM) |
|---|---|---|---|---|---|---|---|---|---|---|---|---|---|
| 11 | 91 | 926 | 1436 | 264 | 1819 | 10235 | 3004 | 79 | 782 | 2139 | 4828 | 64 | ND |
| 15 | 73 | 3392 | 853 | 480 | 14413 | 24515 | 8202 | 344 | 2184 | 8809 | 13151 | 78 | ND |
| 17 | 87 | 996 | 1167 | 221 | 3523 | 38732 | 10269 | 516 | 1808 | 2477 | 22227 | 89 | ND |
| 22 | 28 | 1278 | 1582 | 368 | 906 | 5757 | 2737 | 128 | 1501 | 5664 | 11621 | 63 | ND |
| 34 | 23 | 3756 | 15004 | 1240 | 3679 | 15488 | 8832 | 290 | 2500 | 9922 | 18716 | 111 | ND |
| 49 | 211 | 6646 | 18852 | 678 | 4731 | 25374 | 9244 | 3781 | 5940 | 13964 | 45824 | 328 | ND |
| 60 | 86 | 13604 | 40615 | 4231 | 10838 | * | 7200 | 600 | 26815 | 15295 | 48756 | 538 | 39909 |
| 77 | 79 | 834 | 452 | 217 | 315 | 7783 | 634 | 60 | 910 | 2716 | 504 | 122 | ND |
| 92 | 38 | ND | * | 17175 | 21943 | * | * | * | 41369 | 48180 | 41369 | 29290 | 39909 |
| 94 | 49 | 12715 | 31135 | 4027 | 12718 | 45378 | 47863 | 2145 | 6249 | 423 | * | 727 | ND |
| 95 | 29 | 13137 | 32494 | 3468 | 30072 | * | 48552 | 4394 | 9716 | 466 | * | 2590 | ND |
| 97 | 51 | 16921 | 45845 | 6454 | 13569 | * | * | 25115 | * | 9716 | * | 10069 | ND |
| 98 | 38 | 14500 | 31693 | 1891 | 23236 | * | * | 2524 | 3788 | 592 | * | 1199 | ND |

* = >50000
ND = Not determined

TABLE 10

Antagonist selectivity ratios determined for the human GAL3 receptor vs. alpha-adrenergic, dopamine, and histamine receptors.

| Example | hGAL3 | $h\alpha_{1A}$ | $h\alpha_{1B}$ | $h\alpha_{1D}$ | $h\alpha_{2A}$ | $h\alpha_{2B}$ | $h\alpha_{2C}$ | $hD_1$ | $hD_2$ | $rD_3$ | $hD_4$ | $hD_5$ | $hH_1$ |
|---|---|---|---|---|---|---|---|---|---|---|---|---|---|
| 11 | 1 | 10 | 16 | 3 | 20 | >100 | >30 | 0.9 | 9 | 24 | >30 | 0.7 | ND |
| 15 | 1 | 46 | 12 | 7 | >100 | >100 | >100 | 5 | 30 | >100 | >30 | 1 | ND |
| 17 | 1 | 11 | 13 | 3 | >30 | >100 | >100 | 6 | 21 | 28 | >100 | 1 | ND |
| 22 | 1 | >30 | >30 | 13 | >30 | >100 | >100 | 5 | >30 | >100 | >100 | 2 | ND |
| 34 | 1 | >100 | >100 | >30 | >100 | >100 | >100 | 13 | >100 | >100 | >100 | 5 | ND |
| 49 | 1 | >30 | >30 | 3 | 22 | >100 | >30 | 18 | 28 | >30 | >100 | 2 | ND |
| 60 | 1 | >100 | >100 | >30 | >100 | >100 | >30 | 7 | >100 | >100 | >100 | 6 | >100 |
| 77 | 1 | 11 | 6 | 3 | 4 | >30 | 8 | 0.8 | 11 | >30 | 6 | 2 | ND |
| 92 | 1 | ND | >100 | >100 | >100 | >100 | >100 | >100 | >100 | >100 | >100 | >100 | >100 |
| 94 | 1 | >100 | >100 | >30 | >100 | >100 | >100 | >30 | >100 | 9 | >100 | 15 | ND |
| 95 | 1 | >100 | >100 | >100 | >100 | >100 | >100 | >100 | >100 | 16 | >100 | >30 | ND |
| 97 | 1 | >100 | >100 | >100 | >100 | >100 | >100 | >100 | >100 | >100 | >100 | >100 | ND |
| 98 | 1 | >100 | >100 | >30 | >100 | >100 | >100 | >30 | >100 | 16 | >100 | >30 | ND |

ND = Not determined

GAL3 Receptor Localization

A. Materials and Methods

Preparation of the anti-GAL3 Antiserum

BioSource International, Hopkinton, Mass. performed the immunization and maintenance of rabbits. Following a pre-immune bleed, one peptide for each GAL receptor was injected into a pair of New Zealand white rabbits. The peptide sequences was chosen based on sequence specificity and immunogenicity. The rabbit anti-GAL3 antiserum were raised against C-terminal epitopes corresponding to amino acids 357-370 (Genbank accession number AF073798). The peptides were conjugated to the carrier KLH (keyhole limpet hemocyanin) by a cross linker and subcutaneously injected into the rabbits. The generation of the anti-GAL3 antiserum required OVA followed by a third series of injections with the GAL3 peptide conjugated to tetanus toxoid (TTOX). All injections were done using the Freund's Adjuvant System. Once immunoreactivity was established (see below) the antiserum was affinity purified by passing it over an agarose based column thiol coupled to its antigenic peptide. The column was washed and the antiserum was eluted using a low pH glycine buffer. The purified material was dialyzed, the optical density is taken at 280 λ and the purified antiserum was frozen.

Characterization of the Anti-GAL3 Antiserum Recombinant GAL1, GAL2, and GAL3 Receptor Transfected Cells To determine the ability of the GAL3 antiserum to recognize only the GAL3 receptor protein in vitro, COS-7 cells were grown on poly-L-lysine-coated plastic chamber slides (Nalge Nunc International, Naperville, Ill.) and transfected with recombinant rat GAL receptors (Genbank accession numbers U30290, AF010318, AF073798, respectively) or expression vector only (for mock-transfected cells) as previously described by Borowsky et al. (1999). Receptor expression was confirmed by radioligand binding. Briefly, a subset of slides was washed three times in binding buffer (50 mM Tris, pH 7.5, 5 mM $MgCl_2$, 1 mM EDTA, 0.1% bovine serum albumin, and 0.1% bacitracin) and incubated in 500 μl binding buffer containing porcine $^{125}$I-galanin (625,000 dpm) plus or minus 10 μM porcine galanin. After incubation at room temperature for 1 hour, the binding buffer was aspirated and slides were rinsed three times in ice cold 50 mM Tris, pH 7.5. Cells were solubilized in 1 ml of 0.1 N NaOH and 0.05% sodium deoxycholate for 30 minutes then transferred to test tubes for gamma counting of $^{125}$I. To evaluate antibody activity another subset of slides were washed with phosphate buffered saline (PBS) (Sigma, St. Louis, Mo.) to remove the medium and fixed with 4% paraformaldehyde (PFA) (Sigma, St. Louis, Mo.) then permeabilized using 0.2% Triton X-100/PBS and incubated in 3% normal goat serum for 30 minutes to minimize nonspecific binding of the primary antibody. Cells were incubated overnight at 4° C. with the anti-GAL3 antiserum (1:1000 dilution). The cells were rinsed three times with PBS, incubated for 30 minutes at 25° C. with goat anti-rabbit IgG (1:200 dilution) (Santa Cruz Biotechnology, Santa Cruz, Calif.), rinsed and processed using the peroxidase-antiperoxidase (PAP) reaction of. Sternberger et al. (1982). Control experiments for antibody specificity were (1) incubation of the cells in primary antiserum that had been preabsorbed with the respective antigenic peptide (20 µg/ml), (2) incubation without the primary antiserum, or (3) incubation with the primary antiserum replaced by normal goat serum.

Western Blotting

Membranes were prepared from COS-7 cells transiently transfected with the rat recombinant receptors GAL1, GAL2, and GAL3 as previously described (Borowsky et al., 1999). Transfected cells were lysed by sonication in ice-cold sonication buffer (20 mM Tris-HCl, pH 7.7, 5 mM EDTA). Cell lysates were subjected to centrifugation at 4° C. for 10 minutes at 200 g. The supernatant was then fractionated by centrifugation at 4° C. for 18 minutes at 32,000 g. The resulting membrane pellet was suspended into 50 mM Tris, pH 7.5, 5 mM $MgCl_2$, 1 mM EDTA. Protein samples (1-10 µg) were solubilized in 2× Laemmli buffer (Bio-Rad, Hercules, Calif.) and fractionated by SDS-PAGE in 10% polyacrylamide gels. Proteins were transferred to polyvinylidine difluoride membranes for immunoblot analysis in ice-cold 25 mM Tris, pH 8, 192 mM glycine, 20% methanol as previously described by Harlow and Lane (1999). Blots were incubated for 1 hour at, 25° C. in blocking buffer composed of 5% non-fat dried milk in TTBS (0.1% Tween-20, 500 mM NaCl, 20 mM Tris, pH 7.5) then for 16 hours at 25° C. with the receptor-specific polyclonal antibody (1:1000 dilution in blocking buffer)(0.25 mg/ml for GAL2 or 1.5 mg/ml for GAL3). Immunoreactive bands were detected with the Phototope-HRP Detection Kit for Western Blotting (New England BioLab, Beverly, Mass.) according to the protocol. Briefly, the blots were incubated with horseradish peroxidase-conjugated goat anti-rabbit IgG then developed with a mixture of LumiGLO plus hydrogen peroxide and recorded by chemiluminescence on Kodak Biomax-ML film (Kodak, Rochester, N.Y.).

Immunohistochemistry

Male Sprague-Dawley rats, (200-250 g; Charles Rivers, Rochester, N.Y.) were anesthetized by intraperitoneal injection of ketamine 20 mg/kg (RBI, Natick, Mass.) and xylazine 0.2 mg/kg (Bayer, Shawnee Mission, Kans.) then transcardially perfused with 200 ml PBS, pH 7.4 followed by 200 ml 4% PFA in PBS. The brains and spinal cords were removed, blocked, and postfixed in the same fixative for 4 hours at 4° C. then cryoprotected in 30% sucrose in PBS at 4° C. for 48 hours before freezing on dry ice. Coronal brain sections and transverse spinal cord sections were cut at 30 µm using a freezing microtome. Tissue sections were immediately immersed in PBS and stored at 4° C. until use. Sections were processed free-floating according to the protocol outlined in NEN Life, Science Products TSA (Tyramide Signal Amplification) Indirect Kit. Briefly, tissue sections were permeabilized in 0.2% Triton X-100 (Sigma, St. Louis, Mo.)/PBS, incubated in 1% hydrogen peroxide (Sigma, St. Louis, Mo.)/PBS to remove endogenous peroxidase activity then blocked in TNB Buffer (0.1 M Tris-HCl, pH 7.5, 0.15 M NaCl, and 0.5% Blocking Reagent. Sections were incubated for 24 hours at 4° C. in either the anti-GAL2 or anti-GAL3 antiserum (1:100). Following incubation with the primary antiserum, the tissue sections were washed in TNT Buffer (0.1 M Tris-HCl, pH 7.4, 0.15 M NaCl, 0.05% Tween 20) followed by incubation at 25° C. for 30 minutes with horseradish peroxidase (HRP)-conjugated goat anti-rabbit immunoglobulin (1:200) (Sternberger Monoclonals Inc., Lutherville, Md.). Tissue sections were rinsed in TNT Buffer and incubated in a solution containing biotinylated tyramide to amplify the signal then rinsed in TNT buffer and incubated with HRP-conjugated to streptavidin at 25° C. for 30 minutes. An immunoperoxidase reaction was done by incubating the section in 3,3'-diaminobenzidine (DAB) (0.05%) in 00.1 mM Tris, pH 7.4 and adding hydrogen peroxide to 0.006% immediately before use. The reaction was stopped in water and the sections mounted on microscopic slide with mounting medium (40% ethanol: gelatin) and counterstained with Cresyl violet then coverslipped for light microscopy.

Optimal GAL3 antibody concentrations (1:200) for rat brain sections were determined in preliminary titration experiments. Experimental controls in the tissue sections included (1) incubation in normal rabbit serum or (2) omission of the primary antiserum.

Analysis

COS-7 cells and tissue sections were examined using a Zeiss Axioscope. A total of 6 male rats were examined with the anti-GAL3 antiserum. The identification of GAL3-LI in the transfected cells and brain regions was based on the presence of immunoreactivity appearing as a brownish precipitate in individual cells and their projections or in the neuropil of the tissue by light microscopy. The descriptions of neuroanatomic boundaries are based on the atlas of Paxinos and Watson (1998).

B. Results

Characterization of the GAL3 Antiserum Recombinant GAL1, GAL2, and GAL3 Receptor Transfected Cells The ability of the anti-GAL3 antiserum to recognize only the GAL3 receptor protein in vitro was established by performing immunocytochemistry on COS-7 cells transiently transfected with the recombinant receptor proteins for the rat GAL1, GAL2, and GAL3, or mock-transfected with vector only. Specific porcine $^{125}$I-galanin binding was detected for all transfectants except mock-transfected cells. An immune response was detected only in the COS-7 cells incubated with the antiserum generated for the particular recombinant receptor. Specifically, no immune reaction was observed with the anti-GAL3 antiserum (1:1000) in GAL1 or GAL2 transfected cells. Furthermore, no visible immune reaction was detected in the mock-transfected cells. Incubation of the cells in primary antiserum that had been preabsorbed with the antigenic peptide (2.0 µg/ml) or without the primary antiserum or with the primary replaced by normal goat serum did not result in an immune response.

Taken together, these data demonstrate that the anti-GAL3 antiserum recognizes the receptor against which it was generated and does not show cross reactivity with other known GAL receptors.

Western Blots

To determine the specificity of the anti-GAL3 antiserum, COS-7 cells were transiently transfected either with recombinant rat GAL2 or GAL3 receptors or with expression vector only; membranes were then isolated for evaluation by immunoblotting (see FIG. 1). The anti-GAL3 antiserum labeled proteins in membranes only from rat GAL3-transfected cells; a predominant band was evident with an apparent molecular weight of approximately 56 kDa (FIG. 1), somewhat higher than the amino acid-derived value of 40.4 kDa. (For comparison, apparent molecular weights determined by SDS-PAGE are 56 kDa (Servin et al., 1987) or 54 kDa (Chen et al., 1992) for native GAL receptors purified from rat brain and 54 kDa (Amiranoff et al., 1989) for native GAL receptors purified from Rin m 5F cells. These values are all higher than the amino acid-derived value any known GAL receptor subtype, including the value of 38.9 kDa for rat GAL1 (Parker et al., 1995). The apparently high molecular weight observed for rat GAL3 very likely reflects post-translational processing such as glycosylation; note that rat GAL3 contains multiple N-terminal glycosylation sites (Smith et al., 1998). Relative to the predominant band, additional species of higher molecular weight as well as lower molecular weight were labeled by the corresponding antiserum (FIG. 1). These are presumably receptor-related species composed of protein aggregates of C-terminal fragments, as they are absent in mock-transfected cells.

Immunohistochemical Distribution of GAL3-LI in the CNS

GAL3-like immunoreactivity (GAL3-LI) was observed in many regions of the brain, specifically, the neocortex, septum, hippocampus, amygdala, hypothalamus, brainstem, cerebellum, and spinal cord. Throughout the brain and spinal cord GAL3-LI was found to be associated with neuronal profiles however, there was neuropil staining observed in several brain regions. GAL3-LI was high in the septum, basal forebrain, and spinal cord dorsal horn. Lower GAL3-staining was observed in the neocortex, thalamus, hypothalamus, hippocampus, and ventral horn of the spinal cord. Several regions of the CNS almost exclusively expressed (GAL3-LI, specifically the caudate-putamen, accumbens nucleus, dorsal raphe and regions of the central gray. There was no observable staining of the fiber tracts.

The specificity of the anti-GAL3 antiserum was determined in tissue sections by (1) omission of the primary antiserum or (2) incubation with normal rabbit serum. No specific staining was observed in either condition. Preabsorption of the GAL3 primary antiserum with the antigenic peptide (10 μg/ml) decreased but did not completely block staining in the tissue sections as in the transfected cells. This was most likely related to the different localization approaches. In the transiently transfected COS-7 cells the expression of GAL3 receptor protein was relatively high therefore, indirect immunocytochemistry with no amplification was used. In contrast, GAL3 receptor protein expression is presumed to be relatively lower in the tissue sections and for that reason the TSA (amplification) technique was employed. It is possible that because of the amplification (1000-fold) in the TSA technique even small amounts of unabsorbed antiserum may result in a signal.

Olfactory System

The main olfactory bulb contained a weak GAL3-LI in scattered cells of the glomerular and internal granule layers; the mitral cells did not contain GAL3-LI. In the anterior olfactory nucleus weak GAL3-LI was detected in random cell bodies and fibers. GAL3-LI was not detected above background in the superficial plexiform layer of the piriform cortex, but weak staining was observed in the neuropil of layer 2 and in the cell bodies of layer 3. Weakly stained cells were observed in the islands of Calleja, and tenia tecta; many cells in the olfactory tubercle were moderately stained.

Regions of the Telencephalon

Cerebral Cortex

GAL3-LI was widespread in the cerebral cortex and the distribution pattern extended rostrocaudally. Moderately stained GAL3-positive fibers were detected in layers II and III. Numerous pyramidal-shaped somata in layers II through V contained moderate GAL3-LI, and in some instances staining could be seen extending into the cell's dendritic arborizations. In layer VI, GAL3-LI was present only in the cytoplasm of scattered small cells. A weak to moderate GAL3-LI was seen in numerous cell bodies in the anterior cingulate and retrosplenial cortices. The entorhinal cortex contained GAL3-positive cell bodies and a finely stained neuropil.

Septal Region

An extensive and densely stained fiber network was seen throughout the entire lateral, intermediate and medial septal nuclei. The dorsal division of the lateral septum contained scarce moderately GAL3-positive somata.

Basal Ganglia and Basal Forebrain

GAL3-LI was detected in the receiving regions of the basal ganglia; thus GAL3 may mediate the internal organization of the basal ganglia. Many moderately labeled medium-sized round cells were evenly distributed throughout the caudate-putamen in addition to a weakly immunoreactive neuropil. Moderately positive cells were visible along themedial border of the globus pallidus. Numerous moderately GAL3-positive cell bodies and fibers were present in the shell and core of the accumbens nucleus. The cell bodies of the subthalamic nucleus, a relay nucleus in the basal ganglia, contained weak GAL3-LI.

Moderately GAL3-positive cells were present in several nuclei of the basal forebrain: the horizontal limb of the diagonal band, the basal nucleus of Meynert, and the substantia innominata.

Hippocampal Region

A large number of granule cells in the dorsal dentate gyrus and pyramidal-shaped cells in the polymorphic dentate gyrus displayed a weak to moderate GAL3-LI. Clusters of very fine light to moderately GAL3-immunoreactive fiber networks were evident in the molecular layer of the dentate gyrus. Light to moderate GAL3-LI was observed in the perikarya of the pyramidal-shaped cells in Ammon's horn and as a fine neuropil in the stratum oriens and stratum radiatum of fields CA1, CA2, and CA3. Labeled cells and fibers were observed in the rostral subiculum. Caudally, moderate to weak GAL3-LI was seen in the granule cells of the ventral dentate gyrus with weaker labeling in random cell bodies throughout the dorsal subiculum and the ventral CA1 field.

Amygdala and Extended Amygdala

In general, GAL3-LI was weak throughout the amygdala. Scattered cell bodies and fibers exhibited weak staining in several nuclei: the lateral, medial, posteroventral, posterodorsal medial, and posteromedial cortical nuclei. GAL3-positive cells were present in the anterior cortical amygdaloid nuclei, amygdalopiriform transition and amygdalohippocampal areas. Very fine GAL3-positive fibers with scattered moderately labeled cells were detected in the central amygdaloid nucleus. The divisions of the bed nucleus of the stria terminalis displayed a weak cellular GAL3-LI; moderately stained fibers were present in the nucleus of the lateral olfactory tract.

Regions of the Diencephalon

Hypothalamus and Preoptic Area

GAL3-LI was fairly extensive in the hypothalamus. Moderate GAL3-LI could be seen in the large cell bodies extending into the dendrites in the magnocellular preoptic nucleus. Relatively high GAL3 staining was observed in cells and neuropil of the suprachiasmatic and arcuate nuclei and as a dense fiber network in the median eminence. Moderately stained GAL3-positive fibers could be seen in the optic chiasm near the ventral border of the superchiasmatic nucleus. Moderate labeling was detected in cells and neuropil in several nuclei: the lateroanterior, lateral and anterior hypothalamus, supraoptic, dorsomedial, paraventricular parvocellular, periformical, ventromedial, and medial mammillary nuclei, and in cell bodies and fibers of the ventromedial nucleus.

Thalamus and Epithalamus

GAL3-LI was generally weak throughout the thalamus. The highest GAL3-LI in the thalamus was detected in the cell bodies and neuropil of the geniculate nuclei and the anteromedial thalamic nucleus. The reticular, paraventricular, central, mediodorsal, anterodorsal, anteromedial, anteroventral, lateral posterior, anterior pretectal, and posterior thalamic nuclei, the zona incerta and the nucleus of the fields of Forel contained light to moderately stained cells. The ventroposterior lateral and ventroposterior medial nuclei contained GAL3-positive cells and fibers. Weak labeling was detected in the cell bodies in the medial habenular nucleus with scarce positive cells in the lateral habenular nucleus.

Midborain/Mesencephalon

The neuropil and scattered cells in the zonal layer of the superior colliculus were moderately labeled. Light to moderately stained GAL3-positive cell bodies were observed in the superficial, intermediate gray and deep gray layers with a random positive cell in the optic nerve layer. Moderately labeled cell bodies were present in several midbrain regions: the dorsal and lateral ventral divisions of the central gray, the external cortex of the inferior colliculus, oculomotor, and rhabdoid nuclei and tegmental area. Labeled cells were detected within the dorsal raphe and projections from these cells were seen converging toward the midline of the raphe in the midbrain tegmentum, moderate GAL3-LI was present in the perikarya and dendrites of the large neurons of the red nucleus and retrorubral field. Small-sized pyramidal shaped weakly stained cell bodies were seen throughout the substantia nigra, reticular part with weaker labeling of the neuropil; moderately dense labeling of neuronal perlkarya was detected in the compact part. The pontine nucleus displayed a light to moderate GAL3-positive neuropil.

GAL3-LI was extensive throughout the brain stem. Moderate GAL3-LI was detected in the neuropil and cell bodies of several nuclei: the medial vestibular, prepositus hypoglossal, dorsal cochlear, and facial nuclei. Very weak GAL3-LI was observed in the gracile nucleus and no immunoreactivity was detected in the cuneate and hypoglossal nuclei. Moderate to light labeling was evident in large cell bodies and dendrites in the spinal vestibular and the dorsal motor nucleus vagus; weaker labeling was seen in the gigantocellular reticular, gigantocellular reticular, alpha, and lateral paragigantocellular nuclei. Numerous moderately labeled small round cells and neuropil was detected in the nucleus of the solitary tract; the parvicellular reticular nucleus contained moderately labeled small cells. Intense staining was observed in fibers in the area postrema and in cell bodies in the locus coeruleus. Light to moderate GAL3-LI was observed in scattered somata throughout the layers of the caudal spinal trigeminal nucleus, and labeled fibers were also seen in the superficial layer. Moderately heavy GAL3-LI was present in neuronal perikarya and dendrites in the trapezoid nucleus and in fibers in the subnuclei A, B, and K of the inferior olive. The pontine reticular nucleus contained low to moderate labeling of large-sized neurons.

Cerebellum

In the cerebellar cortex, moderate GAL3-LI appeared to be present in fibers that passed from the granule cell layer through the Purkinje cell layer. The molecular layer contained a weak to moderately stained very fine fiber network. Weak staining was visible in the neuronal perikarya of the deep cerebellar nuclei.

Spinal cord

GAL3-positive cells were detected throughout the dorsal and ventral horns of the spinal cord. In the superficial laminae of the dorsal horn small moderately immunoreactive cells and neuropil were observed. Moderately stained cell bodies were scattered throughout laminae III, IV and the laminae of the ventral horn, while labeled cells and neuropil were seen around the central canal in lamina X. GAL3-positive axons were observed in the ventral funiculus converging toward the ventral root. All levels of the spinal cord exhibited a comparable laminar distribution.

The distribution of rat GAL3 protein in the CNS using receptor subtype selective polyclonal antibodies and tyramide sianal amplification (TSA) immunocytochemistry is illustrated in Table 12. These were qualitative evaluations for the rat GAL3 receptor protein distribution based on the relative intensity of the chromogen (3,3'-diaminobenzidine) observed in individual cells at the microscopic level.

A total of 4 rat brains were analyzed for this study. As shown in Table 12, the strength of the signal obtained in various regions of the rat brain was graded as weak (+) or moderate (++) or intense (+++).

| REGION | cells | fibers | Potential Therapeutic Application |
|---|---|---|---|
| Olfactory System | | | Modulation of olfactory sensation |
| Internal granule cell layer | + | − | |
| Mitral cells | − | − | |
| Glomerular cell layer | + | − | |
| Anterior olfactory nucleus | + | + | |
| Olfactory tubercle | + | | |
| Islands of Calleja | + | | |
| Piriform cortex | + | + | |
| Tenia tecta | + | | |
| Telencephalon | | | Sensory integration |
| Frontal | ++ | | Anxiety/Depression |
| Cingulate | ++ | | Anxiety/Depression |
| Parietal | ++ | | Processing visual stimuli |
| Insular | ++ | | |
| Occipital | ++ | | |
| Temporal | ++ | | Processing auditory stimuli |

-continued

| REGION | cells | fibers | Potential Therapeutic Application |
|---|---|---|---|
| Retrosplenial cortex | ++ | | |
| Entorhinal cortex | ++ | ++ | |
| Basal Ganglia and basal forebrain | | | The control of movement. Parkinson's disease, Huntington's disease and hemibalismus |
| Accumbens nucleus | ++ | − | Treatment of the positive symptoms of schizophrenia Treatment of drug addiction. This region is particularly sensitive to psychoactive drugs. Anxiety/depression |
| Caudate-putamen | ++ | + | Sensory/motor integration |
| Globus pallidus | ++ | − | |
| Entopeduncular nucleus | − | − | |
| Substantia nigra, reticulata | ++ | + | |
| Horizontal limb of the diagonal band | ++ | | |
| Vertical limb of the diagonal band | ++ | | |
| Subthalamic nucleus | + | − | |
| Substantia innominata | ++ | | |
| Basal nucleus of Meynert | ++ | | |
| Septal Region | | | Relief of fear, initiation of motivated behavior, ex. food intake |
| Lateral septal nucleus, dorsal | + | ++ | |
| Lateral septal nucleus, ventral | + | ++ | |
| Intermediate septal nucleus | − | ++ | |
| Medial septal nucleus | | ++ | |
| Hippocampus | | | Memory consolidation and retention, Alzheimer's disease, cognitive disorders |
| Dentate gyrus, granule cell layer | + | − | |
| Dentate gyrus, molecular layer | − | + | |
| Polymorphic dentate gyrus | + | | |
| Ammon's horn: | | | |
| CA1 | ++ | + | |
| CA2 | ++ | + | |
| CA3 | ++ | + | |
| subiculum | + | + | |

-continued

| REGION | cells | fibers | Potential Therapeutic Application |
|---|---|---|---|
| Amygdala and extended Amygdala | | | Treatment of anxiety, panic attack, and depression. Treatment of disorders of integrated behaviors such as defense, ingestion, reproduction, and learning. |
| Basolateral nucleus | | + | |
| Lateral nucleus | + | + | |
| Central nucleus | ++ | ++ | Fear and anxiety |
| Medial nucleus | + | + | |
| Lateral olfactory tract | ++ | − | |
| Bed nucleus of the stria terminalis | + | + | |
| Posteromedial cortical amygdaloid nucleus | + | + | |
| Amygdalohippocampal area | + | − | |
| Amygdalopiriform transition | + | − | |
| Nucleus Lateral olfactory tract | − | ++ | |
| Anterior cortical amygdaloid nucleus | + | − | |
| Diencephalon | | | |
| Hypothalamus | | | Treatment of appetite disorders, ex. obesity. Treatment of endocrine disorders. |
| Medial preoptic area | + | + | |
| Median preoptic nucleus | | | |
| Magnocellular preoptic nucleus | ++ | − | |
| Anterior hypothalamic area | ++ | ++ | |
| Lateroanterior hypothalamic nucleus | ++ | ++ | Sympathetic activating region, regulation of autonomic function |
| Dorsomedial nucleus | ++ | ++ | |
| Ventromedial nucleus | +++ | ++ | |
| Arcuate nucleus | ++ | +++ | Regulation of food intake |
| Paraventricular | ++ | ++ | Regulation of food intake |

-continued

| REGION | cells | fibers | Potential Therapeutic Application |
|---|---|---|---|
| Periformical area | ++ | ++ | |
| Lateral hypothalamus | ++ | ++ | General arousal and sensory sensitization associate with motivated behavior (hunger and thirst). Analgesia |
| Median eminence | − | +++ | |
| Supraoptic nucleus | ++ | ++ | |
| Suprachiasmatic nucleus | +++ | ++ | Treatment of sleep disorders |
| Medial mammillary nucleus | ++ | ++ | |
| Thalamus and epithalamus | | | Analgesia/ Modulation of sensory information |
| Anterodorsal nucleus | + | − | Limbic system. Modulation of motor information to the cerebral cortex/eye movement |
| Anteromedial nucleus | ++ | ++ | Limbic system |
| Anteroventral nucleus | + | − | Motor |
| Anterior pretectal nucleus | ++ | − | |
| Dorsal geniculate nucleus | ++ | ++ | Vision |
| Medial geniculate nucleus | ++ | ++ | Hearing |
| Centromedial nucleus | + | − | Modulation of motor and behavioral responses to pain |
| Mediodorsal nucleus | + | − | |
| Reuniens nucleus | + | − | |
| Paraventricular nucleus | + | − | Modulation of motor and behavioral responses to pain |
| Reticular nucleus | + | − | Alertness/sedation |
| Periformical nucleus | + | + | |
| Ventroposterior nucleus | + | + | Somatic sensation |
| Ventrolateral nucleus | + | + | |
| Nucleus of the Field of Forel | + | − | |
| Zona incerta | + | − | |
| Medial habenular nucleus | + | − | |
| Lateral habenular n | + | − | |
| Parafascicular nucleus | − | − | Motor and behavioral responses to pain. Analgesia |
| Midbrain/Mesencephalon | | | |
| Superior colliculus | ++ | ++ | Modulation of visual stimuli |
| Inferior colliculus | ++ | − | |
| Central gray | ++ | − | Analgesia |
| Rhabdoid nucleus | ++ | − | |
| Dorsal raphe | ++ | − | Depression/ Analgesia |
| Oculomotor nucleus (3) | ++ | − | |
| Dorsal n lateral lemniscus | ++ | ++ | |
| Ventral n lateral lemniscus | ++ | − | |
| Red nucleus | ++ | − | Motor coordination |
| Retrorubral field | ++ | − | |
| Ventral tegmental area | ++ | − | Depression |
| Substantia nigra, pars reticulata | ++ | + | Control of movement |
| Substantia nigra, pars compacta | ++ | + | Control of movement |
| Prerubral field | | | |
| Interpeduncular nucleus, caudal s | ++ | − | |
| Interpeduncular nucleus, rostral | − | + | |
| Trapezoid nucleus | ++ | − | |
| Pontine nuclei | + | − | |
| Brainstem/Pons/Medulla | | | |
| Dorsal cochlear nucleus | ++ | ++ | |
| Prepositus hypoglossal nucleus | ++ | − | |
| Medial vestibular | ++ | ++ | Maintenance of balance and equilibrium |
| Spinal vestibular | + | − | |
| Parvicellular reticular n | ++ | − | |
| Gigantocellular reticular nucleus | + | − | Analgesia |
| Gigantocellular reticular n, alpha | + | − | Analgesia |
| Lateral paragigantocellular n | + | − | Analgesia |
| Reticular tegmental n pons | + | + | |
| Locus coeruleus | +++ | − | Modulation of noradrenergic transmission. Treatment of depression |
| Dorsal motor n vagus (10) | ++ | − | |
| Area postrema | − | +++ | |
| Nucleus of the solitary tract | ++ | ++ | Modulation of general visceral sensation and taste. |
| Spinal trigeminal nucleus, caudal | + | + | |
| Hypoglossal nucleus (12) | − | − | |
| Gracile nucleus | + | − | |
| Cuneate nucleus | − | − | |
| Facial | ++ | ++ | |
| Cerebellum | | | Motor coordination |
| Granule cells layer | + | + | |
| Molecular layer | − | ++ | |
| Purkinje cells | − | − | |
| Deep cerebellar nuclei | + | − | |
| Spinal cord | | | |
| Dorsal horn, superficial layer | ++ | ++ | Analgesia |
| Lamina X | ++ | + | |
| Ventral horn | ++ | − | Spinal reflex |

Discussion

The GAL3 antiserum was characterized using recombinant GAL receptors in transiently transfected COS-7 cells and Western blot analysis and the specificity of the GAL3 antiserum to recognize only the cognate receptor in vitro was established. The anatomical distribution of the GAL3 receptor protein in the rat CNS was determined using a modified immunohistochemical technique to enhance sensitivity and delectability via tyramide signal amplification (Toda et al. 1999).

The results indicate that the expression GAL3-LI was primarily found in neuronal profiles with neuropil labeling detectable in several areas. In general, the distribution of GAL3-LI is in good agreement with the reported distribution for galanin-LI, galanin binding sites, and GAL3 mRNA in the rat brain (for recent review, Branchek et al., 2000). Overall, GAL3-LI was found to be extensively distributed throughout the brain: the neocortex, septum, hippocampus, amygdala, hypothalamus, brain stem, cerebellum and spinal cord. Paralleling the distribution of galanin banding sites, GAL3-LI was observed in ventral regions of the brain, specifically the horizontal diagonal bard, substantia innominata, olfactory tubercle, and ventral hippocampus. However, there was discordance between $^{125}$I-galanin binding and the GAL3 receptor protein distribution particularly in the neocortex, dorsal hippocampus, and cerebellum (Skofitsch and Jacobowitz, 1986), regions where binding sites have not been identified by receptor autoradiography.

The present results showed several interesting observations in the distribution of GAL3-LI relating to potential therapeutic applications for the GAL3 receptor.

Galanin has been reported to be involved in the regulation of cholinergic neuotransmission in the hippocampus and in the basal forebrain via modulation of acetylcholine release. Therefore, the development of a galanin receptor antagonist to block the inhibition of firing of cholinergic neurons may have a potential therapeutic application in the treatment of some of the learning and memory deficits of Alzheimer's disease (AD) (for review, Mufson et al. 1998). GAL3-LI was identified in several cholinergic regions of the rat brain: the horizontal diagonal band, basal nucleus of Meynert, substantia innominata, bed nucleus of the stria terminalis, and the hippocampus. The GAL3 protein has been localized to other regions of the brain, the entorhinal cortex and locus coeruleus, that exhibit increased galanin receptor binding and galanin expression in AD providing further evidence for the potential involvement of GAL3 in AD.

Substantial evidence suggests that galanin is involved in the regulation of energy and nutrient balance. Injections of galanin into the hypothalamus have been shown to increase food intake. Concordant with the localization of GAL3 mRNA in the hypothalamus, GAL3-LI was detected in several hypothalamic nuclei involved in the regulation of feeding: the paraventricular, arcuate, dorsomedial, ventromedial and medial preoptic areas. This localization suggests that the GAL3 receptor may be a potential therapeutic target in the regulation of food intake and body weight and thus be useful in the treatment of eating disorders.

GAL3 may be a potential therapeutic target in the development of analgesic drugs. The presence of the receptor in the target regions of nociceptive primary afferent fibers, the superficial layers of the spinal trigeminal nucleus and dorsal horn of the spinal cord, suggests that GAL3 could potentially modulate nociceptive information from the periphery. GAL3 is in a position to potentially mediate the influence of excitatory glutamatergic nociceptive primary afferents from the dorsal root ganglia in the superficial layers of the spinal cord.

In Vivo Model

Chronic Constriction Nerve Injury Model of Neuropathic Pain

The aim of this study was to assess the potential analgesic effects of Example 92 following intraperitoneal administration at the doses of 3, 10 and 30 mg/kg, respectively, in an animal model of neuropathic pain. A peripheral mononeuropathy was induced in the right hind limb of rats following a chronic constriction nerve injury (Bennett and Xie, 1988), and the development of mechanical allodynia and thermal hyperalgesia was monitored using established behavioral tests (Attal, N., et al., 1990; Hargreaves, K., et al., 1988).

Method

Animals

Male Sprague-Dawley rats within the weight range of 200-225 g, and approximate age 7-9 weeks, were allowed to acclimate for a minimum of 6 days prior to the start of the behavioral testing.

All rats underwent a chronic constriction nerve injury, and of these, those that successfully developed allodynia and hyperalgesia were allocated to treatment groups.

Treatment Groups and Dosing of Test Substance

There were 5 separate treatment groups (with a minimum of 10 rats per group). The treatment groups were as follows:

Group C received Morphine at 10 mg/kg (n=10)
Group D received Vehicle for Example 92* at 1 ml/kg (n=10) (* 100% DMSO)
Group E received Example 92 at 30 mg/kg (n=10)
Group F received Example 92 at 3 mg/kg (n=10)
Group G received Example 92 at 10 mg/kg (n=10)

The dose volume for all treatments was 1 ml/kg. Each rat received a single i.p. dose of the test substance, reference substance or vehicle on Day 12 PO. Test substance and vehicle dosing solutions were encoded (C-G) so that the observers were unaware of the identity of the treatment groups.

Behavioral Testing

The behavioral tests (Von Frey filament and Thermal Plantar Tests—see below) were performed on all rats on 3 separate days prior to surge Id, to establish baseline values. The pre-surgery baseline values were calculated as the mean of the last 2 days testing (the data from the first day of testing were not included as this was classed as part of the acclimating period). The sequence of tests was always mechanical allodynia (Von Frey Test) followed by thermal hyperalgesia (Thermal Plantar Test), with a minimum 5 min period allowed between the 2 tests.

Mechanical Allodynia:

Each animal was placed in a wire mesh cage and a series of Von Frey filaments (ranging from filament handle number 3.61 to 6.10) applied to the plantar surface of the hind paw, from below. The filaments were applied in ascending order (starting with the weakest force) and the withdrawal threshold for both the ipsilateral and contralateral hind paws was evaluated. Each filament was indented on the plantar surface of the foot to the point where it just started to bend, and this was repeated approximately 8-10 times per filament at a frequency of approximately 1 Hz. The withdrawal threshold was defined as the lowest force of two or more consecutive Von Frey filaments to elicit a reflex withdrawal response.

Thermal Hyperalgesia:

Each rat was placed in a clear plastic chamber with a glass floor and allowed a short period to acclimatize to the new environment (approximately 5 min.). The animals were then challenged with a radiant Infrared (IR) heat source, directed at the plantar surface of the hind paw from below, and the withdrawal latency of both the ipsilateral and contralateral hind paws was evaluated. The infrared intensity was set at IR50 and the maximum length of exposure to the IR source was 18 s. Non-responding animals were allocated a withdrawal latency of 18 s.

Surgical Procedure

The animals were surgically prepared over 5 days. Each rat was anaesthetized with sodium pentobarbitone (60 mg/ml; 0.6 ml/kg dose, intraperitonealy; batch number 00230; expiry date 22 May 3) and then supplemented as necessary with isoflurane (1-3% in oxygen). The surface around the incision site was shaved and then sterilized with surgical spirit. Under aseptic conditions the right sciatic nerve was exposed by blunt dissection at mid-thigh level and approximately 1 cm of nerve was freed of adhering connective tissue. Four chromic cat gut (4.0) ligatures, spaced at approximately 1 mm inzervals, were then tied so as to barely constrict the nerve (as viewed under 40× magnification) to induce a peripheral mononeuropathy in the right hind limb. The overlying muscle and skin were then closed in layers using suture material, and the anesthesia discontinued. On recovery from anesthesia, the rats were re-housed with their cage mates on soft padded bedding overnight (to reduce the risk of infection) and subsequently on sawdust bedding following full recovery. The animals were allowed 4 full days to recover before the behavioral testing was recommenced.

Testing Paradigm

Following surgery, the behavioral testing was resumed on Day 5 PO (post-operative), and then repeated on days 7, 9, and 11, to monitor the development of allodynia and hyperalgesia. Only those animals that developed both mechanical allodynia and thermal hyperalgesia in their nerve-injured hind paw were used in the main study. The animals were deemed to have developed mechanical allodynia if their nerve-injured hind paw exhibited a withdrawal response of $\leq 5$ g of force (which corresponds to monofilament number 4.56 or less) on Day 11/12 PO, when challenged with the Von Frey filaments. Similarly, they were deemed to have developed thermal hyperalgesia if their nerve-injured hind paw exhibited a withdrawal latency (sec) which showed a $\geq 30\%$ difference from the mean right paw, pre-surgery value, for the Thermal Plantar Test on Day 11/12 PO.

On Day 12 PO, a single i.p. dose of test substance, reference substance (morphine) or vehicle was administered to each rat. On Day 12, all the animals were then tested with the Von Frey filaments at approximately 30 and 90 min post dose (PD) and with the Plantar Device at approximately 40 and 100 min PD, with a minimum 5 minute period allowed between the 2 tests, to investigate treatment effect.

Statistical Analysis

The Von Frey data were logarithmically transformed [$\log^{10}$ of (force in grams×10000)] prior to analysis. Statistical comparisons were made between treatment groups using parametric (e.g. one-way analysis of variance, Dunnett's t-test, Student's t-test) or non-parametric (e.g. Kruskal-Wallis statistic, Dunn's test, Mann-Whitney U-test) statistical procedures. The choice of parametric or non-parametric test was based on whether the groups to be compared satisfied the homogeneity of variance criterion (evaluated by the Levene Mean test or F-test). Statistical significance was assumed when $P \leq 0.05$.

Results

The majority of the animals which underwent a chronic constriction injury of the right sciatic nerve successfully developed both neuropathic pain states. These animals exhibited a marked increase in sensitivity to both the behavioral tests in the days post-injury, indicative of the development of a peripheral mononeuropathy. This change in sensitivity was evident from as early as day 5 PO, reaching a maximum from approximately day 10 PO onwards.

Mean Von Frey pre-surgery baseline responses for those animals included in the study were 57.65±0.98 g (left paw) and 59.45±1.36 g (right paw). Eighty-nine percent of the animals which underwent a chronic constriction nerve injury successfully developed mechanical allodynia by Day 11/12 PO.

Mean plantar pre-surgery baseline responses for those animals included in the study were 13.1±0.2 s (left paw) and 12.6±0.2 s (right paw). The mean plantar responses prior to dosing were 12.0+0.2 s (left paw) and 5.6±0.1 s (right paw). Eighty-seven percent of the animals which underwent a chronic constriction nerve injury successfully developed thermal hyperalgesia by Day 11/12 PO.

Effects of Example 92 on Behavioral Test Responses

Mechanical Allodynia:

Intraperitoneal administration of Example 92 significantly increased the withdrawal threshold of the nerve-injured hind paw to Von Fey filament challenges at the highest dose tested (30 mg.kg,). Thee changes were significantly different from vehicle (100% DMSO) control group values at the 30 min PD time point only. Administration of 30 mg/kg Example 92, resulted in a significant increase in the withdrawal threshold of the nerve-injured paw to 25.98±8.25 g compared to the vehicle group value of 4.82±2.77 g ($P \leq 0.05$), at 30 min. PD. At 90 min. PD the withdrawal threshold was still slightly raised (11.73±6.43 g compared to 2.43±1.48 g in the vehicle treated group), however this was not found to be significant. Administration of Example 92 at 3 or 10 mg/kg (i.p.) had no significant effect on the withdrawal threshold of the nerve-injured paw at any of the time points tested. No significant changes were observed in the responses of the uninjured (contralateral) left paw at any of the doses or at any of the time points tested, compared with vehicle control group values. (These results are summarized in FIGS. 2 and 3.)

Intraperitoneal administration of % he reference substance, morphine (10 mg/kg), significantly increased the withdrawal threshold of the nerve-injured hind paw to Von Frey filament challenges. (See FIGS. 2 and 3.)

Thermal Hyperalgesia:

Intraperitoneal administration of Example 92 at 3, 10 and 30 mg/kg had no significant effect on the withdrawal latency of the nerve hind paw, to the thermal plantar device at either time points tested (approximately 40 and 100 min. PD). No significant changes were observed in the responses of the uninjured (contralateral) left paw following Example 92 administration at any of the doses or time points tested, compared with vehicle control group values. (These results are summarized in FIGS. 4 and 5.)

Intraperitoneal administration of morphine (10 mg/kg) significantly increased the withdrawal latency of the nerve-injured hind paw to the Thermal Plantar Device at both time points tested (approximately 40 and 100 min. PD). (See FIGS. 4 and 5.)

Discussion

The chronic constriction injury model of Bennett and Xie (1988) is one of the more commonly used animal models of neuropathic pain. Within one week the animals showed altered spontaneous behaviors which are consistent with the presence of neuropathic pain in addition, the affected limb is demostrably hyperalgesic (i.e. displays an increased sensitivity to noxious stimuli), as well as allodynic (i.e. displays a reduced threshold to non-painful stimuli) (Attal et al., 1990). This study provides behavioral evidence that an experimental peripheral mononeuropathy produced by sciatic nerve ligation, produces significant pain-related behavioral changes in the rat, consistent with the development of mechanical allodynia and thermal hyperalgesia (Gautron, M., et al, 1990). These abnormal pain states were evident from as early as day 5 PO, showing maximal changes from approximately day 9 PO onwards. A similar proportion of animals developed mechanical allodynia (89%) compared to thermal hyperalgesia (87%), with 79% successfully developing both pain states in their nerve-injured paw.

From the behavioral data obtained in the present study, it is apparent that i.p. administration of Example 92 at a dose of 30 mg/kg significantly attenuates specific pain-related behaviors in neuropathic rats, namely mechanical allodynia. These results are consistent with analgesic properties.

The withdrawal threshold of the nerve-injured paw to Von Frey filament challenges was significantly increased at approximately 30 min. PD following administration of Example 92 at a dose of 30 mg/kg i.p. Unlike morphine (10 mg/kg i.p.) which also elicited significant contralateral effects in the Von Frey test at 30 and 90 min post-dose, Example 92 showed no significant contralateral effects, at any of the doses tested.

Intraperitoneal administration of the reference substance, morphine, resulted in a significant increase in the withdrawal threshold (Von Frey challenge) of the nerve-injured paw for up to 90 min PD at 10 mg/kg. In addition, significant contralateral effects were observed at both the 30 and 90 min. time points, indicative of the central effects of morphine. Morphine also caused a significant increase in the withdrawal latency to a noxious heat stimulus (thermal plantar test) for up to 100 min PD in both the nerve-injured and contralateral hind paws. These results are consistent with morphine's known pharmacological properties as an opioid analgesic.

These results therefore provide behavioral evidence of a specific analgesic role for Example 92 in neuropathic rats. The analgesic properties were selective, attenuating mechanical allodynia in the nerve-injured paw only (unlike the effects of the reference substance, morphine (10 mg/kg), which also produced significant contralateral effects in the mechanical allodynia test).

REFERENCES

Amiranoff, B., et al., (1989) Galanin receptor in the rat pancreatic beta cell line Rin m 5F. Molecular characterization by chemical cross-linking. *J. Biol. Chem.*, 264 (34): 20714-20717.

Attal, N., et al. (1990) Further evidence for "pain-related" behaviours in a model of unilateral peripheral mononeuropathy. *Pain* 41: 235-251.

*Asymmetric Synthesis* (1983) Vol: 2-5, Academic Press, Editor Morrison, J.

Bakker, R. A., et al., (2000) Constitutive activity of the histamine H1 receptor reveals inverse agonism of histamine H1 receptor antagonists. *Eur. J. Pharmacol.*, 387: R5-R7.

Bennett, G. J. & Xie, Y-K. (1988) A peripheral mononeuropathy in rat that produces disorders of pain sensation like those seen in man. *Pain* 33: 87-107.

Borowsky, B., et al., (1999) Cloning and characterization of the human galanin GALR2 receptor. *Peptides*, 19: 1771-1781.

Bradford, M. M. (1976) A rapid and sensitive method for the quantitation of microgram quantities of protein utilizing the principle of the protein-dye binding. *Anal. Biochem.*, 72: 248-254.

Branchek, T. A., et al., (2000) Galanin receptor subtypes. *Trends in Pharm. Sci.*, 21: 109-116.

Bryant, W. M. III, et al., (1993) *Synthetic Communications*, 23: 1617-1625.

Chen, Y., et al., (1992) Solubilization and molecular characterization of active galarnin receptors from rat brain. *Biochemistry*, 31(8): 2415-2422.

Coppola, G. M. (1987) Journal of *Heterocyclic Chemistry*, 24: 1249.

Cullen, B. (1987) Use of eukaryotic expression technology in the functional analysis of cloned genes. *Methods Enzymol.*, 152: 685-704.

deLigt, R. A., et al., (2000) inverse agonism at G protein-coupled receptors: (patho)physiological relevance and implications for drug discovery. *Br. J. Pharmacol.*, 130 (1): 1-12.

Ennis, M. D. and Ghazal, N. B., (1992) The synthesis of (+) and (−)-flesinoxan: Application of enzymatic resolution methodology. *Tetrahedron Lett.*, 33: 6287-6290.

Fisher, K. et al., (1998) Intrathecal administration of the mGluR compound, (S)-4CPG, attenuates hyperalgesia and allodynia associated with sciatic nerve constriction injury in rats. *Pain* 77(1): 59-66.

Fisher, K., Lefebvre, C., and Couderre, T. J., (2002) Antinociceptive effects following intrathecal pretreatment with selective metabotropic glutamate receptor compounds in a rat model of neuropathic pain. *Pharmacol Biochem Behav* 73(2): 411-418.

Garden, S. J., et al., (1998). *Synthetic Communications*, 28: 1679-1689.

Gautron, M., et al. (1990) Alterations in myelinated fibres in the sciatic nerve of rats after constriction: possible relationships between the presence of abnormal small myelinated fibres and pain-related behaviour. *Neurosci Letters* 111: 28-33.

Green, T. W. and Wuts, P. G. M. (1991) *Protection groups in Organic Synthesis*, second Edition John Wiley & Sons, Near York.

Guy, A. P. and Gardner, C. R. (1985) Pharmacological characterisation of a modified social interaction model of anxiety. *Neuropsychobiology*, 13: 194-200.

Hargreaves, K., et al. (1988) A new and sensitive method for measuring thermal nociception in cutaneous hyperalgesia. *Pain* 32: 77-88.

Harlow, E. and Lane, D. (1999) *Immunoblotting*. In: Barker, P. editor. Using Antibodies: A Laboratory Manual. New York: Cold Spring Harbor Laboratory Press. p 267-309.

Herrick-Davis, K., et al., (2000) Inverse agonist activity of a typical antipsychotic drugs at human 5-Hydroxytryptamine2C receptors. *J. Pharmacol. Exp. Ther.*, 295(1): 226-32.

Hess, B. A. Jr. and Corbino, S. (1971) *Journal of Heterocyclic Chemistry*, 8: 161.

Jansson, A., et al., (1989) Centrally administered galanin reduces dopamine utilization in the median eminence and increases dopamine utilization in the medial neostriatum of the male rat. *Acta Physiol. Scand.*, 135: 199-200.

Javitch, J. A., et al, (1984) ³H-Mazindol binding associated with neuronal dopamine and norepinephrine uptake sites. *Molecular Pharmacology*, 26: 35-44.

Jaques, J., et al., (1981) *Enantiomer, Racemates and Resolutions*. John Wiley & Sons.

Julius, D., et al., (1988) Molecular characterization of a functional cDNA encoding the serotonin 1c receptor. *Science*, 241: 558-564.

Kenakin, T. (1996) The classification of seven transmembrane receptors in recombinant expression systems. *Pharmacol. Rev.*, 48(3): 413-63.

Lutz, M. and Kenakin, T. (1999) *Quantitative Molecular Pharmacology and Informatics in Drug Discovery*, John Wiley & Sons, LTD, West Sussex, England. p. 153.

Monsma, F. J. Jr., et al., (1993) Cloning and expression of a novel serotonin receptor with high affinity for tricyclic psychotropic drugs. *Mol. Pharmacol.*, 43: 320-327.

Nógrádi, M. (1987) *Stereoselective Synthesis*, VCH, Editor Ebel, H.

Owens, M. J. (1997) Neurotransmitter receptor and transporter binding profile of antidepressants and their metabolites. *J. Pharm. Exp. Ther.*, 283: 1305-1322.

Parker, E. M., et al., (1995) Cloning and characterization of the rat GALR1 galanin receptor from Rin14B insulinoma cells. *Mol. Brain Res.*, 34: 179-189.

Paxinos, G. and Watson, C. (1986) The Rat Brain in Stereotaxic Coordinates. San Diego: Academic Press, Inc.

Servin, A. L., et al., (1987) Identification and molecular characterization of galanin receptor sites in rat brain. *Biochem. Biophys. Res. Commun.*, 144(1): 298-306.

Smith, K. E., et al., (1998) Cloned human and rat galanin GALR3 receptors Pharmacology and activation of G-protein inwardly rectifying K+ channels. *J. Biol. Chem.*, 273(36): 23321-223326.

Sternberger, L. A. (1982) Neurotypy: regional individuality in rat brain detected by immunocytochemistry with monoclonal antibodies. *Proc. Natl. Acad. Sci. USA*, 79: 1326-1330.

Toda, Y., et al., (1999) Application of tyramide signal amplification system to immunohistochemistry: a potent method to localize antigens that are not detectable by ordinary method. *Pathol. Int.*, 49(5): 479-483.

Wiesenfeld-Halin, Z., et al., (1992) *Proc. Natl. Acad. Sci. USA.*, 89: 3334-3337.

What is claimed is:

1. A method of treating a subject suffering from neuropathic pain, which comprises administering to the subject an amount of a compound effective to treat the subject's neuropathic pain, wherein the compound has the structure:

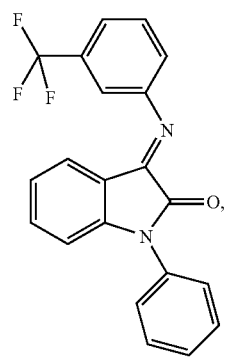

or a pharmaceutically acceptable salt thereof

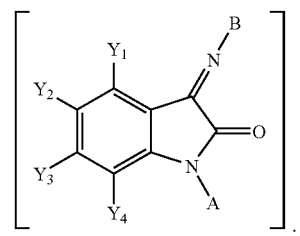

* * * * *

UNITED STATES PATENT AND TRADEMARK OFFICE
CERTIFICATE OF CORRECTION

PATENT NO. : 7,220,775 B2  Page 1 of 1
APPLICATION NO. : 10/637299
DATED : May 22, 2007
INVENTOR(S) : Thomas P. Blackburn It is certified that error appears in the above-identified patent and that said Letters Patent is hereby corrected as shown below:

Claim 1 in column 258, lines 9-40, "A method of treating a subject suffering from neuropathic pain, which comprises administering to the subject an amount of a compound effective to treat the subject's neuropathic pain, wherein the compound has the structure:

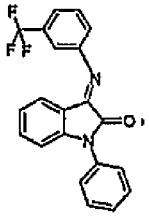

or a pharmaceutically acceptable salt thereof

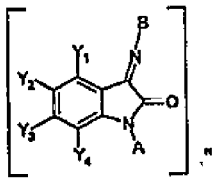

should read --A method of treating a subject suffering from neuropathic pain, which comprises administering to the subject an amount of a compound effective to treat the subject's neuropathic pain, wherein the compound has the structure:

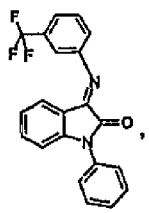

or a pharmaceutically acceptable salt thereof.--

Signed and Sealed this

Thirty-first Day of July, 2007

JON W. DUDAS
*Director of the United States Patent and Trademark Office*